(12) United States Patent
Handfield et al.

(10) Patent No.: US 7,052,860 B2
(45) Date of Patent: May 30, 2006

(54) **IDENTIFICATION OF *ACTINOBACILLUS ACTINOMYCETEMCOMITANS* ANTIGENS FOR USE IN THE DIAGNOSIS, TREATMENT, AND MONITORING OF PERIODONTAL DISEASES**

(75) Inventors: Martin Handfield, Gainesville, FL (US); Jeffrey Daniel Hillman, Gainesville, FL (US); Ann Progulske-Fox, Keystone Heights, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 09/995,493

(22) Filed: Nov. 28, 2001

(65) Prior Publication Data

US 2006/0035293 A1    Feb. 16, 2006

(51) Int. Cl.
G01N 33/569 (2006.01)
G01N 33/554 (2006.01)
C07H 21/04 (2006.01)
A61K 39/02 (2006.01)

(52) U.S. Cl. .................. 435/7.32; 435/69.1; 435/71.1; 435/91.2; 435/243; 435/252.2; 435/320.1; 435/810; 536/23.1; 536/23.7; 536/24.1; 536/24.32; 536/24.33; 424/184.1; 424/234.1; 424/235.1

(58) Field of Classification Search ............... 435/69.1, 435/91.2, 7.32, 810, 71.1, 243, 320.1, 252.2; 536/23.7, 24.1, 24.32, 24.33, 23.1; 424/184.1, 424/234.1, 235.1

See application file for complete search history.

(56) References Cited

U.S. PATENT DOCUMENTS

| 5,985,288 A | 11/1999 | Munson, Jr. et al. .... 424/256.1 |
| 6,713,071 B1 | 3/2004 | Ankenbauer et al. .... 424/234.1 |

FOREIGN PATENT DOCUMENTS

| EP | 0439210 | * | 1/1991 |
| EP | 0439211 | * | 1/1991 |
| EP | 0439212 | * | 1/1991 |
| EP | 0537830 | * | 10/1992 |
| WO | 10111081 | | 2/2001 |
| WO | 0277183 | | 10/2002 |

OTHER PUBLICATIONS

Flemmig et al 1996(Clinical and Diagnostic Laboratory Immunology; 3, 678-681).*
Ebersole et al 1995(J.Dent Res 74 (2) 658-666).*
Houghten et al. (Vaccines, 1986, Edited by Fred Brown: Cold Spring Harbor Laboratory, pp21-25).*
Rudinger et al, in "Peptide Hormones", edited by Parsons, J.A., University Park Press, Jun. 1976, page.*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67.*
Rudikoff et al (Proc Natl Acad Sci USA 1982 vol. 79 p. 1979).*
Malheiros et al Rev Saude Publica. Oct. 2004;38(5):723-728. Epub 2004.*
Löe, et al., "*Early Onset Periodontitis in the United States of America*", J. Periodontol., vol. 62, No. 10, pp. 608-616 (1991).
Handfield, et al., "*IVIAT: a Novel Method to Identify Microbial Genes Expressed Specifically During Human Infections*", Trends in Microbiology, vol. 8, No. 7, pp. 336-339 (2000).
International Search Report dated Feb. 28, 2005 corresponding to PCT/US02/37235 filed Nov. 20, 2002.
Cao, et al., "*In vivo induced antigenic determinants of Actinobacillus actinomycetemcomitans*", FEMS Microbiology Letters, 237 (2004) 97-103.
Wilson, et al., "*Virulence factors of Actinobacillus actinomycetemcomitans relevant to the pathogenesis of inflammatory periodontal diseases*", FEMS Microbiology Reviews, 17 (1995) 365-379.
Meyer, et al., "*The role of Actinobacillus actinomycetemcomitans in the pathogenesis of periodontal disease*", Trends in Microbiology, vol. 5, No. 6, pp. 224-228, 1997.
Murray, et al., "*The microbiology of HIV-associated periodontal lesions*", J. Clin. Periodontol. 16:636-642, 1989.
Komatsuzawa, et al., "*Identification of six major outer membrane proteins from Actinobacillus actinomycetemcomitans*", Gene, 288 (2002) 195-201.
International Search Report dated Nov. 3, 2004 corresponding to PCT/US03/32645.

* cited by examiner

*Primary Examiner*—Lynette R. F. Smith
*Assistant Examiner*—Padma Baskar
(74) *Attorney, Agent, or Firm*—McDonnell Boehnen Hulbert & Berghoff LLP

(57) ABSTRACT

Antibodies, polypeptides, and polynucleotides are provided for the detection, prevention, amelioration and treatment of diseases caused by *Actinobacillus actinomycetemcomitans*.

3 Claims, No Drawings

IDENTIFICATION OF ACTINOBACILLUS ACTINOMYCETEMCOMITANS ANTIGENS FOR USE IN THE DIAGNOSIS, TREATMENT, AND MONITORING OF PERIODONTAL DISEASES

GOVERNMENT INTERESTS

This invention was made with Government support under Grant Number RO1 DE13523 awarded by the National Institutes of Health (National Institute for Dental and Craniofacial Research, NIDCR). The Government has certain rights in the invention.

TECHNICAL AREA OF THE INVENTION

This invention provides methods and compositions for the diagnosis, treatment, preventions, and amelioration of diseases caused by Actinobacillus actinomycetemcomitans.

BACKGROUND OF THE INVENTION

Actinobacillus actinomycetemcomitans (Aa) is the principal etiologic agent of early-onset periodontitis including localized and generalized prepubertal periodontis, localized and generalized juvenile periodontis, and rapidly progressive or refractory adult periodontitis. Currently, diagnosis of these diseases is made by X-ray analysis usually long after the onset of the disease and after considerable damage to the supporting bone and tissue has occurred. Tooth loss is the ultimate detrimental effect of destructive periodontal disease. A national survey of the United States revealed a prevalence of localized juvenile periodontitis of 0.53% and of generalized juvenile periodontitis of 0.13%. Loe & Brown, J. Periodontol. 62:608–616 (1991). Findings from a number of studies corroborate the conclusion that early-onset disease is similar in other industrialized countries and is more frequent in developing countries. Loe & Brown, J. Periodontol. 62:608–616 (1991). Therefore, methods of early diagnosis of early-onset periodontitis, localized and generalized juvenile periodontis, and rapidly progressive or refractory adult periodontitis are needed in the art. In addition, certain types of adult periodontitis, which in general is a very common condition affecting over half the adult population, are likely to be caused by Aa. Furthermore, Aa can cause extra-oral diseases such as endocarditis, thyroid gland abscesses, urinary tract infections, brain abscesses, and vertebral osteomyelitis.

There are antibiotic, surgical, and mechanical therapies for the treatment of Aa induced periodontis, but no means for prevention. Tetracycline has been widely used in the treatment of early-onset periodontis. There remains a concern, however, of strains developing resistance to tetracycline as well as the possibility of overgrowth of other pathogenic microorganisms. Given the incidence of these diseases, a safe vaccine for Aa is needed. A vaccine can be, for example, a multivalent vaccine. Control of periodontal disease is also very important in light of recent attention to the possible role of periodontal infections as risk factors for systemic disease (e.g., coronary heart disease).

While most people have Aa as a normal member of their dental plaque, it usually does not cause disease. However, when Aa does cause disease, the host mounts an enormous immune response that is inevitably futile, presumably because the immune response is directed against the wrong Aa antigens. Providing the most appropriate periodontal treatment requires making an accurate diagnosis, performing optimum treatment, and monitoring the patient's response to therapy.

Currently, standard microbiological tests for Aa detect only the presence of Aa in dental plaque, and do not specifically identify disease activity. For this reason these tests have a low positive predictive value. Because Aa is normally found in the plaque of even healthy individuals, the application of these tests is limited in their usefulness to those who present with certain clinical manifestations of disease, including for example, patients with advanced attachment loss and bone loss before the age of 25, patients aged about 25–35 with rapid destruction of attachment and bone in a relatively short period of time (rapidly progressive periodontitis), and patients who continue to lose attachment despite stringent treatment (refractory periodontitis).

DNA probe technology has been developed to identify the presence of Aa in dental plaque, but this technology is unable to distinguish between Aa that is normally part of the dental plaque community and Aa that is involved in an actual disease process. Therefore, these DNA probes do not identify Aa involved in a disease process.

Therefore, methods of diagnosing, monitoring, treating, preventing, or ameliorating a disease caused by Aa are needed in the art.

SUMMARY OF THE INVENTION

It is an object of the invention to provide methods and compositions for the treatment, amelioration, and prevention of diseases caused by Aa. This and other objects of the invention are provided by one or more of the embodiments described below.

One embodiment of the invention provides a purified immunogenic polypeptide comprising at least 5 contiguous amino acids of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:103, SEQ ID NO:104, SEQ ID NO:105, SEQ ID NO:107, SEQ ID NO:109, SEQ ID NO:110, SEQ ID NO:111, SEQ ID NO:112, SEQ ID NO:113, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, and SEQ ID NO:234 ("the polypeptide SEQ IDs"). While each of these polypeptide sequences are collectively referred to as "the polypeptide SEQ ID" and are presented together in a group, each of these sequences can be separately considered and claimed.

Another embodiment of the invention provides a purified polypeptide comprising an amino acid sequence selected from the group consisting of "the polypeptide SEQ IDs."

Yet another embodiment of the invention provides a purified polynucleotide comprising a sequence that encodes a "polypeptide SEQ ID."

Still another embodiment of the invention provides a purified polynucleotide comprising at least about 15 contiguous nucleic acids of a sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:106, SEQ ID NO:108, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID N0:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231 and SEQ ID NO:233 ("the polynucleotide SEQ IDs"). While each of these polynucleotide sequences are collectively referred to as "the polynucleotide SEQ IDs" and are presented together in a group, each of these sequences can be separately considered and claimed.

Even another embodiment of the invention provides a purified polynucleotide comprising the nucleotide sequence of "the polynucleotide SEQ IDs" or degenerate variants thereof.

Another embodiment of the invention provides an expression vector comprising a "polynucleotide SEQ ID" operably linked to an expression control sequence. The vector can be in a cultured cell.

Still another embodiment of the invention provides an antibody or a fragment thereof that specifically binds to a polypeptide of "the polypeptide SEQ IDs." An antibody fragment can be, for example, a Fab or F(ab')$_2$ fragment. The antibody can be a monoclonal antibody or a polyclonal antibody. The antibody can be present in a pharmaceutical composition along with a pharmaceutically acceptable carrier.

Yet another embodiment of the invention provides a method for treating, ameliorating, or preventing a disease caused by *A. actinomycetemcomitans*. The method comprises administering to an animal an antibody of the invention or fragment thereof. A disease caused by *A. actinomycetemcomitans* is thereby treated, ameliorated, or prevented. A disease caused by *A. actinomycetemcomitans* can be selected from the group consisting of localized prepubertal periodontis, generalized prepubertal periodontis, localized juvenile periodontis, generalized juvenile periodontis, rapidly progressive adult periodontis, refractory adult periodontis, endiocarditis, thyroid gland abscess, urinary tract infection, brain abscess and vertebral osteomyelitis.

Even another embodiment of the invention provides a method of detecting the presence of *A. actinomycetemcomitans* or an *A. actinomycetemcomitans* antigen in a test sample. The method comprises contacting a test sample with an antibody of the invention that specifically binds *A. actinomycetemcomitans* or an *A. actinomycetemcomitans* antigen under conditions that allow formation of an immunocomplex between the antibody and the *A. actinomycetemcomitans* or the *A. actinomycetemcomitans* antigen and detecting an immunocomplex. Detection of the immunocomplex indicates the presence of *A. actinomycetemcomitans* or an *A. actinomycetemcomitans* antigen in the test sample. The detected *A. actinomycetemcomitans* antigen can be an antigen that is expressed in vivo during infection of an animal.

Another embodiment of the invention provides a pharmaceutical composition that comprises a polypeptide of the invention and a pharmaceutically acceptable carrier.

Still another embodiment of the invention provides a method of eliciting an immune response. The method comprises administering a polypeptide of the invention to an animal, wherein an immune response is elicited.

Yet another embodiment of the invention provides a method of treating, preventing, or ameliorating a disease or infection caused by *A. actinomycetemcomitans*. The method comprises administering a polypeptide of the invention to an animal, wherein the disease or infection is treated, prevented, or ameliorated.

Even another embodiment of the invention provides a composition comprising a polynucleotide of the invention and a pharmaceutically acceptable carrier. The polynucleotide can be DNA. The polynucleotide can be in a plasmid.

Another method of the invention provides a method of eliciting an immune response comprising administering a purified polynucleotide of the invention to an animal, wherein an immune response is elicited. Still another embodiment of the invention provides a method of treating, preventing, or ameliorating a disease or infection caused by *A. actinomycetemcomitans*. The method comprises administering a purified polynucleotide of the invention to an animal, wherein the disease or infection is treated, prevented, or ameliorated.

Yet another embodiment of the invention provides a method for identifying the presence of a first *A. actinomycetemcomitans* polynucleotide. The method comprises contacting a test sample suspected of containing a first *A. actinomycetemcomitans* polynucleotide with a second polynucleotide, wherein the second polynucleotide is a polynucleotide of the invention, under hybridization conditions. A hybridized first and second polynucleotide complex is detected. The presence of a hybridized first and second polynucleotide indicates the presence of a first polynucleotide in the test sample.

DETAILED DESCRIPTION OF THE INVENTION

Method of Identification of Polynucleotides and Polypeptides

A method for identifying nucleotide sequences that are important to a microorganism's ability to cause disease has been applied to Aa, the principal etiologic agent of early-onset periodontitis including localized prepubertal periodontis, generalized prepubertal periodontis, localized juvenile periodontis, generalized juvenile periodontis, rapidly progressive adult periodontis, and refractory adult periodontis. Aa can also cause endocarditis, thyroid gland abscess, urinary tract infection, brain abscess and vertebral osteomyelitis. The method used to identify polynucleotide and polypeptide sequences of the invention is termed in vivo induced antigen technology (IVIAT). See Handfield et al., Trends Microbiol. 336:336–339 (2000); WO 01/11081.

Briefly, IVIAT comprises obtaining a sample of antibodies against Aa antigens that are expressed by Aa in vivo and in vitro and adsorbing the antibodies with cells or cellular extracts of Aa that have been grown in vitro. An example of a sample of antibodies that can be used is sera from patients who have been or are infected with Aa. The unadsorbed antibodies are isolated and are used to probe an expression library of Aa DNA. Reactive clones are isolated and the cloned fragments sequenced.

IVIAT was used to identify polynucleotides of Aa that are expressed only when Aa is engaged in actually causing disease in animals, and in particular humans. Important environmental signals that normally cause Aa to turn on virulence genes during an infection are missing when the bacteria are grown in the laboratory. Therefore, many of the best targets for diagnostic and vaccine strategies were unknown. IVIAT methodology was used to identify polynucleotides that are specifically turned on during growth of Aa in a human host and not during routine laboratory growth. These polynucleotides and corresponding polypeptides and antibodies are useful in developing diagnostic tests for Aa to identify, for example, subjects who are in early stages of infection and for monitoring response to therapy, and for developing vaccines or treatments to prevent or treat diseases caused by Aa in susceptible animals.

Aa antigens identified by IVIAT have a high predictive value with regard to diseases caused by Aa, for example, periodontal diseases. Diagnostic tests for Aa can be useful in applications such as screening children whose mothers have a history of periodontis to determine if the children have acquired a predisposition for the disease. Diseases known to be associated with periodontitis before puberty include Papillon-Lefevre syndrome (PLS), hypophosphatasia, neutropenias, leukocyte adhesion deficiency (LAD), Chediak-Higashi syndrome, Down's syndrome, leukemia, histiocytosis X, early-onset Type I diabetes, and acrodynia. Children with these diseases are candidates for Aa testing. Additionally, other preadolescent children who are less prone to periodontis would benefit from an Aa diagnostic test since there are no other predictors or known risk factors.

Polypeptides

Purified polypeptides of the invention can either be full-length polypeptides or fragments of polypeptides. For example, fragments of polypeptides of the invention can comprise about 5, 10, 25, 50, 100, or 200 amino acids of polypeptides of the invention. Examples of polypeptides of the invention include those shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:103, SEQ ID NO:104, SEQ ID NO:105, SEQ ID NO:107, SEQ ID NO:109, SEQ ID NO:110, SEQ ID NO:111, SEQ ID NO:112, SEQ ID NO:113, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, and SEQ ID NO:234. These polypeptides will be referred to as "the polypeptide SEQ IDs." Homologous amino acid sequences that are at least about 75, or about 90, 96, 98, or 99% identical to the polypeptide sequences shown in the polypeptide SEQ IDs are also Aa polypeptides. Homologous amino acid sequences retain biological activity, i.e., are biologically functional equivalents.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482–489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants of polypeptides shown in the polypeptide SEQ IDs and fragments thereof are also included in the invention. A variant is a polypeptide that differs from a polypeptide SEQ ID or fragment thereof, only in conservative substitutions and/or modifications, such that the antigenic properties of the polypeptide are substantially the same as the original polypeptide. Variants can generally be identified by modifying one of the polypeptide sequences of the invention, and evaluating the antigenic properties of the modified polypeptide using, for example, an immunohistochemical assay, an enzyme-linked immunosorbant assay (ELISA), a radioimmunoassay (RIA), or a western blot assay. Polypeptides of the invention can comprise at least 1, 5, 10, 25, 50, or 100 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants can also (or alternatively) be modified by, for example, the deletion or addition of amino acids that have minimal influence on the antigenic properties, secondary structure and hydropathic nature of the polypeptide. For example, a polypeptide can be conjugated to a signal (or leader) sequence at the N-terminal end of the protein which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

Polypeptides of the invention further comprise biologically functional equivalents of at least about 5, 10, 25, 50, 100, or 200 amino acids of the polypeptides shown in the polypeptide SEQ IDs. A polypeptide is a biological equivalent if it reacts substantially the same as a polypeptide of the invention in an assay such as an immunohistochemical assay, an ELISA, an RIA, or a western blot assay, e.g. has 90–110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%.

Polypeptides of the invention can comprise an antigen that is recognized by an antibody reactive against Aa. The antigen can comprise one or more epitopes (or antigenic determinants). An epitope can be a linear epitope, sequential epitope or a conformational epitope. Epitopes within a polypeptide of the invention can be identified by several methods. See, e.g. U.S. Pat. No. 4,554,101; Jameson & Wolf, *CABIOS* 4:181–186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay an Aa polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific adsorbtion is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

Polynucleotides of the invention are shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:106, SEQ ID NO:108, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, and SEQ ID NO:233. These polynucleotides will be referred to as the "polynucleotide SEQ IDs."

Degenerate nucleotide sequences encoding polypeptides of the invention, as well as homologous nucleotide sequences that are at least about 75, or about 90, 96, 98, or 99% identical to the nucleotide sequences shown in the polynucleotide SEQ IDs and the complements thereof are also polynucleotides of the invention. Percent sequence identity can be calculated as described in the "Polypeptides" section. Degenerate nucleotide sequences are polynucleotides that encode a polypeptide shown in the polypeptide SEQ IDs or fragments thereof, but differ in nucleic acid sequence from the sequence given in the polynucleotide SEQ IDs, due to the degeneracy of the genetic code. Complementary DNA (cDNA) molecules, species homologs, and variants of Aa polynucleotides that encode biologically functional Aa polypeptides also are Aa polynucleotides. A polynucleotide of the invention can comprise about 5, 10, 15, 50, 100, or 200 nucleotides of a nucleic acid sequence shown in the polynucleotide SEQ IDs.

Polynucleotides of the invention can be isolated from nucleic acid sequences present in, for example, a biological sample, such as plaque, saliva, crevicular fluid, sputum, blood, serum, plasma, urine, feces, cerebrospinal fluid, amniotic fluid, wound exudate, or tissue, from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences which do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to one or more expression control elements, which direct transcription and/or translation of the polynucleotide.

A vector comprising a polynucleotide of the invention can be transformed into, for example, bacterial, yeast, insect, or mammalian cells so that the polypeptides of the invention can be expressed in and isolated from cell culture. Any of those techniques that are available in the art can be used to introduce polynucleotides into the host cells. These include, but are not limited to, transfection with naked or encapsulated nucleic acids, cellular fusion, protoplast fusion, viral infection, and electroporation.

Polynucleotides of the invention can be used, for example, as probes or primers, for example PCR primers, to detect the presence of Aa polynucleotides in a sample, such as a biological sample. The ability of such probes and primers to specifically hybridize to Aa polynucleotide sequences will enable them to be of use in detecting the presence of complementary sequences in a given sample. Polynucleotide probes and primers of the invention can hybridize to complementary sequences in a sample such as a biological sample, including plaque, saliva, crevicular fluid, sputum, blood, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9 M salt, at temperatures ranging form about 20° C. to about 55° C. The presence of a hybridized complex comprising the probe or primer and a complementary polynucleotide from the test sample indicates the presence of Aa or an Aa polynucleotide sequence in the sample.

Antibodies

Antibodies of the invention are antibody molecules that specifically and stably bind to an Aa polypeptide of the invention or fragment thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23–37 (1998); Dean, *Methods Mol. Biol.* 32:361–79 (1994); Baileg, *Methods Mol. Biol.* 32:381–88 (1994); Gullick, *Methods Mol. Biol.* 32:389–99 (1994); Drenckhahn et al. *Methods Cell. Biol.* 37:7–56 (1993); Morrison, *Ann. Rev. Immunol.* 10:239–65 (1992);

Wright et al. *Crit. Rev. Immunol.* 12:125–68 (1992). For example, polyclonal antibodies can be produced by administering a polypeptide of the invention to an animal, such as a human or other primate, mouse, rat, rabbit, guinea pig, goat, pig, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing Aa-specific antibodies can be identified using RIA or ELISA and isolated by cloning in semi-solid agar or by limiting dilution. Clones producing Aa-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242–246 (1998).

Antibodies, either monoclonal and polyclonal, which are directed against Aa antigens, are particularly useful for detecting the presence of Aa or Aa antigens in a sample, such as a serum sample from an Aa-infected human. An immunoassay for Aa or an Aa antigen can utilize one antibody or several antibodies. An immunoassay for Aa or an Aa antigen can use, for example, a monoclonal antibody directed towards an Aa epitope, a combination of monoclonal antibodies directed towards epitopes of one Aa polypeptide, monoclonal antibodies directed towards epitopes of different Aa polypeptides, polyclonal antibodies directed towards the same Aa antigen, polyclonal antibodies directed towards different Aa antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of Aa or an Aa antigen. Supports include, for example, glass, polystyrene, polypropylene, polyethylene, dextran, nylon, amylases, natural and modified celluloses, polyacrylamides, agaroses and magletite.

Polyclonal or monoclonal antibodies of the invention can further be used to isolate Aa organisms or Aa antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind Aa organisms or Aa antigens from a sample, such as a biological sample including saliva, plaque, crevicular fluid, sputum, blood, urine, feces, cerebrospinal fluid, amniotic fluid, wound exudate, or tissue. The bound Aa organisms or Aa antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by Aa. By measuring the increase or decrease of Aa antibodies to Aa proteins in a test sample from an animal, it can be determined whether a particular therapeutic regiment aimed at ameliorating the disorder is effective. Antibodies can be detected and/or quantified using for example, direct binding assays such as RIA, ELISA, or western blot assays.

An antibody of the invention can be used in a method of the diagnosis of Aa infection by obtaining a test sample from an animal suspected of having an Aa infection. The test sample is contacted with an antibody of the invention under conditions enabling the formation of an antibody-antigen complex (i.e., an immunocomplex). The amount of antibody-antigen complexes can be determined by methodology known in the art. A level that is higher than that formed in a control sample indicates an Aa infection. Alternatively, a polypeptide of the invention can be contacted with a test sample. Aa antibodies in a positive body sample will form an antigen-antibody complex under suitable conditions. The amount of antibody-antigen complexes can be determined by methods known in the art.

Methods of Treatment, Amelioration, or Prevention of a Disease Caused by Aa

Polypeptides, polynucleotides, and antibodies of the invention can be used to treat, ameliorate, or prevent a disease caused by Aa, such as early-onset periodontitis including localized and generalized prepubertal periodontis, localized and generalized juvenile periodontis, and rapidly progressive or refractory adult periodontitis, endocarditis, thyroid gland abscesses, urinary tract infections, brain abscesses, and vertebral osteomyelitis.

For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of Aa infection or in reducing the amount of Aa organisms in a subject.

Polypeptides or polynucleotides of the invention can be used to elicit an immune response in a host. An immonogenic polypeptide or polynucleotide is a polypeptide or polynucleotide of the invention that is capable of inducing an immune response in an animal. An immunogenic polypeptide or polynucleotide of the invention is particularly useful in sensitizing an immune system of an animal such that, as one result, an immune response is produced that ameliorates or prevents the effect of Aa infection. The elicitation of an immune response in animal model can be useful to determine, for example, optimal doses or administration routes. Elicitation of an immune response can also be used to treat, prevent, or ameliorate a disease or infection caused by Aa. An immune response includes humoral immune responses or cell mediated immune responses, or a combination thereof. An immune response can also comprise the promotion of a generalized host response, e.g., by promoting the production of defensins.

The generation of an antibody titer by an animal against Aa can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to Aa can be identified by eliciting antibodies directed against Aa polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Polyic and Poly AU acids), and certain natural substances (e.g. wax D from *Mycobacterium tuberculosis*, as well as substances found in *Corynebacterium parvum*, *Bordetella pertussis* and members of the genus Brucella. Adjuvants which can be used include, but are not limited to MF59-0, aluminum hydroxide, N-acetylmuramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides or polynucleotides can elicit an immune response in the animal that lasts for at least 1 week, 1 month, 3 months, 6 months, 1 year, or longer.

Optionally, an immune response can be maintained in an animal by providing one or more booster injections of the polypeptide or polynucleotide at 1 month, 3 months, 6 months, 1 year, or more after the primary injection. If desired, co-stimulatorymolecules or adjuvants can also be provided before, after, or together with the compositions.

A composition of the invention comprising a polypeptide, polynucleotide, or a combination thereof is administered in a manner compatible with the particular composition used and in an amount that is effective to elicit an immune response as detected by, for example, an ELISA. A polynucleotide can be injected intramuscularly to a large mammal, such as a baboon, chimpanzee, or human, at a dose of 1 ng/kg, 10 ng/kg, 100 ng/kg, 1000 ng/kg, 0.001 mg/kg, 0.1 mg/kg, or 0.5 mg/kg. A polypeptide can be injected intramuscularly to a large mammal, such as a human, at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with Aa or can be administered to an Aa-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

The materials for use in a method of the invention can be present in a kit. A kit can comprise one or more elements used in the method. For example, a kit can contain an antibody of the invention in a container and Aa polypeptides in another container. The kit and containers are laled with their contents and the kit includes instructions for use of the elements in the containers. The constituents of the kit can be present in, for example, liquid or lypholized form.

All references cited in this disclosure are incorporated herein by reference.

We claim:

1. A method of detecting the presence or absence of *A. actinomycetemcomitans* or an *A. actinomycetemcomitans* antigen in a test sample comprising:
  contacting a test sample with an antibody or a fragment thereof that specifically binds to a purified immunogenic polypeptide consisting of SEQ ID NO:52, wherein the antibody or fragment thereof specifically binds *A. actinomycetemcomitans* or an *A. actinomycetemcomitans* antigen under conditions that allow formation of an immunocomplex between the antibody and the *A. actinomycetemcomitans* or the *A. actinomycetemcomitans* antigen; and
  detecting an immunocomplex,
  wherein detection of the immunocomplex indicates the presence of *A. actinomycetemcomitans* or an *A. actinomycetemcomitans* antigen in the test sample.

2. The method of claim 1, wherein the *A. actinomycetemcomitans* antigen is expressed in vivo during infection of an animal.

3. A method of detecting presence or absence of an *A. actinomycetemcomitans* antibody in a test sample comprising:
  contacting a test sample with a purified immunogenic polypeptide consisting of SEQ ID NO:52, wherein the polypeptide specifically binds an *A. actinomycetemcomitans* antibody under conditions that allow formation of an immunocomplex between the antibody and the polypeptide; and
  detecting an immunocomplex,
  wherein detection of the immunocomplex indicates the presence of *A. actinomycetemcomitans* antibody in the test sample.

* * * * *

SEQUENCE LISTING

<160> NUMBER OF SEQ ID NOS: 234

<210> SEQ ID NO 1
<211> LENGTH: 560
<212> TYPE: DNA
<213> ORGANISM: Actinobacillus actinomycetemcomitans
<220> FEATURE:
<221> NAME/KEY: CDS
<222> LOCATION: (1)..(555)

<400> SEQUENCE: 1

```
agc gat tgg ctg gca ttt atg tta agc ggc gaa ctg gcg gtg gaa cct      48
Ser Asp Trp Leu Ala Phe Met Leu Ser Gly Glu Leu Ala Val Glu Pro
1               5                  10                  15 tcc aat gcg ggc acg acc ggc atg ttg aac ctg aca aca cgt caa tgg      96
Ser Asn Ala Gly Thr Thr Gly Met Leu Asn Leu Thr Thr Arg Gln Trp
            20                  25                  30 tcg ccg gaa tta ctg gat atg gcg ggg tta aat tca aat att ctg acg     144
Ser Pro Glu Leu Leu Asp Met Ala Gly Leu Asn Ser Asn Ile Leu Thr
        35                  40                  45 ccg ata aaa gaa acc ggt acg cgt tta ggt gaa gtg act tca gaa gtt     192
Pro Ile Lys Glu Thr Gly Thr Arg Leu Gly Glu Val Thr Ser Glu Val
    50                  55                  60 gca caa caa acc ggt tta ata cag ggc aca ccg gtt gtg gtc ggc ggc     240
Ala Gln Gln Thr Gly Leu Ile Gln Gly Thr Pro Val Val Val Gly Gly
65                  70                  75                  80 ggg gac gtg cag tta ggt tgt att ggt tta ggc gtc acc gag ccc gct     288
Gly Asp Val Gln Leu Gly Cys Ile Gly Leu Gly Val Thr Glu Pro Ala
                85                  90                  95 caa gcg gca gtt atc ggc ggt acg ttc tgg caa caa gtg gtg aat tta     336
Gln Ala Ala Val Ile Gly Gly Thr Phe Trp Gln Gln Val Val Asn Leu
            100                 105                 110 ccg cag gcg gtg acc gac ccg gaa atg aat gta cgt att aac ccg cac     384
Pro Gln Ala Val Thr Asp Pro Glu Met Asn Val Arg Ile Asn Pro His
        115                 120                 125 gtt atc ccg ccg tta gta cag gcg gaa tcc att agc ttt ttc acc aga     432
Val Ile Pro Pro Leu Val Gln Ala Glu Ser Ile Ser Phe Phe Thr Arg
    130                 135                 140 tta acc atg cgc tgg ttc cgt gat gca ttt tgc gaa gaa gaa aag aga     480
Leu Thr Met Arg Trp Phe Arg Asp Ala Phe Cys Glu Glu Glu Lys Arg
145                 150                 155                 160
```

```
ctg gcg gaa aaa ctg ggt acc gat gct tat gcg ttg ctg gaa caa atg      528
Leu Ala Glu Lys Leu Gly Thr Asp Ala Tyr Ala Leu Leu Glu Gln Met
                165                 170                 175 gcg gaa cgc gtg ccc gtc ggc gcc aat gacgt                            560
Ala Glu Arg Val Pro Val Gly Ala Asn
        180                 185
```

<210> SEQ ID NO 2
<211> LENGTH: 185
<212> TYPE: PRT
<213> ORGANISM: Actinobacillus actinomycetemcomitans

<400> SEQUENCE: 2

```
Ser Asp Trp Leu Ala Phe Met Leu Ser Gly Glu Leu Ala Val Glu Pro
1               5                   10                  15

Ser Asn Ala Gly Thr Thr Gly Met Leu Asn Leu Thr Thr Arg Gln Trp
            20                  25                  30

Ser Pro Glu Leu Leu Asp Met Ala Gly Leu Asn Ser Asn Ile Leu Thr
        35                  40                  45

Pro Ile Lys Glu Thr Gly Thr Arg Leu Gly Glu Val Thr Ser Glu Val
50                  55                  60

Ala Gln Gln Thr Gly Leu Ile Gln Gly Thr Pro Val Val Gly Gly
65                  70                  75                  80

Gly Asp Val Gln Leu Gly Cys Ile Gly Leu Gly Val Thr Glu Pro Ala
                85                  90                  95

Gln Ala Ala Val Ile Gly Gly Thr Phe Trp Gln Gln Val Val Asn Leu
            100                 105                 110

Pro Gln Ala Val Thr Asp Pro Glu Met Asn Val Arg Ile Asn Pro His
        115                 120                 125

Val Ile Pro Pro Leu Val Gln Ala Glu Ser Ile Ser Phe Phe Thr Arg
130                 135                 140

Leu Thr Met Arg Trp Phe Arg Asp Ala Phe Cys Glu Glu Lys Arg
145                 150                 155                 160

Leu Ala Glu Lys Leu Gly Thr Asp Ala Tyr Ala Leu Leu Glu Gln Met
                165                 170                 175

Ala Glu Arg Val Pro Val Gly Ala Asn
        180                 185
```

<210> SEQ ID NO 3
<211> LENGTH: 573
<212> TYPE: DNA
<213> ORGANISM: Actinobacillus actinomycetemcomitans
<220> FEATURE:
<221> NAME/KEY: CDS
<222> LOCATION: (1)..(573)

<400> SEQUENCE: 3

```
tgt gat acc gac att gaa cgt tat ctg gat gaa ggg cta atc tcc ctc      48
Cys Asp Thr Asp Ile Glu Arg Tyr Leu Asp Glu Gly Leu Ile Ser Leu
1               5                   10                  15 aat ccg cgc ccg tcg aac gat aaa att aat ggc gcc aca att gat gtg     96
Asn Pro Arg Pro Ser Asn Asp Lys Ile Asn Gly Ala Thr Ile Asp Val
            20                  25                  30 cgt ttg ggc aat tcc ttc cgc gta ttt cgt gaa cat tcc gcc cct tac    144
Arg Leu Gly Asn Ser Phe Arg Val Phe Arg Glu His Ser Ala Pro Tyr
        35                  40                  45 att gat ttg agc ggt ccg aaa gaa gaa gtg tcg gcg cag ttg gaa tcg    192
Ile Asp Leu Ser Gly Pro Lys Glu Glu Val Ser Ala Gln Leu Glu Ser
50                  55                  60
```

-continued

```
gtc atg agc gat gaa atg att atc ggt gat gac gaa gcc ttc ttt tta      240
Val Met Ser Asp Glu Met Ile Ile Gly Asp Asp Glu Ala Phe Phe Leu
 65                  70                  75                  80 cat ccc ggc gtg ctg gcg ctt gcc acg act ttg gaa tca gta aaa ctg      288
His Pro Gly Val Leu Ala Leu Ala Thr Thr Leu Glu Ser Val Lys Leu
                 85                  90                  95 ccg gcg aat att atc ggt tgg ctg gac ggg cgt tct tct ttg gcg cgt      336
Pro Ala Asn Ile Ile Gly Trp Leu Asp Gly Arg Ser Ser Leu Ala Arg
            100                 105                 110 ttg ggg ttg atg gta cac gtc acc gcc cat cgt atc gac cca ggc tgg      384
Leu Gly Leu Met Val His Val Thr Ala His Arg Ile Asp Pro Gly Trp
        115                 120                 125 gaa ggc aaa atc gtg ttg gaa ttt tac aat tcc ggc aaa tta ccg tta      432
Glu Gly Lys Ile Val Leu Glu Phe Tyr Asn Ser Gly Lys Leu Pro Leu
    130                 135                 140 gcg tta cgc ccg aat atg att atc ggc gcc ttg agt ttc gaa gtg tta      480
Ala Leu Arg Pro Asn Met Ile Ile Gly Ala Leu Ser Phe Glu Val Leu
145                 150                 155                 160 agc gga ccg gcg gcg cgt ccg tac agc agc cgc aaa gac gca aaa tac      528
Ser Gly Pro Ala Ala Arg Pro Tyr Ser Ser Arg Lys Asp Ala Lys Tyr
                165                 170                 175 aag aac caa caa aat gcc gtt gcc agc cgc att gat gag gac aaa          573
Lys Asn Gln Gln Asn Ala Val Ala Ser Arg Ile Asp Glu Asp Lys
            180                 185                 190
```

<210> SEQ ID NO 4
<211> LENGTH: 191
<212> TYPE: PRT
<213> ORGANISM: Actinobacillus actinomycetemcomitans

<400> SEQUENCE: 4

```
Cys Asp Thr Asp Ile Glu Arg Tyr Leu Asp Glu Gly Leu Ile Ser Leu
 1               5                  10                  15

Asn Pro Arg Pro Ser Asn Asp Lys Ile Asn Gly Ala Thr Ile Asp Val
            20                  25                  30

Arg Leu Gly Asn Ser Phe Arg Val Phe Arg Glu His Ser Ala Pro Tyr
        35                  40                  45

Ile Asp Leu Ser Gly Pro Lys Glu Glu Val Ser Ala Gln Leu Glu Ser
    50                  55                  60

Val Met Ser Asp Glu Met Ile Ile Gly Asp Asp Glu Ala Phe Phe Leu
 65                  70                  75                  80

His Pro Gly Val Leu Ala Leu Ala Thr Thr Leu Glu Ser Val Lys Leu
                 85                  90                  95

Pro Ala Asn Ile Ile Gly Trp Leu Asp Gly Arg Ser Ser Leu Ala Arg
            100                 105                 110

Leu Gly Leu Met Val His Val Thr Ala His Arg Ile Asp Pro Gly Trp
        115                 120                 125

Glu Gly Lys Ile Val Leu Glu Phe Tyr Asn Ser Gly Lys Leu Pro Leu
    130                 135                 140

Ala Leu Arg Pro Asn Met Ile Ile Gly Ala Leu Ser Phe Glu Val Leu
145                 150                 155                 160

Ser Gly Pro Ala Ala Arg Pro Tyr Ser Ser Arg Lys Asp Ala Lys Tyr
                165                 170                 175

Lys Asn Gln Gln Asn Ala Val Ala Ser Arg Ile Asp Glu Asp Lys
            180                 185                 190
```

<210> SEQ ID NO 5

<211> LENGTH: 798
<212> TYPE: DNA
<213> ORGANISM: Actinobacillus actinomycetemcomitans
<220> FEATURE:
<221> NAME/KEY: CDS
<222> LOCATION: (1)..(798)

<400> SEQUENCE: 5

```
atg aac gct att cag cct gaa gat aag agc ttt tgg ctt ttc act cag       48
Met Asn Ala Ile Gln Pro Glu Asp Lys Ser Phe Trp Leu Phe Thr Gln
1               5                   10                  15 aga tca aaa ata cat tta att gac ggc aag ctt cct ttc ggc aat gcc       96
Arg Ser Lys Ile His Leu Ile Asp Gly Lys Leu Pro Phe Gly Asn Ala
            20                  25                  30 acc gaa ctg ggt ttc gtc ggg ctt cat gct atg cgc atc ggc gaa tgg      144
Thr Glu Leu Gly Phe Val Gly Leu His Ala Met Arg Ile Gly Glu Trp
        35                  40                  45 ctg gag caa ccg tta tat ttg gtg gaa acc caa ccg aac gac aac cgc      192
Leu Glu Gln Pro Leu Tyr Leu Val Glu Thr Gln Pro Asn Asp Asn Arg
    50                  55                  60 acc tat ttt tct tta cgc gat caa ctg ccg ctg ccg caa gcg caa ttt      240
Thr Tyr Phe Ser Leu Arg Asp Gln Leu Pro Leu Pro Gln Ala Gln Phe
65                  70                  75                  80 aat ctg ttg agc tgc ggc gtg gag tta aat cat ttc tat cag acc cat      288
Asn Leu Leu Ser Cys Gly Val Glu Leu Asn His Phe Tyr Gln Thr His
                85                  90                  95 caa ttc tgc gga aag tgc ggt gga aaa acc gag caa atg cag gag gaa      336
Gln Phe Cys Gly Lys Cys Gly Gly Lys Thr Glu Gln Met Gln Glu Glu
            100                 105                 110 tgg gcg gta aaa tgc cgt gcc tgc ggt ttt cat acc tat ccc gtc att      384
Trp Ala Val Lys Cys Arg Ala Cys Gly Phe His Thr Tyr Pro Val Ile
        115                 120                 125 tgc cct tcc att atc gtt gca gta cga cac gat tca caa atc ctg ctg      432
Cys Pro Ser Ile Ile Val Ala Val Arg His Asp Ser Gln Ile Leu Leu
    130                 135                 140 gca aat cat atg cgc cac aaa ggc ggc att tac acc acg ttg gcg ggt      480
Ala Asn His Met Arg His Lys Gly Gly Ile Tyr Thr Thr Leu Ala Gly
145                 150                 155                 160 ttt gtg gaa gta ggc gaa acc ttt gag gat gcg gta cat cgc gaa att      528
Phe Val Glu Val Gly Glu Thr Phe Glu Asp Ala Val His Arg Glu Ile
                165                 170                 175 tgg gag gaa acc caa atc aaa gta aaa aat ttg cgt tat ttc gac agc      576
Trp Glu Glu Thr Gln Ile Lys Val Lys Asn Leu Arg Tyr Phe Asp Ser
            180                 185                 190 cag cct tgg gcg ttt cct aat tcg caa atg gtg ggt ttt tta gcc gat      624
Gln Pro Trp Ala Phe Pro Asn Ser Gln Met Val Gly Phe Leu Ala Asp
        195                 200                 205 tat gaa gga ggc gag att act att cag cgt gaa gaa ctt tat gac gca      672
Tyr Glu Gly Gly Glu Ile Thr Ile Gln Arg Glu Glu Leu Tyr Asp Ala
    210                 215                 220 caa tgg ttt gat tgc gac caa ccg ttg ccc gaa ctg cca ccg cac ggc      720
Gln Trp Phe Asp Cys Asp Gln Pro Leu Pro Glu Leu Pro Pro His Gly
225                 230                 235                 240 acc atc gca cgc aaa tta att gaa acc aca ctt gaa ttg tgt aaa cag      768
Thr Ile Ala Arg Lys Leu Ile Glu Thr Thr Leu Glu Leu Cys Lys Gln
                245                 250                 255 cat aaa ata aac cat aat aag gaa cgg gca                              798
His Lys Ile Asn His Asn Lys Glu Arg Ala
            260                 265
```

<210> SEQ ID NO 6

-continued

```
<211> LENGTH: 266
<212> TYPE: PRT
<213> ORGANISM: Actinobacillus actinomycetemcomitans

<400> SEQUENCE: 6

Met Asn Ala Ile Gln Pro Glu Asp Lys Ser Phe Trp Leu Phe Thr Gln
1               5                   10                  15

Arg Ser Lys Ile His Leu Ile Asp Gly Lys Leu Pro Phe Gly Asn Ala
            20                  25                  30

Thr Glu Leu Gly Phe Val Gly Leu His Ala Met Arg Ile Gly Glu Trp
        35                  40                  45

Leu Glu Gln Pro Leu Tyr Leu Val Glu Thr Gln Pro Asn Asp Asn Arg
    50                  55                  60

Thr Tyr Phe Ser Leu Arg Asp Gln Leu Pro Leu Pro Gln Ala Gln Phe
65                  70                  75                  80

Asn Leu Leu Ser Cys Gly Val Glu Leu Asn His Phe Tyr Gln Thr His
                85                  90                  95

Gln Phe Cys Gly Lys Cys Gly Gly Lys Thr Glu Gln Met Gln Glu Glu
            100                 105                 110

Trp Ala Val Lys Cys Arg Ala Cys Gly Phe His Thr Tyr Pro Val Ile
        115                 120                 125

Cys Pro Ser Ile Ile Val Ala Val Arg His Asp Ser Gln Ile Leu Leu
130                 135                 140

Ala Asn His Met Arg His Lys Gly Gly Ile Tyr Thr Thr Leu Ala Gly
145                 150                 155                 160

Phe Val Glu Val Gly Glu Thr Phe Glu Asp Ala Val His Arg Glu Ile
                165                 170                 175

Trp Glu Glu Thr Gln Ile Lys Val Lys Asn Leu Arg Tyr Phe Asp Ser
            180                 185                 190

Gln Pro Trp Ala Phe Pro Asn Ser Gln Met Val Gly Phe Leu Ala Asp
        195                 200                 205

Tyr Glu Gly Gly Glu Ile Thr Ile Gln Arg Glu Glu Leu Tyr Asp Ala
    210                 215                 220

Gln Trp Phe Asp Cys Asp Gln Pro Leu Pro Glu Leu Pro Pro His Gly
225                 230                 235                 240

Thr Ile Ala Arg Lys Leu Ile Glu Thr Thr Leu Glu Leu Cys Lys Gln
                245                 250                 255

His Lys Ile Asn His Asn Lys Glu Arg Ala
            260                 265

<210> SEQ ID NO 7
<211> LENGTH: 770
<212> TYPE: DNA
<213> ORGANISM: Actinobacillus actinomycetemcomitans
<220> FEATURE:
<221> NAME/KEY: CDS
<222> LOCATION: (1)..(768)

<400> SEQUENCE: 7 aaa atc caa agt ttg ctg cat cct gat gtt aaa ccg atg gtt tta ccg      48
Lys Ile Gln Ser Leu Leu His Pro Asp Val Lys Pro Met Val Leu Pro
1               5                   10                  15 aac ccg att tcc gtt gaa atg tcc gcc atg cgt gtt tca tta ttg acc      96
Asn Pro Ile Ser Val Glu Met Ser Ala Met Arg Val Ser Leu Leu Thr
            20                  25                  30 ggt tta ttg ggc gca gtg att tat aat caa aac cgc caa caa agt cgc     144
Gly Leu Leu Gly Ala Val Ile Tyr Asn Gln Asn Arg Gln Gln Ser Arg
        35                  40                  45
```

-continued

```
gtg cgt ttg ttt gag cac ggt tta cgt ttt att ccg gac gaa aag gcc      192
Val Arg Leu Phe Glu His Gly Leu Arg Phe Ile Pro Asp Glu Lys Ala
 50                  55                  60 gaa ttc ggc gtg cac caa gag ccg gtt ttt gcc gcg gtg atg aca ggg      240
Glu Phe Gly Val His Gln Glu Pro Val Phe Ala Ala Val Met Thr Gly
65                  70                  75                  80 tta aaa tca aac gaa cag tgg agc gaa aaa gcc gta ccg gca gat ttt      288
Leu Lys Ser Asn Glu Gln Trp Ser Glu Lys Ala Val Pro Ala Asp Phe
                 85                  90                  95 tac gac tta aaa ggc tac att gaa aac tta ctt tcg tta agt tct gct      336
Tyr Asp Leu Lys Gly Tyr Ile Glu Asn Leu Leu Ser Leu Ser Ser Ala
            100                 105                 110 gga aat cgg gca aaa ttt gta gca aaa tca tac aca gca ttg cat ccg      384
Gly Asn Arg Ala Lys Phe Val Ala Lys Ser Tyr Thr Ala Leu His Pro
        115                 120                 125 ggt caa tct gcg gcc att atg ctg gat ggt gaa gaa atc gga ttt att      432
Gly Gln Ser Ala Ala Ile Met Leu Asp Gly Glu Glu Ile Gly Phe Ile
    130                 135                 140 ggt caa ctt cac ccg act atc gcg caa aaa att ggt ctt acc gga aaa      480
Gly Gln Leu His Pro Thr Ile Ala Gln Lys Ile Gly Leu Thr Gly Lys
145                 150                 155                 160 gca ttt gtt tgt gaa att tcg gtc gca cac att tct cga cga gaa gtc      528
Ala Phe Val Cys Glu Ile Ser Val Ala His Ile Ser Arg Arg Glu Val
                165                 170                 175 gcc cgt gcc aaa gaa att tcc cgt ttc cct gct aat cgt cgt gat ttg      576
Ala Arg Ala Lys Glu Ile Ser Arg Phe Pro Ala Asn Arg Arg Asp Leu
            180                 185                 190 gcg gtt gtg gtt gcg gat aat atc cct gca aat gac gtg ctg gaa gtg      624
Ala Val Val Val Ala Asp Asn Ile Pro Ala Asn Asp Val Leu Glu Val
        195                 200                 205 tgt cgt aca gca ggc gga gat aaa tta acc caa atc aat tta ttt gat      672
Cys Arg Thr Ala Gly Gly Asp Lys Leu Thr Gln Ile Asn Leu Phe Asp
    210                 215                 220 gtt tac cac gga acc ggt gtt gct gca ggg cat aag agc tta gct atc      720
Val Tyr His Gly Thr Gly Val Ala Ala Gly His Lys Ser Leu Ala Ile
225                 230                 235                 240 agc tta gta att caa gat aat gaa aaa acc ctt gaa gaa gat gaa att      768
Ser Leu Val Ile Gln Asp Asn Glu Lys Thr Leu Glu Glu Asp Glu Ile
                245                 250                 255 aa                                                                    770
```

<210> SEQ ID NO 8
<211> LENGTH: 256
<212> TYPE: PRT
<213> ORGANISM: Actinobacillus actinomycetemcomitans

<400> SEQUENCE: 8

```
Lys Ile Gln Ser Leu Leu His Pro Asp Val Lys Pro Met Val Leu Pro
1               5                   10                  15

Asn Pro Ile Ser Val Glu Met Ser Ala Met Arg Val Ser Leu Leu Thr
            20                  25                  30

Gly Leu Leu Gly Ala Val Ile Tyr Asn Gln Asn Arg Gln Ser Arg
        35                  40                  45

Val Arg Leu Phe Glu His Gly Leu Arg Phe Ile Pro Asp Glu Lys Ala
    50                  55                  60

Glu Phe Gly Val His Gln Glu Pro Val Phe Ala Ala Val Met Thr Gly
65                  70                  75                  80

Leu Lys Ser Asn Glu Gln Trp Ser Glu Lys Ala Val Pro Ala Asp Phe
```

```
                85                  90                  95
Tyr Asp Leu Lys Gly Tyr Ile Glu Asn Leu Leu Ser Leu Ser Ser Ala
            100                 105                 110

Gly Asn Arg Ala Lys Phe Val Ala Lys Ser Tyr Thr Ala Leu His Pro
        115                 120                 125

Gly Gln Ser Ala Ala Ile Met Leu Asp Gly Glu Ile Gly Phe Ile
    130                 135                 140

Gly Gln Leu His Pro Thr Ile Ala Gln Lys Ile Gly Leu Thr Gly Lys
145                 150                 155                 160

Ala Phe Val Cys Glu Ile Ser Val Ala His Ile Ser Arg Arg Glu Val
                165                 170                 175

Ala Arg Ala Lys Glu Ile Ser Arg Phe Pro Ala Asn Arg Arg Asp Leu
            180                 185                 190

Ala Val Val Val Ala Asp Asn Ile Pro Ala Asn Asp Val Leu Glu Val
                195                 200                 205

Cys Arg Thr Ala Gly Gly Asp Lys Leu Thr Gln Ile Asn Leu Phe Asp
    210                 215                 220

Val Tyr His Gly Thr Gly Val Ala Ala Gly His Lys Ser Leu Ala Ile
225                 230                 235                 240

Ser Leu Val Ile Gln Asp Asn Glu Lys Thr Leu Glu Glu Asp Glu Ile
                245                 250                 255

<210> SEQ ID NO 9
<211> LENGTH: 141
<212> TYPE: DNA
<213> ORGANISM: Actinobacillus actinomycetemcomitans
<220> FEATURE:
<221> NAME/KEY: CDS
<222> LOCATION: (1)..(141)

<400> SEQUENCE: 9 gat cag cct gat tat gtc aac gcc gtc gct tgc ctg gaa acg gcg ctt     48
Asp Gln Pro Asp Tyr Val Asn Ala Val Ala Cys Leu Glu Thr Ala Leu
1               5                   10                  15 tct ccc ttc gca ttg ctt gat gaa tta caa cgt att gaa cag gaa caa     96
Ser Pro Phe Ala Leu Leu Asp Glu Leu Gln Arg Ile Glu Gln Glu Gln
            20                  25                  30 ggg cgt gtc cgt ctt cgt cgt tgg ggt gag cgc aca tta gat ctg         141
Gly Arg Val Arg Leu Arg Arg Trp Gly Glu Arg Thr Leu Asp Leu
        35                  40                  45

<210> SEQ ID NO 10
<211> LENGTH: 47
<212> TYPE: PRT
<213> ORGANISM: Actinobacillus actinomycetemcomitans

<400> SEQUENCE: 10

Asp Gln Pro Asp Tyr Val Asn Ala Val Ala Cys Leu Glu Thr Ala Leu
1               5                   10                  15

Ser Pro Phe Ala Leu Leu Asp Glu Leu Gln Arg Ile Glu Gln Glu Gln
            20                  25                  30

Gly Arg Val Arg Leu Arg Arg Trp Gly Glu Arg Thr Leu Asp Leu
        35                  40                  45

<210> SEQ ID NO 11
<211> LENGTH: 597
<212> TYPE: DNA
<213> ORGANISM: Actinobacillus actinomycetemcomitans
<220> FEATURE:
<221> NAME/KEY: CDS
```

<222> LOCATION: (1)..(597)

<400> SEQUENCE: 11

```
ggt ctg agt ttt act ttc ctt tca tca ttg gct ttt gca gaa tct tgg      48
Gly Leu Ser Phe Thr Phe Leu Ser Ser Leu Ala Phe Ala Glu Ser Trp
1               5                   10                  15 act atg cat att tcc gaa gat ggc gtg ata acc gat aaa acc gct caa      96
Thr Met His Ile Ser Glu Asp Gly Val Ile Thr Asp Lys Thr Ala Gln
            20                  25                  30 cag ctt aat ccg gct agg tat gcc gga gct gtg tac aaa caa caa ttt     144
Gln Leu Asn Pro Ala Arg Tyr Ala Gly Ala Val Tyr Lys Gln Gln Phe
        35                  40                  45 tct ttt tct gac agc ggc ggg caa ggt aaa acc act tac att aat caa     192
Ser Phe Ser Asp Ser Gly Gly Gln Gly Lys Thr Thr Tyr Ile Asn Gln
    50                  55                  60 aat aac ggc aag aaa ttc gat cct aaa aat gct gct gat gtg agt gaa     240
Asn Asn Gly Lys Lys Phe Asp Pro Lys Asn Ala Ala Asp Val Ser Glu
65                  70                  75                  80 ttg ggt aaa agc atc gcc ttt gaa gtg ttt gag att aaa gaa aat aaa     288
Leu Gly Lys Ser Ile Ala Phe Glu Val Phe Glu Ile Lys Glu Asn Lys
                85                  90                  95 gac tct cac tca gta ttt gaa tcc ggc gcc ggc att tgt tac ggc ttc     336
Asp Ser His Ser Val Phe Glu Ser Gly Ala Gly Ile Cys Tyr Gly Phe
            100                 105                 110 aaa tat acc gat ggc gtc gcg ttc acc gat tct aca acc tat tat gta     384
Lys Tyr Thr Asp Gly Val Ala Phe Thr Asp Ser Thr Thr Tyr Tyr Val
        115                 120                 125 gat aaa tcc aag cag caa tat tac gcc agt atc atc ggc gcc acc gta     432
Asp Lys Ser Lys Gln Gln Tyr Tyr Ala Ser Ile Ile Gly Ala Thr Val
    130                 135                 140 tct tct gac gtg gaa ccg aaa aac gtg caa tat gcg ccg gtg ttt aat     480
Ser Ser Asp Val Glu Pro Lys Asn Val Gln Tyr Ala Pro Val Phe Asn
145                 150                 155                 160 att cag gat ccc gag tta gat aaa gaa gta aag tcg gaa gaa caa cga     528
Ile Gln Asp Pro Glu Leu Asp Lys Glu Val Lys Ser Glu Glu Gln Arg
                165                 170                 175 aac ggt aaa acc ttg att aat aaa aat ttg caa aag agc aga gaa att     576
Asn Gly Lys Thr Leu Ile Asn Lys Asn Leu Gln Lys Ser Arg Glu Ile
            180                 185                 190 ctt tct aac gta gtt tgt aag                                         597
Leu Ser Asn Val Val Cys Lys
        195
```

<210> SEQ ID NO 12
<211> LENGTH: 199
<212> TYPE: PRT
<213> ORGANISM: Actinobacillus actinomycetemcomitans

<400> SEQUENCE: 12

```
Gly Leu Ser Phe Thr Phe Leu Ser Ser Leu Ala Phe Ala Glu Ser Trp
1               5                   10                  15

Thr Met His Ile Ser Glu Asp Gly Val Ile Thr Asp Lys Thr Ala Gln
            20                  25                  30

Gln Leu Asn Pro Ala Arg Tyr Ala Gly Ala Val Tyr Lys Gln Gln Phe
        35                  40                  45

Ser Phe Ser Asp Ser Gly Gly Gln Gly Lys Thr Thr Tyr Ile Asn Gln
    50                  55                  60

Asn Asn Gly Lys Lys Phe Asp Pro Lys Asn Ala Ala Asp Val Ser Glu
65                  70                  75                  80
```

```
Leu Gly Lys Ser Ile Ala Phe Glu Val Phe Glu Ile Lys Glu Asn Lys
            85                  90                  95

Asp Ser His Ser Val Phe Glu Ser Gly Ala Gly Ile Cys Tyr Gly Phe
            100                 105                 110

Lys Tyr Thr Asp Gly Val Ala Phe Thr Asp Ser Thr Thr Tyr Tyr Val
            115                 120                 125

Asp Lys Ser Lys Gln Gln Tyr Tyr Ala Ser Ile Ile Gly Ala Thr Val
            130                 135                 140

Ser Ser Asp Val Glu Pro Lys Asn Val Gln Tyr Ala Pro Val Phe Asn
145                 150                 155                 160

Ile Gln Asp Pro Glu Leu Asp Lys Glu Val Lys Ser Glu Glu Gln Arg
                    165                 170                 175

Asn Gly Lys Thr Leu Ile Asn Lys Asn Leu Gln Lys Ser Arg Glu Ile
            180                 185                 190

Leu Ser Asn Val Val Cys Lys
            195
```

<210> SEQ ID NO 13
<211> LENGTH: 288
<212> TYPE: DNA
<213> ORGANISM: Actinobacillus actinomycetemcomitans
<220> FEATURE:
<221> NAME/KEY: CDS
<222> LOCATION: (1)..(288)

<400> SEQUENCE: 13

```
atg caa aaa ttg tta ctc gtc aca gtg att agt ggt gtt tta gtt gct      48
Met Gln Lys Leu Leu Leu Val Thr Val Ile Ser Gly Val Leu Val Ala
1               5                   10                  15 tgt tct tct aag gct cca caa atc aat caa gct cct tta gat aag cag      96
Cys Ser Ser Lys Ala Pro Gln Ile Asn Gln Ala Pro Leu Asp Lys Gln
                20                  25                  30 aca gtt gaa gct tat caa gcg aaa gtg tat agc ggt aat acg gtg tcg     144
Thr Val Glu Ala Tyr Gln Ala Lys Val Tyr Ser Gly Asn Thr Val Ser
            35                  40                  45 aag aaa tat caa gta aga gac gtt aaa ccg gaa gac aat gtg tta aat     192
Lys Lys Tyr Gln Val Arg Asp Val Lys Pro Glu Asp Asn Val Leu Asn
        50                  55                  60 gct agt gat tcg gaa ccg aaa acc gtg att tat cgc gag cgt cag cca     240
Ala Ser Asp Ser Glu Pro Lys Thr Val Ile Tyr Arg Glu Arg Gln Pro
65                  70                  75                  80 aga ctg gtt gtg aca ccg agc att ggc tat tat cgc ggt tgg cac tgg     288
Arg Leu Val Val Thr Pro Ser Ile Gly Tyr Tyr Arg Gly Trp His Trp
                85                  90                  95
```

<210> SEQ ID NO 14
<211> LENGTH: 96
<212> TYPE: PRT
<213> ORGANISM: Actinobacillus actinomycetemcomitans

<400> SEQUENCE: 14

```
Met Gln Lys Leu Leu Leu Val Thr Val Ile Ser Gly Val Leu Val Ala
1               5                   10                  15

Cys Ser Ser Lys Ala Pro Gln Ile Asn Gln Ala Pro Leu Asp Lys Gln
                20                  25                  30

Thr Val Glu Ala Tyr Gln Ala Lys Val Tyr Ser Gly Asn Thr Val Ser
            35                  40                  45

Lys Lys Tyr Gln Val Arg Asp Val Lys Pro Glu Asp Asn Val Leu Asn
        50                  55                  60
```

```
<210> SEQ ID NO 15
<211> LENGTH: 403
<212> TYPE: DNA
<213> ORGANISM: Actinobacillus actinomycetemcomitans
<220> FEATURE:
<221> NAME/KEY: CDS
<222> LOCATION: (1)..(402)

<400> SEQUENCE: 15
```

| | | | | | | | | | | | | | | | | |
|---|---|---|---|---|---|---|---|---|---|---|---|---|---|---|---|---|
| cca | aac | tgg | ttg | cgc | cgg | caa | gtc | ggt | gtc | gtc | ttg | caa | gat | aat | gtg | 48 |
| Pro | Asn | Trp | Leu | Arg | Arg | Gln | Val | Gly | Val | Val | Leu | Gln | Asp | Asn | Val | |
| 1 | | | | 5 | | | | | 10 | | | | | 15 | | |

Lines 65–95 (prior sequence, continued):

Ala Ser Asp Ser Glu Pro Lys Thr Val Ile Tyr Arg Glu Arg Gln Pro
 65              70              75              80
Arg Leu Val Val Thr Pro Ser Ile Gly Tyr Tyr Arg Gly Trp His Trp
             85              90              95

(SEQ ID NO 15 continued)

ttg ctt aat cga agt atc aga gag aat att gcg tta acc aat ccg gga    96
Leu Leu Asn Arg Ser Ile Arg Glu Asn Ile Ala Leu Thr Asn Pro Gly
         20              25              30 atg cca atg gaa aag gtt att gcc gcg gca aaa ctt gcg gga gcg cac    144
Met Pro Met Glu Lys Val Ile Ala Ala Ala Lys Leu Ala Gly Ala His
     35              40              45 gat ttt att tct gaa tta aga gaa ggt tat aac acg gtt gtg ggg gaa    192
Asp Phe Ile Ser Glu Leu Arg Glu Gly Tyr Asn Thr Val Val Gly Glu
 50              55              60 cag gga gcc ggt ttg tcc gga gga caa cgt caa cgg atc gcg ata gca    240
Gln Gly Ala Gly Leu Ser Gly Gly Gln Arg Gln Arg Ile Ala Ile Ala
 65              70              75              80 agg gca cta gtc aat aac cca agg att ttg att ttt gat gaa gca acc    288
Arg Ala Leu Val Asn Asn Pro Arg Ile Leu Ile Phe Asp Glu Ala Thr
             85              90              95 agt gca ctt gat tac gaa tct gaa aat atc att atg cat aat atg cat    336
Ser Ala Leu Asp Tyr Glu Ser Glu Asn Ile Ile Met His Asn Met His
         100             105             110 aaa att tgc caa aat cgt act gtg ctt atc att gct cac cgc ctt tct    384
Lys Ile Cys Gln Asn Arg Thr Val Leu Ile Ile Ala His Arg Leu Ser
     115             120             125 act gta aaa aat gct gat c                                          403
Thr Val Lys Asn Ala Asp
         130

```
<210> SEQ ID NO 16
<211> LENGTH: 134
<212> TYPE: PRT
<213> ORGANISM: Actinobacillus actinomycetemcomitans

<400> SEQUENCE: 16
```

Pro Asn Trp Leu Arg Arg Gln Val Gly Val Val Leu Gln Asp Asn Val
 1               5              10              15

Leu Leu Asn Arg Ser Ile Arg Glu Asn Ile Ala Leu Thr Asn Pro Gly
             20              25              30

Met Pro Met Glu Lys Val Ile Ala Ala Ala Lys Leu Ala Gly Ala His
         35              40              45

Asp Phe Ile Ser Glu Leu Arg Glu Gly Tyr Asn Thr Val Val Gly Glu
 50              55              60

Gln Gly Ala Gly Leu Ser Gly Gly Gln Arg Gln Arg Ile Ala Ile Ala
 65              70              75              80

Arg Ala Leu Val Asn Asn Pro Arg Ile Leu Ile Phe Asp Glu Ala Thr
             85              90              95

```
Ser Ala Leu Asp Tyr Glu Ser Glu Asn Ile Ile Met His Asn Met His
            100                 105                 110

Lys Ile Cys Gln Asn Arg Thr Val Leu Ile Ile Ala His Arg Leu Ser
        115                 120                 125

Thr Val Lys Asn Ala Asp
    130

<210> SEQ ID NO 17
<211> LENGTH: 374
<212> TYPE: DNA
<213> ORGANISM: Actinobacillus actinomycetemcomitans
<220> FEATURE:
<221> NAME/KEY: CDS
<222> LOCATION: (1)..(372)

<400> SEQUENCE: 17 cac cgt tta ccg gaa atg att aac caa att cgc ggt ggc aaa agt gct      48
His Arg Leu Pro Glu Met Ile Asn Gln Ile Arg Gly Gly Lys Ser Ala
1               5                   10                  15 gtg gtg gat att agt ttc ccg gaa atc gaa aaa ttc gac cgg ttg ccg      96
Val Val Asp Ile Ser Phe Pro Glu Ile Glu Lys Phe Asp Arg Leu Pro
            20                  25                  30 gaa ccg cgc gca gaa ggc ccg act gcc ttt gtt tct atc atg gaa ggc     144
Glu Pro Arg Ala Glu Gly Pro Thr Ala Phe Val Ser Ile Met Glu Gly
        35                  40                  45 tgt aat aaa tac tgt act tac tgc gtg gtg cct tat acc cgt ggc gag     192
Cys Asn Lys Tyr Cys Thr Tyr Cys Val Val Pro Tyr Thr Arg Gly Glu
    50                  55                  60 gaa gtt agc cgt ccg gtg gat gat att tta ttt gaa att gcc cag ttg     240
Glu Val Ser Arg Pro Val Asp Asp Ile Leu Phe Glu Ile Ala Gln Leu
65                  70                  75                  80 gcg gag caa ggc gtg cgc gaa gtg aat ttg ctc ggc cag aac gtg aac     288
Ala Glu Gln Gly Val Arg Glu Val Asn Leu Leu Gly Gln Asn Val Asn
                85                  90                  95 gcc tat cgt ggt ccg aca ttt gat ggc gat att tgc acc ttc gcc gaa     336
Ala Tyr Arg Gly Pro Thr Phe Asp Gly Asp Ile Cys Thr Phe Ala Glu
            100                 105                 110 ttg ttg cgt ttg gta gcg gcc att gac ggt atc gat cg                  374
Leu Leu Arg Leu Val Ala Ala Ile Asp Gly Ile Asp
        115                 120

<210> SEQ ID NO 18
<211> LENGTH: 124
<212> TYPE: PRT
<213> ORGANISM: Actinobacillus actinomycetemcomitans

<400> SEQUENCE: 18

His Arg Leu Pro Glu Met Ile Asn Gln Ile Arg Gly Gly Lys Ser Ala
1               5                   10                  15

Val Val Asp Ile Ser Phe Pro Glu Ile Glu Lys Phe Asp Arg Leu Pro
            20                  25                  30

Glu Pro Arg Ala Glu Gly Pro Thr Ala Phe Val Ser Ile Met Glu Gly
        35                  40                  45

Cys Asn Lys Tyr Cys Thr Tyr Cys Val Val Pro Tyr Thr Arg Gly Glu
    50                  55                  60

Glu Val Ser Arg Pro Val Asp Asp Ile Leu Phe Glu Ile Ala Gln Leu
65                  70                  75                  80

Ala Glu Gln Gly Val Arg Glu Val Asn Leu Leu Gly Gln Asn Val Asn
                85                  90                  95

Ala Tyr Arg Gly Pro Thr Phe Asp Gly Asp Ile Cys Thr Phe Ala Glu
```

```
                100              105              110
Leu Leu Arg Leu Val Ala Ala Ile Asp Gly Ile Asp
        115              120

<210> SEQ ID NO 19
<211> LENGTH: 158
<212> TYPE: DNA
<213> ORGANISM: Actinobacillus actinomycetemcomitans
<220> FEATURE:
<221> NAME/KEY: CDS
<222> LOCATION: (1)..(156)

<400> SEQUENCE: 19 cta agc gta ttc aac tac gcc cat ttg ccg agc cgt ttt gcc gga cag      48
Leu Ser Val Phe Asn Tyr Ala His Leu Pro Ser Arg Phe Ala Gly Gln
1               5                   10                  15 gcg aaa atc aag gat tgg cag ttg ccg aaa ccg gaa gcg aaa ctg gaa      96
Ala Lys Ile Lys Asp Trp Gln Leu Pro Lys Pro Glu Ala Lys Leu Glu
            20                  25                  30 att ctg caa aaa acc atc gaa acg ctg ggc aac gcc ggt tac aaa ttt     144
Ile Leu Gln Lys Thr Ile Glu Thr Leu Gly Asn Ala Gly Tyr Lys Phe
        35                  40                  45 atc ggc atg gat ca                                                  158
Ile Gly Met Asp
    50

<210> SEQ ID NO 20
<211> LENGTH: 52
<212> TYPE: PRT
<213> ORGANISM: Actinobacillus actinomycetemcomitans

<400> SEQUENCE: 20

Leu Ser Val Phe Asn Tyr Ala His Leu Pro Ser Arg Phe Ala Gly Gln
1               5                   10                  15

Ala Lys Ile Lys Asp Trp Gln Leu Pro Lys Pro Glu Ala Lys Leu Glu
            20                  25                  30

Ile Leu Gln Lys Thr Ile Glu Thr Leu Gly Asn Ala Gly Tyr Lys Phe
        35                  40                  45

Ile Gly Met Asp
    50

<210> SEQ ID NO 21
<211> LENGTH: 1098
<212> TYPE: DNA
<213> ORGANISM: Actinobacillus actinomycetemcomitans
<220> FEATURE:
<221> NAME/KEY: CDS
<222> LOCATION: (1)..(1095)

<400> SEQUENCE: 21 aat cag atg aat aaa acc tta aaa att tca ttg ttt gcc atg att tcc      48
Asn Gln Met Asn Lys Thr Leu Lys Ile Ser Leu Phe Ala Met Ile Ser
1               5                   10                  15 gcg tta gct ttt aat acc atg gca aat aca caa ccg tta gcc gtg ttg      96
Ala Leu Ala Phe Asn Thr Met Ala Asn Thr Gln Pro Leu Ala Val Leu
            20                  25                  30 gaa ccg cag gta aac tat caa cag tta ctc acc caa cgg cag gtg gtg     144
Glu Pro Gln Val Asn Tyr Gln Gln Leu Leu Thr Gln Arg Gln Val Val
        35                  40                  45 gat gat tta atc gcg cag gcg gtg aaa atc caa aat tca ccg gcg cgg     192
Asp Asp Leu Ile Ala Gln Ala Val Lys Ile Gln Asn Ser Pro Ala Arg
    50                  55                  60
```

```
gtg tcc aat gcg ggc ttt acc gca aaa ttg cca agc aac atg gaa cgc         240
Val Ser Asn Ala Gly Phe Thr Ala Lys Leu Pro Ser Asn Met Glu Arg
 65                  70                  75                  80 att gcc gcg att ttg ttg gaa gcc tat gaa ttg gaa cct tac cgc gtt         288
Ile Ala Ala Ile Leu Leu Glu Ala Tyr Glu Leu Glu Pro Tyr Arg Val
                     85                  90                  95 gat ttt ctg ttc ggc gca gca aat gcc aac att tac aac ggc aat acg         336
Asp Phe Leu Phe Gly Ala Ala Asn Ala Asn Ile Tyr Asn Gly Asn Thr
                100                 105                 110 gac aaa gcc atc gag ctt tac caa aaa gtg ctc acg gtg gcg cct gat         384
Asp Lys Ala Ile Glu Leu Tyr Gln Lys Val Leu Thr Val Ala Pro Asp
            115                 120                 125 gat gtg aaa gca cat att tat tta acc gcg tgg aat cgt ttt aaa caa         432
Asp Val Lys Ala His Ile Tyr Leu Thr Ala Trp Asn Arg Phe Lys Gln
130                 135                 140 aac caa ggg gaa acc gac aaa tac ttc acc cgc tta aaa gcg ctg gca         480
Asn Gln Gly Glu Thr Asp Lys Tyr Phe Thr Arg Leu Lys Ala Leu Ala
145                 150                 155                 160 ccg caa aaa gca gcg gaa ctg gag cag gtc ttc aag att att gat aac         528
Pro Gln Lys Ala Ala Glu Leu Glu Gln Val Phe Lys Ile Ile Asp Asn
                165                 170                 175 gcc gca agc caa ccg att agc gat aaa ttg gcg aat aaa ttg ccg gcg         576
Ala Ala Ser Gln Pro Ile Ser Asp Lys Leu Ala Asn Lys Leu Pro Ala
            180                 185                 190 gat tcc gcc att att acc ttg ggt tat gcg tta aat ccg gac ggc agt         624
Asp Ser Ala Ile Ile Thr Leu Gly Tyr Ala Leu Asn Pro Asp Gly Ser
                    195                 200                 205 atg cac gac att ttg att cag cgt ttg gaa aaa acc ttg gaa atc gcc         672
Met His Asp Ile Leu Ile Gln Arg Leu Glu Lys Thr Leu Glu Ile Ala
        210                 215                 220 aaa caa aat cct gat gca ttg att att gtc acc ggc ggc atg ccg caa         720
Lys Gln Asn Pro Asp Ala Leu Ile Ile Val Thr Gly Gly Met Pro Gln
225                 230                 235                 240 aat aat cgt acg gaa ggg gca tta atg aaa caa tgg ctg att aac aaa         768
Asn Asn Arg Thr Glu Gly Ala Leu Met Lys Gln Trp Leu Ile Asn Lys
                245                 250                 255 ggc atc gat gcc aaa cgc att tat gcc gac aat tac gcc cgt tca acg         816
Gly Ile Asp Ala Lys Arg Ile Tyr Ala Asp Asn Tyr Ala Arg Ser Thr
            260                 265                 270 gtg gaa aat gcg tta ttt tcc cgt tac gcc ttg gcg aaa cac cat atc         864
Val Glu Asn Ala Leu Phe Ser Arg Tyr Ala Leu Ala Lys His His Ile
        275                 280                 285 aaa cac gcc tcc ctc atc agc tcc ggt agc cat gtg cgg cgc ggt cag         912
Lys His Ala Ser Leu Ile Ser Ser Gly Ser His Val Arg Arg Gly Gln
290                 295                 300 gcg ttg ttt gaa atc gcc gcc ttg gaa tcc ggt ccg caa aac atc aaa         960
Ala Leu Phe Glu Ile Ala Ala Leu Glu Ser Gly Pro Gln Asn Ile Lys
305                 310                 315                 320 atc gaa acg gtg gcg gcg cta gac aaa ccg tta gac gaa tta caa aaa        1008
Ile Glu Thr Val Ala Ala Leu Asp Lys Pro Leu Asp Glu Leu Gln Lys
                325                 330                 335 gtg agt gaa aaa gat tta ttg gga atc tat cgc gac agc ctg aaa acc        1056
Val Ser Glu Lys Asp Leu Leu Gly Ile Tyr Arg Asp Ser Leu Lys Thr
            340                 345                 350 atg ggc ttg cca atg ttt aat agc gga gca cta caa gat taa               1098
Met Gly Leu Pro Met Phe Asn Ser Gly Ala Leu Gln Asp
        355                 360                 365

<210> SEQ ID NO 22
<211> LENGTH: 365
```

```
<212> TYPE: PRT
<213> ORGANISM: Actinobacillus actinomycetemcomitans

<400> SEQUENCE: 22

Asn Gln Met Asn Lys Thr Leu Lys Ile Ser Leu Phe Ala Met Ile Ser
1               5                   10                  15

Ala Leu Ala Phe Asn Thr Met Ala Asn Thr Gln Pro Leu Ala Val Leu
            20                  25                  30

Glu Pro Gln Val Asn Tyr Gln Gln Leu Leu Thr Gln Arg Gln Val Val
        35                  40                  45

Asp Asp Leu Ile Ala Gln Ala Val Lys Ile Gln Asn Ser Pro Ala Arg
50                  55                  60

Val Ser Asn Ala Gly Phe Thr Ala Lys Leu Pro Ser Asn Met Glu Arg
65                  70                  75                  80

Ile Ala Ala Ile Leu Leu Glu Ala Tyr Glu Leu Glu Pro Tyr Arg Val
                85                  90                  95

Asp Phe Leu Phe Gly Ala Ala Asn Ala Asn Ile Tyr Asn Gly Asn Thr
            100                 105                 110

Asp Lys Ala Ile Glu Leu Tyr Gln Lys Val Leu Thr Val Ala Pro Asp
        115                 120                 125

Asp Val Lys Ala His Ile Tyr Leu Thr Ala Trp Asn Arg Phe Lys Gln
130                 135                 140

Asn Gln Gly Glu Thr Asp Lys Tyr Phe Thr Arg Leu Lys Ala Leu Ala
145                 150                 155                 160

Pro Gln Lys Ala Ala Glu Leu Glu Gln Val Phe Lys Ile Ile Asp Asn
                165                 170                 175

Ala Ala Ser Gln Pro Ile Ser Asp Lys Leu Ala Asn Lys Leu Pro Ala
            180                 185                 190

Asp Ser Ala Ile Ile Thr Leu Gly Tyr Ala Leu Asn Pro Asp Gly Ser
        195                 200                 205

Met His Asp Ile Leu Ile Gln Arg Leu Glu Lys Thr Leu Glu Ile Ala
210                 215                 220

Lys Gln Asn Pro Asp Ala Leu Ile Ile Val Thr Gly Gly Met Pro Gln
225                 230                 235                 240

Asn Asn Arg Thr Glu Gly Ala Leu Met Lys Gln Trp Leu Ile Asn Lys
                245                 250                 255

Gly Ile Asp Ala Lys Arg Ile Tyr Ala Asp Asn Tyr Ala Arg Ser Thr
            260                 265                 270

Val Glu Asn Ala Leu Phe Ser Arg Tyr Ala Leu Ala Lys His His Ile
        275                 280                 285

Lys His Ala Ser Leu Ile Ser Ser Gly Ser His Val Arg Arg Gly Gln
290                 295                 300

Ala Leu Phe Glu Ile Ala Ala Leu Glu Ser Gly Pro Gln Asn Ile Lys
305                 310                 315                 320

Ile Glu Thr Val Ala Ala Leu Asp Lys Pro Leu Asp Glu Leu Gln Lys
                325                 330                 335

Val Ser Glu Lys Asp Leu Leu Gly Ile Tyr Arg Asp Ser Leu Lys Thr
            340                 345                 350

Met Gly Leu Pro Met Phe Asn Ser Gly Ala Leu Gln Asp
        355                 360                 365

<210> SEQ ID NO 23
<211> LENGTH: 134
<212> TYPE: DNA
<213> ORGANISM: Actinobacillus actinomycetemcomitans
```

```
<220> FEATURE:
<221> NAME/KEY: CDS
<222> LOCATION: (1)..(132)

<400> SEQUENCE: 23 ttg gat caa ttc ccg tcc gac gtt tat caa ggc ggc gcg ggc act tcc      48
Leu Asp Gln Phe Pro Ser Asp Val Tyr Gln Gly Gly Ala Gly Thr Ser
1               5                   10                  15 gtc aac atg aat acg aac gaa gtg gtt gcg aat ctg gca ttg gaa att      96
Val Asn Met Asn Thr Asn Glu Val Val Ala Asn Leu Ala Leu Glu Ile
            20                  25                  30 tta gga cac aaa aaa ggc gaa tat aat tat ttg gat cc                  134
Leu Gly His Lys Lys Gly Glu Tyr Asn Tyr Leu Asp
        35                  40

<210> SEQ ID NO 24
<211> LENGTH: 44
<212> TYPE: PRT
<213> ORGANISM: Actinobacillus actinomycetemcomitans

<400> SEQUENCE: 24

Leu Asp Gln Phe Pro Ser Asp Val Tyr Gln Gly Gly Ala Gly Thr Ser
1               5                   10                  15

Val Asn Met Asn Thr Asn Glu Val Val Ala Asn Leu Ala Leu Glu Ile
            20                  25                  30

Leu Gly His Lys Lys Gly Glu Tyr Asn Tyr Leu Asp
        35                  40

<210> SEQ ID NO 25
<211> LENGTH: 380
<212> TYPE: DNA
<213> ORGANISM: Actinobacillus actinomycetemcomitans
<220> FEATURE:
<221> NAME/KEY: CDS
<222> LOCATION: (1)..(378)

<400> SEQUENCE: 25 gat ccg aac agc ttc aaa ctg cgc ggc gaa ttg agc cac ggc aaa gac      48
Asp Pro Asn Ser Phe Lys Leu Arg Gly Glu Leu Ser His Gly Lys Asp
1               5                   10                  15 gtg gaa atc gac atg aac gtg att tta aac ggc aaa gtg cgg tta gga      96
Val Glu Ile Asp Met Asn Val Ile Leu Asn Gly Lys Val Arg Leu Gly
            20                  25                  30 aat cgg gtg aaa atc ggt gca ggt tgt gtg ttg act aac tgc gac atc     144
Asn Arg Val Lys Ile Gly Ala Gly Cys Val Leu Thr Asn Cys Asp Ile
        35                  40                  45 ggc gat gac gtg gaa atc aaa ccg tat tcc gtg ctg gaa gat gcc tcc     192
Gly Asp Asp Val Glu Ile Lys Pro Tyr Ser Val Leu Glu Asp Ala Ser
    50                  55                  60 gta ggc gcc aat gcc gcc atc gga ccg ttc tcc cgc tta cgt ccg ggc     240
Val Gly Ala Asn Ala Ala Ile Gly Pro Phe Ser Arg Leu Arg Pro Gly
65                  70                  75                  80 gcc gac ttg gcg gaa aac acc cac gtg ggc aat ttc gtg gaa atc aaa     288
Ala Asp Leu Ala Glu Asn Thr His Val Gly Asn Phe Val Glu Ile Lys
                85                  90                  95 aaa gcg tac atc ggc aaa ggc tcc aaa gtg aac cac tta acc tat gtg     336
Lys Ala Tyr Ile Gly Lys Gly Ser Lys Val Asn His Leu Thr Tyr Val
            100                 105                 110 ggc gac gcg gaa atc ggc aaa gat tgt aac ata ggc gca ggc gt         380
Gly Asp Ala Glu Ile Gly Lys Asp Cys Asn Ile Gly Ala Gly
        115                 120                 125
```

```
<210> SEQ ID NO 26
<211> LENGTH: 126
<212> TYPE: PRT
<213> ORGANISM: Actinobacillus actinomycetemcomitans

<400> SEQUENCE: 26

Asp Pro Asn Ser Phe Lys Leu Arg Gly Glu Leu Ser His Gly Lys Asp
1               5                   10                  15

Val Glu Ile Asp Met Asn Val Ile Leu Asn Gly Lys Val Arg Leu Gly
            20                  25                  30

Asn Arg Val Lys Ile Gly Ala Gly Cys Val Leu Thr Asn Cys Asp Ile
        35                  40                  45

Gly Asp Asp Val Glu Ile Lys Pro Tyr Ser Val Leu Glu Asp Ala Ser
    50                  55                  60

Val Gly Ala Asn Ala Ala Ile Gly Pro Phe Ser Arg Leu Arg Pro Gly
65                  70                  75                  80

Ala Asp Leu Ala Glu Asn Thr His Val Gly Asn Phe Val Glu Ile Lys
                85                  90                  95

Lys Ala Tyr Ile Gly Lys Gly Ser Lys Val Asn His Leu Thr Tyr Val
            100                 105                 110

Gly Asp Ala Glu Ile Gly Lys Asp Cys Asn Ile Gly Ala Gly
        115                 120                 125

<210> SEQ ID NO 27
<211> LENGTH: 468
<212> TYPE: DNA
<213> ORGANISM: Actinobacillus actinomycetemcomitans
<220> FEATURE:
<221> NAME/KEY: CDS
<222> LOCATION: (1)..(468)

<400> SEQUENCE: 27 att ggt cgc caa ctt gct cag ttg ctc aac atg gat ttt gta gat acc      48
Ile Gly Arg Gln Leu Ala Gln Leu Leu Asn Met Asp Phe Val Asp Thr
1               5                   10                  15 gac gca gaa att gaa gaa cgc gcc ggc gca gat att ggc tgg att ttt      96
Asp Ala Glu Ile Glu Glu Arg Ala Gly Ala Asp Ile Gly Trp Ile Phe
            20                  25                  30 gat gtt gag ggc gaa gcc ggt ttc cgt aaa aga gaa gaa cgt att att     144
Asp Val Glu Gly Glu Ala Gly Phe Arg Lys Arg Glu Glu Arg Ile Ile
        35                  40                  45 aac gaa tta acg caa cgc caa ggc atc gtg tta tct acc ggc ggt         192
Asn Glu Leu Thr Gln Arg Gln Gly Ile Val Leu Ser Thr Gly Gly Gly
    50                  55                  60 gca gtg tta tct aag gac aat cga aac cag ctt gcc gcg cgc ggt att     240
Ala Val Leu Ser Lys Asp Asn Arg Asn Gln Leu Ala Ala Arg Gly Ile
65                  70                  75                  80 gtg att tat ctg gaa acc act gtt gaa aag caa tat caa cgc acc cag     288
Val Ile Tyr Leu Glu Thr Thr Val Glu Lys Gln Tyr Gln Arg Thr Gln
                85                  90                  95 cgg gat aaa aag cgc ccg ctt ttg caa gat gtt gcc gat ccg cgt cag     336
Arg Asp Lys Lys Arg Pro Leu Leu Gln Asp Val Ala Asp Pro Arg Gln
            100                 105                 110 gtg ttg gaa gat ttg gcg aaa atc cgc aat ccg ctg tat gaa gac gta     384
Val Leu Glu Asp Leu Ala Lys Ile Arg Asn Pro Leu Tyr Glu Asp Val
        115                 120                 125 gca gac att acc ctc cct act gat gac caa agt gcc aag gta atg gca     432
Ala Asp Ile Thr Leu Pro Thr Asp Asp Gln Ser Ala Lys Val Met Ala
    130                 135                 140 acg cag att atc gac ttg att gat aac tat aac ggt                     468
Thr Gln Ile Ile Asp Leu Ile Asp Asn Tyr Asn Gly
```

```
Thr Gln Ile Ile Asp Leu Ile Asp Asn Tyr Asn Gly
145                 150                 155

<210> SEQ ID NO 28
<211> LENGTH: 156
<212> TYPE: PRT
<213> ORGANISM: Actinobacillus actinomycetemcomitans

<400> SEQUENCE: 28

Ile Gly Arg Gln Leu Ala Gln Leu Leu Asn Met Asp Phe Val Asp Thr
1               5                   10                  15

Asp Ala Glu Ile Glu Glu Arg Ala Gly Ala Asp Ile Gly Trp Ile Phe
            20                  25                  30

Asp Val Glu Gly Glu Ala Gly Phe Arg Lys Arg Glu Glu Arg Ile Ile
        35                  40                  45

Asn Glu Leu Thr Gln Arg Gln Gly Ile Val Leu Ser Thr Gly Gly Gly
    50                  55                  60

Ala Val Leu Ser Lys Asp Asn Arg Asn Gln Leu Ala Ala Arg Gly Ile
65                  70                  75                  80

Val Ile Tyr Leu Glu Thr Thr Val Glu Lys Gln Tyr Gln Arg Thr Gln
                85                  90                  95

Arg Asp Lys Lys Arg Pro Leu Leu Gln Asp Val Ala Asp Pro Arg Gln
            100                 105                 110

Val Leu Glu Asp Leu Ala Lys Ile Arg Asn Pro Leu Tyr Glu Asp Val
        115                 120                 125

Ala Asp Ile Thr Leu Pro Thr Asp Gln Ser Ala Lys Val Met Ala
    130                 135                 140

Thr Gln Ile Ile Asp Leu Ile Asp Asn Tyr Asn Gly
145                 150                 155

<210> SEQ ID NO 29
<211> LENGTH: 307
<212> TYPE: DNA
<213> ORGANISM: Actinobacillus actinomycetemcomitans
<220> FEATURE:
<221> NAME/KEY: CDS
<222> LOCATION: (1)..(306)

<400> SEQUENCE: 29 gcc tcc cgc agt ggc gat gcc gat gag cgt gtc atg gat tcc aac gat    48
Ala Ser Arg Ser Gly Asp Ala Asp Glu Arg Val Met Asp Ser Asn Asp
1               5                   10                  15 tta gaa aaa gag cgc ggc atc act att tta gcg aaa aat act gcc att    96
Leu Glu Lys Glu Arg Gly Ile Thr Ile Leu Ala Lys Asn Thr Ala Ile
            20                  25                  30 aac tgg aat agc tac cgt att aac att gta gac acc ccg ggg cac gcg   144
Asn Trp Asn Ser Tyr Arg Ile Asn Ile Val Asp Thr Pro Gly His Ala
        35                  40                  45 gac ttc ggt ggc gaa gtg gaa cgc gta ctt tcc atg gtg gat tcc gta   192
Asp Phe Gly Gly Glu Val Glu Arg Val Leu Ser Met Val Asp Ser Val
    50                  55                  60 tta ttg atg gtg gat gcc ttc gac ggc ccg atg ccg caa acc cgt ttt   240
Leu Leu Met Val Asp Ala Phe Asp Gly Pro Met Pro Gln Thr Arg Phe
65                  70                  75                  80 gtt acg caa aaa gcc ttc tcc cac ggt tta aaa cct atc gta gtc atc   288
Val Thr Gln Lys Ala Phe Ser His Gly Leu Lys Pro Ile Val Val Ile
                85                  90                  95 aat aaa gtt gac cgc ccg g                                         307
Asn Lys Val Asp Arg Pro
            100
```

<210> SEQ ID NO 30
<211> LENGTH: 102
<212> TYPE: PRT
<213> ORGANISM: Actinobacillus actinomycetemcomitans

<400> SEQUENCE: 30

| | | | | | | | | | | | | | | | |
|---|---|---|---|---|---|---|---|---|---|---|---|---|---|---|---|
| Ala | Ser | Arg | Ser | Gly | Asp | Ala | Asp | Glu | Arg | Val | Met | Asp | Ser | Asn | Asp |
| 1 | | | | 5 | | | | | 10 | | | | | 15 | |
| Leu | Glu | Lys | Glu | Arg | Gly | Ile | Thr | Ile | Leu | Ala | Lys | Asn | Thr | Ala | Ile |
| | | | 20 | | | | | 25 | | | | | 30 | | |
| Asn | Trp | Asn | Ser | Tyr | Arg | Ile | Asn | Ile | Val | Asp | Thr | Pro | Gly | His | Ala |
| | | | 35 | | | | | 40 | | | | | 45 | | |
| Asp | Phe | Gly | Gly | Glu | Val | Glu | Arg | Val | Leu | Ser | Met | Val | Asp | Ser | Val |
| | | | 50 | | | | | 55 | | | | | 60 | | |
| Leu | Leu | Met | Val | Asp | Ala | Phe | Asp | Gly | Pro | Met | Pro | Gln | Thr | Arg | Phe |
| 65 | | | | | 70 | | | | | 75 | | | | | 80 |
| Val | Thr | Gln | Lys | Ala | Phe | Ser | His | Gly | Leu | Lys | Pro | Ile | Val | Val | Ile |
| | | | | 85 | | | | | 90 | | | | | 95 | |
| Asn | Lys | Val | Asp | Arg | Pro | | | | | | | | | | |
| | | | 100 | | | | | | | | | | | | |

<210> SEQ ID NO 31
<211> LENGTH: 891
<212> TYPE: DNA
<213> ORGANISM: Actinobacillus actinomycetemcomitans
<220> FEATURE:
<221> NAME/KEY: CDS
<222> LOCATION: (1)..(891)
<221> NAME/KEY: misc_feature
<222> LOCATION: (182)..(182)
<223> OTHER INFORMATION: n is any nucleotide a, g, c, or t.
<221> NAME/KEY: misc_feature
<222> LOCATION: (188)..(188)
<223> OTHER INFORMATION: n is any nucleotide a, g, c, or t.

<400> SEQUENCE: 31

```
atg gct atc gta caa tcc aaa tct gcc cgc tac cgt tta tgg gtg acc        48
Met Ala Ile Val Gln Ser Lys Ser Ala Arg Tyr Arg Leu Trp Val Thr
1               5                   10                  15 cat ttg ctg ctg att gca ttt att tgt ctg att att ttc ccg tta ctg        96
His Leu Leu Leu Ile Ala Phe Ile Cys Leu Ile Ile Phe Pro Leu Leu
                20                  25                  30 atg gtg atc ggc att tcc ctg cgc ccg ggc aac ctc gct ttg ggc gat       144
Met Val Ile Gly Ile Ser Leu Arg Pro Gly Asn Leu Ala Leu Gly Asp
            35                  40                  45 ttg att ccg aaa caa att tcc tgg gaa cac tgg cag gcg gcg ctt ggc       192
Leu Ile Pro Lys Gln Ile Ser Trp Glu His Trp Gln Ala Ala Leu Gly
        50                  55                  60 ttt tat gtg gta cac gcc gac ggt tct gtc aca cca ccg ccg ttc ccg       240
Phe Tyr Val Val His Ala Asp Gly Ser Val Thr Pro Pro Pro Phe Pro
65                  70                  75                  80 gtg ttg ttg tgg ttg tgg aac tcc att aaa gtg gcg acc atc acc tcc       288
Val Leu Leu Trp Leu Trp Asn Ser Ile Lys Val Ala Thr Ile Thr Ser
                85                  90                  95 gtg ggt atc gtt gtt atg tcc acc act tgc gcc tac gct ttc gcg cgg       336
Val Gly Ile Val Val Met Ser Thr Thr Cys Ala Tyr Ala Phe Ala Arg
            100                 105                 110 atg aaa ttc aaa ggc aaa aaa acc atc ttg caa ggc atg tta att ttc       384
Met Lys Phe Lys Gly Lys Lys Thr Ile Leu Gln Gly Met Leu Ile Phe
        115                 120                 125
```

-continued

```
caa atg ttc cct gcg gtg ttg tct ttg gtc gcc tta tac gcc tta ttc       432
Gln Met Phe Pro Ala Val Leu Ser Leu Val Ala Leu Tyr Ala Leu Phe
    130                 135                 140 gat cgc ctc ggt caa tat atc ccg ttc ctc ggc tta aac acc cac ggc       480
Asp Arg Leu Gly Gln Tyr Ile Pro Phe Leu Gly Leu Asn Thr His Gly
145                 150                 155                 160 ggc gtg att ttc gct tac ttg ggc ggt atc gcc ttg cac gtt tgg acc       528
Gly Val Ile Phe Ala Tyr Leu Gly Gly Ile Ala Leu His Val Trp Thr
                165                 170                 175 atc aaa ggc tat ttt gaa acc atc gac gga tcc ctg gaa gaa gct gcc       576
Ile Lys Gly Tyr Phe Glu Thr Ile Asp Gly Ser Leu Glu Glu Ala Ala
            180                 185                 190 gcc tta gac ggc gct acc cca tgg cag gca ttc cgc tta att tta cta       624
Ala Leu Asp Gly Ala Thr Pro Trp Gln Ala Phe Arg Leu Ile Leu Leu
        195                 200                 205 cct ctc tcc gta ccg att ctg gcg gtg gtc ttc att ctt tcc ttc atc       672
Pro Leu Ser Val Pro Ile Leu Ala Val Val Phe Ile Leu Ser Phe Ile
    210                 215                 220 gcc gcc att acc gaa gtg ccg gtc gcc tcg cta tta tta cgc gat gtc       720
Ala Ala Ile Thr Glu Val Pro Val Ala Ser Leu Leu Leu Arg Asp Val
225                 230                 235                 240 aac agc tac acc ctg gcg gtg gga atg caa caa tat ctc tac ccg caa       768
Asn Ser Tyr Thr Leu Ala Val Gly Met Gln Gln Tyr Leu Tyr Pro Gln
                245                 250                 255 aac tac ctt tgg ggc gac ttc gcc gct gca gcg gtg ctt tcc gct att       816
Asn Tyr Leu Trp Gly Asp Phe Ala Ala Ala Ala Val Leu Ser Ala Ile
            260                 265                 270 cct att acc ctc gtg ttc tta ctg gca caa cgc tgg tta atc ggc gga       864
Pro Ile Thr Leu Val Phe Leu Leu Ala Gln Arg Trp Leu Ile Gly Gly
        275                 280                 285 tta acg gca ggt ggg gtn aar ggn tga                                   891
Leu Thr Ala Gly Gly Val Lys Gly
    290                 295
```

<210> SEQ ID NO 32
<211> LENGTH: 296
<212> TYPE: PRT
<213> ORGANISM: Actinobacillus actinomycetemcomitans
<220> FEATURE:
<221> NAME/KEY: misc_feature
<222> LOCATION: (182)..(182)
<223> OTHER INFORMATION: n is any nucleotide a, g, c, or t.
<221> NAME/KEY: misc_feature
<222> LOCATION: (188)..(188)
<223> OTHER INFORMATION: n is any nucleotide a, g, c, or t.

<400> SEQUENCE: 32

```
Met Ala Ile Val Gln Ser Lys Ser Ala Arg Tyr Arg Leu Trp Val Thr
1               5                   10                  15

His Leu Leu Leu Ile Ala Phe Ile Cys Leu Ile Ile Phe Pro Leu Leu
            20                  25                  30

Met Val Ile Gly Ile Ser Leu Arg Pro Gly Asn Leu Ala Leu Gly Asp
        35                  40                  45

Leu Ile Pro Lys Gln Ile Ser Trp Glu His Trp Gln Ala Ala Leu Gly
    50                  55                  60

Phe Tyr Val Val His Ala Asp Gly Ser Val Thr Pro Pro Phe Pro
65                  70                  75                  80

Val Leu Leu Trp Leu Trp Asn Ser Ile Lys Val Ala Thr Ile Thr Ser
                85                  90                  95

Val Gly Ile Val Val Met Ser Thr Cys Ala Tyr Ala Phe Ala Arg
            100                 105                 110
```

```
Met Lys Phe Lys Gly Lys Lys Thr Ile Leu Gln Gly Met Leu Ile Phe
        115                 120                 125

Gln Met Phe Pro Ala Val Leu Ser Leu Val Ala Leu Tyr Ala Leu Phe
    130                 135                 140

Asp Arg Leu Gly Gln Tyr Ile Pro Phe Leu Gly Leu Asn Thr His Gly
145                 150                 155                 160

Gly Val Ile Phe Ala Tyr Leu Gly Gly Ile Ala Leu His Val Trp Thr
                165                 170                 175

Ile Lys Gly Tyr Phe Glu Thr Ile Asp Gly Ser Leu Glu Glu Ala Ala
            180                 185                 190

Ala Leu Asp Gly Ala Thr Pro Trp Gln Ala Phe Arg Leu Ile Leu Leu
        195                 200                 205

Pro Leu Ser Val Pro Ile Leu Ala Val Val Phe Ile Leu Ser Phe Ile
    210                 215                 220

Ala Ala Ile Thr Glu Val Pro Val Ala Ser Leu Leu Leu Arg Asp Val
225                 230                 235                 240

Asn Ser Tyr Thr Leu Ala Val Gly Met Gln Gln Tyr Leu Tyr Pro Gln
                245                 250                 255

Asn Tyr Leu Trp Gly Asp Phe Ala Ala Ala Val Leu Ser Ala Ile
            260                 265                 270

Pro Ile Thr Leu Val Phe Leu Leu Ala Gln Arg Trp Leu Ile Gly Gly
        275                 280                 285

Leu Thr Ala Gly Gly Val Lys Gly
        290                 295

<210> SEQ ID NO 33
<211> LENGTH: 323
<212> TYPE: DNA
<213> ORGANISM: Actinobacillus actinomycetemcomitans
<220> FEATURE:
<221> NAME/KEY: CDS
<222> LOCATION: (1)..(321)

<400> SEQUENCE: 33 aat gtt tat ggc ggt acc aaa gcc ttt gta aaa caa ttt agc tta aac     48
Asn Val Tyr Gly Gly Thr Lys Ala Phe Val Lys Gln Phe Ser Leu Asn
1               5                   10                  15 cta cgt gcc gat ctt gcc gga acc aat att cgc gtt tcc aat gta gaa     96
Leu Arg Ala Asp Leu Ala Gly Thr Asn Ile Arg Val Ser Asn Val Glu
            20                  25                  30 ccg gga ctg tgc ggc ggc acg gaa ttt tct aac gta cgt ttt aaa ggc    144
Pro Gly Leu Cys Gly Gly Thr Glu Phe Ser Asn Val Arg Phe Lys Gly
        35                  40                  45 gat aac gcc cgc gcg gaa aaa ctc tac gaa aac gta caa tat gtt acg    192
Asp Asn Ala Arg Ala Glu Lys Leu Tyr Glu Asn Val Gln Tyr Val Thr
    50                  55                  60 cca caa gat att gcc aat atc gtg ttg tgg ctc aat caa caa ccg gaa    240
Pro Gln Asp Ile Ala Asn Ile Val Leu Trp Leu Asn Gln Gln Pro Glu
65                  70                  75                  80 cac gtc aac att aac cgc att gaa gtg atg ccg acg gcg caa acc ttc    288
His Val Asn Ile Asn Arg Ile Glu Val Met Pro Thr Ala Gln Thr Phe
                85                  90                  95 gcc ccg ctt aat gta gca agg aat tta aat tta ga                     323
Ala Pro Leu Asn Val Ala Arg Asn Leu Asn Leu
            100                 105

<210> SEQ ID NO 34
<211> LENGTH: 107
```

```
<212> TYPE: PRT
<213> ORGANISM: Actinobacillus actinomycetemcomitans

<400> SEQUENCE: 34

Asn Val Tyr Gly Gly Thr Lys Ala Phe Val Lys Gln Phe Ser Leu Asn
1               5                   10                  15

Leu Arg Ala Asp Leu Ala Gly Thr Asn Ile Arg Val Ser Asn Val Glu
            20                  25                  30

Pro Gly Leu Cys Gly Gly Thr Glu Phe Ser Asn Val Arg Phe Lys Gly
        35                  40                  45

Asp Asn Ala Arg Ala Glu Lys Leu Tyr Glu Asn Val Gln Tyr Val Thr
    50                  55                  60

Pro Gln Asp Ile Ala Asn Ile Val Leu Trp Leu Asn Gln Gln Pro Glu
65                  70                  75                  80

His Val Asn Ile Asn Arg Ile Glu Val Met Pro Thr Ala Gln Thr Phe
                85                  90                  95

Ala Pro Leu Asn Val Ala Arg Asn Leu Asn Leu
            100                 105

<210> SEQ ID NO 35
<211> LENGTH: 585
<212> TYPE: DNA
<213> ORGANISM: Actinobacillus actinomycetemcomitans
<220> FEATURE:
<221> NAME/KEY: CDS
<222> LOCATION: (1)..(585)

<400> SEQUENCE: 35 atg gcg gaa acg att tta aac ccg tat ttc ggg gaa ttc ggc gga atg     48
Met Ala Glu Thr Ile Leu Asn Pro Tyr Phe Gly Glu Phe Gly Gly Met
1               5                   10                  15 tat gtg ccg gaa att cta gtg ccg gtg ttg caa cag ttg gaa aaa gcg     96
Tyr Val Pro Glu Ile Leu Val Pro Val Leu Gln Gln Leu Glu Lys Ala
            20                  25                  30 ttt gta gaa gcc aag gcg gat cct gca ttt cag cgc gaa ttt cag gat    144
Phe Val Glu Ala Lys Ala Asp Pro Ala Phe Gln Arg Glu Phe Gln Asp
        35                  40                  45 tta ttg aaa aat tat gcc ggc aga ccc acc gca ctt acc ctt tgt cgc    192
Leu Leu Lys Asn Tyr Ala Gly Arg Pro Thr Ala Leu Thr Leu Cys Arg
    50                  55                  60 aat ctc acc aaa ggc acc aac gcc aaa atc tat tta aaa cgg gaa gat    240
Asn Leu Thr Lys Gly Thr Asn Ala Lys Ile Tyr Leu Lys Arg Glu Asp
65                  70                  75                  80 tta tta cac ggc ggc gca cat aaa acc aac cag gta tta ggt cag att    288
Leu Leu His Gly Gly Ala His Lys Thr Asn Gln Val Leu Gly Gln Ile
                85                  90                  95 ttg ctt gcc aaa cgc atg ggc aaa acc cgc att att gcc gaa acc ggc    336
Leu Leu Ala Lys Arg Met Gly Lys Thr Arg Ile Ile Ala Glu Thr Gly
            100                 105                 110 gcg gga cag cac ggt gtc gcc act gct ctc gcc tgc gcc atg ttg gat    384
Ala Gly Gln His Gly Val Ala Thr Ala Leu Ala Cys Ala Met Leu Asp
        115                 120                 125 atg ccg tgc cgt gtt tat atg ggc gcg aaa gat gtg gaa cgc caa tcg    432
Met Pro Cys Arg Val Tyr Met Gly Ala Lys Asp Val Glu Arg Gln Ser
    130                 135                 140 ccg aat gtg ttt cgt atg cgt tta atg ggc acg gaa gtg gta ccg gtg    480
Pro Asn Val Phe Arg Met Arg Leu Met Gly Thr Glu Val Val Pro Val
145                 150                 155                 160 caa aaa ggt tcc tgt tct ttg aaa gac gct tgc tgc gaa gcc atg cgt    528
Gln Lys Gly Ser Cys Ser Leu Lys Asp Ala Cys Cys Glu Ala Met Arg
```

```
                        165                 170                 175
gac tgg tcg gca aat tat gaa aat acg cac tat ttg ctc ggc aca gcg    576
Asp Trp Ser Ala Asn Tyr Glu Asn Thr His Tyr Leu Leu Gly Thr Ala
            180                 185                 190 gca ggt ccg                                                        585
Ala Gly Pro
        195

<210> SEQ ID NO 36
<211> LENGTH: 195
<212> TYPE: PRT
<213> ORGANISM: Actinobacillus actinomycetemcomitans

<400> SEQUENCE: 36

Met Ala Glu Thr Ile Leu Asn Pro Tyr Phe Gly Glu Phe Gly Gly Met
1               5                   10                  15

Tyr Val Pro Glu Ile Leu Val Pro Val Leu Gln Gln Leu Glu Lys Ala
            20                  25                  30

Phe Val Glu Ala Lys Ala Asp Pro Ala Phe Gln Arg Glu Phe Gln Asp
        35                  40                  45

Leu Leu Lys Asn Tyr Ala Gly Arg Pro Thr Ala Leu Thr Leu Cys Arg
    50                  55                  60

Asn Leu Thr Lys Gly Thr Asn Ala Lys Ile Tyr Leu Lys Arg Glu Asp
65                  70                  75                  80

Leu Leu His Gly Gly Ala His Lys Thr Asn Gln Val Leu Gly Gln Ile
                85                  90                  95

Leu Leu Ala Lys Arg Met Gly Lys Thr Arg Ile Ile Ala Glu Thr Gly
            100                 105                 110

Ala Gly Gln His Gly Val Ala Thr Ala Leu Ala Cys Ala Met Leu Asp
        115                 120                 125

Met Pro Cys Arg Val Tyr Met Gly Ala Lys Asp Val Glu Arg Gln Ser
    130                 135                 140

Pro Asn Val Phe Arg Met Arg Leu Met Gly Thr Glu Val Val Pro Val
145                 150                 155                 160

Gln Lys Gly Ser Cys Ser Leu Lys Asp Ala Cys Cys Glu Ala Met Arg
                165                 170                 175

Asp Trp Ser Ala Asn Tyr Glu Asn Thr His Tyr Leu Leu Gly Thr Ala
            180                 185                 190

Ala Gly Pro
        195

<210> SEQ ID NO 37
<211> LENGTH: 543
<212> TYPE: DNA
<213> ORGANISM: Actinobacillus actinomycetemcomitans
<220> FEATURE:
<221> NAME/KEY: CDS
<222> LOCATION: (1)..(543)

<400> SEQUENCE: 37 atg tcg cac gta ttt caa atc tca aga gaa att atg aca gct tta aat    48
Met Ser His Val Phe Gln Ile Ser Arg Glu Ile Met Thr Ala Leu Asn
1               5                   10                  15 gta ctt att tac ccg gaa gag cac ctt aaa gtg gtt tgc gat ccg gtc    96
Val Leu Ile Tyr Pro Glu Glu His Leu Lys Val Val Cys Asp Pro Val
            20                  25                  30 gtg gaa gtc aat gac aac acg cgt aag att att gat aat atg ttt gat   144
Val Glu Val Asn Asp Asn Thr Arg Lys Ile Ile Asp Asn Met Phe Asp
        35                  40                  45
```

```
acc atg tat cag gaa ggc ggt atc ggc cta gcg gca ccg cag gtg gat      192
Thr Met Tyr Gln Glu Gly Gly Ile Gly Leu Ala Ala Pro Gln Val Asp
     50                  55                  60 att tta cag cgt att atc act att gat att gag ggt gac aaa caa aac      240
Ile Leu Gln Arg Ile Ile Thr Ile Asp Ile Glu Gly Asp Lys Gln Asn
 65                  70                  75                  80 cag tta gtg ttg att aac cct gaa att ttg gaa tcg gaa ggt gaa acc      288
Gln Leu Val Leu Ile Asn Pro Glu Ile Leu Glu Ser Glu Gly Glu Thr
                 85                  90                  95 gga att gaa gag ggt tgt ttg tcg att ccc gga ttt cgt gcg tta gtg      336
Gly Ile Glu Glu Gly Cys Leu Ser Ile Pro Gly Phe Arg Ala Leu Val
            100                 105                 110 cca cgt aaa gag aaa gtg act gta aaa gcg ctg gat cgt cat ggt aaa      384
Pro Arg Lys Glu Lys Val Thr Val Lys Ala Leu Asp Arg His Gly Lys
        115                 120                 125 gaa ttc acc tta aaa gcc gat ggt ctg ttg gca att tgt att cag cat      432
Glu Phe Thr Leu Lys Ala Asp Gly Leu Leu Ala Ile Cys Ile Gln His
    130                 135                 140 gaa att gat cat tta aac ggt att ctt ttt gtg gat tat ctc tct cca      480
Glu Ile Asp His Leu Asn Gly Ile Leu Phe Val Asp Tyr Leu Ser Pro
145                 150                 155                 160 ttg aaa cgt cag cgg att aaa gaa aag ctg att aaa atg aaa aag cag      528
Leu Lys Arg Gln Arg Ile Lys Glu Lys Leu Ile Lys Met Lys Lys Gln
                165                 170                 175 atg gaa aag caa aaa                                                  543
Met Glu Lys Gln Lys
            180

<210> SEQ ID NO 38
<211> LENGTH: 181
<212> TYPE: PRT
<213> ORGANISM: Actinobacillus actinomycetemcomitans

<400> SEQUENCE: 38

Met Ser His Val Phe Gln Ile Ser Arg Glu Ile Met Thr Ala Leu Asn
 1               5                  10                  15

Val Leu Ile Tyr Pro Glu Glu His Leu Lys Val Val Cys Asp Pro Val
             20                  25                  30

Val Glu Val Asn Asp Asn Thr Arg Lys Ile Ile Asp Asn Met Phe Asp
         35                  40                  45

Thr Met Tyr Gln Glu Gly Gly Ile Gly Leu Ala Ala Pro Gln Val Asp
     50                  55                  60

Ile Leu Gln Arg Ile Ile Thr Ile Asp Ile Glu Gly Asp Lys Gln Asn
 65                  70                  75                  80

Gln Leu Val Leu Ile Asn Pro Glu Ile Leu Glu Ser Glu Gly Glu Thr
                 85                  90                  95

Gly Ile Glu Glu Gly Cys Leu Ser Ile Pro Gly Phe Arg Ala Leu Val
            100                 105                 110

Pro Arg Lys Glu Lys Val Thr Val Lys Ala Leu Asp Arg His Gly Lys
        115                 120                 125

Glu Phe Thr Leu Lys Ala Asp Gly Leu Leu Ala Ile Cys Ile Gln His
    130                 135                 140

Glu Ile Asp His Leu Asn Gly Ile Leu Phe Val Asp Tyr Leu Ser Pro
145                 150                 155                 160

Leu Lys Arg Gln Arg Ile Lys Glu Lys Leu Ile Lys Met Lys Lys Gln
                165                 170                 175

Met Glu Lys Gln Lys
            180
```

<210> SEQ ID NO 39
<211> LENGTH: 353
<212> TYPE: DNA
<213> ORGANISM: Actinobacillus actinomycetemcomitans
<220> FEATURE:
<221> NAME/KEY: CDS
<222> LOCATION: (1)..(351)

<400> SEQUENCE: 39

| | | | | | | | | | | | | | | | | |
|---|---|---|---|---|---|---|---|---|---|---|---|---|---|---|---|---|
| cgc | ggc | gtg | aca | ccg | gaa | cta | ttc | gcc | gac | tgg | tta | aaa | cag | tta | cat | 48 |
| Arg | Gly | Val | Thr | Pro | Glu | Leu | Phe | Ala | Asp | Trp | Leu | Lys | Gln | Leu | His | |
| 1 | | | | 5 | | | | | 10 | | | | | 15 | | |
| cag | gcg | ggc | gta | aaa | gtg | gtg | ttg | gac | agc | agt | aac | gcc | gca | ttg | acc | 96 |
| Gln | Ala | Gly | Val | Lys | Val | Val | Leu | Asp | Ser | Ser | Asn | Ala | Ala | Leu | Thr | |
| | | | 20 | | | | | 25 | | | | | 30 | | | |
| gcc | ggc | tta | acg | gcg | caa | cct | tgg | ttg | gtt | aaa | ccg | aat | cat | cgt | gag | 144 |
| Ala | Gly | Leu | Thr | Ala | Gln | Pro | Trp | Leu | Val | Lys | Pro | Asn | His | Arg | Glu | |
| | | 35 | | | | | 40 | | | | | 45 | | | | |
| ttg | gaa | gcc | tgg | att | ggt | cat | gcg | ctg | ccg | acc | ttg | gac | gac | att | atc | 192 |
| Leu | Glu | Ala | Trp | Ile | Gly | His | Ala | Leu | Pro | Thr | Leu | Asp | Asp | Ile | Ile | |
| 50 | | | | | 55 | | | | | 60 | | | | | | |
| gcg | gcg | gcg | aaa | aaa | ctg | aaa | gca | caa | ggc | att | gct | aac | gtg | att | att | 240 |
| Ala | Ala | Ala | Lys | Lys | Leu | Lys | Ala | Gln | Gly | Ile | Ala | Asn | Val | Ile | Ile | |
| 65 | | | | | 70 | | | | | 75 | | | | | 80 | |
| tcc | atg | ggc | gcc | aac | ggt | tcg | ttg | tgg | ttg | agc | gat | aca | gcc | gtc | gta | 288 |
| Ser | Met | Gly | Ala | Asn | Gly | Ser | Leu | Trp | Leu | Ser | Asp | Thr | Ala | Val | Val | |
| | | | | 85 | | | | | 90 | | | | | 95 | | |
| cag | gcg | caa | ccg | ccg | aaa | tgc | gaa | aac | gtg | gtc | agc | acc | gtg | ggc | gcg | 336 |
| Gln | Ala | Gln | Pro | Pro | Lys | Cys | Glu | Asn | Val | Val | Ser | Thr | Val | Gly | Ala | |
| | | | 100 | | | | | 105 | | | | | 110 | | | |
| ggc | gat | tct | atg | gtg | gc | | | | | | | | | | | 353 |
| Gly | Asp | Ser | Met | Val | | | | | | | | | | | | |
| | | | 115 | | | | | | | | | | | | | |

<210> SEQ ID NO 40
<211> LENGTH: 117
<212> TYPE: PRT
<213> ORGANISM: Actinobacillus actinomycetemcomitans

<400> SEQUENCE: 40

Arg Gly Val Thr Pro Glu Leu Phe Ala Asp Trp Leu Lys Gln Leu His
1               5                   10                  15

Gln Ala Gly Val Lys Val Val Leu Asp Ser Ser Asn Ala Ala Leu Thr
            20                  25                  30

Ala Gly Leu Thr Ala Gln Pro Trp Leu Val Lys Pro Asn His Arg Glu
        35                  40                  45

Leu Glu Ala Trp Ile Gly His Ala Leu Pro Thr Leu Asp Asp Ile Ile
50                  55                  60

Ala Ala Ala Lys Lys Leu Lys Ala Gln Gly Ile Ala Asn Val Ile Ile
65                  70                  75                  80

Ser Met Gly Ala Asn Gly Ser Leu Trp Leu Ser Asp Thr Ala Val Val
                85                  90                  95

Gln Ala Gln Pro Pro Lys Cys Glu Asn Val Val Ser Thr Val Gly Ala
            100                 105                 110

Gly Asp Ser Met Val
            115

<210> SEQ ID NO 41

```
<211> LENGTH: 367
<212> TYPE: DNA
<213> ORGANISM: Actinobacillus actinomycetemcomitans
<220> FEATURE:
<221> NAME/KEY: CDS
<222> LOCATION: (1)..(366)

<400> SEQUENCE: 41 atg aaa aaa tgg ttt atg ctg tta ctt ccg ctg aca ttt atc ggc agc      48
Met Lys Lys Trp Phe Met Leu Leu Pro Leu Thr Phe Ile Gly Ser
1               5                   10                  15 ctt tgg gcg cag gaa gcg cct tcc ccc ttt ctt gcc ggg gaa tta ccg      96
Leu Trp Ala Gln Glu Ala Pro Ser Pro Phe Leu Ala Gly Glu Leu Pro
            20                  25                  30 gca gcg caa aaa atc gaa aaa gtc tta agc gcc ggt aat ccg agt gat     144
Ala Ala Gln Lys Ile Glu Lys Val Leu Ser Ala Gly Asn Pro Ser Asp
        35                  40                  45 gcg tta ttg ctg gcc gcc gcg ccg caa aaa atg gtc gga ctg gcg ggc     192
Ala Leu Leu Leu Ala Ala Ala Pro Gln Lys Met Val Gly Leu Ala Gly
    50                  55                  60 ttt aag atg gca tcc aaa ggc ggc aaa tta ttt cct gtg caa caa caa     240
Phe Lys Met Ala Ser Lys Gly Gly Lys Leu Phe Pro Val Gln Gln Gln
65                  70                  75                  80 gcg ttg ccg acc atc ggc aaa att gcc gga aag ggc agt acg ttt tcc     288
Ala Leu Pro Thr Ile Gly Lys Ile Ala Gly Lys Gly Ser Thr Phe Ser
                85                  90                  95 gcc gaa aaa atc gtg gcg ctt caa ccg aat ttg att att gat gtg ggc     336
Ala Glu Lys Ile Val Ala Leu Gln Pro Asn Leu Ile Ile Asp Val Gly
            100                 105                 110 aat gtg gcg ccg aat tac atc gat cag gca a                            367
Asn Val Ala Pro Asn Tyr Ile Asp Gln Ala
        115                 120

<210> SEQ ID NO 42
<211> LENGTH: 122
<212> TYPE: PRT
<213> ORGANISM: Actinobacillus actinomycetemcomitans

<400> SEQUENCE: 42

Met Lys Lys Trp Phe Met Leu Leu Pro Leu Thr Phe Ile Gly Ser
1               5                   10                  15

Leu Trp Ala Gln Glu Ala Pro Ser Pro Phe Leu Ala Gly Glu Leu Pro
            20                  25                  30

Ala Ala Gln Lys Ile Glu Lys Val Leu Ser Ala Gly Asn Pro Ser Asp
        35                  40                  45

Ala Leu Leu Leu Ala Ala Ala Pro Gln Lys Met Val Gly Leu Ala Gly
    50                  55                  60

Phe Lys Met Ala Ser Lys Gly Gly Lys Leu Phe Pro Val Gln Gln Gln
65                  70                  75                  80

Ala Leu Pro Thr Ile Gly Lys Ile Ala Gly Lys Gly Ser Thr Phe Ser
                85                  90                  95

Ala Glu Lys Ile Val Ala Leu Gln Pro Asn Leu Ile Ile Asp Val Gly
            100                 105                 110

Asn Val Ala Pro Asn Tyr Ile Asp Gln Ala
        115                 120

<210> SEQ ID NO 43
<211> LENGTH: 4593
<212> TYPE: DNA
<213> ORGANISM: Actinobacillus actinomycetemcomitans
<220> FEATURE:
```

-continued

```
<221> NAME/KEY: CDS
<222> LOCATION: (1)..(4593)

<400> SEQUENCE: 43 gtc ttt aaa gta atc tgg tgt aaa aca tct cag aca tgg att gcc gta      48
Val Phe Lys Val Ile Trp Cys Lys Thr Ser Gln Thr Trp Ile Ala Val
1               5                   10                  15 tct gaa cta tct aaa gct ttt tcc ctt tct acc act aca gat ata cct      96
Ser Glu Leu Ser Lys Ala Phe Ser Leu Ser Thr Thr Thr Asp Ile Pro
            20                  25                  30 aaa aaa act aaa ata ttc att gct gca gcc ccg tta tta ttt ctc tcc     144
Lys Lys Thr Lys Ile Phe Ile Ala Ala Ala Pro Leu Leu Phe Leu Ser
        35                  40                  45 ttt aat acc aac gct tac att gct ata ggt tct gtt gaa aac aat tct     192
Phe Asn Thr Asn Ala Tyr Ile Ala Ile Gly Ser Val Glu Asn Asn Ser
    50                  55                  60 gtg aaa tcc gag ggg gca gaa gcc tcc cca aac aag aga aag gga agc     240
Val Lys Ser Glu Gly Ala Glu Ala Ser Pro Asn Lys Arg Lys Gly Ser
65                  70                  75                  80 caa gca tta aat tat tac aac ccc ggt agt aaa tca tat gat gat aaa     288
Gln Ala Leu Asn Tyr Tyr Asn Pro Gly Ser Lys Ser Tyr Asp Asp Lys
                85                  90                  95 gac aaa ccg agc aat cct gaa aga aga tac agc aat ggg gag gca tat     336
Asp Lys Pro Ser Asn Pro Glu Arg Arg Tyr Ser Asn Gly Glu Ala Tyr
            100                 105                 110 ggt atc gct atc ggt aaa aat acc gat gtt cgt gac tca agt aag gat     384
Gly Ile Ala Ile Gly Lys Asn Thr Asp Val Arg Asp Ser Ser Lys Asp
        115                 120                 125 tca aat ggt atc gcc tta ggc gat tat tct aaa gct acc ggt ggg ctt     432
Ser Asn Gly Ile Ala Leu Gly Asp Tyr Ser Lys Ala Thr Gly Gly Leu
    130                 135                 140 gcc atg gcc tta ggt tca ttt tcc aga gca gaa aaa aat ggc ggt att     480
Ala Met Ala Leu Gly Ser Phe Ser Arg Ala Glu Lys Asn Gly Gly Ile
145                 150                 155                 160 gca atc ggt ata gct tcc aga tca tca gga att aat tct ctt gcg atg     528
Ala Ile Gly Ile Ala Ser Arg Ser Ser Gly Ile Asn Ser Leu Ala Met
                165                 170                 175 atg cgt caa tct gca gca acc ggg gat tat tct act gcc att ggt tct     576
Met Arg Gln Ser Ala Ala Thr Gly Asp Tyr Ser Thr Ala Ile Gly Ser
            180                 185                 190 gtc gca tgg gct gca ggt caa tca agc ttc gca ctg ggg gct tct gct     624
Val Ala Trp Ala Ala Gly Gln Ser Ser Phe Ala Leu Gly Ala Ser Ala
        195                 200                 205 act gct aaa ggc aac caa tcc att gca att ggc agc ttg gaa caa aaa     672
Thr Ala Lys Gly Asn Gln Ser Ile Ala Ile Gly Ser Leu Glu Gln Lys
    210                 215                 220 ata tct ccg aat ggt tct ggt gtg cca atc aca aaa tac aac ggg tta     720
Ile Ser Pro Asn Gly Ser Gly Val Pro Ile Thr Lys Tyr Asn Gly Leu
225                 230                 235                 240 gac aac aca caa acc aat ggt aac cgt tcc atg gca ttg ggt acg gca     768
Asp Asn Thr Gln Thr Asn Gly Asn Arg Ser Met Ala Leu Gly Thr Ala
                245                 250                 255 gct aaa acc aat ggt gat gat tca ttt gct att ggt tat aaa gca cac     816
Ala Lys Thr Asn Gly Asp Asp Ser Phe Ala Ile Gly Tyr Lys Ala His
            260                 265                 270 acc ggt gag ttt aaa gtg gaa cat gac aac tat cta aaa gag aat gtt     864
Thr Gly Glu Phe Lys Val Glu His Asp Asn Tyr Leu Lys Glu Asn Val
        275                 280                 285 acc tct ccg gat ctg tct aaa aaa gct gat aaa gcc att gct gtc ggt     912
Thr Ser Pro Asp Leu Ser Lys Lys Ala Asp Lys Ala Ile Ala Val Gly
```

```
            290                 295                 300
acg agt gcc ctt gcg caa aaa gaa tct gct atc gca ttt ggc tac caa     960
Thr Ser Ala Leu Ala Gln Lys Glu Ser Ala Ile Ala Phe Gly Tyr Gln
305                 310                 315                 320 gct aat gct tcc ggc att aat gca att tct ctt ggc gca aat gca aaa    1008
Ala Asn Ala Ser Gly Ile Asn Ala Ile Ser Leu Gly Ala Asn Ala Lys
                325                 330                 335 gca tct caa gat aac gtt gta gca ata ggt aaa tat gct aca gcc act    1056
Ala Ser Gln Asp Asn Val Val Ala Ile Gly Lys Tyr Ala Thr Ala Thr
            340                 345                 350 gaa tct ggt tca atg gcc att ggt cag gga gct aaa tct acc ttt aaa    1104
Glu Ser Gly Ser Met Ala Ile Gly Gln Gly Ala Lys Ser Thr Phe Lys
        355                 360                 365 aac tca ttg gca tta ggt aca ggt acc att gtc aac agt gtc gat ggc    1152
Asn Ser Leu Ala Leu Gly Thr Gly Thr Ile Val Asn Ser Val Asp Gly
    370                 375                 380 ggg caa tct aaa ttt act gca caa aat tat gat gct aat aat ggt gtt    1200
Gly Gln Ser Lys Phe Thr Ala Gln Asn Tyr Asp Ala Asn Asn Gly Val
385                 390                 395                 400 gta gct gtt gca aac gcc ggt aaa gag cgt cga att att aat gtt gcc    1248
Val Ala Val Ala Asn Ala Gly Lys Glu Arg Arg Ile Ile Asn Val Ala
                405                 410                 415 ggt ggt cgt aat gat act gat gca gtg aat att gcc cag tta aaa ttc    1296
Gly Gly Arg Asn Asp Thr Asp Ala Val Asn Ile Ala Gln Leu Lys Phe
            420                 425                 430 gtg aat gat aac tta gcc aag tcc atc gca ggc gcc ggt tat aac ggc    1344
Val Asn Asp Asn Leu Ala Lys Ser Ile Ala Gly Ala Gly Tyr Asn Gly
        435                 440                 445 tat gaa aca gac gga cat act tac aaa gca ccg gta ttt agt att aaa    1392
Tyr Glu Thr Asp Gly His Thr Tyr Lys Ala Pro Val Phe Ser Ile Lys
    450                 455                 460 aat acc aac tat cac gat gtc aaa aca gct gtt gaa gcg gca caa acc    1440
Asn Thr Asn Tyr His Asp Val Lys Thr Ala Val Glu Ala Ala Gln Thr
465                 470                 475                 480 aat tat gta agt gta aat agc act aat aca gca gcc gat agt aat tac    1488
Asn Tyr Val Ser Val Asn Ser Thr Asn Thr Ala Ala Asp Ser Asn Tyr
                485                 490                 495 gac aat aaa ggg gct aaa gca gta ggt tct att gcg tta ggc gaa aaa    1536
Asp Asn Lys Gly Ala Lys Ala Val Gly Ser Ile Ala Leu Gly Glu Lys
            500                 505                 510 gcc aca aca gga acg gcg gca atg aac tct att gcc att ggt tta aac    1584
Ala Thr Thr Gly Thr Ala Ala Met Asn Ser Ile Ala Ile Gly Leu Asn
        515                 520                 525 agc aat gtt agc ggc caa aat acc gtt gca ttg ggt gcc aat atc acc    1632
Ser Asn Val Ser Gly Gln Asn Thr Val Ala Leu Gly Ala Asn Ile Thr
    530                 535                 540 gcg aca acc aac ggt tcc gtc att tta gga aat tcc tcc acc acg gaa    1680
Ala Thr Thr Asn Gly Ser Val Ile Leu Gly Asn Ser Ser Thr Thr Glu
545                 550                 555                 560 ggt tca cat cct gtt tca aat gtt agc agt gcg act gtt aac gga tat    1728
Gly Ser His Pro Val Ser Asn Val Ser Ser Ala Thr Val Asn Gly Tyr
                565                 570                 575 acc tac tca ggt ttt acc ggc acg gta aaa gag tcg gga cat ttt gtg    1776
Thr Tyr Ser Gly Phe Thr Gly Thr Val Lys Glu Ser Gly His Phe Val
            580                 585                 590 agc att ggt tca aaa ggc aat gag cgt caa att aaa aat gtg gca gca    1824
Ser Ile Gly Ser Lys Gly Asn Glu Arg Gln Ile Lys Asn Val Ala Ala
        595                 600                 605 ggt aat gtt gcg gca aac tca acc gat gcc gtt aat ggc tct caa tta    1872
```

```
                Gly Asn Val Ala Ala Asn Ser Thr Asp Ala Val Asn Gly Ser Gln Leu
                            610                 615                 620 ttt gct gtc gcc agt cgt gta gaa caa ggt tgg caa atc act tcc ggc              1920
Phe Ala Val Ala Ser Arg Val Glu Gln Gly Trp Gln Ile Thr Ser Gly
625                 630                 635                 640 gta gaa aat ggt ggt act caa aat ggc gca gcc tca aca gca aca atc              1968
Val Glu Asn Gly Gly Thr Gln Asn Gly Ala Ala Ser Thr Ala Thr Ile
                645                 650                 655 aaa ccg agt aac caa gtg aag cta ctg gca gga aag aat tta gca gtc              2016
Lys Pro Ser Asn Gln Val Lys Leu Leu Ala Gly Lys Asn Leu Ala Val
                660                 665                 670 aaa caa aac ggc act aac ttc acc ttc tca acc caa gaa aat gtc acg              2064
Lys Gln Asn Gly Thr Asn Phe Thr Phe Ser Thr Gln Glu Asn Val Thr
                675                 680                 685 ttc act aat gtt acg acc caa gat cta act gca aca ggc aac acc act              2112
Phe Thr Asn Val Thr Thr Gln Asp Leu Thr Ala Thr Gly Asn Thr Thr
690                 695                 700 gtt aag aac ttc agc gtt caa aat ggc gga acc atc aat atg gga aat              2160
Val Lys Asn Phe Ser Val Gln Asn Gly Gly Thr Ile Asn Met Gly Asn
705                 710                 715                 720 aat cgc att acc ggt gtc gct gaa ggc act caa gat gac gac gcg gtt              2208
Asn Arg Ile Thr Gly Val Ala Glu Gly Thr Gln Asp Asp Asp Ala Val
                725                 730                 735 aac ttt aaa caa tta aaa agc ctt ctt ggt ggc tcc gca tca acg gaa              2256
Asn Phe Lys Gln Leu Lys Ser Leu Leu Gly Gly Ser Ala Ser Thr Glu
                740                 745                 750 att gtt gag aaa aaa gca gct caa gcc gga gat gaa aac ctg gcg gat              2304
Ile Val Glu Lys Lys Ala Ala Gln Ala Gly Asp Glu Asn Leu Ala Asp
                755                 760                 765 att agc gta gca aat ggt aaa aac gcc ggc gat atg ggt gcg aaa tac              2352
Ile Ser Val Ala Asn Gly Lys Asn Ala Gly Asp Met Gly Ala Lys Tyr
                770                 775                 780 gaa gta tct gta tcc aaa aaa gcc gta caa agt gcc gca aaa gaa gcg              2400
Glu Val Ser Val Ser Lys Lys Ala Val Gln Ser Ala Ala Lys Glu Ala
785                 790                 795                 800 gtt aaa gtg aca ggt tcg gca ccg att aat gta aac aaa aca gat gta              2448
Val Lys Val Thr Gly Ser Ala Pro Ile Asn Val Asn Lys Thr Asp Val
                805                 810                 815 aat ggc gtt gat act tat gcc gta acc ttt aat ggc aca gaa gcg gcg              2496
Asn Gly Val Asp Thr Tyr Ala Val Thr Phe Asn Gly Thr Glu Ala Ala
                820                 825                 830 aaa tct atc cca tta act tat aaa gct aac ggt agc ggt gat aaa acc              2544
Lys Ser Ile Pro Leu Thr Tyr Lys Ala Asn Gly Ser Gly Asp Lys Thr
                835                 840                 845 gtc atg ttg gat aaa gga tta aac ttt acc aat ggt atg atg aca acc              2592
Val Met Leu Asp Lys Gly Leu Asn Phe Thr Asn Gly Met Met Thr Thr
850                 855                 860 gct tcc gtg gca aat gac ggt gtg gtg aaa tat gac gtc aat tta tcc              2640
Ala Ser Val Ala Asn Asp Gly Val Val Lys Tyr Asp Val Asn Leu Ser
865                 870                 875                 880 acc att aaa gta gaa gat ggc aag gct gcc gta gcc ggt aca ccg ggc              2688
Thr Ile Lys Val Glu Asp Gly Lys Ala Ala Val Ala Gly Thr Pro Gly
                885                 890                 895 aca aat ggc gcc aac ggc act gat ggc aaa gat ggc gta gcg acg gtt              2736
Thr Asn Gly Ala Asn Gly Thr Asp Gly Lys Asp Gly Val Ala Thr Val
                900                 905                 910 aaa aat gtg gta gag gcg tta aat aat gcc gca tgg aca ata act gcc              2784
Lys Asn Val Val Glu Ala Leu Asn Asn Ala Ala Trp Thr Ile Thr Ala
                915                 920                 925
```

-continued

| | |
|---|---|
| tct aaa tct gac ggc gaa gtc gtc agc aat gca tct aat tcc gtt aaa<br>Ser Lys Ser Asp Gly Glu Val Val Ser Asn Ala Ser Asn Ser Val Lys<br>930                  935                  940 | 2832 |
| aat ggg gat acg gtg act tat gat gcc ggc aaa aac atc aaa att act<br>Asn Gly Asp Thr Val Thr Tyr Asp Ala Gly Lys Asn Ile Lys Ile Thr<br>945                  950                  955                  960 | 2880 |
| caa aga gat aaa aaa ttc tct ttt gcc acc aaa gat aat gtt gaa ttt<br>Gln Arg Asp Lys Lys Phe Ser Phe Ala Thr Lys Asp Asn Val Glu Phe<br>                  965                  970                  975 | 2928 |
| act tct gtg acc acg ggc aat acc aaa tta acc ggt aat ggt gta gaa<br>Thr Ser Val Thr Thr Gly Asn Thr Lys Leu Thr Gly Asn Gly Val Glu<br>980                  985                  990 | 2976 |
| atc acc aac ggc cct aaa ctt acc caa tca ggt gtg gat gca ggc ggt<br>Ile Thr Asn Gly Pro Lys Leu Thr Gln Ser Gly Val Asp Ala Gly Gly<br>995                  1000                1005 | 3024 |
| aag aaa atc acc aat gta gca gat ggc gtt att gca gct aac agc<br>Lys Lys Ile Thr Asn Val Ala Asp Gly Val Ile Ala Ala Asn Ser<br>1010                  1015                1020 | 3069 |
| aaa gat gcc gtg aat ggc ggt caa tta ttc gct gaa act gca aaa<br>Lys Asp Ala Val Asn Gly Gly Gln Leu Phe Ala Glu Thr Ala Lys<br>1025                  1030                1035 | 3114 |
| gcc aaa act acg gtt gag aaa ggt gat gat aat att caa atc aca<br>Ala Lys Thr Thr Val Glu Lys Gly Asp Asp Asn Ile Gln Ile Thr<br>1040                  1045                1050 | 3159 |
| tca gaa act gca acg gac gga cat att aac tat aaa gtg gca tta<br>Ser Glu Thr Ala Thr Asp Gly His Ile Asn Tyr Lys Val Ala Leu<br>1055                  1060                1065 | 3204 |
| aat cct agc ttg acc gtc gga cca aga aca aat ggt cac ccg atc<br>Asn Pro Ser Leu Thr Val Gly Pro Arg Thr Asn Gly His Pro Ile<br>1070                  1075                1080 | 3249 |
| acc att gat ggt aat aac ggc tat att acc ggt tta acc aat aca<br>Thr Ile Asp Gly Asn Asn Gly Tyr Ile Thr Gly Leu Thr Asn Thr<br>1085                  1090                1095 | 3294 |
| agc tgg acg ggc gcg cca aca acc ggt cgt gca gca acg gaa gat<br>Ser Trp Thr Gly Ala Pro Thr Thr Gly Arg Ala Ala Thr Glu Asp<br>1100                  1105                1110 | 3339 |
| caa tta tct ata gtc gat aaa aaa ttc gat aat aag gtt tct tta<br>Gln Leu Ser Ile Val Asp Lys Lys Phe Asp Asn Lys Val Ser Leu<br>1115                  1120                1125 | 3384 |
| ggc ggt gac aac ggt agt acc aca gag aaa tcc ttg tct cac aac<br>Gly Gly Asp Asn Gly Ser Thr Thr Glu Lys Ser Leu Ser His Asn<br>1130                  1135                1140 | 3429 |
| gga gga atc aaa ttt aat atc aaa ggc gga gac agc caa aaa tat<br>Gly Gly Ile Lys Phe Asn Ile Lys Gly Gly Asp Ser Gln Lys Tyr<br>1145                  1150                1155 | 3474 |
| gtg acg aca tca gga tcc ggc gat gat gtc acg gtg gat ctt gcc<br>Val Thr Thr Ser Gly Ser Gly Asp Asp Val Thr Val Asp Leu Ala<br>1160                  1165                1170 | 3519 |
| caa acc aca aaa aat aag atc gac aat gcg gca gat aaa gat ctc<br>Gln Thr Thr Lys Asn Lys Ile Asp Asn Ala Ala Asp Lys Asp Leu<br>1175                  1180                1185 | 3564 |
| gcc aac att acc gat aat ggt aaa aaa gtt att acc gct tta ggc<br>Ala Asn Ile Thr Asp Asn Gly Lys Lys Val Ile Thr Ala Leu Gly<br>1190                  1195                1200 | 3609 |
| gct gta gtg aaa gcg gct gat tct acg att acg gta act gac gaa<br>Ala Val Val Lys Ala Ala Asp Ser Thr Ile Thr Val Thr Asp Glu<br>1205                  1210                1215 | 3654 |
| acc gat aat acg aca gga caa aaa acc tac aaa atc aaa gcc aat<br>Thr Asp Asn Thr Thr Gly Gln Lys Thr Tyr Lys Ile Lys Ala Asn<br>1220                  1225                1230 | 3699 |

-continued

| | | |
|---|---|---|
| att cca aca ccg gaa aaa aca gca atg gct ccc ggc aac aat aca<br>Ile Pro Thr Pro Glu Lys Thr Ala Met Ala Pro Gly Asn Asn Thr<br>1235                  1240                1245 | 3744 |
| acc att gaa ggt gat ggc tca gcc gcc aat ccg ttt aaa gtg aat<br>Thr Ile Glu Gly Asp Gly Ser Ala Ala Asn Pro Phe Lys Val Asn<br>1250                  1255                1260 | 3789 |
| ctg aaa gat gat tta gcg cta ggt caa aaa gac gct aac ggc gta<br>Leu Lys Asp Asp Leu Ala Leu Gly Gln Lys Asp Ala Asn Gly Val<br>1265                  1270                1275 | 3834 |
| acc ggt aaa gat tct tcc att aaa gtg aac ggc aaa gat ggc tcc<br>Thr Gly Lys Asp Ser Ser Ile Lys Val Asn Gly Lys Asp Gly Ser<br>1280                  1285                1290 | 3879 |
| ggt gtg gcg att aac ggt aaa gac ggt tcc att gca tta aat ggc<br>Gly Val Ala Ile Asn Gly Lys Asp Gly Ser Ile Ala Leu Asn Gly<br>1295                  1300                1305 | 3924 |
| aaa gac ggt gcg aat cct gtc acc atc aaa acg gcg caa ggt cct<br>Lys Asp Gly Ala Asn Pro Val Thr Ile Lys Thr Ala Gln Gly Pro<br>1310                  1315                1320 | 3969 |
| gcc ggt gtg aat gaa acc aat ccc aaa gac cgt tta atg gtg aat<br>Ala Gly Val Asn Glu Thr Asn Pro Lys Asp Arg Leu Met Val Asn<br>1325                  1330                1335 | 4014 |
| aac gac gct gtt gca acc ctt aaa gac ggc tta aaa ttc gcc gga<br>Asn Asp Ala Val Ala Thr Leu Lys Asp Gly Leu Lys Phe Ala Gly<br>1340                  1345                1350 | 4059 |
| gat aac agc acc gaa gtc atc act aaa acc tta aat caa aaa ctg<br>Asp Asn Ser Thr Glu Val Ile Thr Lys Thr Leu Asn Gln Lys Leu<br>1355                  1360                1365 | 4104 |
| gaa att gtg ggt ggt gca gat aaa aac aaa tta tct gac aac aat<br>Glu Ile Val Gly Gly Ala Asp Lys Asn Lys Leu Ser Asp Asn Asn<br>1370                  1375                1380 | 4149 |
| atc ggc gta aat gcc aat aac ggc aaa ctg gaa gtg aaa tta gcc<br>Ile Gly Val Asn Ala Asn Asn Gly Lys Leu Glu Val Lys Leu Ala<br>1385                  1390                1395 | 4194 |
| aaa gag ttg aat gag tta acc agt gcg caa ttc aag aat ggc gac<br>Lys Glu Leu Asn Glu Leu Thr Ser Ala Gln Phe Lys Asn Gly Asp<br>1400                  1405                1410 | 4239 |
| aac aca acg gtt atc aat ggc aat ggc ata aca att acc ccg aaa<br>Asn Thr Thr Val Ile Asn Gly Asn Gly Ile Thr Ile Thr Pro Lys<br>1415                  1420                1425 | 4284 |
| gat ccg aca aag gcg gtc agc tta acg gat aaa gga cta aac aat<br>Asp Pro Thr Lys Ala Val Ser Leu Thr Asp Lys Gly Leu Asn Asn<br>1430                  1435                1440 | 4329 |
| ggt ggt aat caa att gtg aac att gac agc gga tta aaa caa gcc<br>Gly Gly Asn Gln Ile Val Asn Ile Asp Ser Gly Leu Lys Gln Ala<br>1445                  1450                1455 | 4374 |
| gac ggt tca aca gtt gct tta aaa gac gcc tca ggt gat acc tta<br>Asp Gly Ser Thr Val Ala Leu Lys Asp Ala Ser Gly Asp Thr Leu<br>1460                  1465                1470 | 4419 |
| aaa aat gcg gcg aat atc ggc gat tta caa aaa tcc att aac gac<br>Lys Asn Ala Ala Asn Ile Gly Asp Leu Gln Lys Ser Ile Asn Asp<br>1475                  1480                1485 | 4464 |
| att acc gac gca agt aaa aac ggc ggc ttc ggt tta agc gat gac<br>Ile Thr Asp Ala Ser Lys Asn Gly Gly Phe Gly Leu Ser Asp Asp<br>1490                  1495                1500 | 4509 |
| aat ggc gca acc gct aaa gcc aac tta ggt gaa acc cgt gaa agt<br>Asn Gly Ala Thr Ala Lys Ala Asn Leu Gly Glu Thr Arg Glu Ser<br>1505                  1510                1515 | 4554 |
| gaa agg cga tgg cag tgt tat tac aaa agt agt tac cga<br>Glu Arg Arg Trp Gln Cys Tyr Tyr Lys Ser Ser Tyr Arg | 4593 |

```
<210> SEQ ID NO 44
<211> LENGTH: 1531
<212> TYPE: PRT
<213> ORGANISM: Actinobacillus actinomycetemcomitans

<400> SEQUENCE: 44
```

| | | | | | | | | | | | | | | | |
|---|---|---|---|---|---|---|---|---|---|---|---|---|---|---|---|
| Val | Phe | Lys | Val | Ile | Trp | Cys | Lys | Thr | Ser | Gln | Thr | Trp | Ile | Ala | Val |
| 1 | | | | 5 | | | | | 10 | | | | | 15 | |
| Ser | Glu | Leu | Ser | Lys | Ala | Phe | Ser | Leu | Ser | Thr | Thr | Thr | Asp | Ile | Pro |
| | | | 20 | | | | | 25 | | | | | 30 | | |
| Lys | Lys | Thr | Lys | Ile | Phe | Ile | Ala | Ala | Pro | Leu | Leu | Phe | Leu | Ser | |
| | | 35 | | | | | 40 | | | | | 45 | | | |
| Phe | Asn | Thr | Asn | Ala | Tyr | Ile | Ala | Ile | Gly | Ser | Val | Glu | Asn | Asn | Ser |
| | 50 | | | | | 55 | | | | | 60 | | | | |
| Val | Lys | Ser | Glu | Gly | Ala | Glu | Ala | Ser | Pro | Asn | Lys | Arg | Lys | Gly | Ser |
| 65 | | | | 70 | | | | | 75 | | | | | 80 | |
| Gln | Ala | Leu | Asn | Tyr | Tyr | Asn | Pro | Gly | Ser | Lys | Ser | Tyr | Asp | Asp | Lys |
| | | | | 85 | | | | | 90 | | | | | 95 | |
| Asp | Lys | Pro | Ser | Asn | Pro | Glu | Arg | Arg | Tyr | Ser | Asn | Gly | Glu | Ala | Tyr |
| | | | 100 | | | | | 105 | | | | | 110 | | |
| Gly | Ile | Ala | Ile | Gly | Lys | Asn | Thr | Asp | Val | Arg | Asp | Ser | Ser | Lys | Asp |
| | | | 115 | | | | | 120 | | | | | 125 | | |
| Ser | Asn | Gly | Ile | Ala | Leu | Gly | Asp | Tyr | Ser | Lys | Ala | Thr | Gly | Gly | Leu |
| | 130 | | | | | 135 | | | | | 140 | | | | |
| Ala | Met | Ala | Leu | Gly | Ser | Phe | Ser | Arg | Ala | Glu | Lys | Asn | Gly | Gly | Ile |
| 145 | | | | | 150 | | | | | 155 | | | | | 160 |
| Ala | Ile | Gly | Ile | Ala | Ser | Arg | Ser | Ser | Gly | Ile | Asn | Ser | Leu | Ala | Met |
| | | | | 165 | | | | | 170 | | | | | 175 | |
| Met | Arg | Gln | Ser | Ala | Ala | Thr | Gly | Asp | Tyr | Ser | Thr | Ala | Ile | Gly | Ser |
| | | | | 180 | | | | | 185 | | | | | 190 | |
| Val | Ala | Trp | Ala | Ala | Gly | Gln | Ser | Ser | Phe | Ala | Leu | Gly | Ala | Ser | Ala |
| | | | 195 | | | | | 200 | | | | | 205 | | |
| Thr | Ala | Lys | Gly | Asn | Gln | Ser | Ile | Ala | Ile | Gly | Ser | Leu | Glu | Gln | Lys |
| | 210 | | | | | 215 | | | | | 220 | | | | |
| Ile | Ser | Pro | Asn | Gly | Ser | Gly | Val | Pro | Ile | Thr | Lys | Tyr | Asn | Gly | Leu |
| 225 | | | | | 230 | | | | | 235 | | | | | 240 |
| Asp | Asn | Thr | Gln | Thr | Asn | Gly | Asn | Arg | Ser | Met | Ala | Leu | Gly | Thr | Ala |
| | | | | 245 | | | | | 250 | | | | | 255 | |
| Ala | Lys | Thr | Asn | Gly | Asp | Asp | Ser | Phe | Ala | Ile | Gly | Tyr | Lys | Ala | His |
| | | | | 260 | | | | | 265 | | | | | 270 | |
| Thr | Gly | Glu | Phe | Lys | Val | Glu | His | Asp | Asn | Tyr | Leu | Lys | Glu | Asn | Val |
| | | | 275 | | | | | 280 | | | | | 285 | | |
| Thr | Ser | Pro | Asp | Leu | Ser | Lys | Lys | Ala | Asp | Lys | Ala | Ile | Ala | Val | Gly |
| | 290 | | | | | 295 | | | | | 300 | | | | |
| Thr | Ser | Ala | Leu | Ala | Gln | Lys | Glu | Ser | Ala | Ile | Ala | Phe | Gly | Tyr | Gln |
| 305 | | | | | 310 | | | | | 315 | | | | | 320 |
| Ala | Asn | Ala | Ser | Gly | Ile | Asn | Ala | Ile | Ser | Leu | Gly | Ala | Asn | Ala | Lys |
| | | | | 325 | | | | | 330 | | | | | 335 | |
| Ala | Ser | Gln | Asp | Asn | Val | Val | Ala | Ile | Gly | Lys | Tyr | Ala | Thr | Ala | Thr |
| | | | 340 | | | | | 345 | | | | | 350 | | |
| Glu | Ser | Gly | Ser | Met | Ala | Ile | Gly | Gln | Gly | Ala | Lys | Ser | Thr | Phe | Lys |
| | | | 355 | | | | | 360 | | | | | 365 | | |

-continued

```
Asn Ser Leu Ala Leu Gly Thr Gly Thr Ile Val Asn Ser Val Asp Gly
    370                 375                 380

Gly Gln Ser Lys Phe Thr Ala Gln Asn Tyr Asp Ala Asn Asn Gly Val
385                 390                 395                 400

Val Ala Val Ala Asn Ala Gly Lys Glu Arg Arg Ile Ile Asn Val Ala
                405                 410                 415

Gly Gly Arg Asn Asp Thr Asp Ala Val Asn Ile Ala Gln Leu Lys Phe
            420                 425                 430

Val Asn Asp Asn Leu Ala Lys Ser Ile Ala Gly Ala Gly Tyr Asn Gly
        435                 440                 445

Tyr Glu Thr Asp Gly His Thr Tyr Lys Ala Pro Val Phe Ser Ile Lys
    450                 455                 460

Asn Thr Asn Tyr His Asp Val Lys Thr Ala Val Glu Ala Ala Gln Thr
465                 470                 475                 480

Asn Tyr Val Ser Val Asn Ser Thr Asn Thr Ala Ala Asp Ser Asn Tyr
                485                 490                 495

Asp Asn Lys Gly Ala Lys Ala Val Gly Ser Ile Ala Leu Gly Glu Lys
            500                 505                 510

Ala Thr Thr Gly Thr Ala Ala Met Asn Ser Ile Ala Ile Gly Leu Asn
        515                 520                 525

Ser Asn Val Ser Gly Gln Asn Thr Val Ala Leu Gly Ala Asn Ile Thr
    530                 535                 540

Ala Thr Thr Asn Gly Ser Val Ile Leu Gly Asn Ser Ser Thr Thr Glu
545                 550                 555                 560

Gly Ser His Pro Val Ser Asn Val Ser Ser Ala Thr Val Asn Gly Tyr
                565                 570                 575

Thr Tyr Ser Gly Phe Thr Gly Thr Val Lys Glu Ser Gly His Phe Val
            580                 585                 590

Ser Ile Gly Ser Lys Gly Asn Glu Arg Gln Ile Lys Asn Val Ala Ala
        595                 600                 605

Gly Asn Val Ala Ala Asn Ser Thr Asp Ala Val Asn Gly Ser Gln Leu
    610                 615                 620

Phe Ala Val Ala Ser Arg Val Glu Gln Gly Trp Gln Ile Thr Ser Gly
625                 630                 635                 640

Val Glu Asn Gly Gly Thr Gln Asn Gly Ala Ala Ser Thr Ala Thr Ile
                645                 650                 655

Lys Pro Ser Asn Gln Val Lys Leu Leu Ala Gly Lys Asn Leu Ala Val
            660                 665                 670

Lys Gln Asn Gly Thr Asn Phe Thr Phe Ser Thr Gln Glu Asn Val Thr
        675                 680                 685

Phe Thr Asn Val Thr Thr Gln Asp Leu Thr Ala Thr Gly Asn Thr Thr
    690                 695                 700

Val Lys Asn Phe Ser Val Gln Asn Gly Gly Thr Ile Asn Met Gly Asn
705                 710                 715                 720

Asn Arg Ile Thr Gly Val Ala Glu Gly Thr Gln Asp Asp Ala Val
                725                 730                 735

Asn Phe Lys Gln Leu Lys Ser Leu Leu Gly Gly Ser Ala Ser Thr Glu
            740                 745                 750

Ile Val Glu Lys Lys Ala Ala Gln Ala Gly Asp Glu Asn Leu Ala Asp
        755                 760                 765

Ile Ser Val Ala Asn Gly Lys Asn Ala Gly Asp Met Gly Ala Lys Tyr
    770                 775                 780

Glu Val Ser Val Ser Lys Lys Ala Val Gln Ser Ala Ala Lys Glu Ala
```

-continued

```
           785                 790                 795                 800
Val Lys Val Thr Gly Ser Ala Pro Ile Asn Val Asn Lys Thr Asp Val
                    805                 810                 815
Asn Gly Val Asp Thr Tyr Ala Val Thr Phe Asn Gly Thr Glu Ala Ala
                    820                 825                 830
Lys Ser Ile Pro Leu Thr Tyr Lys Ala Asn Gly Ser Gly Asp Lys Thr
                    835                 840                 845
Val Met Leu Asp Lys Gly Leu Asn Phe Thr Asn Gly Met Met Thr Thr
850                 855                 860
Ala Ser Val Ala Asn Asp Gly Val Val Lys Tyr Asp Val Asn Leu Ser
865                 870                 875                 880
Thr Ile Lys Val Glu Asp Gly Lys Ala Ala Val Ala Gly Thr Pro Gly
                    885                 890                 895
Thr Asn Gly Ala Asn Gly Thr Asp Gly Lys Asp Gly Val Ala Thr Val
                    900                 905                 910
Lys Asn Val Val Glu Ala Leu Asn Asn Ala Ala Trp Thr Ile Thr Ala
                    915                 920                 925
Ser Lys Ser Asp Gly Glu Val Val Ser Asn Ala Ser Asn Ser Val Lys
                    930                 935                 940
Asn Gly Asp Thr Val Thr Tyr Asp Ala Gly Lys Asn Ile Lys Ile Thr
945                 950                 955                 960
Gln Arg Asp Lys Lys Phe Ser Phe Ala Thr Lys Asp Asn Val Glu Phe
                    965                 970                 975
Thr Ser Val Thr Thr Gly Asn Thr Lys Leu Thr Gly Asn Gly Val Glu
                    980                 985                 990
Ile Thr Asn Gly Pro Lys Leu Thr Gln Ser Gly Val Asp Ala Gly Gly
                    995                 1000                1005
Lys Lys Ile Thr Asn Val Ala Asp Gly Val Ile Ala Ala Asn Ser
1010                1015                1020
Lys Asp Ala Val Asn Gly Gly Gln Leu Phe Ala Glu Thr Ala Lys
1025                1030                1035
Ala Lys Thr Thr Val Glu Lys Gly Asp Asp Asn Ile Gln Ile Thr
1040                1045                1050
Ser Glu Thr Ala Thr Asp Gly His Ile Asn Tyr Lys Val Ala Leu
1055                1060                1065
Asn Pro Ser Leu Thr Val Gly Pro Arg Thr Asn Gly His Pro Ile
1070                1075                1080
Thr Ile Asp Gly Asn Asn Gly Tyr Ile Thr Gly Leu Thr Asn Thr
1085                1090                1095
Ser Trp Thr Gly Ala Pro Thr Thr Gly Arg Ala Ala Thr Glu Asp
1100                1105                1110
Gln Leu Ser Ile Val Asp Lys Lys Phe Asp Asn Lys Val Ser Leu
1115                1120                1125
Gly Gly Asp Asn Gly Ser Thr Thr Glu Lys Ser Leu Ser His Asn
1130                1135                1140
Gly Gly Ile Lys Phe Asn Ile Lys Gly Gly Asp Ser Gln Lys Tyr
1145                1150                1155
Val Thr Thr Ser Gly Ser Gly Asp Asp Val Thr Val Asp Leu Ala
1160                1165                1170
Gln Thr Thr Lys Asn Lys Ile Asp Asn Ala Ala Asp Lys Asp Leu
1175                1180                1185
Ala Asn Ile Thr Asp Asn Gly Lys Lys Val Ile Thr Ala Leu Gly
1190                1195                1200
```

```
Ala Val Val Lys Ala Ala Asp Ser Thr Ile Thr Val Thr Asp Glu
    1205                1210                1215

Thr Asp Asn Thr Thr Gly Gln Lys Thr Tyr Lys Ile Lys Ala Asn
    1220                1225                1230

Ile Pro Thr Pro Glu Lys Thr Ala Met Ala Pro Gly Asn Asn Thr
    1235                1240                1245

Thr Ile Glu Gly Asp Gly Ser Ala Ala Asn Pro Phe Lys Val Asn
    1250                1255                1260

Leu Lys Asp Asp Leu Ala Leu Gly Gln Lys Asp Ala Asn Gly Val
    1265                1270                1275

Thr Gly Lys Asp Ser Ser Ile Lys Val Asn Gly Lys Asp Gly Ser
    1280                1285                1290

Gly Val Ala Ile Asn Gly Lys Asp Gly Ser Ile Ala Leu Asn Gly
    1295                1300                1305

Lys Asp Gly Ala Asn Pro Val Thr Ile Lys Thr Ala Gln Gly Pro
    1310                1315                1320

Ala Gly Val Asn Glu Thr Asn Pro Lys Asp Arg Leu Met Val Asn
    1325                1330                1335

Asn Asp Ala Val Ala Thr Leu Lys Asp Gly Leu Lys Phe Ala Gly
    1340                1345                1350

Asp Asn Ser Thr Glu Val Ile Thr Lys Thr Leu Asn Gln Lys Leu
    1355                1360                1365

Glu Ile Val Gly Gly Ala Asp Lys Asn Lys Leu Ser Asp Asn Asn
    1370                1375                1380

Ile Gly Val Asn Ala Asn Asn Gly Lys Leu Glu Val Lys Leu Ala
    1385                1390                1395

Lys Glu Leu Asn Glu Leu Thr Ser Ala Gln Phe Lys Asn Gly Asp
    1400                1405                1410

Asn Thr Thr Val Ile Asn Gly Asn Gly Ile Thr Ile Thr Pro Lys
    1415                1420                1425

Asp Pro Thr Lys Ala Val Ser Leu Thr Asp Lys Gly Leu Asn Asn
    1430                1435                1440

Gly Gly Asn Gln Ile Val Asn Ile Asp Ser Gly Leu Lys Gln Ala
    1445                1450                1455

Asp Gly Ser Thr Val Ala Leu Lys Asp Ala Ser Gly Asp Thr Leu
    1460                1465                1470

Lys Asn Ala Ala Asn Ile Gly Asp Leu Gln Lys Ser Ile Asn Asp
    1475                1480                1485

Ile Thr Asp Ala Ser Lys Asn Gly Gly Phe Gly Leu Ser Asp Asp
    1490                1495                1500

Asn Gly Ala Thr Ala Lys Ala Asn Leu Gly Glu Thr Arg Glu Ser
    1505                1510                1515

Glu Arg Arg Trp Gln Cys Tyr Tyr Lys Ser Ser Tyr Arg
    1520                1525                1530
```

<210> SEQ ID NO 45
<211> LENGTH: 565
<212> TYPE: DNA
<213> ORGANISM: Actinobacillus actinomycetemcomitans
<220> FEATURE:
<221> NAME/KEY: CDS
<222> LOCATION: (1)..(564)

<400> SEQUENCE: 45 caa gaa atc att aac cta gcg cct aaa ggc tta att acc gcc gcc agc    48

```
Gln Glu Ile Ile Asn Leu Ala Pro Lys Gly Leu Ile Thr Ala Ala Ser
1               5                   10                  15 cct tat tta tac ggt gta acc cgt agt gat ttg gaa aaa atc gtc atc      96
Pro Tyr Leu Tyr Gly Val Thr Arg Ser Asp Leu Glu Lys Ile Val Ile
                20                  25                  30 atg ggc gtg tgg ttt gaa gac atg aaa acc ctc gcg ccc tac tgg caa     144
Met Gly Val Trp Phe Glu Asp Met Lys Thr Leu Ala Pro Tyr Trp Gln
            35                  40                  45 atc acc ggc acg ccc acc ggt gtc aac ttt gac gaa cgc aac gcc atg     192
Ile Thr Gly Thr Pro Thr Gly Val Asn Phe Asp Glu Arg Asn Ala Met
        50                  55                  60 atc ggc aaa acc ctc gcc gaa cgc tta aac ctg aaa gtg ggc agt aag     240
Ile Gly Lys Thr Leu Ala Glu Arg Leu Asn Leu Lys Val Gly Ser Lys
65                  70                  75                  80 ctg acc tta agc ctg aat tcg gta gat aaa cac cag ttt acg att aaa     288
Leu Thr Leu Ser Leu Asn Ser Val Asp Lys His Gln Phe Thr Ile Lys
                85                  90                  95 gcc atc gtg gaa gcg ggc gac gcc acc gac aat atg ctc atc gtg agc     336
Ala Ile Val Glu Ala Gly Asp Ala Thr Asp Asn Met Leu Ile Val Ser
                100                 105                 110 ctg gat ttc gcg caa aac tgg ctg gaa aaa gaa aac ttt gcc acc aat     384
Leu Asp Phe Ala Gln Asn Trp Leu Glu Lys Glu Asn Phe Ala Thr Asn
            115                 120                 125 gcc ctg ctt aac gtg aaa aat gat cag ggg caa gtg gaa caa ttc gca     432
Ala Leu Leu Asn Val Lys Asn Asp Gln Gly Gln Val Glu Gln Phe Ala
        130                 135                 140 cag caa ctt cag caa caa tat ccc gat ttg gat att cat ccg atc cgc     480
Gln Gln Leu Gln Gln Gln Tyr Pro Asp Leu Asp Ile His Pro Ile Arg
145                 150                 155                 160 aaa gtc tcc gcc tcc gaa ggg caa att ctg gat aag att aaa ggc ttg     528
Lys Val Ser Ala Ser Glu Gly Gln Ile Leu Asp Lys Ile Lys Gly Leu
                165                 170                 175 atg ggc ttg att tcc gtg gtg att ctg att tta gcc a                   565
Met Gly Leu Ile Ser Val Val Ile Leu Ile Leu Ala
                180                 185
```

<210> SEQ ID NO 46
<211> LENGTH: 188
<212> TYPE: PRT
<213> ORGANISM: Actinobacillus actinomycetemcomitans

<400> SEQUENCE: 46

```
Gln Glu Ile Ile Asn Leu Ala Pro Lys Gly Leu Ile Thr Ala Ala Ser
1               5                   10                  15

Pro Tyr Leu Tyr Gly Val Thr Arg Ser Asp Leu Glu Lys Ile Val Ile
                20                  25                  30

Met Gly Val Trp Phe Glu Asp Met Lys Thr Leu Ala Pro Tyr Trp Gln
            35                  40                  45

Ile Thr Gly Thr Pro Thr Gly Val Asn Phe Asp Glu Arg Asn Ala Met
        50                  55                  60

Ile Gly Lys Thr Leu Ala Glu Arg Leu Asn Leu Lys Val Gly Ser Lys
65                  70                  75                  80

Leu Thr Leu Ser Leu Asn Ser Val Asp Lys His Gln Phe Thr Ile Lys
                85                  90                  95

Ala Ile Val Glu Ala Gly Asp Ala Thr Asp Asn Met Leu Ile Val Ser
                100                 105                 110

Leu Asp Phe Ala Gln Asn Trp Leu Glu Lys Glu Asn Phe Ala Thr Asn
            115                 120                 125
```

```
Ala Leu Leu Asn Val Lys Asn Asp Gln Gly Gln Val Glu Gln Phe Ala
    130                 135                 140

Gln Gln Leu Gln Gln Gln Tyr Pro Asp Leu Asp Ile His Pro Ile Arg
145                 150                 155                 160

Lys Val Ser Ala Ser Glu Gly Gln Ile Leu Asp Lys Ile Lys Gly Leu
                165                 170                 175

Met Gly Leu Ile Ser Val Val Ile Leu Ile Leu Ala
            180                 185

<210> SEQ ID NO 47
<211> LENGTH: 668
<212> TYPE: DNA
<213> ORGANISM: Actinobacillus actinomycetemcomitans
<220> FEATURE:
<221> NAME/KEY: CDS
<222> LOCATION: (1)..(666)

<400> SEQUENCE: 47 gcc aat cgg atc att gaa atc aaa gat ggt gaa att atc agt gat acg      48
Ala Asn Arg Ile Ile Glu Ile Lys Asp Gly Glu Ile Ile Ser Asp Thr
1               5                   10                  15 caa aaa cgt cag gta aaa agt gcg gtt aaa aat cca agt gtt ttt aaa      96
Gln Lys Arg Gln Val Lys Ser Ala Val Lys Asn Pro Ser Val Phe Lys
            20                  25                  30 ggt cgt ttc ggt ttc agc aaa gat caa ctt atg gaa gcc ttc cgt atg     144
Gly Arg Phe Gly Phe Ser Lys Asp Gln Leu Met Glu Ala Phe Arg Met
        35                  40                  45 tcc gtc agt gcc att gta gcg cac aaa atg cgc tca ttg ctg acc atg     192
Ser Val Ser Ala Ile Val Ala His Lys Met Arg Ser Leu Leu Thr Met
    50                  55                  60 ctg gga att atc atc ggg atc act tcc gtc gtt tcc gtg gtg gcg tta     240
Leu Gly Ile Ile Ile Gly Ile Thr Ser Val Val Ser Val Val Ala Leu
65                  70                  75                  80 gga aat ggt tca caa caa aag att ttg gaa aat att cgc ggt atc ggc     288
Gly Asn Gly Ser Gln Gln Lys Ile Leu Glu Asn Ile Arg Gly Ile Gly
                85                  90                  95 aca aac aca atg acg att ttt aac ggt aat ggt ttc ggt gac cgt cgt     336
Thr Asn Thr Met Thr Ile Phe Asn Gly Asn Gly Phe Gly Asp Arg Arg
            100                 105                 110 tca cgg cac att caa aac cta aaa atc agc gat gcc aat acg tta tcg     384
Ser Arg His Ile Gln Asn Leu Lys Ile Ser Asp Ala Asn Thr Leu Ser
        115                 120                 125 aaa caa agt tat att caa agc gtt act cca aat acc tct tcc agc ggc     432
Lys Gln Ser Tyr Ile Gln Ser Val Thr Pro Asn Thr Ser Ser Ser Gly
    130                 135                 140 att tta gtg gtc ggt aac aaa tcc ttc aca tcc gcc aat tta tat ggt     480
Ile Leu Val Val Gly Asn Lys Ser Phe Thr Ser Ala Asn Leu Tyr Gly
145                 150                 155                 160 atc ggt gaa caa tat ttt gat gta gaa ggc ttg aag tta aaa cag ggc     528
Ile Gly Glu Gln Tyr Phe Asp Val Glu Gly Leu Lys Leu Lys Gln Gly
                165                 170                 175 cgt tta tta acc gag gac gat gtg gat caa agc aac cag gtg gtc gtg     576
Arg Leu Leu Thr Glu Asp Asp Val Asp Gln Ser Asn Gln Val Val Val
            180                 185                 190 ctg gac gaa agt gca aaa aaa gcc att ttt gcc aac gaa aat ccc ctt     624
Leu Asp Glu Ser Ala Lys Lys Ala Ile Phe Ala Asn Glu Asn Pro Leu
        195                 200                 205 ggc aaa acg gtg att ttt aat aag cga cca ttt cgt gtc att gg          668
Gly Lys Thr Val Ile Phe Asn Lys Arg Pro Phe Arg Val Ile
    210                 215                 220
```

<210> SEQ ID NO 48
<211> LENGTH: 222
<212> TYPE: PRT
<213> ORGANISM: Actinobacillus actinomycetemcomitans

<400> SEQUENCE: 48

Ala Asn Arg Ile Ile Glu Ile Lys Asp Gly Glu Ile Ile Ser Asp Thr
1               5                   10                  15

Gln Lys Arg Gln Val Lys Ser Ala Val Lys Asn Pro Ser Val Phe Lys
            20                  25                  30

Gly Arg Phe Gly Phe Ser Lys Asp Gln Leu Met Glu Ala Phe Arg Met
        35                  40                  45

Ser Val Ser Ala Ile Val Ala His Lys Met Arg Ser Leu Leu Thr Met
    50                  55                  60

Leu Gly Ile Ile Ile Gly Ile Thr Ser Val Val Ser Val Val Ala Leu
65                  70                  75                  80

Gly Asn Gly Ser Gln Gln Lys Ile Leu Glu Asn Ile Arg Gly Ile Gly
                85                  90                  95

Thr Asn Thr Met Thr Ile Phe Asn Gly Asn Gly Phe Gly Asp Arg Arg
            100                 105                 110

Ser Arg His Ile Gln Asn Leu Lys Ile Ser Asp Ala Asn Thr Leu Ser
        115                 120                 125

Lys Gln Ser Tyr Ile Gln Ser Val Thr Pro Asn Thr Ser Ser Ser Gly
    130                 135                 140

Ile Leu Val Val Gly Asn Lys Ser Phe Thr Ser Ala Asn Leu Tyr Gly
145                 150                 155                 160

Ile Gly Glu Gln Tyr Phe Asp Val Glu Gly Leu Lys Leu Lys Gln Gly
                165                 170                 175

Arg Leu Leu Thr Glu Asp Asp Val Asp Gln Ser Asn Gln Val Val Val
            180                 185                 190

Leu Asp Glu Ser Ala Lys Lys Ala Ile Phe Ala Asn Glu Asn Pro Leu
        195                 200                 205

Gly Lys Thr Val Ile Phe Asn Lys Arg Pro Phe Arg Val Ile
    210                 215                 220

<210> SEQ ID NO 49
<211> LENGTH: 276
<212> TYPE: DNA
<213> ORGANISM: Actinobacillus actinomycetemcomitans
<220> FEATURE:
<221> NAME/KEY: CDS
<222> LOCATION: (1)..(276)

<400> SEQUENCE: 49 atg aga atg cac aat cct cca cac ccg gga gaa ctg tta aaa gaa tat    48
Met Arg Met His Asn Pro Pro His Pro Gly Glu Leu Leu Lys Glu Tyr
1               5                   10                  15 att gat ggc gtg agt gtc acg aag gtt gcc caa aaa tta ggt gtt tcg    96
Ile Asp Gly Val Ser Val Thr Lys Val Ala Gln Lys Leu Gly Val Ser
            20                  25                  30 cgt gtt acg ctt tcc cgc att ctt aat ggg aaa gca agt ata acg cct   144
Arg Val Thr Leu Ser Arg Ile Leu Asn Gly Lys Ala Ser Ile Thr Pro
        35                  40                  45 gaa atg gct gtg cga tta agc gaa tta ttg aat acc aca aca ccg aaa   192
Glu Met Ala Val Arg Leu Ser Glu Leu Leu Asn Thr Thr Thr Pro Lys
    50                  55                  60 tta tgg ctg ggt atg caa gca gac tac gat tta tgg caa att gaa caa   240
Leu Trp Leu Gly Met Gln Ala Asp Tyr Asp Leu Trp Gln Ile Glu Gln

```
                                                                    276
caa cac gcc gta ttc aac atc caa cca tta ttt aat
Gln His Ala Val Phe Asn Ile Gln Pro Leu Phe Asn
                85                  90
```

<210> SEQ ID NO 50
<211> LENGTH: 92
<212> TYPE: PRT
<213> ORGANISM: Actinobacillus actinomycetemcomitans

<400> SEQUENCE: 50

```
Met Arg Met His Asn Pro Pro His Pro Gly Glu Leu Leu Lys Glu Tyr
1               5                   10                  15

Ile Asp Gly Val Ser Val Thr Lys Val Ala Gln Lys Leu Gly Val Ser
            20                  25                  30

Arg Val Thr Leu Ser Arg Ile Leu Asn Gly Lys Ala Ser Ile Thr Pro
        35                  40                  45

Glu Met Ala Val Arg Leu Ser Glu Leu Leu Asn Thr Thr Thr Pro Lys
    50                  55                  60

Leu Trp Leu Gly Met Gln Ala Asp Tyr Asp Leu Trp Gln Ile Glu Gln
65                  70                  75                  80

Gln His Ala Val Phe Asn Ile Gln Pro Leu Phe Asn
                85                  90
```

<210> SEQ ID NO 51
<211> LENGTH: 537
<212> TYPE: DNA
<213> ORGANISM: Actinobacillus actinomycetemcomitans
<220> FEATURE:
<221> NAME/KEY: CDS
<222> LOCATION: (1)..(537)

<400> SEQUENCE: 51

```
                                                                    48
caa cat aat ggt gta cta ggt cct tat atc ggt aaa ggc agt tta acc
Gln His Asn Gly Val Leu Gly Pro Tyr Ile Gly Lys Gly Ser Leu Thr
1               5                   10                  15

96
tta aaa tta ccg gct tac tgg gaa cta tca gga ttc cat caa tta acc
Leu Lys Leu Pro Ala Tyr Trp Glu Leu Ser Gly Phe His Gln Leu Thr
            20                  25                  30

144
gat caa tgg gct atc cac tat agc tat aaa tat aca gaa tgg agt cgt
Asp Gln Trp Ala Ile His Tyr Ser Tyr Lys Tyr Thr Glu Trp Ser Arg
        35                  40                  45

192
ttt aaa gaa tta cgc ggc aaa tat caa gat ggt tcc ggc tat gag gcc
Phe Lys Glu Leu Arg Gly Lys Tyr Gln Asp Gly Ser Gly Tyr Glu Ala
    50                  55                  60

240
ttt acc aag aaa gag gaa tac aaa gac aac tcc cgt ttt gct att ggt
Phe Thr Lys Lys Glu Glu Tyr Lys Asp Asn Ser Arg Phe Ala Ile Gly
65                  70                  75                  80

288
aca aca tat agc cta aat gat gct tta aca tta cgt gca ggt ttg gct
Thr Thr Tyr Ser Leu Asn Asp Ala Leu Thr Leu Arg Ala Gly Leu Ala
                85                  90                  95

336
tac gat aaa gcc gcg agt aaa acg cat tta tct gcg tcc att cct gat
Tyr Asp Lys Ala Ala Ser Lys Thr His Leu Ser Ala Ser Ile Pro Asp
            100                 105                 110

384
acc gac cgt atg tgg tat agt ata gga gcc acc tat aaa ttc acc ccg
Thr Asp Arg Met Trp Tyr Ser Ile Gly Ala Thr Tyr Lys Phe Thr Pro
        115                 120                 125

432
aat tta tct gtt gat gtc ggc ttc gct cat tta cgt ggt aag aag aaa
Asn Leu Ser Val Asp Val Gly Phe Ala His Leu Arg Gly Lys Lys Lys
    130                 135                 140
```

| | | |
|---|---|---|
| cat ttt gtt gag acc caa aat atc aag ggg tta ttg ctt gtt gag gcg | | 480 |
| His Phe Val Glu Thr Gln Asn Ile Lys Gly Leu Leu Leu Val Glu Ala | | |
| 145 150 155 160 | | |
| | | |
| gat tac acc act aaa gcc acc gct aac ctc tac ggt ttg aat cta aat | | 528 |
| Asp Tyr Thr Thr Lys Ala Thr Ala Asn Leu Tyr Gly Leu Asn Leu Asn | | |
| 165 170 175 | | |
| | | |
| tac cgt ttc | | 537 |
| Tyr Arg Phe | | |

<210> SEQ ID NO 52
<211> LENGTH: 179
<212> TYPE: PRT
<213> ORGANISM: Actinobacillus actinomycetemcomitans

<400> SEQUENCE: 52

```
Gln His Asn Gly Val Leu Gly Pro Tyr Ile Gly Lys Gly Ser Leu Thr
1               5                   10                  15

Leu Lys Leu Pro Ala Tyr Trp Glu Leu Ser Gly Phe His Gln Leu Thr
            20                  25                  30

Asp Gln Trp Ala Ile His Tyr Ser Tyr Lys Tyr Thr Glu Trp Ser Arg
        35                  40                  45

Phe Lys Glu Leu Arg Gly Lys Tyr Gln Asp Gly Ser Gly Tyr Glu Ala
    50                  55                  60

Phe Thr Lys Lys Glu Glu Tyr Lys Asp Asn Ser Arg Phe Ala Ile Gly
65                  70                  75                  80

Thr Thr Tyr Ser Leu Asn Asp Ala Leu Thr Leu Arg Ala Gly Leu Ala
                85                  90                  95

Tyr Asp Lys Ala Ala Ser Lys Thr His Leu Ser Ala Ser Ile Pro Asp
            100                 105                 110

Thr Asp Arg Met Trp Tyr Ser Ile Gly Ala Thr Tyr Lys Phe Thr Pro
        115                 120                 125

Asn Leu Ser Val Asp Val Gly Phe Ala His Leu Arg Gly Lys Lys Lys
    130                 135                 140

His Phe Val Glu Thr Gln Asn Ile Lys Gly Leu Leu Leu Val Glu Ala
145                 150                 155                 160

Asp Tyr Thr Thr Lys Ala Thr Ala Asn Leu Tyr Gly Leu Asn Leu Asn
                165                 170                 175

Tyr Arg Phe
```

<210> SEQ ID NO 53
<211> LENGTH: 548
<212> TYPE: DNA
<213> ORGANISM: Actinobacillus actinomycetemcomitans
<220> FEATURE:
<221> NAME/KEY: CDS
<222> LOCATION: (1)..(546)

<400> SEQUENCE: 53

| | | |
|---|---|---|
| gga cca agt gtc acc aag gac ggc att cac gcc aat gat aag aaa atc | | 48 |
| Gly Pro Ser Val Thr Lys Asp Gly Ile His Ala Asn Asp Lys Lys Ile | | |
| 1               5                   10                  15 | | |
| | | |
| acc ggt gta aaa gac ggt gaa att tca gcc cat agt aaa gag gcg gtg | | 96 |
| Thr Gly Val Lys Asp Gly Glu Ile Ser Ala His Ser Lys Glu Ala Val | | |
| 20                  25                  30 | | |
| | | |
| aac ggt agc caa tta cat caa acc aac caa aat gtg acg aat tta gcc | | 144 |
| Asn Gly Ser Gln Leu His Gln Thr Asn Gln Asn Val Thr Asn Leu Ala | | |
| 35                  40                  45 | | |
| | | |
| aac aat gtg gac aaa ggg ctg aat ttc caa gga gac aat caa gaa gtc | | 192 |
| Asn Asn Val Asp Lys Gly Leu Asn Phe Gln Gly Asp Asn Gln Glu Val | | |

```
              50                  55                  60
aca gtt aat cgt aaa tta ggc gat caa ctt aac att cgc ggc ggt gcg      240
Thr Val Asn Arg Lys Leu Gly Asp Gln Leu Asn Ile Arg Gly Gly Ala
 65                  70                  75                  80 gat ccg aag aaa tta aca caa aat aat atc ggc gtg acc gca gat aaa      288
Asp Pro Lys Lys Leu Thr Gln Asn Asn Ile Gly Val Thr Ala Asp Lys
                 85                  90                  95 aac ggc acc atg acc gtt cag ctg gcg aag gaa gtt aat ctc ggc gca      336
Asn Gly Thr Met Thr Val Gln Leu Ala Lys Glu Val Asn Leu Gly Ala
            100                 105                 110 gat ggc agc ctt act gta ggc aat acc acg gtc aat aac gac ggt gtt      384
Asp Gly Ser Leu Thr Val Gly Asn Thr Thr Val Asn Asn Asp Gly Val
        115                 120                 125 acg att aaa gac ggt cca agc atg aca agc cac ggc atc aac gcc ggc      432
Thr Ile Lys Asp Gly Pro Ser Met Thr Ser His Gly Ile Asn Ala Gly
    130                 135                 140 ggc aaa cga att gct aac gtt gcg aaa ggg aaa gca ccg acg gat gca      480
Gly Lys Arg Ile Ala Asn Val Ala Lys Gly Lys Ala Pro Thr Asp Ala
145                 150                 155                 160 gta aat atg agt cag ctt caa gac gtc ggc agt gcc att aat aat cgc      528
Val Asn Met Ser Gln Leu Gln Asp Val Gly Ser Ala Ile Asn Asn Arg
                165                 170                 175 att gat aac att gat aag cg                                            548
Ile Asp Asn Ile Asp Lys
            180

<210> SEQ ID NO 54
<211> LENGTH: 182
<212> TYPE: PRT
<213> ORGANISM: Actinobacillus actinomycetemcomitans

<400> SEQUENCE: 54

Gly Pro Ser Val Thr Lys Asp Gly Ile His Ala Asn Asp Lys Lys Ile
 1               5                  10                  15

Thr Gly Val Lys Asp Gly Glu Ile Ser Ala His Ser Lys Glu Ala Val
                20                  25                  30

Asn Gly Ser Gln Leu His Gln Thr Asn Gln Asn Val Thr Asn Leu Ala
            35                  40                  45

Asn Asn Val Asp Lys Gly Leu Asn Phe Gln Gly Asp Asn Gln Glu Val
        50                  55                  60

Thr Val Asn Arg Lys Leu Gly Asp Gln Leu Asn Ile Arg Gly Gly Ala
 65                  70                  75                  80

Asp Pro Lys Lys Leu Thr Gln Asn Asn Ile Gly Val Thr Ala Asp Lys
                85                  90                  95

Asn Gly Thr Met Thr Val Gln Leu Ala Lys Glu Val Asn Leu Gly Ala
            100                 105                 110

Asp Gly Ser Leu Thr Val Gly Asn Thr Thr Val Asn Asn Asp Gly Val
        115                 120                 125

Thr Ile Lys Asp Gly Pro Ser Met Thr Ser His Gly Ile Asn Ala Gly
    130                 135                 140

Gly Lys Arg Ile Ala Asn Val Ala Lys Gly Lys Ala Pro Thr Asp Ala
145                 150                 155                 160

Val Asn Met Ser Gln Leu Gln Asp Val Gly Ser Ala Ile Asn Asn Arg
                165                 170                 175

Ile Asp Asn Ile Asp Lys
            180
```

```
<210> SEQ ID NO 55
<211> LENGTH: 168
<212> TYPE: DNA
<213> ORGANISM: Actinobacillus actinomycetemcomitans
<220> FEATURE:
<221> NAME/KEY: CDS
<222> LOCATION: (1)..(168)

<400> SEQUENCE: 55 atg gat cac ttt ccg ccg ctt tgg ctt ttt cgg tta aac agc tta atg       48
Met Asp His Phe Pro Pro Leu Trp Leu Phe Arg Leu Asn Ser Leu Met
1               5                   10                  15 ctt ctt ttg ctg ctt ctt ccg ttg cat aaa cct gtt caa aat cca ccg       96
Leu Leu Leu Leu Leu Leu Pro Leu His Lys Pro Val Gln Asn Pro Pro
            20                  25                  30 tgc agt cag aac cgt caa tca ccg tac cca cct cga cac aac agc aaa      144
Cys Ser Gln Asn Arg Gln Ser Pro Tyr Pro Pro Arg His Asn Ser Lys
        35                  40                  45 ctt ttg ctt ctt ccg cct gac att                                      168
Leu Leu Leu Leu Pro Pro Asp Ile
    50                  55

<210> SEQ ID NO 56
<211> LENGTH: 56
<212> TYPE: PRT
<213> ORGANISM: Actinobacillus actinomycetemcomitans

<400> SEQUENCE: 56

Met Asp His Phe Pro Pro Leu Trp Leu Phe Arg Leu Asn Ser Leu Met
1               5                   10                  15

Leu Leu Leu Leu Leu Leu Pro Leu His Lys Pro Val Gln Asn Pro Pro
            20                  25                  30

Cys Ser Gln Asn Arg Gln Ser Pro Tyr Pro Pro Arg His Asn Ser Lys
        35                  40                  45

Leu Leu Leu Leu Pro Pro Asp Ile
    50                  55

<210> SEQ ID NO 57
<211> LENGTH: 492
<212> TYPE: DNA
<213> ORGANISM: Actinobacillus actinomycetemcomitans
<220> FEATURE:
<221> NAME/KEY: CDS
<222> LOCATION: (1)..(492)

<400> SEQUENCE: 57 atg acg aac aaa cca aaa tcc ggg ctc tca ttt ttg tgg tta agt acg       48
Met Thr Asn Lys Pro Lys Ser Gly Leu Ser Phe Leu Trp Leu Ser Thr
1               5                   10                  15 ctg gca ttt atc gcc gat att ttt acc aaa tac tta atc gta agc cat       96
Leu Ala Phe Ile Ala Asp Ile Phe Thr Lys Tyr Leu Ile Val Ser His
            20                  25                  30 ttt gaa tac ggc gaa agc gta aat atc ctg ccg att ttt aat ttg acc      144
Phe Glu Tyr Gly Glu Ser Val Asn Ile Leu Pro Ile Phe Asn Leu Thr
        35                  40                  45 tat gtg ggt aac ttt ggc gcc gct ttt agt ttc ctg gcg gat cat gac      192
Tyr Val Gly Asn Phe Gly Ala Ala Phe Ser Phe Leu Ala Asp His Asp
    50                  55                  60 ggt tgg caa aaa ttc ttt ttc ctt gcg ttg gca gtg ggg att tcc gcc      240
Gly Trp Gln Lys Phe Phe Phe Leu Ala Leu Ala Val Gly Ile Ser Ala
65                  70                  75                  80 atg ttg gtt tat ttt tta atg aaa aat cgc cat gaa caa aaa ctg ctg      288
Met Leu Val Tyr Phe Leu Met Lys Asn Arg His Glu Gln Lys Leu Leu
```

-continued

```
                        85                  90                  95
aat gcc gcc tac gct ttg att atc ggc ggc gct ttg ggc aat gcg gcg      336
Asn Ala Ala Tyr Ala Leu Ile Ile Gly Gly Ala Leu Gly Asn Ala Ala
                100                 105                 110 gat cgt ctg tat cac ggc tat gtg gtg gat ttt tta gat ttc tat tgg      384
Asp Arg Leu Tyr His Gly Tyr Val Val Asp Phe Leu Asp Phe Tyr Trp
            115                 120                 125 cgg gat tgg cat tat ccc gtg ttt aac ctg gcg gat att gcc att tgt      432
Arg Asp Trp His Tyr Pro Val Phe Asn Leu Ala Asp Ile Ala Ile Cys
    130                 135                 140 gtg ggt gcc ggt ttg att gcc ttg gat gcg ttc aaa aac ggc aat aaa      480
Val Gly Ala Gly Leu Ile Ala Leu Asp Ala Phe Lys Asn Gly Asn Lys
145                 150                 155                 160 cag gaa tgt aaa                                                      492
Gln Glu Cys Lys
```

<210> SEQ ID NO 58
<211> LENGTH: 164
<212> TYPE: PRT
<213> ORGANISM: Actinobacillus actinomycetemcomitans

<400> SEQUENCE: 58

```
Met Thr Asn Lys Pro Lys Ser Gly Leu Ser Phe Leu Trp Leu Ser Thr
1               5                   10                  15

Leu Ala Phe Ile Ala Asp Ile Phe Thr Lys Tyr Leu Ile Val Ser His
                20                  25                  30

Phe Glu Tyr Gly Glu Ser Val Asn Ile Leu Pro Ile Phe Asn Leu Thr
            35                  40                  45

Tyr Val Gly Asn Phe Gly Ala Ala Phe Ser Phe Leu Ala Asp His Asp
        50                  55                  60

Gly Trp Gln Lys Phe Phe Phe Leu Ala Leu Ala Val Gly Ile Ser Ala
65                  70                  75                  80

Met Leu Val Tyr Phe Leu Met Lys Asn Arg His Glu Gln Lys Leu Leu
                85                  90                  95

Asn Ala Ala Tyr Ala Leu Ile Ile Gly Gly Ala Leu Gly Asn Ala Ala
                100                 105                 110

Asp Arg Leu Tyr His Gly Tyr Val Val Asp Phe Leu Asp Phe Tyr Trp
            115                 120                 125

Arg Asp Trp His Tyr Pro Val Phe Asn Leu Ala Asp Ile Ala Ile Cys
    130                 135                 140

Val Gly Ala Gly Leu Ile Ala Leu Asp Ala Phe Lys Asn Gly Asn Lys
145                 150                 155                 160

Gln Glu Cys Lys
```

<210> SEQ ID NO 59
<211> LENGTH: 453
<212> TYPE: DNA
<213> ORGANISM: Actinobacillus actinomycetemcomitans
<220> FEATURE:
<221> NAME/KEY: CDS
<222> LOCATION: (1)..(453)

<400> SEQUENCE: 59

```
atg gct aaa ttg tat ttt tac tat tcc acc atg aat gca gga aaa tcc       48
Met Ala Lys Leu Tyr Phe Tyr Tyr Ser Thr Met Asn Ala Gly Lys Ser
1               5                   10                  15 acc acc ttg ttg caa tct tcc tat aat tac cgc gaa cgt aac atg aac       96
Thr Thr Leu Leu Gln Ser Ser Tyr Asn Tyr Arg Glu Arg Asn Met Asn
                20                  25                  30
```

```
acg ctg gtt tat aca gcg gcg ata gac gat cgt ttc ggc gta ggg cag      144
Thr Leu Val Tyr Thr Ala Ala Ile Asp Asp Arg Phe Gly Val Gly Gln
        35                  40                  45 gtg act tcc cgc atc ggg att agc gaa cgg gcg aat acc ttt acc cgc      192
Val Thr Ser Arg Ile Gly Ile Ser Glu Arg Ala Asn Thr Phe Thr Arg
 50                  55                  60 aat acg aat ttg ttc gct gaa att gaa caa cat ctg gcg cag gag ccg      240
Asn Thr Asn Leu Phe Ala Glu Ile Glu Gln His Leu Ala Gln Glu Pro
 65                  70                  75                  80 ctt cat tgt att ttg gtg gat gag gca cag ttt tta acc aaa gaa cag      288
Leu His Cys Ile Leu Val Asp Glu Ala Gln Phe Leu Thr Lys Glu Gln
                 85                  90                  95 gtt tat caa ctg agc gat gtg gtg gat aaa cta cat att ccc gtg ttg      336
Val Tyr Gln Leu Ser Asp Val Val Asp Lys Leu His Ile Pro Val Leu
            100                 105                 110 tgc tac ggt ttg cgc acc gat ttc caa gcg gaa tta ttt gaa ggc agt      384
Cys Tyr Gly Leu Arg Thr Asp Phe Gln Ala Glu Leu Phe Glu Gly Ser
        115                 120                 125 cgc tat tta ctg gcg tgg gcg gat cag ctg gaa gaa ctc aaa acc att      432
Arg Tyr Leu Leu Ala Trp Ala Asp Gln Leu Glu Glu Leu Lys Thr Ile
130                 135                 140 tgt tac tgc ggt cgc aaa gcc                                          453
Cys Tyr Cys Gly Arg Lys Ala
145                 150

<210> SEQ ID NO 60
<211> LENGTH: 151
<212> TYPE: PRT
<213> ORGANISM: Actinobacillus actinomycetemcomitans

<400> SEQUENCE: 60

Met Ala Lys Leu Tyr Phe Tyr Ser Thr Met Asn Ala Gly Lys Ser
1               5                   10                  15

Thr Thr Leu Leu Gln Ser Ser Tyr Asn Tyr Arg Glu Arg Asn Met Asn
            20                  25                  30

Thr Leu Val Tyr Thr Ala Ala Ile Asp Asp Arg Phe Gly Val Gly Gln
        35                  40                  45

Val Thr Ser Arg Ile Gly Ile Ser Glu Arg Ala Asn Thr Phe Thr Arg
 50                  55                  60

Asn Thr Asn Leu Phe Ala Glu Ile Glu Gln His Leu Ala Gln Glu Pro
 65                  70                  75                  80

Leu His Cys Ile Leu Val Asp Glu Ala Gln Phe Leu Thr Lys Glu Gln
                 85                  90                  95

Val Tyr Gln Leu Ser Asp Val Val Asp Lys Leu His Ile Pro Val Leu
            100                 105                 110

Cys Tyr Gly Leu Arg Thr Asp Phe Gln Ala Glu Leu Phe Glu Gly Ser
        115                 120                 125

Arg Tyr Leu Leu Ala Trp Ala Asp Gln Leu Glu Glu Leu Lys Thr Ile
130                 135                 140

Cys Tyr Cys Gly Arg Lys Ala
145                 150

<210> SEQ ID NO 61
<211> LENGTH: 643
<212> TYPE: DNA
<213> ORGANISM: Actinobacillus actinomycetemcomitans
<220> FEATURE:
<221> NAME/KEY: CDS
<222> LOCATION: (1)..(642)
```

```
<400> SEQUENCE: 61 tat aac gaa aaa act tac gaa aat gac tta acc gca aaa gaa atc ttc         48
Tyr Asn Glu Lys Thr Tyr Glu Asn Asp Leu Thr Ala Lys Glu Ile Phe
1               5                   10                  15 gta act tat gta ttg aaa aac aaa ttg tta tgg tac atc gcc att gct         96
Val Thr Tyr Val Leu Lys Asn Lys Leu Leu Trp Tyr Ile Ala Ile Ala
            20                  25                  30 aac gtg ttc gtt tac tta atc cgc tac ggc gta ttg aaa tgg tct ccg        144
Asn Val Phe Val Tyr Leu Ile Arg Tyr Gly Val Leu Lys Trp Ser Pro
        35                  40                  45 gtt tac ttg agt gaa gtg aaa cac ttc aac atc aaa ggt acc gca tgg        192
Val Tyr Leu Ser Glu Val Lys His Phe Asn Ile Lys Gly Thr Ala Trp
    50                  55                  60 gca tac acc att tat gaa ttg gcg gcc gtt ccg ggt aca tta ctt tgc        240
Ala Tyr Thr Ile Tyr Glu Leu Ala Ala Val Pro Gly Thr Leu Leu Cys
65                  70                  75                  80 ggt tgg gta tct gac cat gta ttc aaa ggt aaa cgt ggc tta acc ggt        288
Gly Trp Val Ser Asp His Val Phe Lys Gly Lys Arg Gly Leu Thr Gly
                85                  90                  95 ttc atc ttt atg att tta acc acc gca gcg gta gcc aca tac tgg atg        336
Phe Ile Phe Met Ile Leu Thr Thr Ala Ala Val Ala Thr Tyr Trp Met
            100                 105                 110 aac cct gca aca ccg gaa gct gag ctt gca aac tac agc gca tgg tat        384
Asn Pro Ala Thr Pro Glu Ala Glu Leu Ala Asn Tyr Ser Ala Trp Tyr
        115                 120                 125 gaa aac cca tac caa tta acc gac ttt att ttg atg acc tta atc ggt        432
Glu Asn Pro Tyr Gln Leu Thr Asp Phe Ile Leu Met Thr Leu Ile Gly
    130                 135                 140 ttc tta atc tac ggc cct gtg atg cta atc ggc ttg cac gcc ctt gaa        480
Phe Leu Ile Tyr Gly Pro Val Met Leu Ile Gly Leu His Ala Leu Glu
145                 150                 155                 160 ctt gca ccg aaa aaa gcg gca ggt acc gca gca ggt ttc acc ggt tta        528
Leu Ala Pro Lys Lys Ala Ala Gly Thr Ala Ala Gly Phe Thr Gly Leu
                165                 170                 175 ttc ggt tac tta ggc ggt acc gtg tct gca tca gca gtt atc ggt tgg        576
Phe Gly Tyr Leu Gly Gly Thr Val Ser Ala Ser Ala Val Ile Gly Trp
            180                 185                 190 gca gcc caa cac tac ggc tgg gac ggc ggt ttt tac gtg atg atc ggc        624
Ala Ala Gln His Tyr Gly Trp Asp Gly Gly Phe Tyr Val Met Ile Gly
        195                 200                 205 ggt ggt atc tta ccg gtc a                                              643
Gly Gly Ile Leu Pro Val
    210

<210> SEQ ID NO 62
<211> LENGTH: 214
<212> TYPE: PRT
<213> ORGANISM: Actinobacillus actinomycetemcomitans

<400> SEQUENCE: 62

Tyr Asn Glu Lys Thr Tyr Glu Asn Asp Leu Thr Ala Lys Glu Ile Phe
1               5                   10                  15

Val Thr Tyr Val Leu Lys Asn Lys Leu Leu Trp Tyr Ile Ala Ile Ala
            20                  25                  30

Asn Val Phe Val Tyr Leu Ile Arg Tyr Gly Val Leu Lys Trp Ser Pro
        35                  40                  45

Val Tyr Leu Ser Glu Val Lys His Phe Asn Ile Lys Gly Thr Ala Trp
    50                  55                  60
```

```
Ala Tyr Thr Ile Tyr Glu Leu Ala Ala Val Pro Gly Thr Leu Leu Cys
 65                  70                  75                  80

Gly Trp Val Ser Asp His Val Phe Lys Gly Lys Arg Gly Leu Thr Gly
                 85                  90                  95

Phe Ile Phe Met Ile Leu Thr Thr Ala Val Ala Thr Tyr Trp Met
            100                 105                 110

Asn Pro Ala Thr Pro Glu Ala Glu Leu Ala Asn Tyr Ser Ala Trp Tyr
            115                 120                 125

Glu Asn Pro Tyr Gln Leu Thr Asp Phe Ile Leu Met Thr Leu Ile Gly
        130                 135                 140

Phe Leu Ile Tyr Gly Pro Val Met Leu Ile Gly Leu His Ala Leu Glu
145                 150                 155                 160

Leu Ala Pro Lys Lys Ala Ala Gly Thr Ala Ala Gly Phe Thr Gly Leu
                165                 170                 175

Phe Gly Tyr Leu Gly Gly Thr Val Ser Ala Ser Ala Val Ile Gly Trp
            180                 185                 190

Ala Ala Gln His Tyr Gly Trp Asp Gly Gly Phe Tyr Val Met Ile Gly
        195                 200                 205

Gly Gly Ile Leu Pro Val
        210
```

<210> SEQ ID NO 63
<211> LENGTH: 333
<212> TYPE: DNA
<213> ORGANISM: Actinobacillus actinomycetemcomitans
<220> FEATURE:
<221> NAME/KEY: CDS
<222> LOCATION: (1)..(333)

<400> SEQUENCE: 63

```
gaa tgg gcg gga acg cct tat cgt atc ggc gga caa agt cgc agt ggc    48
Glu Trp Ala Gly Thr Pro Tyr Arg Ile Gly Gly Gln Ser Arg Ser Gly
 1               5                  10                  15 gtg gat tgc tcc ggt ttc gtg caa acc acc ttt ttc gat cgc ttc ggc    96
Val Asp Cys Ser Gly Phe Val Gln Thr Thr Phe Phe Asp Arg Phe Gly
             20                  25                  30 ata aaa ttg ccg cga caa acc aaa gat cag gca aat tac ggt cag tat   144
Ile Lys Leu Pro Arg Gln Thr Lys Asp Gln Ala Asn Tyr Gly Gln Tyr
         35                  40                  45 att gaa aaa ggc gat att caa acc ggt gat ttg gtg ttc ttt aaa acc   192
Ile Glu Lys Gly Asp Ile Gln Thr Gly Asp Leu Val Phe Phe Lys Thr
     50                  55                  60 ggt cgc ggt cct cat ggc tat cat gtg ggc att tat gtg aag gaa gac   240
Gly Arg Gly Pro His Gly Tyr His Val Gly Ile Tyr Val Lys Glu Asp
 65                  70                  75                  80 aaa ttt ctg cac gcg tct act aag ggt ggc gtg att tat tcc tcg ttg   288
Lys Phe Leu His Ala Ser Thr Lys Gly Gly Val Ile Tyr Ser Ser Leu
                 85                  90                  95 aac agc gat tat tgg cgt aag gca tat tgg cag gca aga cga att        333
Asn Ser Asp Tyr Trp Arg Lys Ala Tyr Trp Gln Ala Arg Arg Ile
            100                 105                 110
```

<210> SEQ ID NO 64
<211> LENGTH: 111
<212> TYPE: PRT
<213> ORGANISM: Actinobacillus actinomycetemcomitans

<400> SEQUENCE: 64

```
Glu Trp Ala Gly Thr Pro Tyr Arg Ile Gly Gly Gln Ser Arg Ser Gly
 1               5                  10                  15
```

```
Val Asp Cys Ser Gly Phe Val Gln Thr Thr Phe Phe Asp Arg Phe Gly
         20                  25                  30

Ile Lys Leu Pro Arg Gln Thr Lys Asp Gln Ala Asn Tyr Gly Gln Tyr
             35                  40                  45

Ile Glu Lys Gly Asp Ile Gln Thr Gly Asp Leu Val Phe Phe Lys Thr
         50                  55                  60

Gly Arg Gly Pro His Gly Tyr His Val Gly Ile Tyr Val Lys Glu Asp
 65                  70                  75                  80

Lys Phe Leu His Ala Ser Thr Lys Gly Gly Val Ile Tyr Ser Ser Leu
                 85                  90                  95

Asn Ser Asp Tyr Trp Arg Lys Ala Tyr Trp Gln Ala Arg Arg Ile
            100                 105                 110

<210> SEQ ID NO 65
<211> LENGTH: 423
<212> TYPE: DNA
<213> ORGANISM: Actinobacillus actinomycetemcomitans
<220> FEATURE:
<221> NAME/KEY: CDS
<222> LOCATION: (1)..(423)

<400> SEQUENCE: 65 atg aaa aaa cgt tgc aca tgg gcg gaa aac tca caa att tat cag gat       48
Met Lys Lys Arg Cys Thr Trp Ala Glu Asn Ser Gln Ile Tyr Gln Asp
  1               5                  10                  15 tac cac gac aac gaa tgg ggt aaa cca caa ttt gat gat cgc aaa tta       96
Tyr His Asp Asn Glu Trp Gly Lys Pro Gln Phe Asp Asp Arg Lys Leu
             20                  25                  30 ttt gaa aaa ctg tgt ctg gaa ggg cag caa gcg ggc ctg tcg tgg att      144
Phe Glu Lys Leu Cys Leu Glu Gly Gln Gln Ala Gly Leu Ser Trp Ile
         35                  40                  45 acg gta tta aaa aaa cgg gaa gct tat cgg cag gcg ttt ttc cat ttt      192
Thr Val Leu Lys Lys Arg Glu Ala Tyr Arg Gln Ala Phe Phe His Phe
     50                  55                  60 gat ccg cac aaa gtc gca gca atg act gat gcc gat atc gat cac tgt      240
Asp Pro His Lys Val Ala Ala Met Thr Asp Ala Asp Ile Asp His Cys
 65                  70                  75                  80 atg caa aat aca ggc tta att cgc cat cgc gct aaa tta cag gca atc      288
Met Gln Asn Thr Gly Leu Ile Arg His Arg Ala Lys Leu Gln Ala Ile
                 85                  90                  95 gtc acc aat gcg cgg gcg ttt ctt gcc atg caa aag tgc ggt gaa aat      336
Val Thr Asn Ala Arg Ala Phe Leu Ala Met Gln Lys Cys Gly Glu Asn
            100                 105                 110 ttc agt cat ttt att tgg tct ttc gtg aat cat cag ccg caa att cat      384
Phe Ser His Phe Ile Trp Ser Phe Val Asn His Gln Pro Gln Ile His
        115                 120                 125 gac gtg ccc gag tta agc cat gtg ccg gcg caa acg gca                  423
Asp Val Pro Glu Leu Ser His Val Pro Ala Gln Thr Ala
    130                 135                 140

<210> SEQ ID NO 66
<211> LENGTH: 141
<212> TYPE: PRT
<213> ORGANISM: Actinobacillus actinomycetemcomitans

<400> SEQUENCE: 66

Met Lys Lys Arg Cys Thr Trp Ala Glu Asn Ser Gln Ile Tyr Gln Asp
  1               5                  10                  15

Tyr His Asp Asn Glu Trp Gly Lys Pro Gln Phe Asp Asp Arg Lys Leu
             20                  25                  30
```

```
Phe Glu Lys Leu Cys Leu Glu Gly Gln Gln Ala Gly Leu Ser Trp Ile
        35                  40                  45

Thr Val Leu Lys Lys Arg Glu Ala Tyr Arg Gln Ala Phe Phe His Phe
    50                  55                  60

Asp Pro His Lys Val Ala Ala Met Thr Asp Ala Asp Ile Asp His Cys
65                  70                  75                  80

Met Gln Asn Thr Gly Leu Ile Arg His Arg Ala Lys Leu Gln Ala Ile
                85                  90                  95

Val Thr Asn Ala Arg Ala Phe Leu Ala Met Gln Lys Cys Gly Glu Asn
            100                 105                 110

Phe Ser His Phe Ile Trp Ser Phe Val Asn His Gln Pro Gln Ile His
        115                 120                 125

Asp Val Pro Glu Leu Ser His Val Pro Ala Gln Thr Ala
    130                 135                 140

<210> SEQ ID NO 67
<211> LENGTH: 375
<212> TYPE: DNA
<213> ORGANISM: Actinobacillus actinomycetemcomitans
<220> FEATURE:
<221> NAME/KEY: CDS
<222> LOCATION: (1)..(375)

<400> SEQUENCE: 67 gac atc gtt aca ttt acc caa aaa cgc tgc ccg ttt aat cac atg acg       48
Asp Ile Val Thr Phe Thr Gln Lys Arg Cys Pro Phe Asn His Met Thr
1               5                   10                  15 gtg gcg tat caa aaa agt gcg gtc ata aat tgc ggc gga tat gag gat       96
Val Ala Tyr Gln Lys Ser Ala Val Ile Asn Cys Gly Gly Tyr Glu Asp
            20                  25                  30 tta cag gaa gat tat tat ttg tgg atc aaa ctg gtg gcg caa ggg cag      144
Leu Gln Glu Asp Tyr Tyr Leu Trp Ile Lys Leu Val Ala Gln Gly Gln
        35                  40                  45 cgc gta gca aat tta ccc gat att ttg gtc tat gcg cgc gtc ggc aac      192
Arg Val Ala Asn Leu Pro Asp Ile Leu Val Tyr Ala Arg Val Gly Asn
    50                  55                  60 ggc atg gta ggg cga cgc cgt ggt tta aac caa gcc aaa gcg gaa tgg      240
Gly Met Val Gly Arg Arg Arg Gly Leu Asn Gln Ala Lys Ala Glu Trp
65                  70                  75                  80 cgc tta ttt aag cta aaa cac cat ctt ggc att cag gga ttt tta tcc      288
Arg Leu Phe Lys Leu Lys His His Leu Gly Ile Gln Gly Phe Leu Ser
                85                  90                  95 ggg cta ttc act ttt gtc ctg cgt tcc ggt gcc aga tta ttg ccg aca      336
Gly Leu Phe Thr Phe Val Leu Arg Ser Gly Ala Arg Leu Leu Pro Thr
            100                 105                 110 tca tta ctg aaa aac atc tat caa acc ttt tta aga aaa                  375
Ser Leu Leu Lys Asn Ile Tyr Gln Thr Phe Leu Arg Lys
        115                 120                 125

<210> SEQ ID NO 68
<211> LENGTH: 125
<212> TYPE: PRT
<213> ORGANISM: Actinobacillus actinomycetemcomitans

<400> SEQUENCE: 68

Asp Ile Val Thr Phe Thr Gln Lys Arg Cys Pro Phe Asn His Met Thr
1               5                   10                  15

Val Ala Tyr Gln Lys Ser Ala Val Ile Asn Cys Gly Gly Tyr Glu Asp
            20                  25                  30
```

```
Leu Gln Glu Asp Tyr Tyr Leu Trp Ile Lys Leu Val Ala Gln Gly Gln
            35                  40                  45

Arg Val Ala Asn Leu Pro Asp Ile Leu Val Tyr Ala Arg Val Gly Asn
    50                  55                  60

Gly Met Val Gly Arg Arg Gly Leu Asn Gln Ala Lys Ala Glu Trp
65                  70                  75                  80

Arg Leu Phe Lys Leu Lys His His Leu Gly Ile Gln Gly Phe Leu Ser
                85                  90                  95

Gly Leu Phe Thr Phe Val Leu Arg Ser Gly Ala Arg Leu Leu Pro Thr
                100                 105                 110

Ser Leu Leu Lys Asn Ile Tyr Gln Thr Phe Leu Arg Lys
                115                 120                 125

<210> SEQ ID NO 69
<211> LENGTH: 1005
<212> TYPE: DNA
<213> ORGANISM: Actinobacillus actinomycetemcomitans
<220> FEATURE:
<221> NAME/KEY: CDS
<222> LOCATION: (1)..(1005)

<400> SEQUENCE: 69 tcc ggt aaa tcc gtc ggc gta aat acc atg att tta agc ctg ctt tac      48
Ser Gly Lys Ser Val Gly Val Asn Thr Met Ile Leu Ser Leu Leu Tyr
1               5                   10                  15 cgc gtt aaa ccg gaa gaa gtg aaa ttc atc atg att gac ccg aaa gtg      96
Arg Val Lys Pro Glu Glu Val Lys Phe Ile Met Ile Asp Pro Lys Val
                20                  25                  30 gtg gaa ttg tct att tat aat gat att ccg cat ctt tta acg gaa gtg     144
Val Glu Leu Ser Ile Tyr Asn Asp Ile Pro His Leu Leu Thr Glu Val
            35                  40                  45 gtc acg gac atg aaa aaa gcg gca aac gcg ttg cgc tgg tgt gta gac     192
Val Thr Asp Met Lys Lys Ala Ala Asn Ala Leu Arg Trp Cys Val Asp
        50                  55                  60 gaa atg gag cgc cgt tat caa tta ttg tct gct ttg cgg gtg cgt aat     240
Glu Met Glu Arg Arg Tyr Gln Leu Leu Ser Ala Leu Arg Val Arg Asn
65                  70                  75                  80 att gaa gga ttt aac gag aaa gtt gat gaa tat gag gcc tta aat atg     288
Ile Glu Gly Phe Asn Glu Lys Val Asp Glu Tyr Glu Ala Leu Asn Met
                85                  90                  95 ccg att ccg aac ccg tta tgg aag ccg ggc gat tcc atg gat act ttg     336
Pro Ile Pro Asn Pro Leu Trp Lys Pro Gly Asp Ser Met Asp Thr Leu
                100                 105                 110 ccg cca cca tta gaa aaa ctg agt tac att gtg gtg att gtg gat gaa     384
Pro Pro Pro Leu Glu Lys Leu Ser Tyr Ile Val Val Ile Val Asp Glu
            115                 120                 125 ttc gcc gat ttg atg atg gtg gca ggc aaa cag gtg gaa gag ctt atc     432
Phe Ala Asp Leu Met Met Val Ala Gly Lys Gln Val Glu Glu Leu Ile
130                 135                 140 gca cgt ttg gcg caa aaa gcc cgt gcg gtg ggg att cac tta att ttg     480
Ala Arg Leu Ala Gln Lys Ala Arg Ala Val Gly Ile His Leu Ile Leu
145                 150                 155                 160 gca acc caa cgc cct tcc gta gat gtg att acc ggt ttg att aaa gcg     528
Ala Thr Gln Arg Pro Ser Val Asp Val Ile Thr Gly Leu Ile Lys Ala
                165                 170                 175 aac gta ccg agt cga att gcg ttt act gtg gcg act aaa att gac tcg     576
Asn Val Pro Ser Arg Ile Ala Phe Thr Val Ala Thr Lys Ile Asp Ser
            180                 185                 190 cgt act att ctt gat gca ggc ggt gcg gaa tcc tta ttg ggt aaa ggt     624
Arg Thr Ile Leu Asp Ala Gly Gly Ala Glu Ser Leu Leu Gly Lys Gly
```

-continued

```
            195                 200                 205
gat atg ctg tat tcc cca cag ggt tct acc gaa tta gtc cgt att cac     672
Asp Met Leu Tyr Ser Pro Gln Gly Ser Thr Glu Leu Val Arg Ile His
    210                 215                 220 ggt gcc ttt atg act gat gac gaa gtc gtg cgc gtg gta gat gat tgg     720
Gly Ala Phe Met Thr Asp Asp Glu Val Val Arg Val Val Asp Asp Trp
225                 230                 235                 240 aaa gca cgc ggt aaa ccg aat tac att gat ggt att tta gag ggt gat     768
Lys Ala Arg Gly Lys Pro Asn Tyr Ile Asp Gly Ile Leu Glu Gly Asp
                245                 250                 255 gaa gaa gat gcc ggt gcg gaa cgc tta agt gag cgt ggc ggc gaa acc     816
Glu Glu Asp Ala Gly Ala Glu Arg Leu Ser Glu Arg Gly Gly Glu Thr
            260                 265                 270 gac ggg ttg ttt gat gaa gtg gta gag ttt gtg gtc agc aca ggc acc     864
Asp Gly Leu Phe Asp Glu Val Val Glu Phe Val Val Ser Thr Gly Thr
        275                 280                 285 acg tct att tct gcg att caa cgc cgt ttc cga gta ggc ttt aac cgt     912
Thr Ser Ile Ser Ala Ile Gln Arg Arg Phe Arg Val Gly Phe Asn Arg
    290                 295                 300 gcc gcc aat att atg gat cag ctg gaa gag cag ggc att gtt tcg ccg     960
Ala Ala Asn Ile Met Asp Gln Leu Glu Glu Gln Gly Ile Val Ser Pro
305                 310                 315                 320 gtg caa aac ggt aaa cgt gaa gtg ttg gcg cgc agt gcg gat tat        1005
Val Gln Asn Gly Lys Arg Glu Val Leu Ala Arg Ser Ala Asp Tyr
                325                 330                 335
```

<210> SEQ ID NO 70
<211> LENGTH: 335
<212> TYPE: PRT
<213> ORGANISM: Actinobacillus actinomycetemcomitans

<400> SEQUENCE: 70

```
Ser Gly Lys Ser Val Gly Val Asn Thr Met Ile Leu Ser Leu Leu Tyr
1               5                   10                  15

Arg Val Lys Pro Glu Glu Val Lys Phe Ile Met Ile Asp Pro Lys Val
            20                  25                  30

Val Glu Leu Ser Ile Tyr Asn Asp Ile Pro His Leu Leu Thr Glu Val
        35                  40                  45

Val Thr Asp Met Lys Lys Ala Ala Asn Ala Leu Arg Trp Cys Val Asp
    50                  55                  60

Glu Met Glu Arg Arg Tyr Gln Leu Leu Ser Ala Leu Arg Val Arg Asn
65                  70                  75                  80

Ile Glu Gly Phe Asn Glu Lys Val Asp Glu Tyr Glu Ala Leu Asn Met
                85                  90                  95

Pro Ile Pro Asn Pro Leu Trp Lys Pro Gly Asp Ser Met Asp Thr Leu
            100                 105                 110

Pro Pro Pro Leu Glu Lys Leu Ser Tyr Ile Val Val Ile Val Asp Glu
        115                 120                 125

Phe Ala Asp Leu Met Met Val Ala Gly Lys Gln Val Glu Glu Leu Ile
    130                 135                 140

Ala Arg Leu Ala Gln Lys Ala Arg Ala Val Gly Ile His Leu Ile Leu
145                 150                 155                 160

Ala Thr Gln Arg Pro Ser Val Asp Val Ile Thr Gly Leu Ile Lys Ala
                165                 170                 175

Asn Val Pro Ser Arg Ile Ala Phe Thr Val Ala Thr Lys Ile Asp Ser
            180                 185                 190

Arg Thr Ile Leu Asp Ala Gly Gly Ala Glu Ser Leu Leu Gly Lys Gly
```

```
                    195                 200                 205
Asp Met Leu Tyr Ser Pro Gln Gly Ser Thr Glu Leu Val Arg Ile His
    210                 215                 220

Gly Ala Phe Met Thr Asp Asp Glu Val Val Arg Val Val Asp Asp Trp
225                 230                 235                 240

Lys Ala Arg Gly Lys Pro Asn Tyr Ile Asp Gly Ile Leu Glu Gly Asp
                245                 250                 255

Glu Glu Asp Ala Gly Ala Glu Arg Leu Ser Glu Arg Gly Gly Glu Thr
            260                 265                 270

Asp Gly Leu Phe Asp Glu Val Val Glu Phe Val Val Ser Thr Gly Thr
        275                 280                 285

Thr Ser Ile Ser Ala Ile Gln Arg Arg Phe Arg Val Gly Phe Asn Arg
    290                 295                 300

Ala Ala Asn Ile Met Asp Gln Leu Glu Glu Gln Gly Ile Val Ser Pro
305                 310                 315                 320

Val Gln Asn Gly Lys Arg Glu Val Leu Ala Arg Ser Ala Asp Tyr
                325                 330                 335

<210> SEQ ID NO 71
<211> LENGTH: 426
<212> TYPE: DNA
<213> ORGANISM: Actinobacillus actinomycetemcomitans
<220> FEATURE:
<221> NAME/KEY: CDS
<222> LOCATION: (1)..(426)

<400> SEQUENCE: 71 atg tcg cct aat tat cct tat att aaa aca ttg gtt ata ttt cct ctg     48
Met Ser Pro Asn Tyr Pro Tyr Ile Lys Thr Leu Val Ile Phe Pro Leu
1               5                   10                  15 ctt gct caa ctt atc ggc acc atc atc agc att tgt gtg gat gac aat     96
Leu Ala Gln Leu Ile Gly Thr Ile Ile Ser Ile Cys Val Asp Asp Asn
            20                  25                  30 act gac agt ttt ctc ggc act gcc gac gtg atc ctt ttt agt ctg tta    144
Thr Asp Ser Phe Leu Gly Thr Ala Asp Val Ile Leu Phe Ser Leu Leu
        35                  40                  45 tcg act ttt atc gtg gca acc gtg ccc gct ttt ttg att gca ctg tgg    192
Ser Thr Phe Ile Val Ala Thr Val Pro Ala Phe Leu Ile Ala Leu Trp
    50                  55                  60 aca aaa att tat cgc tat acg cgc tat aac atg atg gcg att gtg tta    240
Thr Lys Ile Tyr Arg Tyr Thr Arg Tyr Asn Met Met Ala Ile Val Leu
65                  70                  75                  80 atc tcg ctg att atc gct ttt tgt tat ggc aac gta gct agc ttt atc    288
Ile Ser Leu Ile Ile Ala Phe Cys Tyr Gly Asn Val Ala Ser Phe Ile
                85                  90                  95 tac atg acg ttc tct cag cca aac atg acg ttt ggt att tgg ctg cgt    336
Tyr Met Thr Phe Ser Gln Pro Asn Met Thr Phe Gly Ile Trp Leu Arg
            100                 105                 110 agc ggc ggc att gat atg gcg ttt tta ctg agt ttc ggc atg gcg ttg    384
Ser Gly Gly Ile Asp Met Ala Phe Leu Leu Ser Phe Gly Met Ala Leu
        115                 120                 125 tat tca gtt ctt gtc ttg cct ttg ttg tta ccg caa acc aga            426
Tyr Ser Val Leu Val Leu Pro Leu Leu Leu Pro Gln Thr Arg
    130                 135                 140

<210> SEQ ID NO 72
<211> LENGTH: 142
<212> TYPE: PRT
<213> ORGANISM: Actinobacillus actinomycetemcomitans
```

-continued

```
<400> SEQUENCE: 72

Met Ser Pro Asn Tyr Pro Tyr Ile Lys Thr Leu Val Ile Phe Pro Leu
1               5                   10                  15

Leu Ala Gln Leu Ile Gly Thr Ile Ile Ser Ile Cys Val Asp Asp Asn
            20                  25                  30

Thr Asp Ser Phe Leu Gly Thr Ala Asp Val Ile Leu Phe Ser Leu Leu
        35                  40                  45

Ser Thr Phe Ile Val Ala Thr Val Pro Ala Phe Leu Ile Ala Leu Trp
    50                  55                  60

Thr Lys Ile Tyr Arg Tyr Thr Arg Tyr Asn Met Met Ala Ile Val Leu
65                  70                  75                  80

Ile Ser Leu Ile Ile Ala Phe Cys Tyr Gly Asn Val Ala Ser Phe Ile
                85                  90                  95

Tyr Met Thr Phe Ser Gln Pro Asn Met Thr Phe Gly Ile Trp Leu Arg
            100                 105                 110

Ser Gly Gly Ile Asp Met Ala Phe Leu Leu Ser Phe Gly Met Ala Leu
        115                 120                 125

Tyr Ser Val Leu Val Leu Pro Leu Leu Leu Pro Gln Thr Arg
    130                 135                 140

<210> SEQ ID NO 73
<211> LENGTH: 600
<212> TYPE: DNA
<213> ORGANISM: Actinobacillus actinomycetemcomitans
<220> FEATURE:
<221> NAME/KEY: CDS
<222> LOCATION: (1)..(600)

<400> SEQUENCE: 73 gta tct caa caa aac cgc tgc gga ttc cac cac gga ttc aat aat gaa      48
Val Ser Gln Gln Asn Arg Cys Gly Phe His His Gly Phe Asn Asn Glu
1               5                   10                  15 aga gga aaa ata atc atg ttg gca aga atg tta ttt caa tcc tgg cgt      96
Arg Gly Lys Ile Ile Met Leu Ala Arg Met Leu Phe Gln Ser Trp Arg
            20                  25                  30 tat gat tta aag cgc aaa ctc ctc gcc att gtg acc att ttc ctc gct     144
Tyr Asp Leu Lys Arg Lys Leu Leu Ala Ile Val Thr Ile Phe Leu Ala
        35                  40                  45 gcc gga tta att tcc gcc ttg ctt gcg gtg tcc atc gac atc ggc gac     192
Ala Gly Leu Ile Ser Ala Leu Leu Ala Val Ser Ile Asp Ile Gly Asp
    50                  55                  60 aaa atg gcg aaa gag ctt aaa tcc tac ggc gcc aat att ctg gtg gag     240
Lys Met Ala Lys Glu Leu Lys Ser Tyr Gly Ala Asn Ile Leu Val Glu
65                  70                  75                  80 ccc gcc agc agc gcc att ttg cct gat gaa gtg agc cgt aat aat tct     288
Pro Ala Ser Ser Ala Ile Leu Pro Asp Glu Val Ser Arg Asn Asn Ser
                85                  90                  95 ctc gcc acg caa gat ttt ttg gac gaa aaa gaa ctg ccg aac att aaa     336
Leu Ala Thr Gln Asp Phe Leu Asp Glu Lys Glu Leu Pro Asn Ile Lys
            100                 105                 110 gac att ttt tgg cgt aac aat att gta ggc ttc gcc ccg tta ctc agc     384
Asp Ile Phe Trp Arg Asn Asn Ile Val Gly Phe Ala Pro Leu Leu Ser
        115                 120                 125 gca caa gtc aaa gcc gat gga cca aac ggc aag gcg caa gac atc gac     432
Ala Gln Val Lys Ala Asp Gly Pro Asn Gly Lys Ala Gln Asp Ile Asp
    130                 135                 140 att ctc ggc acg ttt ttt gat cat caa atc gcc gtg ccg gat gaa gac     480
Ile Leu Gly Thr Phe Phe Asp His Gln Ile Ala Val Pro Asp Glu Asp
145                 150                 155                 160
```

| | | |
|---|---|---|
| gat tac cac acc ggg caa aaa atc atc aac cct tat tgg cag gtg gaa<br>Asp Tyr His Thr Gly Gln Lys Ile Ile Asn Pro Tyr Trp Gln Val Glu<br>165                      170                    175 | | 528 |
| ggc gaa tgg gtg aac gat gcc acc gat gat ttc agc gaa cag gtt cct<br>Gly Glu Trp Val Asn Asp Ala Thr Asp Asp Phe Ser Glu Gln Val Pro<br>         180                    185                    190 | | 576 |
| gcg tta ctc ggc gca caa ctt gcc<br>Ala Leu Leu Gly Ala Gln Leu Ala<br>195                    200 | | 600 |

<210> SEQ ID NO 74
<211> LENGTH: 200
<212> TYPE: PRT
<213> ORGANISM: Actinobacillus actinomycetemcomitans

<400> SEQUENCE: 74

Val Ser Gln Gln Asn Arg Cys Gly Phe His His Gly Phe Asn Asn Glu
1               5                   10                  15

Arg Gly Lys Ile Ile Met Leu Ala Arg Met Leu Phe Gln Ser Trp Arg
            20                  25                  30

Tyr Asp Leu Lys Arg Lys Leu Leu Ala Ile Val Thr Ile Phe Leu Ala
        35                  40                  45

Ala Gly Leu Ile Ser Ala Leu Leu Ala Val Ser Ile Asp Ile Gly Asp
    50                  55                  60

Lys Met Ala Lys Glu Leu Lys Ser Tyr Gly Ala Asn Ile Leu Val Glu
65                  70                  75                  80

Pro Ala Ser Ser Ala Ile Leu Pro Asp Glu Val Ser Arg Asn Asn Ser
                85                  90                  95

Leu Ala Thr Gln Asp Phe Leu Asp Glu Lys Glu Leu Pro Asn Ile Lys
            100                 105                 110

Asp Ile Phe Trp Arg Asn Asn Ile Val Gly Phe Ala Pro Leu Leu Ser
        115                 120                 125

Ala Gln Val Lys Ala Asp Gly Pro Asn Gly Lys Ala Gln Asp Ile Asp
    130                 135                 140

Ile Leu Gly Thr Phe Phe Asp His Gln Ile Ala Val Pro Asp Glu Asp
145                 150                 155                 160

Asp Tyr His Thr Gly Gln Lys Ile Ile Asn Pro Tyr Trp Gln Val Glu
                165                 170                 175

Gly Glu Trp Val Asn Asp Ala Thr Asp Asp Phe Ser Glu Gln Val Pro
            180                 185                 190

Ala Leu Leu Gly Ala Gln Leu Ala
        195                 200

<210> SEQ ID NO 75
<211> LENGTH: 603
<212> TYPE: DNA
<213> ORGANISM: Actinobacillus actinomycetemcomitans
<220> FEATURE:
<221> NAME/KEY: CDS
<222> LOCATION: (1)..(603)

<400> SEQUENCE: 75

| | | |
|---|---|---|
| gaa cct cga atc act gca ttg cac caa gaa aat caa ggc aaa gcc agt<br>Glu Pro Arg Ile Thr Ala Leu His Gln Glu Asn Gln Gly Lys Ala Ser<br>1               5                   10                 15 | | 48 |
| gca ttg aat cat ggt tta acg gtt gcc aag gga aaa tac gtt gcc tgt<br>Ala Leu Asn His Gly Leu Thr Val Ala Lys Gly Lys Tyr Val Ala Cys<br>         20                    25                    30 | | 96 |

-continued

```
atc gac ggt gat gcg gta ttg gat tac tac gcg ctg gac tac atg gtt      144
Ile Asp Gly Asp Ala Val Leu Asp Tyr Tyr Ala Leu Asp Tyr Met Val
         35                  40                  45 caa gcc tta gag caa gat ccg aaa tat gct gct acc aca ggt aat ccg      192
Gln Ala Leu Glu Gln Asp Pro Lys Tyr Ala Ala Thr Thr Gly Asn Pro
 50                  55                  60 cgt gta cgt aac cgt agt act att ttg ggg cgt tta cag gta tcc gag      240
Arg Val Arg Asn Arg Ser Thr Ile Leu Gly Arg Leu Gln Val Ser Glu
 65                  70                  75                  80 ttc agc tcc atc atc ggt cta att aag cgg gca caa ggt cta atg ggc      288
Phe Ser Ser Ile Ile Gly Leu Ile Lys Arg Ala Gln Gly Leu Met Gly
                 85                  90                  95 aca atc ttt acc gtt tcc ggc gtg tgt tgt tta ttc cgt aaa gat gtc      336
Thr Ile Phe Thr Val Ser Gly Val Cys Cys Leu Phe Arg Lys Asp Val
            100                 105                 110 atg gaa gaa atc ggt gga tgg agt act aac atg atc acc gaa gac att      384
Met Glu Glu Ile Gly Gly Trp Ser Thr Asn Met Ile Thr Glu Asp Ile
        115                 120                 125 gat att agc tgg aaa att caa att gcc ggt tac aac atc atg tac gaa      432
Asp Ile Ser Trp Lys Ile Gln Ile Ala Gly Tyr Asn Ile Met Tyr Glu
130                 135                 140 cca cgc gca ctc tgc tgg gtg ctt atg ccg gaa agc ata aaa ggg ctt      480
Pro Arg Ala Leu Cys Trp Val Leu Met Pro Glu Ser Ile Lys Gly Leu
145                 150                 155                 160 tat aaa cag cgt ttg cgt tgg gca caa ggc ggt gcg gaa act atc atg      528
Tyr Lys Gln Arg Leu Arg Trp Ala Gln Gly Gly Ala Glu Thr Ile Met
                165                 170                 175 aag tat ttt tcg aaa ata tgg cat tgg cgg aat cgt cgc ttg tgg cca      576
Lys Tyr Phe Ser Lys Ile Trp His Trp Arg Asn Arg Arg Leu Trp Pro
            180                 185                 190 atg tat att gag tat ttt gct acc gtt                                  603
Met Tyr Ile Glu Tyr Phe Ala Thr Val
        195                 200
```

<210> SEQ ID NO 76
<211> LENGTH: 201
<212> TYPE: PRT
<213> ORGANISM: Actinobacillus actinomycetemcomitans

<400> SEQUENCE: 76

```
Glu Pro Arg Ile Thr Ala Leu His Gln Glu Asn Gln Gly Lys Ala Ser
 1               5                  10                  15

Ala Leu Asn His Gly Leu Thr Val Ala Lys Gly Lys Tyr Val Ala Cys
                20                  25                  30

Ile Asp Gly Asp Ala Val Leu Asp Tyr Tyr Ala Leu Asp Tyr Met Val
         35                  40                  45

Gln Ala Leu Glu Gln Asp Pro Lys Tyr Ala Ala Thr Thr Gly Asn Pro
 50                  55                  60

Arg Val Arg Asn Arg Ser Thr Ile Leu Gly Arg Leu Gln Val Ser Glu
 65                  70                  75                  80

Phe Ser Ser Ile Ile Gly Leu Ile Lys Arg Ala Gln Gly Leu Met Gly
                 85                  90                  95

Thr Ile Phe Thr Val Ser Gly Val Cys Cys Leu Phe Arg Lys Asp Val
            100                 105                 110

Met Glu Glu Ile Gly Gly Trp Ser Thr Asn Met Ile Thr Glu Asp Ile
        115                 120                 125

Asp Ile Ser Trp Lys Ile Gln Ile Ala Gly Tyr Asn Ile Met Tyr Glu
130                 135                 140
```

```
Pro Arg Ala Leu Cys Trp Val Leu Met Pro Glu Ser Ile Lys Gly Leu
145                 150                 155                 160

Tyr Lys Gln Arg Leu Arg Trp Ala Gln Gly Gly Ala Glu Thr Ile Met
                165                 170                 175

Lys Tyr Phe Ser Lys Ile Trp His Trp Arg Asn Arg Arg Leu Trp Pro
            180                 185                 190

Met Tyr Ile Glu Tyr Phe Ala Thr Val
        195                 200

<210> SEQ ID NO 77
<211> LENGTH: 759
<212> TYPE: DNA
<213> ORGANISM: Actinobacillus actinomycetemcomitans
<220> FEATURE:
<221> NAME/KEY: CDS
<222> LOCATION: (1)..(759)

<400> SEQUENCE: 77 atg cga tat ttg aaa caa aca aca att tca ctg tta att ttg acc gca      48
Met Arg Tyr Leu Lys Gln Thr Thr Ile Ser Leu Leu Ile Leu Thr Ala
1               5                   10                  15 ctt tcc tcc tcc ttt gcc aat cag cac aag gcg aca acg cat aaa gcg      96
Leu Ser Ser Ser Phe Ala Asn Gln His Lys Ala Thr Thr His Lys Ala
            20                  25                  30 aat gtt gcc cat acg cac gcc aaa ccg gag caa cac cac gca gaa tta     144
Asn Val Ala His Thr His Ala Lys Pro Glu Gln His His Ala Glu Leu
        35                  40                  45 gaa cgg cta aaa cag cgt gca act ttt ctg cag tta gaa agc ctg ctg     192
Glu Arg Leu Lys Gln Arg Ala Thr Phe Leu Gln Leu Glu Ser Leu Leu
    50                  55                  60 aaa agt gcg gtc aaa aat aac ggc gtt ttt atc aac caa act gta ttc     240
Lys Ser Ala Val Lys Asn Asn Gly Val Phe Ile Asn Gln Thr Val Phe
65                  70                  75                  80 ctg aaa ctg att gag gat ttg aaa ggc tat ccg ttg caa aca gat gcc     288
Leu Lys Leu Ile Glu Asp Leu Lys Gly Tyr Pro Leu Gln Thr Asp Ala
                85                  90                  95 ata gcg gct tat ttc gac gcc tgc att aaa agc gta aat cac gac aca     336
Ile Ala Ala Tyr Phe Asp Ala Cys Ile Lys Ser Val Asn His Asp Thr
            100                 105                 110 tcg aag gga gaa gtt aag gcg cta aaa cag gac att gag caa ttt atc     384
Ser Lys Gly Glu Val Lys Ala Leu Lys Gln Asp Ile Glu Gln Phe Ile
        115                 120                 125 gaa aag cat ccg act cat ttt cta cgg gaa aaa ttg gaa caa aga ctt     432
Glu Lys His Pro Thr His Phe Leu Arg Glu Lys Leu Glu Gln Arg Leu
    130                 135                 140 ttt acc tta ttt atc aac acg gaa gat ctt gaa ggc tta gtt ggt tac     480
Phe Thr Leu Phe Ile Asn Thr Glu Asp Leu Glu Gly Leu Val Gly Tyr
145                 150                 155                 160 gcg caa cgg gtt aaa ccg aaa ggg ttg gaa gcc caa ctt gca gtg ttg     528
Ala Gln Arg Val Lys Pro Lys Gly Leu Glu Ala Gln Leu Ala Val Leu
                165                 170                 175 aat gcc gaa tat caa ctg ggg cgc aaa cgt gcc gaa tct gat aaa aat     576
Asn Ala Glu Tyr Gln Leu Gly Arg Lys Arg Ala Glu Ser Asp Lys Asn
            180                 185                 190 ccg aat gcg aat gtg tcg aaa atc atc gcc cgt tat gag caa ctt tgg     624
Pro Asn Ala Asn Val Ser Lys Ile Ile Ala Arg Tyr Glu Gln Leu Trp
        195                 200                 205 tta aac aat agt gaa ctg cca aac gat gcg cag cta cgg gca aaa tgg     672
Leu Asn Asn Ser Glu Leu Pro Asn Asp Ala Gln Leu Arg Ala Lys Trp
    210                 215                 220
```

-continued

```
tat tcc gac ggc ggc aga atg gca gaa aaa gtg tat caa aaa gct gag        720
Tyr Ser Asp Gly Gly Arg Met Ala Glu Lys Val Tyr Gln Lys Ala Glu
225                 230                 235                 240 aat ctc ttt atc aaa aac aat gta aaa ggc ttg gaa ttg                    759
Asn Leu Phe Ile Lys Asn Asn Val Lys Gly Leu Glu Leu
                245                 250
```

<210> SEQ ID NO 78
<211> LENGTH: 253
<212> TYPE: PRT
<213> ORGANISM: Actinobacillus actinomycetemcomitans

<400> SEQUENCE: 78

```
Met Arg Tyr Leu Lys Gln Thr Thr Ile Ser Leu Leu Ile Leu Thr Ala
1               5                   10                  15

Leu Ser Ser Ser Phe Ala Asn Gln His Lys Ala Thr Thr His Lys Ala
                20                  25                  30

Asn Val Ala His Thr His Ala Lys Pro Glu Gln His His Ala Glu Leu
            35                  40                  45

Glu Arg Leu Lys Gln Arg Ala Thr Phe Leu Gln Leu Glu Ser Leu Leu
        50                  55                  60

Lys Ser Ala Val Lys Asn Asn Gly Val Phe Ile Asn Gln Thr Val Phe
65                  70                  75                  80

Leu Lys Leu Ile Glu Asp Leu Lys Gly Tyr Pro Leu Gln Thr Asp Ala
                85                  90                  95

Ile Ala Ala Tyr Phe Asp Ala Cys Ile Lys Ser Val Asn His Asp Thr
            100                 105                 110

Ser Lys Gly Glu Val Lys Ala Leu Lys Gln Asp Ile Glu Gln Phe Ile
        115                 120                 125

Glu Lys His Pro Thr His Phe Leu Arg Glu Lys Leu Glu Gln Arg Leu
130                 135                 140

Phe Thr Leu Phe Ile Asn Thr Glu Asp Leu Glu Gly Leu Val Gly Tyr
145                 150                 155                 160

Ala Gln Arg Val Lys Pro Lys Gly Leu Glu Ala Gln Leu Ala Val Leu
                165                 170                 175

Asn Ala Glu Tyr Gln Leu Gly Arg Lys Arg Ala Glu Ser Asp Lys Asn
            180                 185                 190

Pro Asn Ala Asn Val Ser Lys Ile Ile Ala Arg Tyr Glu Gln Leu Trp
        195                 200                 205

Leu Asn Asn Ser Glu Leu Pro Asn Asp Ala Gln Leu Arg Ala Lys Trp
    210                 215                 220

Tyr Ser Asp Gly Gly Arg Met Ala Glu Lys Val Tyr Gln Lys Ala Glu
225                 230                 235                 240

Asn Leu Phe Ile Lys Asn Asn Val Lys Gly Leu Glu Leu
                245                 250
```

<210> SEQ ID NO 79
<211> LENGTH: 624
<212> TYPE: DNA
<213> ORGANISM: Actinobacillus actinomycetemcomitans
<220> FEATURE:
<221> NAME/KEY: CDS
<222> LOCATION: (1)..(624)

<400> SEQUENCE: 79

```
gtc ggt caa tgg acg gag aaa ggt aac caa acg gaa aat cgc gat aat         48
Val Gly Gln Trp Thr Glu Lys Gly Asn Gln Thr Glu Asn Arg Asp Asn
1               5                   10                  15
```

| | | |
|---|---|---|
| tcc gat ccg tcc ggt tta ggt tgt act ctt ggt tgg ggc ttt gca tgg<br>Ser Asp Pro Ser Gly Leu Gly Cys Thr Leu Gly Trp Gly Phe Ala Trp<br>          20                       25                    30 | 96 |
| cca gca aac cgc cgc gtg ctt tat agc cgc gcc tct ttg gat att aac<br>Pro Ala Asn Arg Arg Val Leu Tyr Ser Arg Ala Ser Leu Asp Ile Asn<br>       35                   40                 45 | 144 |
| ggt aat cct tgg gat aaa cac cgt caa ctg atc aaa tgg aac ggt aaa<br>Gly Asn Pro Trp Asp Lys His Arg Gln Leu Ile Lys Trp Asn Gly Lys<br>50                   55                   60 | 192 |
| aac tgg aac tgg ttt gat att gcc gac tac ggc act caa cca cca ggt<br>Asn Trp Asn Trp Phe Asp Ile Ala Asp Tyr Gly Thr Gln Pro Pro Gly<br>65                   70                 75                80 | 240 |
| tcc gat acc aga cca ttt atg atg tca gcc gaa ggt gtt gga cgc tta<br>Ser Asp Thr Arg Pro Phe Met Met Ser Ala Glu Gly Val Gly Arg Leu<br>          85                       90                 95 | 288 |
| ttt gcc gtt gat aaa att aat agc gga ccg ttc ccg gaa cac tat gaa<br>Phe Ala Val Asp Lys Ile Asn Ser Gly Pro Phe Pro Glu His Tyr Glu<br>                100                  105              110 | 336 |
| ccg att gaa agt ccg att gat acg aat ccg ctt cat ccg aat gtg gta<br>Pro Ile Glu Ser Pro Ile Asp Thr Asn Pro Leu His Pro Asn Val Val<br>         115                    120                125 | 384 |
| tca gat ccg acg gtg cgt att tac aaa gaa gat cgc gag ttt atc ggc<br>Ser Asp Pro Thr Val Arg Ile Tyr Lys Glu Asp Arg Glu Phe Ile Gly<br>130                  135                  140 | 432 |
| tca aat aaa gaa tat ccg ttt gtg gca aca act tat cgt cta acc gaa<br>Ser Asn Lys Glu Tyr Pro Phe Val Ala Thr Thr Tyr Arg Leu Thr Glu<br>145                  150                 155              160 | 480 |
| cat ttc cac agt tgg acc gcg caa tct gcc att aac atc atc gca caa<br>His Phe His Ser Trp Thr Ala Gln Ser Ala Ile Asn Ile Ile Ala Gln<br>                  165                  170              175 | 528 |
| ccg caa caa ttt gtg gaa atc ggt gaa aaa ttg gca gaa gaa aaa ggt<br>Pro Gln Gln Phe Val Glu Ile Gly Glu Lys Leu Ala Glu Glu Lys Gly<br>         180                    185                190 | 576 |
| atc caa aaa ggc gat atg gta cgt att acc tcc aaa cgg ggc tat att<br>Ile Gln Lys Gly Asp Met Val Arg Ile Thr Ser Lys Arg Gly Tyr Ile<br>195                  200                  205 | 624 |

<210> SEQ ID NO 80
<211> LENGTH: 208
<212> TYPE: PRT
<213> ORGANISM: Actinobacillus actinomycetemcomitans

<400> SEQUENCE: 80

Val Gly Gln Trp Thr Glu Lys Gly Asn Gln Thr Glu Asn Arg Asp Asn
1               5                   10                  15

Ser Asp Pro Ser Gly Leu Gly Cys Thr Leu Gly Trp Gly Phe Ala Trp
            20                  25                  30

Pro Ala Asn Arg Arg Val Leu Tyr Ser Arg Ala Ser Leu Asp Ile Asn
        35                  40                  45

Gly Asn Pro Trp Asp Lys His Arg Gln Leu Ile Lys Trp Asn Gly Lys
    50                  55                  60

Asn Trp Asn Trp Phe Asp Ile Ala Asp Tyr Gly Thr Gln Pro Pro Gly
65                  70                  75                  80

Ser Asp Thr Arg Pro Phe Met Met Ser Ala Glu Gly Val Gly Arg Leu
                85                  90                  95

Phe Ala Val Asp Lys Ile Asn Ser Gly Pro Phe Pro Glu His Tyr Glu
            100                 105                 110

Pro Ile Glu Ser Pro Ile Asp Thr Asn Pro Leu His Pro Asn Val Val
        115                 120                 125

```
Ser Asp Pro Thr Val Arg Ile Tyr Lys Glu Asp Arg Glu Phe Ile Gly
        130                 135                 140

Ser Asn Lys Glu Tyr Pro Phe Val Ala Thr Thr Tyr Arg Leu Thr Glu
145                 150                 155                 160

His Phe His Ser Trp Thr Ala Gln Ser Ala Ile Asn Ile Ile Ala Gln
                165                 170                 175

Pro Gln Gln Phe Val Glu Ile Gly Glu Lys Leu Ala Glu Lys Gly
            180                 185                 190

Ile Gln Lys Gly Asp Met Val Arg Ile Thr Ser Lys Arg Gly Tyr Ile
        195                 200                 205

<210> SEQ ID NO 81
<211> LENGTH: 534
<212> TYPE: DNA
<213> ORGANISM: Actinobacillus actinomycetemcomitans
<220> FEATURE:
<221> NAME/KEY: CDS
<222> LOCATION: (1)..(534)

<400> SEQUENCE: 81 att cct ggc tta att gaa ggc gca tcg gaa gga gca ggc ttg ggt atc      48
Ile Pro Gly Leu Ile Glu Gly Ala Ser Glu Gly Ala Gly Leu Gly Ile
1               5                   10                  15 cgc ttc ctg aaa cac ttg gaa cgt tgc cgc gtg ttg att cat ttg gtg      96
Arg Phe Leu Lys His Leu Glu Arg Cys Arg Val Leu Ile His Leu Val
            20                  25                  30 gat atc aac cca att gat gat tcc aac ccg gcg gat aac gtg gcg att     144
Asp Ile Asn Pro Ile Asp Asp Ser Asn Pro Ala Asp Asn Val Ala Ile
        35                  40                  45 atc gaa tcg gaa ttg ttc caa tac agc gag tcc ttg gcg gaa aaa ccg     192
Ile Glu Ser Glu Leu Phe Gln Tyr Ser Glu Ser Leu Ala Glu Lys Pro
    50                  55                  60 cgc tgg ctg gtg ttc aac aaa atc gat acg ctc agt gat gaa gaa gcc     240
Arg Trp Leu Val Phe Asn Lys Ile Asp Thr Leu Ser Asp Glu Glu Ala
65                  70                  75                  80 cat gcg cga gcg aaa gag atc acc gaa cgt ctg ggc cgg gag gaa ggt     288
His Ala Arg Ala Lys Glu Ile Thr Glu Arg Leu Gly Arg Glu Glu Gly
                85                  90                  95 tat tat tta att tcc gcc gcc acc ggt aaa aac gcc ccg caa ctg tgc     336
Tyr Tyr Leu Ile Ser Ala Ala Thr Gly Lys Asn Ala Pro Gln Leu Cys
            100                 105                 110 cgc gat att atg gac ttc ctg gaa gcc cac ccg cgc aaa aca gaa aaa     384
Arg Asp Ile Met Asp Phe Leu Glu Ala His Pro Arg Lys Thr Glu Lys
        115                 120                 125 acg ccg gta gaa aat gaa gaa gtc aaa ttc aaa tgg gaa gat tat cat     432
Thr Pro Val Glu Asn Glu Glu Val Lys Phe Lys Trp Glu Asp Tyr His
    130                 135                 140 cag gag caa ttg gaa aat gcc gat gtt gat gat gaa gag gat aat gac     480
Gln Glu Gln Leu Glu Asn Ala Asp Val Asp Asp Glu Glu Asp Asn Asp
145                 150                 155                 160 tgg gat gac tgg tcg gaa gac gat gaa gaa ggc gtg gaa att atc tat     528
Trp Asp Asp Trp Ser Glu Asp Asp Glu Glu Gly Val Glu Ile Ile Tyr
                165                 170                 175 aag cct                                                              534
Lys Pro <210> SEQ ID NO 82
<211> LENGTH: 178
<212> TYPE: PRT
<213> ORGANISM: Actinobacillus actinomycetemcomitans
```

```
<400> SEQUENCE: 82

Ile Pro Gly Leu Ile Glu Gly Ala Ser Glu Gly Ala Gly Leu Gly Ile
1               5                   10                  15

Arg Phe Leu Lys His Leu Glu Arg Cys Arg Val Leu Ile His Leu Val
                20                  25                  30

Asp Ile Asn Pro Ile Asp Asp Ser Asn Pro Ala Asp Asn Val Ala Ile
            35                  40                  45

Ile Glu Ser Glu Leu Phe Gln Tyr Ser Glu Ser Leu Ala Glu Lys Pro
        50                  55                  60

Arg Trp Leu Val Phe Asn Lys Ile Asp Thr Leu Ser Asp Glu Glu Ala
65                  70                  75                  80

His Ala Arg Ala Lys Glu Ile Thr Glu Arg Leu Gly Arg Glu Glu Gly
                85                  90                  95

Tyr Tyr Leu Ile Ser Ala Ala Thr Gly Lys Asn Ala Pro Gln Leu Cys
                100                 105                 110

Arg Asp Ile Met Asp Phe Leu Glu Ala His Pro Arg Lys Thr Glu Lys
            115                 120                 125

Thr Pro Val Glu Asn Glu Val Lys Phe Lys Trp Glu Asp Tyr His
        130                 135                 140

Gln Glu Gln Leu Glu Asn Ala Asp Val Asp Asp Glu Gly Asp Asn Asp
145                 150                 155                 160

Trp Asp Asp Trp Ser Glu Asp Glu Glu Gly Val Glu Ile Ile Tyr
                165                 170                 175

Lys Pro

<210> SEQ ID NO 83
<211> LENGTH: 372
<212> TYPE: DNA
<213> ORGANISM: Actinobacillus actinomycetemcomitans
<220> FEATURE:
<221> NAME/KEY: CDS
<222> LOCATION: (1)..(372)

<400> SEQUENCE: 83 atg tta acg gaa agt gcg gtc gtt att gag tac gaa tcc ggc aga gcc      48
Met Leu Thr Glu Ser Ala Val Val Ile Glu Tyr Glu Ser Gly Arg Ala
1               5                   10                  15 aaa gtg aaa tgc caa tca caa agc gca tgc ggc gct tgc gcg gca aaa      96
Lys Val Lys Cys Gln Ser Gln Ser Ala Cys Gly Ala Cys Ala Ala Lys
                20                  25                  30 ccg gcg tgc ggt aat tct gcc ttg tcg gaa tta gcc agc agc ggc gcg     144
Pro Ala Cys Gly Asn Ser Ala Leu Ser Glu Leu Ala Ser Ser Gly Ala
            35                  40                  45 cgc ggc gaa cat att ttc acc atc gag acc att acg cca ctg aaa atc     192
Arg Gly Glu His Ile Phe Thr Ile Glu Thr Ile Thr Pro Leu Lys Ile
        50                  55                  60 ggg caa cgg gtg gaa atc ggt ttg tcc gaa cgt tcc tta atc aaa tcc     240
Gly Gln Arg Val Glu Ile Gly Leu Ser Glu Arg Ser Leu Ile Lys Ser
65                  70                  75                  80 gcc ttg ctc atg tat tgc gtg ccg cta ttt act tta tta ttc agc acg     288
Ala Leu Leu Met Tyr Cys Val Pro Leu Phe Thr Leu Leu Phe Ser Thr
                85                  90                  95 tta tta ttt gat tcg ctg ttt gcc cat gag ctc gtc agc gtc ttt ttt     336
Leu Leu Phe Asp Ser Leu Phe Ala His Glu Leu Val Ser Val Phe Phe
            100                 105                 110 atc ttc att tcc act gca ctt tct ttc ctt ggt gtg                     372
Ile Phe Ile Ser Thr Ala Leu Ser Phe Leu Gly Val
```

<210> SEQ ID NO 84
<211> LENGTH: 124
<212> TYPE: PRT
<213> ORGANISM: Actinobacillus actinomycetemcomitans

<400> SEQUENCE: 84

```
Met Leu Thr Glu Ser Ala Val Val Ile Glu Tyr Glu Ser Gly Arg Ala
 1               5                  10                  15

Lys Val Lys Cys Gln Ser Gln Ser Ala Cys Gly Ala Cys Ala Ala Lys
            20                  25                  30

Pro Ala Cys Gly Asn Ser Ala Leu Ser Glu Leu Ala Ser Ser Gly Ala
        35                  40                  45

Arg Gly Glu His Ile Phe Thr Ile Glu Thr Ile Thr Pro Leu Lys Ile
    50                  55                  60

Gly Gln Arg Val Glu Ile Gly Leu Ser Glu Arg Ser Leu Ile Lys Ser
65                  70                  75                  80

Ala Leu Leu Met Tyr Cys Val Pro Leu Phe Thr Leu Leu Phe Ser Thr
                85                  90                  95

Leu Leu Phe Asp Ser Leu Phe Ala His Glu Leu Val Ser Val Phe Phe
            100                 105                 110

Ile Phe Ile Ser Thr Ala Leu Ser Phe Leu Gly Val
        115                 120
```

<210> SEQ ID NO 85
<211> LENGTH: 629
<212> TYPE: DNA
<213> ORGANISM: Actinobacillus actinomycetemcomitans
<220> FEATURE:
<221> NAME/KEY: CDS
<222> LOCATION: (1)..(627)

<400> SEQUENCE: 85

```
att tct tcc ggt tcc tta ttg ctt gcc gtg ctt tat aaa cgc aat cgc      48
Ile Ser Ser Gly Ser Leu Leu Leu Ala Val Leu Tyr Lys Arg Asn Arg
 1               5                  10                  15 aaa ccg gaa aaa aca agc gaa aac tgg att att cgc agt gct gcg atc      96
Lys Pro Glu Lys Thr Ser Glu Asn Trp Ile Ile Arg Ser Ala Ala Ile
            20                  25                  30 tta gcg cct ggc acg gtg att atc ggt tta ttg ctg ttg att ttc cac     144
Leu Ala Pro Gly Thr Val Ile Ile Gly Leu Leu Leu Leu Ile Phe His
        35                  40                  45 ttg gcg cgc cct tgg acg ttc tgg tat ttg atg ttt aac tac cag ttc     192
Leu Ala Arg Pro Trp Thr Phe Trp Tyr Leu Met Phe Asn Tyr Gln Phe
    50                  55                  60 aat tcc gtg atg tcc atg ggg gta ctg tta ttc caa atc tat atg gcg     240
Asn Ser Val Met Ser Met Gly Val Leu Leu Phe Gln Ile Tyr Met Ala
65                  70                  75                  80 gcg gtt ctc ctc tgg att gcg att ctc ttt aaa aat gaa ctt gcc gcc     288
Ala Val Leu Leu Trp Ile Ala Ile Leu Phe Lys Asn Glu Leu Ala Ala
                85                  90                  95 ttg ctc gat aga ttt tta ccg aaa tta aaa ttt atc gtg aaa tgg att     336
Leu Leu Asp Arg Phe Leu Pro Lys Leu Lys Phe Ile Val Lys Trp Ile
            100                 105                 110 ttc gcc tgt gaa cgc att acc aac ccg ttg gaa ctg ttc ctg ttg ttc     384
Phe Ala Cys Glu Arg Ile Thr Asn Pro Leu Glu Leu Phe Leu Leu Phe
        115                 120                 125 ctt gcg gtg ttg cta ggc gct tat acc ggt ttc tta ttg tcg gcg tta     432
Leu Ala Val Leu Leu Gly Ala Tyr Thr Gly Phe Leu Leu Ser Ala Leu
```

```
                 130                 135                 140
atc agc tac ccg atg cta aac aat ccc gta ttg ccg gca tta ttc ctc      480
Ile Ser Tyr Pro Met Leu Asn Asn Pro Val Leu Pro Ala Leu Phe Leu
145                 150                 155                 160 gct tcg ggc acg tct tcc ggt atc gcg gcg gta ttc tta acc atc ctg      528
Ala Ser Gly Thr Ser Ser Gly Ile Ala Ala Val Phe Leu Thr Ile Leu
                165                 170                 175 att gtg ggc aaa tta aaa ggg cat tcc gac gaa gtg aat ttc atg cat      576
Ile Val Gly Lys Leu Lys Gly His Ser Asp Glu Val Asn Phe Met His
            180                 185                 190 aaa ttt gaa gtg ccg atc atg ctc gcc gaa ctc ttt tgc atc ggc tgc      624
Lys Phe Glu Val Pro Ile Met Leu Ala Glu Leu Phe Cys Ile Gly Cys
        195                 200                 205 ttc tt                                                                629
Phe

<210> SEQ ID NO 86
<211> LENGTH: 209
<212> TYPE: PRT
<213> ORGANISM: Actinobacillus actinomycetemcomitans

<400> SEQUENCE: 86

Ile Ser Ser Gly Ser Leu Leu Leu Ala Val Leu Tyr Lys Arg Asn Arg
1               5                   10                  15

Lys Pro Glu Lys Thr Ser Glu Asn Trp Ile Ile Arg Ser Ala Ala Ile
            20                  25                  30

Leu Ala Pro Gly Thr Val Ile Ile Gly Leu Leu Leu Ile Phe His
        35                  40                  45

Leu Ala Arg Pro Trp Thr Phe Trp Tyr Leu Met Phe Asn Tyr Gln Phe
    50                  55                  60

Asn Ser Val Met Ser Met Gly Val Leu Leu Phe Gln Ile Tyr Met Ala
65              70                  75                  80

Ala Val Leu Leu Trp Ile Ala Ile Leu Phe Lys Asn Glu Leu Ala Ala
                85                  90                  95

Leu Leu Asp Arg Phe Leu Pro Lys Leu Lys Phe Ile Val Lys Trp Ile
            100                 105                 110

Phe Ala Cys Glu Arg Ile Thr Asn Pro Leu Glu Leu Phe Leu Leu Phe
        115                 120                 125

Leu Ala Val Leu Leu Gly Ala Tyr Thr Gly Phe Leu Leu Ser Ala Leu
    130                 135                 140

Ile Ser Tyr Pro Met Leu Asn Asn Pro Val Leu Pro Ala Leu Phe Leu
145                 150                 155                 160

Ala Ser Gly Thr Ser Ser Gly Ile Ala Ala Val Phe Leu Thr Ile Leu
                165                 170                 175

Ile Val Gly Lys Leu Lys Gly His Ser Asp Glu Val Asn Phe Met His
            180                 185                 190

Lys Phe Glu Val Pro Ile Met Leu Ala Glu Leu Phe Cys Ile Gly Cys
        195                 200                 205

Phe

<210> SEQ ID NO 87
<211> LENGTH: 266
<212> TYPE: DNA
<213> ORGANISM: Actinobacillus actinomycetemcomitans
<220> FEATURE:
<221> NAME/KEY: CDS
<222> LOCATION: (1)..(264)
```

```
<400> SEQUENCE: 87 tgg gat gcc att gag aaa tgt att cag gaa tgg caa ccg gcg cgt att      48
Trp Asp Ala Ile Glu Lys Cys Ile Gln Glu Trp Gln Pro Ala Arg Ile
1               5                   10                  15 gtg gtc ggt ttg cca ctg aat atg gat ggt acg gaa cag ccc tta acg      96
Val Val Gly Leu Pro Leu Asn Met Asp Gly Thr Glu Gln Pro Leu Thr
            20                  25                  30 ttg cgt gcc aaa aag ttt gct aag cgt ttg cac gga cgt ttt aac gtg     144
Leu Arg Ala Lys Lys Phe Ala Lys Arg Leu His Gly Arg Phe Asn Val
        35                  40                  45 ccg gtg gat tta cag gac gaa cgt ctt acc acc acc gaa gcg cgt agc     192
Pro Val Asp Leu Gln Asp Glu Arg Leu Thr Thr Thr Glu Ala Arg Ser
    50                  55                  60 gaa att ttc agt cgt ggt ggt tat cgc gcc tta aat aaa agc aaa gtg     240
Glu Ile Phe Ser Arg Gly Gly Tyr Arg Ala Leu Asn Lys Ser Lys Val
65                  70                  75                  80 gac ggc att tcc gcc tgt ttg att tt                                   266
Asp Gly Ile Ser Ala Cys Leu Ile
                85

<210> SEQ ID NO 88
<211> LENGTH: 88
<212> TYPE: PRT
<213> ORGANISM: Actinobacillus actinomycetemcomitans

<400> SEQUENCE: 88

Trp Asp Ala Ile Glu Lys Cys Ile Gln Glu Trp Gln Pro Ala Arg Ile
1               5                   10                  15

Val Val Gly Leu Pro Leu Asn Met Asp Gly Thr Glu Gln Pro Leu Thr
            20                  25                  30

Leu Arg Ala Lys Lys Phe Ala Lys Arg Leu His Gly Arg Phe Asn Val
        35                  40                  45

Pro Val Asp Leu Gln Asp Glu Arg Leu Thr Thr Thr Glu Ala Arg Ser
    50                  55                  60

Glu Ile Phe Ser Arg Gly Gly Tyr Arg Ala Leu Asn Lys Ser Lys Val
65                  70                  75                  80

Asp Gly Ile Ser Ala Cys Leu Ile
                85

<210> SEQ ID NO 89
<211> LENGTH: 567
<212> TYPE: DNA
<213> ORGANISM: Actinobacillus actinomycetemcomitans
<220> FEATURE:
<221> NAME/KEY: CDS
<222> LOCATION: (1)..(567)

<400> SEQUENCE: 89 caa caa gta aaa gcg ccg gga gaa gcc aaa tcc gac gta tgg caa ttg      48
Gln Gln Val Lys Ala Pro Gly Glu Ala Lys Ser Asp Val Trp Gln Leu
1               5                   10                  15 gta gaa ttc tcc aaa tat ttc acc acc gat gaa atg tgg ccg gcg gaa      96
Val Glu Phe Ser Lys Tyr Phe Thr Thr Asp Glu Met Trp Pro Ala Glu
            20                  25                  30 att ctg gac aaa aat ccg gaa tac aaa ggc aaa acc tta tat gac gtg     144
Ile Leu Asp Lys Asn Pro Glu Tyr Lys Gly Lys Thr Leu Tyr Asp Val
        35                  40                  45 tta tac cgc aac ggt caa gta gat aaa ttc ccg tta agc gaa ttg gcg     192
Leu Tyr Arg Asn Gly Gln Val Asp Lys Phe Pro Leu Ser Glu Leu Ala
    50                  55                  60
```

-continued

```
gaa gga caa ttg aat gat gag tcc tat cac ttc ggt ttc tac ttg caa      240
Glu Gly Gln Leu Asn Asp Glu Ser Tyr His Phe Gly Phe Tyr Leu Gln
 65                  70                  75                  80 aaa ggc tta ttt gag gaa tac gcc tcc ttc ggt cgc ggt cac gga cat      288
Lys Gly Leu Phe Glu Glu Tyr Ala Ser Phe Gly Arg Gly His Gly His
                 85                  90                  95 gac ttg gca tcg ttc gat act tac cac aaa gca cgc ggt tta cgc tgg      336
Asp Leu Ala Ser Phe Asp Thr Tyr His Lys Ala Arg Gly Leu Arg Trp
            100                 105                 110 ccg gtg gtg gac ggc aaa gaa acc tta tgg cgt tat cgc gaa ggc tac      384
Pro Val Val Asp Gly Lys Glu Thr Leu Trp Arg Tyr Arg Glu Gly Tyr
        115                 120                 125 gac ccg tat gtc aaa gaa ggg gaa ggt gtg gcg ttc tac ggc tat ccg      432
Asp Pro Tyr Val Lys Glu Gly Glu Gly Val Ala Phe Tyr Gly Tyr Pro
    130                 135                 140 gat aaa aaa gcg att att ctt gcc gtg cct tat gag ccg cct gcg gaa      480
Asp Lys Lys Ala Ile Ile Leu Ala Val Pro Tyr Glu Pro Pro Ala Glu
145                 150                 155                 160 tca ccg gac gaa gaa tac gat ttg tgg tta tgt acc ggt cgc gtg ttg      528
Ser Pro Asp Glu Glu Tyr Asp Leu Trp Leu Cys Thr Gly Arg Val Leu
                165                 170                 175 gaa cac tgg cac acc ggc acc atg acc cgt cgt gta cca                  567
Glu His Trp His Thr Gly Thr Met Thr Arg Arg Val Pro
            180                 185
```

<210> SEQ ID NO 90
<211> LENGTH: 189
<212> TYPE: PRT
<213> ORGANISM: Actinobacillus actinomycetemcomitans

<400> SEQUENCE: 90

```
Gln Gln Val Lys Ala Pro Gly Glu Ala Lys Ser Asp Val Trp Gln Leu
1               5                   10                  15

Val Glu Phe Ser Lys Tyr Phe Thr Thr Asp Glu Met Trp Pro Ala Glu
                20                  25                  30

Ile Leu Asp Lys Asn Pro Glu Tyr Lys Gly Lys Thr Leu Tyr Asp Val
            35                  40                  45

Leu Tyr Arg Asn Gly Gln Val Asp Lys Phe Pro Leu Ser Glu Leu Ala
        50                  55                  60

Glu Gly Gln Leu Asn Asp Glu Ser Tyr His Phe Gly Phe Tyr Leu Gln
65                  70                  75                  80

Lys Gly Leu Phe Glu Glu Tyr Ala Ser Phe Gly Arg Gly His Gly His
                85                  90                  95

Asp Leu Ala Ser Phe Asp Thr Tyr His Lys Ala Arg Gly Leu Arg Trp
            100                 105                 110

Pro Val Val Asp Gly Lys Glu Thr Leu Trp Arg Tyr Arg Glu Gly Tyr
        115                 120                 125

Asp Pro Tyr Val Lys Glu Gly Glu Gly Val Ala Phe Tyr Gly Tyr Pro
    130                 135                 140

Asp Lys Lys Ala Ile Ile Leu Ala Val Pro Tyr Glu Pro Pro Ala Glu
145                 150                 155                 160

Ser Pro Asp Glu Glu Tyr Asp Leu Trp Leu Cys Thr Gly Arg Val Leu
                165                 170                 175

Glu His Trp His Thr Gly Thr Met Thr Arg Arg Val Pro
            180                 185
```

<210> SEQ ID NO 91
<211> LENGTH: 563

```
<212> TYPE: DNA
<213> ORGANISM: Actinobacillus actinomycetemcomitans
<220> FEATURE:
<221> NAME/KEY: CDS
<222> LOCATION: (1)..(561)

<400> SEQUENCE: 91 ccg aaa cct ttc tat ttt tcc gct gaa aaa gat ggc att ggt gta gaa      48
Pro Lys Pro Phe Tyr Phe Ser Ala Glu Lys Asp Gly Ile Gly Val Glu
1               5                   10                  15 att gcg ttg caa tgg aac gac ggt tac gcg gaa aac att tat tgt ttc      96
Ile Ala Leu Gln Trp Asn Asp Gly Tyr Ala Glu Asn Ile Tyr Cys Phe
                20                  25                  30 acc aac aac att ccg caa cgg gac ggc ggt acg cac tta gcc ggt ttc     144
Thr Asn Asn Ile Pro Gln Arg Asp Gly Gly Thr His Leu Ala Gly Phe
            35                  40                  45 cgt ggc gca atg acc cgc acc ttg aac aac tac atg gaa aac gaa ggc     192
Arg Gly Ala Met Thr Arg Thr Leu Asn Asn Tyr Met Glu Asn Glu Gly
50                  55                  60 tac acc aag aaa tcc aaa gtg gcg act tcc ggt gat gat gcc cgt gaa     240
Tyr Thr Lys Lys Ser Lys Val Ala Thr Ser Gly Asp Asp Ala Arg Glu
65                  70                  75                  80 ggc ttg gtg gcg gtg att tcc gtg aaa gta ccg gat ccg aaa ttc tct     288
Gly Leu Val Ala Val Ile Ser Val Lys Val Pro Asp Pro Lys Phe Ser
                85                  90                  95 tct caa aca aaa gac aaa ctg gtt tcc tcc gaa gtg aaa agt gcg gtg     336
Ser Gln Thr Lys Asp Lys Leu Val Ser Ser Glu Val Lys Ser Ala Val
            100                 105                 110 gaa tcc ctg atg aac gaa tat tta caa acc tat ttg ttg gaa aac ccg     384
Glu Ser Leu Met Asn Glu Tyr Leu Gln Thr Tyr Leu Leu Glu Asn Pro
        115                 120                 125 aac gat gta aaa atc atc gtg acc aaa att att gat gcc gcg cgt gcc     432
Asn Asp Val Lys Ile Ile Val Thr Lys Ile Ile Asp Ala Ala Arg Ala
130                 135                 140 cgt gaa gcc gcc cgc aaa gcc cgc gaa atg acc cgt cgt aaa ggc gcg     480
Arg Glu Ala Ala Arg Lys Ala Arg Glu Met Thr Arg Arg Lys Gly Ala
145                 150                 155                 160 ttg gat tta ggc ggc ttg ccg ggc aaa ttg gcg gat tgt cag gaa cgc     528
Leu Asp Leu Gly Gly Leu Pro Gly Lys Leu Ala Asp Cys Gln Glu Arg
                165                 170                 175 gat ccg gcg tta tcc gag ctt tac atc gtg gag gg                      563
Asp Pro Ala Leu Ser Glu Leu Tyr Ile Val Glu
            180                 185

<210> SEQ ID NO 92
<211> LENGTH: 187
<212> TYPE: PRT
<213> ORGANISM: Actinobacillus actinomycetemcomitans

<400> SEQUENCE: 92

Pro Lys Pro Phe Tyr Phe Ser Ala Glu Lys Asp Gly Ile Gly Val Glu
1               5                   10                  15

Ile Ala Leu Gln Trp Asn Asp Gly Tyr Ala Glu Asn Ile Tyr Cys Phe
                20                  25                  30

Thr Asn Asn Ile Pro Gln Arg Asp Gly Gly Thr His Leu Ala Gly Phe
            35                  40                  45

Arg Gly Ala Met Thr Arg Thr Leu Asn Asn Tyr Met Glu Asn Glu Gly
50                  55                  60

Tyr Thr Lys Lys Ser Lys Val Ala Thr Ser Gly Asp Asp Ala Arg Glu
65                  70                  75                  80
```

```
Gly Leu Val Ala Val Ile Ser Val Lys Val Pro Asp Pro Lys Phe Ser
                85                  90                  95

Ser Gln Thr Lys Asp Lys Leu Val Ser Ser Glu Val Lys Ser Ala Val
            100                 105                 110

Glu Ser Leu Met Asn Glu Tyr Leu Gln Thr Tyr Leu Leu Glu Asn Pro
        115                 120                 125

Asn Asp Val Lys Ile Ile Val Thr Lys Ile Ile Asp Ala Ala Arg Ala
130                 135                 140

Arg Glu Ala Ala Arg Lys Ala Arg Glu Met Thr Arg Lys Gly Ala
145                 150                 155                 160

Leu Asp Leu Gly Gly Leu Pro Gly Lys Leu Ala Asp Cys Gln Glu Arg
                165                 170                 175

Asp Pro Ala Leu Ser Glu Leu Tyr Ile Val Glu
            180                 185

<210> SEQ ID NO 93
<211> LENGTH: 627
<212> TYPE: DNA
<213> ORGANISM: Actinobacillus actinomycetemcomitans
<220> FEATURE:
<221> NAME/KEY: CDS
<222> LOCATION: (1)..(627)

<400> SEQUENCE: 93 aaa cag caa tta gcc gct gca ctt gcc cga caa gaa caa aaa caa att        48
Lys Gln Gln Leu Ala Ala Ala Leu Ala Arg Gln Glu Gln Lys Gln Ile
1               5                   10                  15 atc gtt tta caa aaa aag tta acg tct ttg tct tcc cta tcc cca caa        96
Ile Val Leu Gln Lys Lys Leu Thr Ser Leu Ser Ser Leu Ser Pro Gln
            20                  25                  30 cgt ctt gcg caa caa att cgg act acc gaa aaa att ctg acc cgt att       144
Arg Leu Ala Gln Gln Ile Arg Thr Thr Glu Lys Ile Leu Thr Arg Ile
        35                  40                  45 ttt aaa aca gag aaa aat ctg aca ccc aaa ttt att gat tac ctg tat       192
Phe Lys Thr Glu Lys Asn Leu Thr Pro Lys Phe Ile Asp Tyr Leu Tyr
    50                  55                  60 ttt gag cca att gaa acg gct gat gac acc tta atg cag gaa atg aaa       240
Phe Glu Pro Ile Glu Thr Ala Asp Asp Thr Leu Met Gln Glu Met Lys
65                  70                  75                  80 aaa aat ctt ttg atc tct ttc ttg gca aat gaa cgc gct caa atc tat       288
Lys Asn Leu Leu Ile Ser Phe Leu Ala Asn Glu Arg Ala Gln Ile Tyr
                85                  90                  95 att aaa gac atg cca aac gct aat caa ttt gtt cag ctt tta aca gaa       336
Ile Lys Asp Met Pro Asn Ala Asn Gln Phe Val Gln Leu Leu Thr Glu
            100                 105                 110 aaa gga gca aag act acg caa ata tcc gta ttg gca gaa cct gct aaa       384
Lys Gly Ala Lys Thr Thr Gln Ile Ser Val Leu Ala Glu Pro Ala Lys
        115                 120                 125 acc att ttc cag cga atc cgc gaa caa atg tac caa gat ttt cct aat       432
Thr Ile Phe Gln Arg Ile Arg Glu Gln Met Tyr Gln Asp Phe Pro Asn
    130                 135                 140 aaa aaa cag ttt act atc act gaa aat cga gta agt gtt att gcc cct       480
Lys Lys Gln Phe Thr Ile Thr Glu Asn Arg Val Ser Val Ile Ala Pro
145                 150                 155                 160 tcc tcc gtt att aag cca cgc ctt gcc ttg gca gct gca att ttt gat       528
Ser Ser Val Ile Lys Pro Arg Leu Ala Leu Ala Ala Ala Ile Phe Asp
                165                 170                 175 cag cag ttt aaa ggg gtt gaa gtt gat gat ttt tct tac ttg gat caa       576
Gln Gln Phe Lys Gly Val Glu Val Asp Asp Phe Ser Tyr Leu Asp Gln
            180                 185                 190
```

```
ccg cgt gaa aat ttg caa cac aat aat gat aca acc cgt tat aaa acc    624
Pro Arg Glu Asn Leu Gln His Asn Asn Asp Thr Thr Arg Tyr Lys Thr
        195                 200                 205 ttt                                                                 627
Phe
```

<210> SEQ ID NO 94
<211> LENGTH: 209
<212> TYPE: PRT
<213> ORGANISM: Actinobacillus actinomycetemcomitans

<400> SEQUENCE: 94

```
Lys Gln Gln Leu Ala Ala Ala Leu Ala Arg Gln Glu Gln Lys Gln Ile
1               5                   10                  15

Ile Val Leu Gln Lys Lys Leu Thr Ser Leu Ser Ser Leu Ser Pro Gln
            20                  25                  30

Arg Leu Ala Gln Gln Ile Arg Thr Thr Glu Lys Ile Leu Thr Arg Ile
        35                  40                  45

Phe Lys Thr Glu Lys Asn Leu Thr Pro Lys Phe Ile Asp Tyr Leu Tyr
    50                  55                  60

Phe Glu Pro Ile Glu Thr Ala Asp Asp Thr Leu Met Gln Glu Met Lys
65                  70                  75                  80

Lys Asn Leu Leu Ile Ser Phe Leu Ala Asn Glu Arg Ala Gln Ile Tyr
                85                  90                  95

Ile Lys Asp Met Pro Asn Ala Asn Gln Phe Val Gln Leu Leu Thr Glu
            100                 105                 110

Lys Gly Ala Lys Thr Thr Gln Ile Ser Val Leu Ala Glu Pro Ala Lys
        115                 120                 125

Thr Ile Phe Gln Arg Ile Arg Glu Gln Met Tyr Gln Asp Phe Pro Asn
    130                 135                 140

Lys Lys Gln Phe Thr Ile Thr Glu Asn Arg Val Ser Val Ile Ala Pro
145                 150                 155                 160

Ser Ser Val Ile Lys Pro Arg Leu Ala Leu Ala Ala Ile Phe Asp
                165                 170                 175

Gln Gln Phe Lys Gly Val Glu Val Asp Asp Phe Ser Tyr Leu Asp Gln
            180                 185                 190

Pro Arg Glu Asn Leu Gln His Asn Asn Asp Thr Thr Arg Tyr Lys Thr
        195                 200                 205

Phe
```

<210> SEQ ID NO 95
<211> LENGTH: 270
<212> TYPE: DNA
<213> ORGANISM: Actinobacillus actinomycetemcomitans
<220> FEATURE:
<221> NAME/KEY: CDS
<222> LOCATION: (1)..(270)

<400> SEQUENCE: 95

```
tct gac aat acg caa tat ttt tgc ccg gcg gga tta agc gag gag cgt    48
Ser Asp Asn Thr Gln Tyr Phe Cys Pro Ala Gly Leu Ser Glu Glu Arg
1               5                   10                  15 gaa cag gag ctc cgc cgt ttg gta aaa cag gcc tat gat gtg gtg ggc    96
Glu Gln Glu Leu Arg Arg Leu Val Lys Gln Ala Tyr Asp Val Val Gly
            20                  25                  30 tgt cgt ggt tgg agc cgt att gat gtg atg gcg gat gcg gaa gga aag   144
Cys Arg Gly Trp Ser Arg Ile Asp Val Met Ala Asp Ala Glu Gly Lys
        35                  40                  45
```

```
ttc cgt ttg gtg gaa gtt aat acc aac cct ggc atg acc agc cac agt    192
Phe Arg Leu Val Glu Val Asn Thr Asn Pro Gly Met Thr Ser His Ser
     50                  55                  60 tta ttc ccg aaa tcg gcg gca acg gtc ggc tat tct ttt gcg cag ttg    240
Leu Phe Pro Lys Ser Ala Ala Thr Val Gly Tyr Ser Phe Ala Gln Leu
65                  70                  75                  80 gtt gag aaa att tta gag ttg agc gcg gaa                            270
Val Glu Lys Ile Leu Glu Leu Ser Ala Glu
                 85                  90

<210> SEQ ID NO 96
<211> LENGTH: 90
<212> TYPE: PRT
<213> ORGANISM: Actinobacillus actinomycetemcomitans

<400> SEQUENCE: 96

Ser Asp Asn Thr Gln Tyr Phe Cys Pro Ala Gly Leu Ser Glu Glu Arg
1               5                  10                  15

Glu Gln Glu Leu Arg Arg Leu Val Lys Gln Ala Tyr Asp Val Val Gly
             20                  25                  30

Cys Arg Gly Trp Ser Arg Ile Asp Val Met Ala Asp Ala Glu Gly Lys
         35                  40                  45

Phe Arg Leu Val Glu Val Asn Thr Asn Pro Gly Met Thr Ser His Ser
     50                  55                  60

Leu Phe Pro Lys Ser Ala Ala Thr Val Gly Tyr Ser Phe Ala Gln Leu
65                  70                  75                  80

Val Glu Lys Ile Leu Glu Leu Ser Ala Glu
                 85                  90

<210> SEQ ID NO 97
<211> LENGTH: 379
<212> TYPE: DNA
<213> ORGANISM: Actinobacillus actinomycetemcomitans
<220> FEATURE:
<221> NAME/KEY: CDS
<222> LOCATION: (1)..(378)

<400> SEQUENCE: 97 ggg gaa tat ttc ggt cct tat ccg aat gcc ggt gca gtg cgc gaa acc    48
Gly Glu Tyr Phe Gly Pro Tyr Pro Asn Ala Gly Ala Val Arg Glu Thr
1               5                  10                  15 ctg tct tta tta caa aaa ctg ttc ccc att cgg cag tgt gaa aac tcc    96
Leu Ser Leu Leu Gln Lys Leu Phe Pro Ile Arg Gln Cys Glu Asn Ser
             20                  25                  30 gtg tat aac aac cgt tcg cgc ccc tgt ttg cag tat caa atc ggg cgt   144
Val Tyr Asn Asn Arg Ser Arg Pro Cys Leu Gln Tyr Gln Ile Gly Arg
         35                  40                  45 tgt ctg gcg cct tgc gta aag ggc tat gtg acc gat gaa gcc tat gcg   192
Cys Leu Ala Pro Cys Val Lys Gly Tyr Val Thr Asp Glu Ala Tyr Ala
     50                  55                  60 cag cag gtc aat ttc gcc cgc ttg ttt tta caa gga aaa gat caa cag   240
Gln Gln Val Asn Phe Ala Arg Leu Phe Leu Gln Gly Lys Asp Gln Gln
65                  70                  75                  80 gtg ctg gat cat ttg gtg aag caa atg gaa cag gca agt cag caa ctg   288
Val Leu Asp His Leu Val Lys Gln Met Glu Gln Ala Ser Gln Gln Leu
                 85                  90                  95 aat ttt gaa gaa gcg gca cgc gtt cgt gat caa att cag gca gtg cgg   336
Asn Phe Glu Glu Ala Ala Arg Val Arg Asp Gln Ile Gln Ala Val Arg
            100                 105                 110 gca gta att gaa aaa caa ttt gtc gcc aac gat cgc cat gac g         379
```

<210> SEQ ID NO 98
<211> LENGTH: 126
<212> TYPE: PRT
<213> ORGANISM: Actinobacillus actinomycetemcomitans

<400> SEQUENCE: 98

```
Gly Glu Tyr Phe Gly Pro Tyr Pro Asn Ala Gly Ala Val Arg Glu Thr
1               5                   10                  15

Leu Ser Leu Leu Gln Lys Leu Phe Pro Ile Arg Gln Cys Glu Asn Ser
            20                  25                  30

Val Tyr Asn Asn Arg Ser Arg Pro Cys Leu Gln Tyr Gln Ile Gly Arg
        35                  40                  45

Cys Leu Ala Pro Cys Val Lys Gly Tyr Val Thr Asp Glu Ala Tyr Ala
    50                  55                  60

Gln Gln Val Asn Phe Ala Arg Leu Phe Leu Gly Lys Asp Gln Gln
65                  70                  75                  80

Val Leu Asp His Leu Val Lys Gln Met Glu Gln Ala Ser Gln Gln Leu
                85                  90                  95

Asn Phe Glu Glu Ala Ala Arg Val Arg Asp Gln Ile Gln Ala Val Arg
            100                 105                 110

Ala Val Ile Glu Lys Gln Phe Val Ala Asn Asp Arg His Asp
        115                 120                 125
```

<210> SEQ ID NO 99
<211> LENGTH: 625
<212> TYPE: DNA
<213> ORGANISM: Actinobacillus actinomycetemcomitans
<220> FEATURE:
<221> NAME/KEY: CDS
<222> LOCATION: (1)..(624)

<400> SEQUENCE: 99

```
gca aaa acc tta gat ttt cag tcc gca ggg ccg gaa aaa ctc ccg aaa      48
Ala Lys Thr Leu Asp Phe Gln Ser Ala Gly Pro Glu Lys Leu Pro Lys
1               5                   10                  15 ttt caa ccg cac ttt ttg gcg caa agc caa caa tta atc gac att tgc      96
Phe Gln Pro His Phe Leu Ala Gln Ser Gln Gln Leu Ile Asp Ile Cys
            20                  25                  30 cgc cgc ctg aca ccg gcg gat att gct tcg ctc atg tct atc agc gac     144
Arg Arg Leu Thr Pro Ala Asp Ile Ala Ser Leu Met Ser Ile Ser Asp
        35                  40                  45 aaa ctt gcc ggg ttg aat gcc gca cgt ttc gcc gaa tgg cag ttg gaa     192
Lys Leu Ala Gly Leu Asn Ala Ala Arg Phe Ala Glu Trp Gln Leu Glu
    50                  55                  60 cat aac gaa cac aat gcc aaa gcg gcg gtg tat gcc ttt aga ggc gat     240
His Asn Glu His Asn Ala Lys Ala Ala Val Tyr Ala Phe Arg Gly Asp
65                  70                  75                  80 gtt tac acc ggc ttg gac gtg gat tcc tta agc aat gac gat atg ttg     288
Val Tyr Thr Gly Leu Asp Val Asp Ser Leu Ser Asn Asp Asp Met Leu
                85                  90                  95 ttt gca caa cag cat ttg cgc att ttg tcc ggg tta tat ggg ctg tta     336
Phe Ala Gln Gln His Leu Arg Ile Leu Ser Gly Leu Tyr Gly Leu Leu
            100                 105                 110 acg ccg ctg gat ttg att cag cct tat cgt ttg gaa atg ggc acc aaa     384
Thr Pro Leu Asp Leu Ile Gln Pro Tyr Arg Leu Glu Met Gly Thr Lys
        115                 120                 125 tta gcc aac ggc aaa ggc gcc gat ttg tat gcc ttt tgg cat ggt ttg     432
```

```
Leu Ala Asn Gly Lys Gly Ala Asp Leu Tyr Ala Phe Trp His Gly Leu
    130                 135                 140 gtg atg cag gcg tta caa cag gcg att gat gaa caa cag gac gat gtt      480
Val Met Gln Ala Leu Gln Gln Ala Ile Asp Glu Gln Gln Asp Asp Val
145                 150                 155                 160 ttg gtg aat ctg gcg tcc gat gaa tat tat aaa tcg gta caa ccg tcg      528
Leu Val Asn Leu Ala Ser Asp Glu Tyr Tyr Lys Ser Val Gln Pro Ser
                165                 170                 175 aat tta acg gcg caa atc att aaa ccg gtg ttc ctg gat aat aaa aac      576
Asn Leu Thr Ala Gln Ile Ile Lys Pro Val Phe Leu Asp Asn Lys Asn
            180                 185                 190 ggc aaa tat aaa att atc agt ttc tac gcg aaa aaa gcc cgc ggt tta a    625
Gly Lys Tyr Lys Ile Ile Ser Phe Tyr Ala Lys Lys Ala Arg Gly Leu
        195                 200                 205
```

<210> SEQ ID NO 100
<211> LENGTH: 208
<212> TYPE: PRT
<213> ORGANISM: Actinobacillus actinomycetemcomitans

<400> SEQUENCE: 100

```
Ala Lys Thr Leu Asp Phe Gln Ser Ala Gly Pro Glu Lys Leu Pro Lys
1               5                   10                  15

Phe Gln Pro His Phe Leu Ala Gln Ser Gln Gln Leu Ile Asp Ile Cys
            20                  25                  30

Arg Arg Leu Thr Pro Ala Asp Ile Ala Ser Leu Met Ser Ile Ser Asp
        35                  40                  45

Lys Leu Ala Gly Leu Asn Ala Ala Arg Phe Ala Glu Trp Gln Leu Glu
    50                  55                  60

His Asn Glu His Asn Ala Lys Ala Ala Val Tyr Ala Phe Arg Gly Asp
65                  70                  75                  80

Val Tyr Thr Gly Leu Asp Val Asp Ser Leu Ser Asn Asp Asp Met Leu
                85                  90                  95

Phe Ala Gln Gln His Leu Arg Ile Leu Ser Gly Leu Tyr Gly Leu Leu
            100                 105                 110

Thr Pro Leu Asp Leu Ile Gln Pro Tyr Arg Leu Glu Met Gly Thr Lys
        115                 120                 125

Leu Ala Asn Gly Lys Gly Ala Asp Leu Tyr Ala Phe Trp His Gly Leu
    130                 135                 140

Val Met Gln Ala Leu Gln Gln Ala Ile Asp Glu Gln Gln Asp Asp Val
145                 150                 155                 160

Leu Val Asn Leu Ala Ser Asp Glu Tyr Tyr Lys Ser Val Gln Pro Ser
                165                 170                 175

Asn Leu Thr Ala Gln Ile Ile Lys Pro Val Phe Leu Asp Asn Lys Asn
            180                 185                 190

Gly Lys Tyr Lys Ile Ile Ser Phe Tyr Ala Lys Lys Ala Arg Gly Leu
        195                 200                 205
```

<210> SEQ ID NO 101
<211> LENGTH: 500
<212> TYPE: DNA
<213> ORGANISM: Actinobacillus actinomycetemcomitans
<220> FEATURE:
<221> NAME/KEY: CDS
<222> LOCATION: (1)..(498)

<400> SEQUENCE: 101

```
cac tgc ttt ata ccg cca tcg cta tgg ctt gct tac cgg cgt atg ccg      48
His Cys Phe Ile Pro Pro Ser Leu Trp Leu Ala Tyr Arg Arg Met Pro
```

```
                1               5                   10                  15
aag aag ttt tta ccc ttg ggc aaa ttg agg tga ttg ccg ata gat caa      96
Lys Lys Phe Leu Pro Leu Gly Lys Leu Arg     Leu Pro Ile Asp Gln
             20                  25                  30 cgg att taa gca cca cac gca ttg aac agg ctg act tac aga aaa aca     144
Arg Ile     Ala Pro His Ala Leu Asn Arg Leu Thr Tyr Arg Lys Thr
                 35                  40                  45 atc aaa cca atg tcg ccg agg tgg cga aaa cca cac cgg gcg tat ttt     192
Ile Lys Pro Met Ser Pro Arg Trp Arg Lys Pro His Arg Ala Tyr Phe
             50                  55                  60 tgg atc gta gcg gcg cac gca atg aac ata att tgt tgg tac gcg gat     240
Trp Ile Val Ala Ala His Ala Met Asn Ile Ile Cys Trp Tyr Ala Asp
             65                  70                  75 tta aag cca atc gcg tgc cag tgt tta ttg acg gca ttc cgg tgt atg     288
Leu Lys Pro Ile Ala Cys Gln Cys Leu Leu Thr Ala Phe Arg Cys Met
             80                  85                  90 tgc cct atg acg gca ata tgg aca ttg gtc gct tca cca cct tcg att     336
Cys Pro Met Thr Ala Ile Trp Thr Leu Val Ala Ser Pro Pro Ser Ile
95                  100                 105                 110 tat ccc gca ttg ata ttt cca agg gcg caa gtt ccg tgc ttt atg gcg     384
Tyr Pro Ala Leu Ile Phe Pro Arg Ala Gln Val Pro Cys Phe Met Ala
                115                 120                 125 cca aca cgc tgg gcg gtg cgg taa atc tca tta cgc aaa aac cga cca     432
Pro Thr Arg Trp Ala Val Arg     Ile Ser Leu Arg Lys Asn Arg Pro
            130                 135                 140 aac cgt ttg aag gca cta tcg gct acg gat ttg ctc acg gta gaa gcg     480
Asn Arg Leu Lys Ala Leu Ser Ala Thr Asp Leu Leu Thr Val Glu Ala
            145                 150                 155 gca gca cgg gca cca atc aa                                          500
Ala Ala Arg Ala Pro Ile
            160

<210> SEQ ID NO 102
<211> LENGTH: 26
<212> TYPE: PRT
<213> ORGANISM: Actinobacillus actinomycetemcomitans

<400> SEQUENCE: 102

His Cys Phe Ile Pro Pro Ser Leu Trp Leu Ala Tyr Arg Arg Met Pro
1               5                   10                  15

Lys Lys Phe Leu Pro Leu Gly Lys Leu Arg
            20                  25

<210> SEQ ID NO 103
<211> LENGTH: 7
<212> TYPE: PRT
<213> ORGANISM: Actinobacillus actinomycetemcomitans

<400> SEQUENCE: 103

Leu Pro Ile Asp Gln Arg Ile
1               5

<210> SEQ ID NO 104
<211> LENGTH: 100
<212> TYPE: PRT
<213> ORGANISM: Actinobacillus actinomycetemcomitans

<400> SEQUENCE: 104

Ala Pro His Ala Leu Asn Arg Leu Thr Tyr Arg Lys Thr Ile Lys Pro
1               5                   10                  15

Met Ser Pro Arg Trp Arg Lys Pro His Arg Ala Tyr Phe Trp Ile Val
```

-continued

```
                    20                  25                  30
Ala Ala His Ala Met Asn Ile Ile Cys Trp Tyr Ala Asp Leu Lys Pro
        35                  40                  45

Ile Ala Cys Gln Cys Leu Leu Thr Ala Phe Arg Cys Met Cys Pro Met
 50                  55                  60

Thr Ala Ile Trp Thr Leu Val Ala Ser Pro Ser Ile Tyr Pro Ala
 65                  70                  75                  80

Leu Ile Phe Pro Arg Ala Gln Val Pro Cys Phe Met Ala Pro Thr Arg
                85                  90                  95

Trp Ala Val Arg
            100

<210> SEQ ID NO 105
<211> LENGTH: 30
<212> TYPE: PRT
<213> ORGANISM: Actinobacillus actinomycetemcomitans

<400> SEQUENCE: 105

Ile Ser Leu Arg Lys Asn Arg Pro Asn Arg Leu Lys Ala Leu Ser Ala
1               5                  10                  15

Thr Asp Leu Leu Thr Val Glu Ala Ala Arg Ala Pro Ile
            20                  25                  30

<210> SEQ ID NO 106
<211> LENGTH: 303
<212> TYPE: DNA
<213> ORGANISM: Actinobacillus actinomycetemcomitans
<220> FEATURE:
<221> NAME/KEY: CDS
<222> LOCATION: (1)..(303)

<400> SEQUENCE: 106 gca ttc ttc tcc tta ttt tcc att atc atg agc ggc aga tta aaa gaa      48
Ala Phe Phe Ser Leu Phe Ser Ile Ile Met Ser Gly Arg Leu Lys Glu
1               5                  10                  15 ttg ggc gaa cac tta aac gaa acc ggc tct ttc aaa gtg ggc atg att      96
Leu Gly Glu His Leu Asn Glu Thr Gly Ser Phe Lys Val Gly Met Ile
            20                  25                  30 tgg aaa gct ttt atc gtc atc acc acc ggt gta ctg gct ttc atg cta     144
Trp Lys Ala Phe Ile Val Ile Thr Thr Gly Val Leu Ala Phe Met Leu
        35                  40                  45 tac aaa gaa gca ggc aaa gtg ctc acc aaa ggc tac gaa ggc tat ccg     192
Tyr Lys Glu Ala Gly Lys Val Leu Thr Lys Gly Tyr Glu Gly Tyr Pro
 50                  55                  60 gac cgg ttc gtc aac acc ttc ggc tgg ggc atg gca atc gct ttg gtg     240
Asp Arg Phe Val Asn Thr Phe Gly Trp Gly Met Ala Ile Ala Leu Val
 65                  70                  75                  80 atc atc gca ttc ctg ctt tcc cgc ctg ccg tgg aaa cac tta acg caa     288
Ile Ile Ala Phe Leu Leu Ser Arg Leu Pro Trp Lys His Leu Thr Gln
                85                  90                  95 aca caa gga gaa aaa                                                  303
Thr Gln Gly Glu Lys
            100

<210> SEQ ID NO 107
<211> LENGTH: 101
<212> TYPE: PRT
<213> ORGANISM: Actinobacillus actinomycetemcomitans

<400> SEQUENCE: 107

Ala Phe Phe Ser Leu Phe Ser Ile Ile Met Ser Gly Arg Leu Lys Glu
```

```
                1               5                   10                  15
            Leu Gly Glu His Leu Asn Glu Thr Gly Ser Phe Lys Val Gly Met Ile
                            20                  25                  30

Trp Lys Ala Phe Ile Val Ile Thr Thr Gly Val Leu Ala Phe Met Leu
                        35                  40                  45

Tyr Lys Glu Ala Gly Lys Val Leu Thr Lys Gly Tyr Glu Gly Tyr Pro
                    50                  55                  60

Asp Arg Phe Val Asn Thr Phe Gly Trp Gly Met Ala Ile Ala Leu Val
            65                  70                  75                  80

Ile Ile Ala Phe Leu Leu Ser Arg Leu Pro Trp Lys His Leu Thr Gln
                            85                  90                  95

Thr Gln Gly Glu Lys
                        100

<210> SEQ ID NO 108
<211> LENGTH: 465
<212> TYPE: DNA
<213> ORGANISM: Actinobacillus actinomycetemcomitans
<220> FEATURE:
<221> NAME/KEY: CDS
<222> LOCATION: (1)..(465)

<400> SEQUENCE: 108 gtg ttt ata acc gct tgc aac aat ata aac ttc ccg aga tcg gtc tcg        48
Val Phe Ile Thr Ala Cys Asn Asn Ile Asn Phe Pro Arg Ser Val Ser
1               5                   10                  15 gga ggc ttc agg ttt acg aac ttt gac tac act aaa cag aga acg gat       96
Gly Gly Phe Arg Phe Thr Asn Phe Asp Tyr Thr Lys Gln Arg Thr Asp
                20                  25                  30 ctc ttt taa gta ttc atc aaa acc ttc ccc ctg aaa aac ttt tac tac      144
Leu Phe     Val Phe Ile Lys Thr Phe Pro Leu Lys Asn Phe Tyr Tyr
            35                  40                  45 aaa act tcc ttt att agc gag aat ctg ctt gca cat atc aag cgc aag      192
Lys Thr Ser Phe Ile Ser Glu Asn Leu Leu Ala His Ile Lys Arg Lys
        50                  55                  60 ttc tac caa ata cat cgc acg cgg aat atc cac tga tgg cat ccc act      240
Phe Tyr Gln Ile His Arg Thr Arg Asn Ile His     Trp His Pro Thr
65                  70                  75 gaa att cgg tgc cat atc tga cat cac cac atc tac ttt gcc ttc acc      288
Glu Ile Arg Cys His Ile     His His His Ile Tyr Phe Ala Phe Thr
            80                  85                  90 gac ccg ctc caa taa aat gtt taa cac att ttc atc acg gaa atc gcc      336
Asp Pro Leu Gln     Asn Val     His Ile Phe Ile Thr Glu Ile Ala
        95              100                 105 ttg tag aaa atc cac gcc tac aat agg atc cat ttc cag aag atc aca      384
Leu     Lys Ile His Ala Tyr Asn Arg Ile His Phe Gln Lys Ile Thr
            110                 115                 120 ggc aat aat ccg tcc att gcg ccc aat ttg gct tac cac ata ctg cga      432
Gly Asn Asn Pro Ser Ile Ala Pro Asn Leu Ala Tyr His Ile Leu Arg
        125                 130                 135 cca tcc gcc cgg cgc tgc acc taa atc aac cac                          465
Pro Ser Ala Arg Arg Cys Thr     Ile Asn His
        140                 145

<210> SEQ ID NO 109
<211> LENGTH: 34
<212> TYPE: PRT
<213> ORGANISM: Actinobacillus actinomycetemcomitans

<400> SEQUENCE: 109
```

-continued

Val Phe Ile Thr Ala Cys Asn Asn Ile Asn Phe Pro Arg Ser Val Ser
1               5                   10                  15

Gly Gly Phe Arg Phe Thr Asn Phe Asp Tyr Thr Lys Gln Arg Thr Asp
            20                  25                  30

Leu Phe

<210> SEQ ID NO 110
<211> LENGTH: 40
<212> TYPE: PRT
<213> ORGANISM: Actinobacillus actinomycetemcomitans

<400> SEQUENCE: 110

Val Phe Ile Lys Thr Phe Pro Leu Lys Asn Phe Tyr Tyr Lys Thr Ser
1               5                   10                  15

Phe Ile Ser Glu Asn Leu Leu Ala His Ile Lys Arg Lys Phe Tyr Gln
            20                  25                  30

Ile His Arg Thr Arg Asn Ile His
        35                  40

<210> SEQ ID NO 111
<211> LENGTH: 10
<212> TYPE: PRT
<213> ORGANISM: Actinobacillus actinomycetemcomitans

<400> SEQUENCE: 111

Trp His Pro Thr Glu Ile Arg Cys His Ile
1               5                   10

<210> SEQ ID NO 112
<211> LENGTH: 13
<212> TYPE: PRT
<213> ORGANISM: Actinobacillus actinomycetemcomitans

<400> SEQUENCE: 112

His His His Ile Tyr Phe Ala Phe Thr Asp Pro Leu Gln
1               5                   10

<210> SEQ ID NO 113
<211> LENGTH: 9
<212> TYPE: PRT
<213> ORGANISM: Actinobacillus actinomycetemcomitans

<400> SEQUENCE: 113

His Ile Phe Ile Thr Glu Ile Ala Leu
1               5

<210> SEQ ID NO 114
<211> LENGTH: 37
<212> TYPE: PRT
<213> ORGANISM: Actinobacillus actinomycetemcomitans

<400> SEQUENCE: 114

Lys Ile His Ala Tyr Asn Arg Ile His Phe Gln Lys Ile Thr Gly Asn
1               5                   10                  15

Asn Pro Ser Ile Ala Pro Asn Leu Ala Tyr His Ile Leu Arg Pro Ser
            20                  25                  30

Ala Arg Arg Cys Thr
        35

<210> SEQ ID NO 115
<211> LENGTH: 630
<212> TYPE: DNA

<213> ORGANISM: Actinobacillus actinomycetemcomitans
<220> FEATURE:
<221> NAME/KEY: CDS
<222> LOCATION: (1)..(630)

<400> SEQUENCE: 115

| | | | | | | | | | | | | | | | | |
|---|---|---|---|---|---|---|---|---|---|---|---|---|---|---|---|---|
| gaa | ctg | ggc | tgg | gga | ggt | tgg | tgg | ttc | tgg | gat | ccg | gtg | gaa | aat | gcg | 48 |
| Glu | Leu | Gly | Trp | Gly | Gly | Trp | Trp | Phe | Trp | Asp | Pro | Val | Glu | Asn | Ala | |
| 1 | | | | 5 | | | | | 10 | | | | | 15 | | |
| tcg | ctc | atg | ccg | tgg | ttg | ctc | ggc | ttg | gca | ttg | ttg | cac | agt | tta | atc | 96 |
| Ser | Leu | Met | Pro | Trp | Leu | Leu | Gly | Leu | Ala | Leu | Leu | His | Ser | Leu | Ile | |
| | | | 20 | | | | | 25 | | | | | 30 | | | |
| gtc | agc | gaa | aaa | cgc | gga | att | ttt | aat | tac | tgg | acg | acc | tta | ttt | tcc | 144 |
| Val | Ser | Glu | Lys | Arg | Gly | Ile | Phe | Asn | Tyr | Trp | Thr | Thr | Leu | Phe | Ser | |
| | | 35 | | | | | 40 | | | | | 45 | | | | |
| ttg | ttg | gca | ttt | gcc | ttc | agc | gta | tta | ggc | acg | ttt | atc | gtg | cgc | tcc | 192 |
| Leu | Leu | Ala | Phe | Ala | Phe | Ser | Val | Leu | Gly | Thr | Phe | Ile | Val | Arg | Ser | |
| | 50 | | | | | 55 | | | | | 60 | | | | | |
| ggc | gcg | ctt | acc | tcc | gta | cac | gct | ttc | gct | gtg | gac | agc | caa | cgc | ggc | 240 |
| Gly | Ala | Leu | Thr | Ser | Val | His | Ala | Phe | Ala | Val | Asp | Ser | Gln | Arg | Gly | |
| 65 | | | | | 70 | | | | | 75 | | | | | 80 | |
| tcg | gca | tta | tta | ctg | att | ttc | ttc | ctg | ctc | acc | gtg | ggt | tct | ctc | ggt | 288 |
| Ser | Ala | Leu | Leu | Leu | Ile | Phe | Phe | Leu | Leu | Thr | Val | Gly | Ser | Leu | Gly | |
| | | | | 85 | | | | | 90 | | | | | 95 | | |
| tta | ttc | gcg | ttc | aaa | gcc | aat | ttg | cag | caa | cgc | cgc | gtc | aaa | tta | acg | 336 |
| Leu | Phe | Ala | Phe | Lys | Ala | Asn | Leu | Gln | Gln | Arg | Arg | Val | Lys | Leu | Thr | |
| | | | 100 | | | | | 105 | | | | | 110 | | | |
| ctg | ctt | tcc | aaa | gaa | agt | gcg | gtg | ctt | ttt | ttg | aat | gtt | tta | ttg | agt | 384 |
| Leu | Leu | Ser | Lys | Glu | Ser | Ala | Val | Leu | Phe | Leu | Asn | Val | Leu | Leu | Ser | |
| | | | 115 | | | | | 120 | | | | | 125 | | | |
| atc | gcc | acc | gtt | agc | acc | ttt | ctc | ggc | acc | ttt | tat | ccc | atg | ctg | ttc | 432 |
| Ile | Ala | Thr | Val | Ser | Thr | Phe | Leu | Gly | Thr | Phe | Tyr | Pro | Met | Leu | Phe | |
| | | 130 | | | | | 135 | | | | | 140 | | | | |
| caa | gcc | atg | aat | tgg | ggt | tcc | att | tcc | gtc | ggt | gcg | cct | tat | ttc | aac | 480 |
| Gln | Ala | Met | Asn | Trp | Gly | Ser | Ile | Ser | Val | Gly | Ala | Pro | Tyr | Phe | Asn | |
| 145 | | | | | 150 | | | | | 155 | | | | | 160 | |
| agt | att | ttc | ttg | ccg | ctg | ctt | acg | ctg | att | tta | atc | gcc | atg | gtg | ttt | 528 |
| Ser | Ile | Phe | Leu | Pro | Leu | Leu | Thr | Leu | Ile | Leu | Ile | Ala | Met | Val | Phe | |
| | | | | 165 | | | | | 170 | | | | | 175 | | |
| tcc | ctc | ggc | ttg | cac | tgg | gcg | aag | gcg | gac | aaa | ggc | att | ttg | ttt | aaa | 576 |
| Ser | Leu | Gly | Leu | His | Trp | Ala | Lys | Ala | Asp | Lys | Gly | Ile | Leu | Phe | Lys | |
| | | | 180 | | | | | 185 | | | | | 190 | | | |
| cgc | gcg | gcg | tta | cta | ccg | tct | ttg | ttg | atc | gct | tat | ttt | atg | att | | 624 |
| Arg | Ala | Ala | Leu | Leu | Leu | Pro | Ser | Leu | Leu | Ile | Ala | Tyr | Phe | Met | Ile | |
| | | | 195 | | | | | 200 | | | | | 205 | | | |
| cgt | cag | | | | | | | | | | | | | | | 630 |
| Arg | Gln | | | | | | | | | | | | | | | |
| | 210 | | | | | | | | | | | | | | | |

<210> SEQ ID NO 116
<211> LENGTH: 210
<212> TYPE: PRT
<213> ORGANISM: Actinobacillus actinomycetemcomitans

<400> SEQUENCE: 116

Glu Leu Gly Trp Gly Gly Trp Trp Phe Trp Asp Pro Val Glu Asn Ala
1               5                   10                  15

Ser Leu Met Pro Trp Leu Leu Gly Leu Ala Leu Leu His Ser Leu Ile
            20                  25                  30

Val Ser Glu Lys Arg Gly Ile Phe Asn Tyr Trp Thr Thr Leu Phe Ser
        35                  40                  45

-continued

```
Leu Leu Ala Phe Ala Phe Ser Val Leu Gly Thr Phe Ile Val Arg Ser
 50                  55                  60

Gly Ala Leu Thr Ser Val His Ala Phe Ala Val Asp Ser Gln Arg Gly
 65                  70                  75                  80

Ser Ala Leu Leu Leu Ile Phe Phe Leu Leu Thr Val Gly Ser Leu Gly
                 85                  90                  95

Leu Phe Ala Phe Lys Ala Asn Leu Gln Gln Arg Arg Val Lys Leu Thr
                100                 105                 110

Leu Leu Ser Lys Glu Ser Ala Val Leu Phe Leu Asn Val Leu Leu Ser
            115                 120                 125

Ile Ala Thr Val Ser Thr Phe Leu Gly Thr Phe Tyr Pro Met Leu Phe
130                 135                 140

Gln Ala Met Asn Trp Gly Ser Ile Ser Val Gly Ala Pro Tyr Phe Asn
145                 150                 155                 160

Ser Ile Phe Leu Pro Leu Leu Thr Leu Ile Leu Ile Ala Met Val Phe
                165                 170                 175

Ser Leu Gly Leu His Trp Ala Lys Ala Asp Lys Gly Ile Leu Phe Lys
            180                 185                 190

Arg Ala Ala Leu Leu Leu Pro Ser Leu Leu Ile Ala Tyr Phe Met Ile
        195                 200                 205

Arg Gln
    210

<210> SEQ ID NO 117
<211> LENGTH: 876
<212> TYPE: DNA
<213> ORGANISM: Actinobacillus actinomycetemcomitans
<220> FEATURE:
<221> NAME/KEY: CDS
<222> LOCATION: (1)..(876)

<400> SEQUENCE: 117 act cac cct gtg cat att tcg atg caa tat atg gca gat gaa gtt aaa      48
Thr His Pro Val His Ile Ser Met Gln Tyr Met Ala Asp Glu Val Lys
 1               5                  10                  15 aaa tta aca aat ggt gaa gtg gtg atc cga att tac cca aat agc cag      96
Lys Leu Thr Asn Gly Glu Val Val Ile Arg Ile Tyr Pro Asn Ser Gln
             20                  25                  30 ctt ggt agc cag cgt gaa tca atg gaa tta ttg caa tcc ggg tca cta     144
Leu Gly Ser Gln Arg Glu Ser Met Glu Leu Leu Gln Ser Gly Ser Leu
         35                  40                  45 gat atg gca aaa tca aac gca agt gaa tta gaa gca ttt gag cca tct     192
Asp Met Ala Lys Ser Asn Ala Ser Glu Leu Glu Ala Phe Glu Pro Ser
 50                  55                  60 tat ggt gca tac aat att ccg tat ctt ttc cat aat gtt gat cat tat     240
Tyr Gly Ala Tyr Asn Ile Pro Tyr Leu Phe His Asn Val Asp His Tyr
 65                  70                  75                  80 tat cgt gct cta ctt gat cct gaa gtt ggg caa aaa att ctt gat tca     288
Tyr Arg Ala Leu Leu Asp Pro Glu Val Gly Gln Lys Ile Leu Asp Ser
                 85                  90                  95 tca aag ggc aaa ggt ttc att ggg ttg act tat tat gat ggt ggt gcg     336
Ser Lys Gly Lys Gly Phe Ile Gly Leu Thr Tyr Tyr Asp Gly Gly Ala
                100                 105                 110 cgt agt ttc tat gcg ggt aag gca att aaa tcg cct gcg gac ctc aaa     384
Arg Ser Phe Tyr Ala Gly Lys Ala Ile Lys Ser Pro Ala Asp Leu Lys
            115                 120                 125 ggt atg aaa att cgc gtt caa cca agc cca acc gca gta gaa atg atc     432
Gly Met Lys Ile Arg Val Gln Pro Ser Pro Thr Ala Val Glu Met Ile
```

```
          130                 135                 140
aaa  tta  atg  ggt  gct  tct  cca  aca  cct  tta  gct  tat  ggt  gaa  ctc  tat       480
Lys  Leu  Met  Gly  Ala  Ser  Pro  Thr  Pro  Leu  Ala  Tyr  Gly  Glu  Leu  Tyr
145                      150                 155                 160 acc  gca  ctc  caa  caa  aaa  gtg  gtt  gat  ggc  gcg  gaa  aat  aac  caa  aca       528
Thr  Ala  Leu  Gln  Gln  Lys  Val  Val  Asp  Gly  Ala  Glu  Asn  Asn  Gln  Thr
                    165                 170                 175 gca  tta  acc  tta  tct  cgt  cat  ggt  gaa  gtg  gct  aaa  ttc  ttt  agt  gaa       576
Ala  Leu  Thr  Leu  Ser  Arg  His  Gly  Glu  Val  Ala  Lys  Phe  Phe  Ser  Glu
               180                 185                 190 gat  gaa  cat  act  atg  att  cct  gat  gtg  ctc  gta  att  ggt  caa  aaa  tct       624
Asp  Glu  His  Thr  Met  Ile  Pro  Asp  Val  Leu  Val  Ile  Gly  Gln  Lys  Ser
          195                 200                 205 tgg  gat  aaa  tta  act  cca  gaa  caa  caa  aat  gca  ctt  aaa  aaa  gcc  gct       672
Trp  Asp  Lys  Leu  Thr  Pro  Glu  Gln  Gln  Asn  Ala  Leu  Lys  Lys  Ala  Ala
     210                 215                 220 gat  gat  tca  atg  atg  tat  cac  aaa  gat  tta  tgg  caa  aaa  atg  att  gct       720
Asp  Asp  Ser  Met  Met  Tyr  His  Lys  Asp  Leu  Trp  Gln  Lys  Met  Ile  Ala
225                 230                 235                 240 gaa  acc  act  caa  gaa  gct  aaa  gat  aaa  ttg  ggt  gta  gaa  ttt  gtg  aaa       768
Glu  Thr  Thr  Gln  Glu  Ala  Lys  Asp  Lys  Leu  Gly  Val  Glu  Phe  Val  Lys
                    245                 250                 255 gta  gat  aaa  caa  cct  ttc  att  gat  gca  aca  aaa  agc  atg  cat  gat  gcg       816
Val  Asp  Lys  Gln  Pro  Phe  Ile  Asp  Ala  Thr  Lys  Ser  Met  His  Asp  Ala
               260                 265                 270 gca  aaa  gcc  aat  cct  ttg  ctt  aaa  gaa  tac  att  gaa  cgt  att  gat  agt       864
Ala  Lys  Ala  Asn  Pro  Leu  Leu  Lys  Glu  Tyr  Ile  Glu  Arg  Ile  Asp  Ser
          275                 280                 285 ttg  gca  acc  aag                                                                    876
Leu  Ala  Thr  Lys
         290

<210> SEQ ID NO 118
<211> LENGTH: 292
<212> TYPE: PRT
<213> ORGANISM: Actinobacillus actinomycetemcomitans

<400> SEQUENCE: 118

Thr  His  Pro  Val  His  Ile  Ser  Met  Gln  Tyr  Met  Ala  Asp  Glu  Val  Lys
1                   5                   10                  15

Lys  Leu  Thr  Asn  Gly  Glu  Val  Val  Ile  Arg  Ile  Tyr  Pro  Asn  Ser  Gln
               20                  25                  30

Leu  Gly  Ser  Gln  Arg  Glu  Ser  Met  Glu  Leu  Leu  Gln  Ser  Gly  Ser  Leu
          35                  40                  45

Asp  Met  Ala  Lys  Ser  Asn  Ala  Ser  Glu  Leu  Glu  Ala  Phe  Glu  Pro  Ser
     50                  55                  60

Tyr  Gly  Ala  Tyr  Asn  Ile  Pro  Tyr  Leu  Phe  His  Asn  Val  Asp  His  Tyr
65                  70                  75                  80

Tyr  Arg  Ala  Leu  Leu  Asp  Pro  Glu  Val  Gly  Gln  Lys  Ile  Leu  Asp  Ser
               85                  90                  95

Ser  Lys  Gly  Lys  Gly  Phe  Ile  Gly  Leu  Thr  Tyr  Tyr  Asp  Gly  Gly  Ala
          100                 105                 110

Arg  Ser  Phe  Tyr  Ala  Gly  Lys  Ala  Ile  Lys  Ser  Pro  Ala  Asp  Leu  Lys
     115                 120                 125

Gly  Met  Lys  Ile  Arg  Val  Gln  Pro  Ser  Pro  Thr  Ala  Val  Glu  Met  Ile
130                 135                 140

Lys  Leu  Met  Gly  Ala  Ser  Pro  Thr  Pro  Leu  Ala  Tyr  Gly  Glu  Leu  Tyr
145                 150                 155                 160
```

```
Thr Ala Leu Gln Gln Lys Val Val Asp Gly Ala Glu Asn Asn Gln Thr
                165                 170                 175
Ala Leu Thr Leu Ser Arg His Gly Glu Val Ala Lys Phe Phe Ser Glu
            180                 185                 190
Asp Glu His Thr Met Ile Pro Asp Val Leu Val Ile Gly Gln Lys Ser
        195                 200                 205
Trp Asp Lys Leu Thr Pro Glu Gln Gln Asn Ala Leu Lys Lys Ala Ala
    210                 215                 220
Asp Asp Ser Met Met Tyr His Lys Asp Leu Trp Gln Lys Met Ile Ala
225                 230                 235                 240
Glu Thr Thr Gln Glu Ala Lys Asp Lys Leu Gly Val Glu Phe Val Lys
                245                 250                 255
Val Asp Lys Gln Pro Phe Ile Asp Ala Thr Lys Ser Met His Asp Ala
            260                 265                 270
Ala Lys Ala Asn Pro Leu Leu Lys Glu Tyr Ile Glu Arg Ile Asp Ser
        275                 280                 285
Leu Ala Thr Lys
    290

<210> SEQ ID NO 119
<211> LENGTH: 303
<212> TYPE: DNA
<213> ORGANISM: Actinobacillus actinomycetemcomitans
<220> FEATURE:
<221> NAME/KEY: CDS
<222> LOCATION: (1)..(303)

<400> SEQUENCE: 119 atg agt gtt tta agt tat gcc caa aaa atc ggg caa gcc tta atg gta      48
Met Ser Val Leu Ser Tyr Ala Gln Lys Ile Gly Gln Ala Leu Met Val
1               5                   10                  15 ccc gtt gcc gtt ttg ccg gca gcc gcc gta tta atg ggg atc ggc tat      96
Pro Val Ala Val Leu Pro Ala Ala Ala Val Leu Met Gly Ile Gly Tyr
                20                  25                  30 tgg ctt gac ccg gac ggc tgg ggc gca aac agc caa ctt gcc gcc tta     144
Trp Leu Asp Pro Asp Gly Trp Gly Ala Asn Ser Gln Leu Ala Ala Leu
            35                  40                  45 tta atc aag tcc ggc gcg gca atc atc gat aac atg ggc tta tta ttc     192
Leu Ile Lys Ser Gly Ala Ala Ile Ile Asp Asn Met Gly Leu Leu Phe
        50                  55                  60 gcc gtg ggc gta gca ttc ggg ttg tcc aaa gac aag cac ggt tct gct     240
Ala Val Gly Val Ala Phe Gly Leu Ser Lys Asp Lys His Gly Ser Ala
65                  70                  75                  80 gcg ctt tcc ggt tta gtg ggc tat tat gtg gtc act acc cta ctc gcc     288
Ala Leu Ser Gly Leu Val Gly Tyr Tyr Val Val Thr Thr Leu Leu Ala
                85                  90                  95 cct ggc ggc gta gcg                                                  303
Pro Gly Gly Val Ala
            100

<210> SEQ ID NO 120
<211> LENGTH: 101
<212> TYPE: PRT
<213> ORGANISM: Actinobacillus actinomycetemcomitans

<400> SEQUENCE: 120

Met Ser Val Leu Ser Tyr Ala Gln Lys Ile Gly Gln Ala Leu Met Val
1               5                   10                  15

Pro Val Ala Val Leu Pro Ala Ala Ala Val Leu Met Gly Ile Gly Tyr
```

```
                      20                  25                  30
         Trp Leu Asp Pro Asp Gly Trp Gly Ala Asn Ser Gln Leu Ala Ala Leu
                  35                  40                  45

Leu Ile Lys Ser Gly Ala Ala Ile Ile Asp Asn Met Gly Leu Leu Phe
              50                  55                  60

Ala Val Gly Val Ala Phe Gly Leu Ser Lys Asp Lys His Gly Ser Ala
          65                  70                  75                  80

Ala Leu Ser Gly Leu Val Gly Tyr Tyr Val Thr Thr Leu Leu Ala
                          85                  90                  95

Pro Gly Gly Val Ala
                     100

<210> SEQ ID NO 121
<211> LENGTH: 590
<212> TYPE: DNA
<213> ORGANISM: Actinobacillus actinomycetemcomitans
<220> FEATURE:
<221> NAME/KEY: CDS
<222> LOCATION: (1)..(588)

<400> SEQUENCE: 121 gaa tat aaa aat ctt gct gtt gct tat atc cgt atg tct acg gag cat       48
Glu Tyr Lys Asn Leu Ala Val Ala Tyr Ile Arg Met Ser Thr Glu His
 1               5                  10                  15 cag gaa ttt tca ccg gat ata caa cgt cgc ttc att caa aaa tat gct       96
Gln Glu Phe Ser Pro Asp Ile Gln Arg Arg Phe Ile Gln Lys Tyr Ala
             20                  25                  30 aag gaa caa ggg ctt ata ctc act agg gaa tac cta gat gag gga agg      144
Lys Glu Gln Gly Leu Ile Leu Thr Arg Glu Tyr Leu Asp Glu Gly Arg
         35                  40                  45 agt gga tta agc gca gaa aaa cgt cct cag ttt tta tca ctc att aat      192
Ser Gly Leu Ser Ala Glu Lys Arg Pro Gln Phe Leu Ser Leu Ile Asn
     50                  55                  60 ttt gta caa tcc ggt aat gct gat ttt tca cat att ctt gtt tat gac      240
Phe Val Gln Ser Gly Asn Ala Asp Phe Ser His Ile Leu Val Tyr Asp
 65                  70                  75                  80 att agc cga tgg ggg cgc ttt cta aat att gat gaa tct gca cat tat      288
Ile Ser Arg Trp Gly Arg Phe Leu Asn Ile Asp Glu Ser Ala His Tyr
                 85                  90                  95 gaa caa att tgt tca aaa atg ggg att aaa gtg cat tac tgt gca gaa      336
Glu Gln Ile Cys Ser Lys Met Gly Ile Lys Val His Tyr Cys Ala Glu
            100                 105                 110 cct ttt aag gga aac gac att ggt tct caa att ttt aaa gcg gta aaa      384
Pro Phe Lys Gly Asn Asp Ile Gly Ser Gln Ile Phe Lys Ala Val Lys
        115                 120                 125 cgt tgg tct gcc gga gaa tac tgt cgt gag cta ggt gaa aaa gtt ttt      432
Arg Trp Ser Ala Gly Glu Tyr Cys Arg Glu Leu Gly Glu Lys Val Phe
    130                 135                 140 aat ggg cag aag aat ttg att gag cgc gga ttt cgt caa ggt gga cca      480
Asn Gly Gln Lys Asn Leu Ile Glu Arg Gly Phe Arg Gln Gly Gly Pro
145                 150                 155                 160 gct gga ttt ggg tta aga cgc cta tta tta agt gct gat ggt tcg cca      528
Ala Gly Phe Gly Leu Arg Arg Leu Leu Leu Ser Ala Asp Gly Ser Pro
                165                 170                 175 aaa ttt gaa cta aaa acg ggt gac agg aag agt ttg cag tcg gat cgt      576
Lys Phe Glu Leu Lys Thr Gly Asp Arg Lys Ser Leu Gln Ser Asp Arg
            180                 185                 190 gtc att ctt att gc                                                    590
Val Ile Leu Ile
        195
```

<210> SEQ ID NO 122
<211> LENGTH: 196
<212> TYPE: PRT
<213> ORGANISM: Actinobacillus actinomycetemcomitans

<400> SEQUENCE: 122

```
Glu Tyr Lys Asn Leu Ala Val Ala Tyr Ile Arg Met Ser Thr Glu His
1               5                  10                  15

Gln Glu Phe Ser Pro Asp Ile Gln Arg Arg Phe Ile Gln Lys Tyr Ala
            20                  25                  30

Lys Glu Gln Gly Leu Ile Leu Thr Arg Glu Tyr Leu Asp Glu Gly Arg
        35                  40                  45

Ser Gly Leu Ser Ala Glu Lys Arg Pro Gln Phe Leu Ser Leu Ile Asn
    50                  55                  60

Phe Val Gln Ser Gly Asn Ala Asp Phe Ser His Ile Leu Val Tyr Asp
65                  70                  75                  80

Ile Ser Arg Trp Gly Arg Phe Leu Asn Ile Asp Glu Ser Ala His Tyr
                85                  90                  95

Glu Gln Ile Cys Ser Lys Met Gly Ile Lys Val His Tyr Cys Ala Glu
            100                 105                 110

Pro Phe Lys Gly Asn Asp Ile Gly Ser Gln Ile Phe Lys Ala Val Lys
        115                 120                 125

Arg Trp Ser Ala Gly Glu Tyr Cys Arg Glu Leu Gly Glu Lys Val Phe
    130                 135                 140

Asn Gly Gln Lys Asn Leu Ile Glu Arg Gly Phe Arg Gln Gly Gly Pro
145                 150                 155                 160

Ala Gly Phe Gly Leu Arg Arg Leu Leu Leu Ser Ala Asp Gly Ser Pro
                165                 170                 175

Lys Phe Glu Leu Lys Thr Gly Asp Arg Lys Ser Leu Gln Ser Asp Arg
            180                 185                 190

Val Ile Leu Ile
        195
```

<210> SEQ ID NO 123
<211> LENGTH: 531
<212> TYPE: DNA
<213> ORGANISM: Actinobacillus actinomycetemcomitans
<220> FEATURE:
<221> NAME/KEY: CDS
<222> LOCATION: (1)..(531)

<400> SEQUENCE: 123

```
ttt tta acc aaa gat aaa atc aag cag gca ata cag gca cag caa cag     48
Phe Leu Thr Lys Asp Lys Ile Lys Gln Ala Ile Gln Ala Gln Gln Gln
1               5                  10                  15 gaa ctg tta cta caa gtg atc ccg cag gat tac ttc aat aat gat ctg     96
Glu Leu Leu Leu Gln Val Ile Pro Gln Asp Tyr Phe Asn Asn Asp Leu
            20                  25                  30 acg cag gct tgt tat gca ccg caa gcg ggg aca tta caa gtc gtg gag    144
Thr Gln Ala Cys Tyr Ala Pro Gln Ala Gly Thr Leu Gln Val Val Glu
        35                  40                  45 ata agc aaa ata tgc acg gca aag aaa gac ggc gtg act act gcc tat    192
Ile Ser Lys Ile Cys Thr Ala Lys Lys Asp Gly Val Thr Thr Ala Tyr
    50                  55                  60 gcc ttt gaa agc acg gcg cat gat ggc tat tcc ggc gat att cat att    240
Ala Phe Glu Ser Thr Ala His Asp Gly Tyr Ser Gly Asp Ile His Ile
65                  70                  75                  80
```

```
ttg gtg ggc atg aaa cct gat ggc gaa gtg ctt ggc gtg cgc att acg      288
Leu Val Gly Met Lys Pro Asp Gly Glu Val Leu Gly Val Arg Ile Thr
             85                  90                  95 gaa cac cac gaa acc ccg gga tta ggc gat aaa att gaa acc cgc att      336
Glu His His Glu Thr Pro Gly Leu Gly Asp Lys Ile Glu Thr Arg Ile
        100                 105                 110 tcc aac tgg gtt tta agt ttt gat cat cag gtt atc agc aac gaa aat      384
Ser Asn Trp Val Leu Ser Phe Asp His Gln Val Ile Ser Asn Glu Asn
    115                 120                 125 gcc gca gaa tgg gcg gtg aaa aaa gac ggc ggt aaa ttc gat caa ttc      432
Ala Ala Glu Trp Ala Val Lys Lys Asp Gly Gly Lys Phe Asp Gln Phe
130                 135                 140 gcc ggt gcc acc atc acg ccc cgc gct gtg gtt aac caa gtg aaa cgg      480
Ala Gly Ala Thr Ile Thr Pro Arg Ala Val Val Asn Gln Val Lys Arg
145                 150                 155                 160 gcg gca ttg gct atg ctg gat aat ctg ccg aaa gag aga gaa agt gat      528
Ala Ala Leu Ala Met Leu Asp Asn Leu Pro Lys Glu Arg Glu Ser Asp
                165                 170                 175 gga                                                                   531
Gly
```

<210> SEQ ID NO 124
<211> LENGTH: 177
<212> TYPE: PRT
<213> ORGANISM: Actinobacillus actinomycetemcomitans

<400> SEQUENCE: 124

Phe Leu Thr Lys Asp Lys Ile Lys Gln Ala Ile Gln Ala Gln Gln Gln
1               5                   10                  15

Glu Leu Leu Leu Gln Val Ile Pro Gln Asp Tyr Phe Asn Asn Asp Leu
            20                  25                  30

Thr Gln Ala Cys Tyr Ala Pro Gln Ala Gly Thr Leu Gln Val Val Glu
        35                  40                  45

Ile Ser Lys Ile Cys Thr Ala Lys Lys Asp Gly Val Thr Thr Ala Tyr
    50                  55                  60

Ala Phe Glu Ser Thr Ala His Asp Gly Tyr Ser Gly Asp Ile His Ile
65                  70                  75                  80

Leu Val Gly Met Lys Pro Asp Gly Glu Val Leu Gly Val Arg Ile Thr
                85                  90                  95

Glu His His Glu Thr Pro Gly Leu Gly Asp Lys Ile Glu Thr Arg Ile
            100                 105                 110

Ser Asn Trp Val Leu Ser Phe Asp His Gln Val Ile Ser Asn Glu Asn
        115                 120                 125

Ala Ala Glu Trp Ala Val Lys Lys Asp Gly Gly Lys Phe Asp Gln Phe
    130                 135                 140

Ala Gly Ala Thr Ile Thr Pro Arg Ala Val Val Asn Gln Val Lys Arg
145                 150                 155                 160

Ala Ala Leu Ala Met Leu Asp Asn Leu Pro Lys Glu Arg Glu Ser Asp
                165                 170                 175

Gly

<210> SEQ ID NO 125
<211> LENGTH: 783
<212> TYPE: DNA
<213> ORGANISM: Actinobacillus actinomycetemcomitans
<220> FEATURE:
<221> NAME/KEY: CDS
<222> LOCATION: (1)..(783)

-continued

```
<400> SEQUENCE: 125 atg gat aaa tta gac gaa aca caa gaa ctg caa caa acc gaa gcc aaa      48
Met Asp Lys Leu Asp Glu Thr Gln Glu Leu Gln Gln Thr Glu Ala Lys
1               5                   10                  15 agt gcg gtt gac aaa aaa caa cat ttt ttg aac gtt ggt tct gcc aac      96
Ser Ala Val Asp Lys Lys Gln His Phe Leu Asn Val Gly Ser Ala Asn
            20                  25                  30 ggc ccc gaa ggg gtg aat aag cga aca agt gag ctt atg aat aat att     144
Gly Pro Glu Gly Val Asn Lys Arg Thr Ser Glu Leu Met Asn Asn Ile
        35                  40                  45 tca aat gaa aaa agc att tgg aaa acg att ttc att cag ggc atc tgg     192
Ser Asn Glu Lys Ser Ile Trp Lys Thr Ile Phe Ile Gln Gly Ile Trp
 50                  55                  60 acc aac aat tcc acc gtg gtg caa ctg ctt ggg ttg tgt ccg ctg ctg     240
Thr Asn Asn Ser Thr Val Val Gln Leu Leu Gly Leu Cys Pro Leu Leu
 65                  70                  75                  80 gcg gtg tcc aac tcc gtg acc aac gcc ctc ggg ctg ggt tta gcc acc     288
Ala Val Ser Asn Ser Val Thr Asn Ala Leu Gly Leu Gly Leu Ala Thr
                 85                  90                  95 atg ctt gtg ctg acg tgt acg aac acg gta gtt tct ctt ttc cgt aag     336
Met Leu Val Leu Thr Cys Thr Asn Thr Val Val Ser Leu Phe Arg Lys
            100                 105                 110 cac atc ccc aat gaa atc cgc att ccg att tat gtg atg atc atc gca     384
His Ile Pro Asn Glu Ile Arg Ile Pro Ile Tyr Val Met Ile Ile Ala
        115                 120                 125 acc acg gta acc gct gtg caa tta ttg atg aat gcc tat acc tac gcg     432
Thr Thr Val Thr Ala Val Gln Leu Leu Met Asn Ala Tyr Thr Tyr Ala
    130                 135                 140 ctt tat caa tct ctc ggg att ttt att ccg ctc atc gtc acc aac tgt     480
Leu Tyr Gln Ser Leu Gly Ile Phe Ile Pro Leu Ile Val Thr Asn Cys
145                 150                 155                 160 att gtg atc ggt cgc gcc gaa gcc ttt gct tcc aag aac agc att tcc     528
Ile Val Ile Gly Arg Ala Glu Ala Phe Ala Ser Lys Asn Ser Ile Ser
                165                 170                 175 cat tcc gcc ttt gac ggt ttt tcc atg gga tta ggg atg tta ttc agt     576
His Ser Ala Phe Asp Gly Phe Ser Met Gly Leu Gly Met Leu Phe Ser
            180                 185                 190 tta gta gcg ctc ggc ggc atc cgc gaa atc atc ggc aac ggt act tta     624
Leu Val Ala Leu Gly Gly Ile Arg Glu Ile Ile Gly Asn Gly Thr Leu
        195                 200                 205 ttt gac ggc atc gaa aat ttg ctg ggc gat tgg gct aaa ttc atg cgg     672
Phe Asp Gly Ile Glu Asn Leu Leu Gly Asp Trp Ala Lys Phe Met Arg
    210                 215                 220 att gaa ttt ttc cac aat gac agt aat ctg tta ctt gcg att ttg cct     720
Ile Glu Phe Phe His Asn Asp Ser Asn Leu Leu Leu Ala Ile Leu Pro
225                 230                 235                 240 ccc ggc gca ttt att ggt tta gct ttg ttg tta gcc tta aaa aat gta     768
Pro Gly Ala Phe Ile Gly Leu Ala Leu Leu Leu Ala Leu Lys Asn Val
                245                 250                 255 ata gat aca aaa aag                                                 783
Ile Asp Thr Lys Lys
            260

<210> SEQ ID NO 126
<211> LENGTH: 261
<212> TYPE: PRT
<213> ORGANISM: Actinobacillus actinomycetemcomitans

<400> SEQUENCE: 126

Met Asp Lys Leu Asp Glu Thr Gln Glu Leu Gln Gln Thr Glu Ala Lys
```

```
        1               5                   10                  15
      Ser Ala Val Asp Lys Lys Gln His Phe Leu Asn Val Gly Ser Ala Asn
                      20                  25                  30
      Gly Pro Glu Gly Val Asn Lys Arg Thr Ser Glu Leu Met Asn Asn Ile
                      35                  40                  45
      Ser Asn Glu Lys Ser Ile Trp Lys Thr Ile Phe Ile Gln Gly Ile Trp
       50                  55                  60
      Thr Asn Asn Ser Thr Val Val Gln Leu Leu Gly Leu Cys Pro Leu Leu
       65                  70                  75                  80
      Ala Val Ser Asn Ser Val Thr Asn Ala Leu Gly Leu Gly Leu Ala Thr
                      85                  90                  95
      Met Leu Val Leu Thr Cys Thr Asn Thr Val Val Ser Leu Phe Arg Lys
                      100                 105                 110
      His Ile Pro Asn Glu Ile Arg Ile Pro Ile Tyr Val Met Ile Ile Ala
                      115                 120                 125
      Thr Thr Val Thr Ala Val Gln Leu Leu Met Asn Ala Tyr Thr Tyr Ala
                      130                 135                 140
      Leu Tyr Gln Ser Leu Gly Ile Phe Ile Pro Leu Ile Val Thr Asn Cys
      145                 150                 155                 160
      Ile Val Ile Gly Arg Ala Glu Ala Phe Ala Ser Lys Asn Ser Ile Ser
                      165                 170                 175
      His Ser Ala Phe Asp Gly Phe Ser Met Gly Leu Gly Met Leu Phe Ser
                      180                 185                 190
      Leu Val Ala Leu Gly Gly Ile Arg Glu Ile Ile Gly Asn Gly Thr Leu
                      195                 200                 205
      Phe Asp Gly Ile Glu Asn Leu Leu Gly Asp Trp Ala Lys Phe Met Arg
                      210                 215                 220
      Ile Glu Phe Phe His Asn Asp Ser Asn Leu Leu Leu Ala Ile Leu Pro
      225                 230                 235                 240
      Pro Gly Ala Phe Ile Gly Leu Ala Leu Leu Leu Ala Leu Lys Asn Val
                      245                 250                 255
      Ile Asp Thr Lys Lys
                      260

<210> SEQ ID NO 127
<211> LENGTH: 627
<212> TYPE: DNA
<213> ORGANISM: Actinobacillus actinomycetemcomitans
<220> FEATURE:
<221> NAME/KEY: CDS
<222> LOCATION: (1)..(627)

<400> SEQUENCE: 127 atg aat ttt act aaa acg cta tat att ttt aaa tat act ggc gaa ctt     48
Met Asn Phe Thr Lys Thr Leu Tyr Ile Phe Lys Tyr Thr Gly Glu Leu
 1               5                  10                  15 ttc gcg att ttt att tat aat gaa gac gct atg ttt tta aat ata cat     96
Phe Ala Ile Phe Ile Tyr Asn Glu Asp Ala Met Phe Leu Asn Ile His
                 20                  25                  30 cgt tat att ttt ctc aca ttc tgt tgg ggt aac atc atg aaa ttt gaa    144
Arg Tyr Ile Phe Leu Thr Phe Cys Trp Gly Asn Ile Met Lys Phe Glu
             35                  40                  45 gtc att tac aaa ttc ctg ttg ttg tgt gtg ctg att atc agt ttg ttg    192
Val Ile Tyr Lys Phe Leu Leu Leu Cys Val Leu Ile Ile Ser Leu Leu
         50                  55                  60 tgt gtt gtg ata agc ggc gcc gga tta ttc tac ggt tgg caa ttg agc    240
Cys Val Val Ile Ser Gly Ala Gly Leu Phe Tyr Gly Trp Gln Leu Ser
```

```
                   65                  70                  75                  80
atg ctg ttc aat att cat gtg agc ttt gcc gtt ttg ctg gtc gcc gcg    288
Met Leu Phe Asn Ile His Val Ser Phe Ala Val Leu Leu Val Ala Ala
                        85                  90                  95 ttg tta ctg cat att ctg aac cgc aaa aat aaa ttg gcg aaa atc aat    336
Leu Leu Leu His Ile Leu Asn Arg Lys Asn Lys Leu Ala Lys Ile Asn
                100                 105                 110 acc caa ttt gcc gat ttg gtc tta cac aat aaa tac ccg agt tat tgc    384
Thr Gln Phe Ala Asp Leu Val Leu His Asn Lys Tyr Pro Ser Tyr Cys
            115                 120                 125 aat tta gac cgc ttg atc atg acg ttc gag cat ttt tcc gtt gtg caa    432
Asn Leu Asp Arg Leu Ile Met Thr Phe Glu His Phe Ser Val Val Gln
        130                 135                 140 att gcc gaa cag tta aac ctg gat ttg gat gcg ctg cta aaa gaa ctc    480
Ile Ala Glu Gln Leu Asn Leu Asp Leu Asp Ala Leu Leu Lys Glu Leu
145                 150                 155                 160 gcc gaa gga aaa ata aac gtc aaa aat tcc cac agc act tta cgg gag    528
Ala Glu Gly Lys Ile Asn Val Lys Asn Ser His Ser Thr Leu Arg Glu
                165                 170                 175 aat ttt ccc cat aat gat gaa aag att ttt gct gcg atc acc atc gtg    576
Asn Phe Pro His Asn Asp Glu Lys Ile Phe Ala Ala Ile Thr Ile Val
            180                 185                 190 ctg caa ctt cgt tta att aat cct atc cct gct ttt aac tta aaa gga    624
Leu Gln Leu Arg Leu Ile Asn Pro Ile Pro Ala Phe Asn Leu Lys Gly
        195                 200                 205 cat                                                                 627
His

<210> SEQ ID NO 128
<211> LENGTH: 209
<212> TYPE: PRT
<213> ORGANISM: Actinobacillus actinomycetemcomitans

<400> SEQUENCE: 128

Met Asn Phe Thr Lys Thr Leu Tyr Ile Phe Lys Tyr Thr Gly Glu Leu
1               5                   10                  15

Phe Ala Ile Phe Ile Tyr Asn Glu Asp Ala Met Phe Leu Asn Ile His
            20                  25                  30

Arg Tyr Ile Phe Leu Thr Phe Cys Trp Gly Asn Ile Met Lys Phe Glu
        35                  40                  45

Val Ile Tyr Lys Phe Leu Leu Leu Cys Val Leu Ile Ile Ser Leu Leu
    50                  55                  60

Cys Val Val Ile Ser Gly Ala Gly Leu Phe Tyr Gly Trp Gln Leu Ser
65                  70                  75                  80

Met Leu Phe Asn Ile His Val Ser Phe Ala Val Leu Leu Val Ala Ala
                85                  90                  95

Leu Leu Leu His Ile Leu Asn Arg Lys Asn Lys Leu Ala Lys Ile Asn
            100                 105                 110

Thr Gln Phe Ala Asp Leu Val Leu His Asn Lys Tyr Pro Ser Tyr Cys
        115                 120                 125

Asn Leu Asp Arg Leu Ile Met Thr Phe Glu His Phe Ser Val Val Gln
    130                 135                 140

Ile Ala Glu Gln Leu Asn Leu Asp Leu Asp Ala Leu Leu Lys Glu Leu
145                 150                 155                 160

Ala Glu Gly Lys Ile Asn Val Lys Asn Ser His Ser Thr Leu Arg Glu
                165                 170                 175

Asn Phe Pro His Asn Asp Glu Lys Ile Phe Ala Ala Ile Thr Ile Val
```

```
                      180              185              190
       Leu Gln Leu Arg Leu Ile Asn Pro Ile Pro Ala Phe Asn Leu Lys Gly
               195                  200                  205
       His

<210> SEQ ID NO 129
<211> LENGTH: 663
<212> TYPE: DNA
<213> ORGANISM: Actinobacillus actinomycetemcomitans
<220> FEATURE:
<221> NAME/KEY: CDS
<222> LOCATION: (1)..(663)

<400> SEQUENCE: 129 gtg caa tct tac gag cag caa agt aat aac ggc gtg ccg att caa ttc       48
Val Gln Ser Tyr Glu Gln Gln Ser Asn Asn Gly Val Pro Ile Gln Phe
 1               5                  10                  15 cag cag tta gac caa tca caa acc gtt gaa ccg acc gtg ttg gat aat       96
Gln Gln Leu Asp Gln Ser Gln Thr Val Glu Pro Thr Val Leu Asp Asn
             20                  25                  30 ctg acc ccg caa acc gat aac act gtc gcg caa caa cct gct gcg gaa      144
Leu Thr Pro Gln Thr Asp Asn Thr Val Ala Gln Gln Pro Ala Ala Glu
         35                  40                  45 acc aat acg caa aat gtc aat gcc ggc gcc ata gaa ccg caa gcg gtg      192
Thr Asn Thr Gln Asn Val Asn Ala Gly Ala Ile Glu Pro Gln Ala Val
     50                  55                  60 gaa caa ggg gca acc acc tcc gtt gct gag caa acg aca act gcg gcg      240
Glu Gln Gly Ala Thr Thr Ser Val Ala Glu Gln Thr Thr Thr Ala Ala
 65                  70                  75                  80 gta gaa aat aaa ccg gca gaa gtc aaa ccg gaa gag gtc gaa acc gtt      288
Val Glu Asn Lys Pro Ala Glu Val Lys Pro Glu Glu Val Glu Thr Val
                 85                  90                  95 aaa ccg agt gag cct gca aaa gcg caa gaa gcc gtc aaa ccg cgt caa      336
Lys Pro Ser Glu Pro Ala Lys Ala Gln Glu Ala Val Lys Pro Arg Gln
            100                 105                 110 cat cag gaa agc gtg aaa aaa gag ccg gtg aaa acc gat aaa gtg aaa      384
His Gln Glu Ser Val Lys Lys Glu Pro Val Lys Thr Asp Lys Val Lys
        115                 120                 125 cag gct gaa aaa gcg act gct aaa aat caa ccg act aaa tcg gca aaa      432
Gln Ala Glu Lys Ala Thr Ala Lys Asn Gln Pro Thr Lys Ser Ala Lys
    130                 135                 140 acc gaa aaa gaa gta cgg gat att tta gaa ggc aaa aca acg act atc      480
Thr Glu Lys Glu Val Arg Asp Ile Leu Glu Gly Lys Thr Thr Thr Ile
145                 150                 155                 160 acc aaa gca gca gcc ggt agc aaa acc tta acc att ccg caa ggc gtg      528
Thr Lys Ala Ala Ala Gly Ser Lys Thr Leu Thr Ile Pro Gln Gly Val
                165                 170                 175 acc tta atg cag gtg ttc cgt gac aac cat cta cct gtc ggt gat gtg      576
Thr Leu Met Gln Val Phe Arg Asp Asn His Leu Pro Val Gly Asp Val
            180                 185                 190 aat gcc atg acc aaa gcc aaa ggc gta ggc aag gtg tta agc agc ttc      624
Asn Ala Met Thr Lys Ala Lys Gly Val Gly Lys Val Leu Ser Ser Phe
        195                 200                 205 aag ccg ggt gat aag gta cag gtt tcc ctg aat gca caa                  663
Lys Pro Gly Asp Lys Val Gln Val Ser Leu Asn Ala Gln
    210                 215                 220

<210> SEQ ID NO 130
<211> LENGTH: 221
<212> TYPE: PRT
<213> ORGANISM: Actinobacillus actinomycetemcomitans
```

-continued

```
<400> SEQUENCE: 130

Val Gln Ser Tyr Glu Gln Ser Asn Asn Gly Val Pro Ile Gln Phe
1               5                   10                  15

Gln Gln Leu Asp Gln Ser Gln Thr Val Glu Pro Thr Val Leu Asp Asn
            20                  25                  30

Leu Thr Pro Gln Thr Asp Asn Thr Val Ala Gln Pro Ala Ala Glu
        35                  40                  45

Thr Asn Thr Gln Asn Val Asn Ala Gly Ala Ile Glu Pro Gln Ala Val
    50                  55                  60

Glu Gln Gly Ala Thr Thr Ser Val Ala Glu Gln Thr Thr Thr Ala Ala
65                  70                  75                  80

Val Glu Asn Lys Pro Ala Glu Val Lys Pro Glu Glu Val Glu Thr Val
                85                  90                  95

Lys Pro Ser Glu Pro Ala Lys Ala Gln Glu Ala Val Lys Pro Arg Gln
            100                 105                 110

His Gln Glu Ser Val Lys Lys Glu Pro Val Lys Thr Asp Lys Val Lys
        115                 120                 125

Gln Ala Glu Lys Ala Thr Ala Lys Asn Gln Pro Thr Lys Ser Ala Lys
    130                 135                 140

Thr Glu Lys Glu Val Arg Asp Ile Leu Glu Gly Lys Thr Thr Ile
145                 150                 155                 160

Thr Lys Ala Ala Ala Gly Ser Lys Thr Leu Thr Ile Pro Gln Gly Val
                165                 170                 175

Thr Leu Met Gln Val Phe Arg Asp Asn His Leu Pro Val Gly Asp Val
            180                 185                 190

Asn Ala Met Thr Lys Ala Lys Gly Val Gly Lys Val Leu Ser Ser Phe
        195                 200                 205

Lys Pro Gly Asp Lys Val Gln Val Ser Leu Asn Ala Gln
    210                 215                 220

<210> SEQ ID NO 131
<211> LENGTH: 478
<212> TYPE: DNA
<213> ORGANISM: Actinobacillus actinomycetemcomitans
<220> FEATURE:
<221> NAME/KEY: CDS
<222> LOCATION: (1)..(477)

<400> SEQUENCE: 131 atg tta aaa aaa atc tta cat tcc gca ctc atc ggt ttg gtt acg gca      48
Met Leu Lys Lys Ile Leu His Ser Ala Leu Ile Gly Leu Val Thr Ala
1               5                   10                  15 ggt gtg att ttg ttt gtg cta ccg aaa atc acc ggg aaa tcc gtg tta      96
Gly Val Ile Leu Phe Val Leu Pro Lys Ile Thr Gly Lys Ser Val Leu
            20                  25                  30 ccg gag caa gaa atc gcc tct tat aaa gat gca gtg cgt att gct tcg     144
Pro Glu Gln Glu Ile Ala Ser Tyr Lys Asp Ala Val Arg Ile Ala Ser
        35                  40                  45 ccg gcg gtt gtg aac gtt tat aat cag gcg ttt act tct tcg tcc gcg     192
Pro Ala Val Val Asn Val Tyr Asn Gln Ala Phe Thr Ser Ser Ser Ala
    50                  55                  60 caa ttg cag gtg aat aac ctc ggt tcg ggc gtg atc atg tca aaa gac     240
Gln Leu Gln Val Asn Asn Leu Gly Ser Gly Val Ile Met Ser Lys Asp
65                  70                  75                  80 ggt tat att ctg acg aac aaa cac gtt att caa aat gcc gat caa att     288
Gly Tyr Ile Leu Thr Asn Lys His Val Ile Gln Asn Ala Asp Gln Ile
                85                  90                  95
```

| | | |
|---|---|---|
| gta gta gcg ttg caa aac ggg cat att ttt gat gcg gcg ctc att ggt<br>Val Val Ala Leu Gln Asn Gly His Ile Phe Asp Ala Ala Leu Ile Gly<br>100                              105                         110 | | 336 |
| tcc gat tct tta acg gat ttg gca gta tta aaa att aaa gcg gat aat<br>Ser Asp Ser Leu Thr Asp Leu Ala Val Leu Lys Ile Lys Ala Asp Asn<br>         115                       120                       125 | | 384 |
| tta tcc acg att ccg caa aat ctc agc cgt ccg gtg cat gtg gga gat<br>Leu Ser Thr Ile Pro Gln Asn Leu Ser Arg Pro Val His Val Gly Asp<br>130                              135                         140 | | 432 |
| gtg gcg ctg gca atc ggc aat ccg tat aac ctg ggg caa agc gtg t<br>Val Ala Leu Ala Ile Gly Asn Pro Tyr Asn Leu Gly Gln Ser Val<br>145                              150                         155 | | 478 |

<210> SEQ ID NO 132
<211> LENGTH: 159
<212> TYPE: PRT
<213> ORGANISM: Actinobacillus actinomycetemcomitans

<400> SEQUENCE: 132

Met Leu Lys Lys Ile Leu His Ser Ala Leu Ile Gly Leu Val Thr Ala
1                 5                    10                   15

Gly Val Ile Leu Phe Val Leu Pro Lys Ile Thr Gly Lys Ser Val Leu
                 20                    25                   30

Pro Glu Gln Glu Ile Ala Ser Tyr Lys Asp Ala Val Arg Ile Ala Ser
               35                    40                   45

Pro Ala Val Val Asn Val Tyr Asn Gln Ala Phe Thr Ser Ser Ser Ala
    50                    55                    60

Gln Leu Gln Val Asn Asn Leu Gly Ser Gly Val Ile Met Ser Lys Asp
65                70                    75                    80

Gly Tyr Ile Leu Thr Asn Lys His Val Ile Gln Asn Ala Asp Gln Ile
                 85                    90                   95

Val Val Ala Leu Gln Asn Gly His Ile Phe Asp Ala Ala Leu Ile Gly
              100                   105                   110

Ser Asp Ser Leu Thr Asp Leu Ala Val Leu Lys Ile Lys Ala Asp Asn
         115                       120                       125

Leu Ser Thr Ile Pro Gln Asn Leu Ser Arg Pro Val His Val Gly Asp
    130                    135                    140

Val Ala Leu Ala Ile Gly Asn Pro Tyr Asn Leu Gly Gln Ser Val
145                150                    155

<210> SEQ ID NO 133
<211> LENGTH: 537
<212> TYPE: DNA
<213> ORGANISM: Actinobacillus actinomycetemcomitans
<220> FEATURE:
<221> NAME/KEY: CDS
<222> LOCATION: (1)..(537)

<400> SEQUENCE: 133

| | | |
|---|---|---|
| gcc ggc tgg cag ata aaa aat aac aaa cct ttt gac ggt aaa gac tgg<br>Ala Gly Trp Gln Ile Lys Asn Asn Lys Pro Phe Asp Gly Lys Asp Trp<br>1                 5                    10                   15 | | 48 |
| acc cgt tgg gtc gat gcg aga gaa tcc gga gcc att gcc ggt gca gta<br>Thr Arg Trp Val Asp Ala Arg Glu Ser Gly Ala Ile Ala Gly Ala Val<br>                 20                    25                   30 | | 96 |
| gaa ttt aac aat tat gtc aat tct cat aaa ggc aaa atg ttc tat gtg<br>Glu Phe Asn Asn Tyr Val Asn Ser His Lys Gly Lys Met Phe Tyr Val<br>               35                    40                   45 | | 144 |
| tca aat cgc aaa gac agt aat gaa aaa gca ggt acc att gat gac atg | | 192 |

| | | | | | | | | | | | | | | |
|---|---|---|---|---|---|---|---|---|---|---|---|---|---|---|
| Ser | Asn | Arg | Lys | Asp | Ser | Asn | Glu | Lys | Ala | Gly | Thr | Ile | Asp | Asp | Met |
| | 50 | | | | | 55 | | | | | 60 | | | | |

```
aaa cgt tta ggc ttt acc ggt gtt gat gaa tca tcc ctt tat ctg aaa    240
Lys Arg Leu Gly Phe Thr Gly Val Asp Glu Ser Ser Leu Tyr Leu Lys
65              70                  75                  80 aaa gat aaa tcc gcc aaa tct gcc cgt ttt gca gaa att gaa agt caa    288
Lys Asp Lys Ser Ala Lys Ser Ala Arg Phe Ala Glu Ile Glu Ser Gln
                85                  90                  95 ggc tat gac atc gtg ctt tat gta ggc gac aac ctg gat gat ttc ggt    336
Gly Tyr Asp Ile Val Leu Tyr Val Gly Asp Asn Leu Asp Asp Phe Gly
            100                 105                 110 gat gca aca cac ggt aaa tta aat gcg gat cgt cga gac ttt gtt gct    384
Asp Ala Thr His Gly Lys Leu Asn Ala Asp Arg Arg Asp Phe Val Ala
        115                 120                 125 aaa aac cag gcg aaa ttc ggt aaa act tat atc gtt tta cct aat ccg    432
Lys Asn Gln Ala Lys Phe Gly Lys Thr Tyr Ile Val Leu Pro Asn Pro
130                 135                 140 aat tac ggt ggt tgg gaa ggc ggt tta gcc aaa gac tac ttt aaa ggt    480
Asn Tyr Gly Gly Trp Glu Gly Gly Leu Ala Lys Asp Tyr Phe Lys Gly
145                 150                 155                 160 gat tcc caa agc aaa gtt gat gcc cgc tta aat gta att aag gca tgg    528
Asp Ser Gln Ser Lys Val Asp Ala Arg Leu Asn Val Ile Lys Ala Trp
                165                 170                 175 agt gga aaa                                                        537
Ser Gly Lys
```

<210> SEQ ID NO 134
<211> LENGTH: 179
<212> TYPE: PRT
<213> ORGANISM: Actinobacillus actinomycetemcomitans

<400> SEQUENCE: 134

```
Ala Gly Trp Gln Ile Lys Asn Asn Lys Pro Phe Asp Gly Lys Asp Trp
1               5                   10                  15

Thr Arg Trp Val Asp Ala Arg Glu Ser Gly Ala Ile Ala Gly Ala Val
                20                  25                  30

Glu Phe Asn Asn Tyr Val Asn Ser His Lys Gly Lys Met Phe Tyr Val
            35                  40                  45

Ser Asn Arg Lys Asp Ser Asn Glu Lys Ala Gly Thr Ile Asp Asp Met
        50                  55                  60

Lys Arg Leu Gly Phe Thr Gly Val Asp Glu Ser Ser Leu Tyr Leu Lys
65              70                  75                  80

Lys Asp Lys Ser Ala Lys Ser Ala Arg Phe Ala Glu Ile Glu Ser Gln
                85                  90                  95

Gly Tyr Asp Ile Val Leu Tyr Val Gly Asp Asn Leu Asp Asp Phe Gly
            100                 105                 110

Asp Ala Thr His Gly Lys Leu Asn Ala Asp Arg Arg Asp Phe Val Ala
        115                 120                 125

Lys Asn Gln Ala Lys Phe Gly Lys Thr Tyr Ile Val Leu Pro Asn Pro
130                 135                 140

Asn Tyr Gly Gly Trp Glu Gly Gly Leu Ala Lys Asp Tyr Phe Lys Gly
145                 150                 155                 160

Asp Ser Gln Ser Lys Val Asp Ala Arg Leu Asn Val Ile Lys Ala Trp
                165                 170                 175

Ser Gly Lys
```

<210> SEQ ID NO 135

```
<211> LENGTH: 765
<212> TYPE: DNA
<213> ORGANISM: Actinobacillus actinomycetemcomitans
<220> FEATURE:
<221> NAME/KEY: CDS
<222> LOCATION: (1)..(765)

<400> SEQUENCE: 135 atg tgg ata ttt tac aac acc cgg aca ttc gtg ccg aat tac cgg ctt        48
Met Trp Ile Phe Tyr Asn Thr Arg Thr Phe Val Pro Asn Tyr Arg Leu
1               5                   10                  15 atg cca act ggc cga cat tcc cgc aat tat ggg tgg aag gcg agc tca        96
Met Pro Thr Gly Arg His Ser Arg Asn Tyr Gly Trp Lys Ala Ser Ser
                20                  25                  30 tcg gtg gtt gcg aca tcg tgt tgg aaa tgt acc aac aag gtg agc tta       144
Ser Val Val Ala Thr Ser Cys Trp Lys Cys Thr Asn Lys Val Ser Leu
            35                  40                  45 aaa cct tgt tac aag agg ttg ccg caa gac atc cgc aag cgt aaa aac       192
Lys Pro Cys Tyr Lys Arg Leu Pro Gln Asp Ile Arg Lys Arg Lys Asn
50                  55                  60 gcg ttt caa aat gac cgt act ttg gtt tcc gga gtg cgg ttt ttt gct       240
Ala Phe Gln Asn Asp Arg Thr Leu Val Ser Gly Val Arg Phe Phe Ala
65                  70                  75                  80 gct tgg cgc agg gaa aaa cag gcg gtt tgt gct ata att ctc cgc aaa       288
Ala Trp Arg Arg Glu Lys Gln Ala Val Cys Ala Ile Ile Leu Arg Lys
                85                  90                  95 ttt tta ccg cac ttt agg atc aat atg tcg ttt caa ttc aac gcg atc       336
Phe Leu Pro His Phe Arg Ile Asn Met Ser Phe Gln Phe Asn Ala Ile
                100                 105                 110 gcc tta ctt ttg gtg att tta att tta tta ggt gta ctc agc cac aac       384
Ala Leu Leu Leu Val Ile Leu Ile Leu Leu Gly Val Leu Ser His Asn
            115                 120                 125 agt tcc atc acc att tcc gct gcc gta ttg ctc atc atg caa caa acc       432
Ser Ser Ile Thr Ile Ser Ala Ala Val Leu Leu Ile Met Gln Gln Thr
130                 135                 140 ttg ctc gca aaa tat att cct tac ttg gaa aaa tac ggc ttg agc atc       480
Leu Leu Ala Lys Tyr Ile Pro Tyr Leu Glu Lys Tyr Gly Leu Ser Ile
145                 150                 155                 160 ggt atc gta att tta acc atc ggc gta cta agc ccg ttg gtt tcc ggc       528
Gly Ile Val Ile Leu Thr Ile Gly Val Leu Ser Pro Leu Val Ser Gly
                165                 170                 175 aga att caa ctg cct ggc ttg tcg gca ttt ttt agc tgg cga atg ttt       576
Arg Ile Gln Leu Pro Gly Leu Ser Ala Phe Phe Ser Trp Arg Met Phe
                180                 185                 190 gtt gcc att ggc gtc ggc gta tta gtg gcg tgg ctt gcc ggc aaa ggc       624
Val Ala Ile Gly Val Gly Val Leu Val Ala Trp Leu Ala Gly Lys Gly
            195                 200                 205 gtt ccg ctc atg ggg gaa gag cct gtt ctg gta acc ggc ttg gtt atc       672
Val Pro Leu Met Gly Glu Glu Pro Val Leu Val Thr Gly Leu Val Ile
210                 215                 220 ggc acc att atc ggc gtt tct ttt ctc ggt ggt att ccc gtt ggt ccc       720
Gly Thr Ile Ile Gly Val Ser Phe Leu Gly Gly Ile Pro Val Gly Pro
225                 230                 235                 240 ctt att gcg gca ggg att ttg gca tta tta ata gga aaa ttt taa           765
Leu Ile Ala Ala Gly Ile Leu Ala Leu Leu Ile Gly Lys Phe
                245                 250

<210> SEQ ID NO 136
<211> LENGTH: 254
<212> TYPE: PRT
<213> ORGANISM: Actinobacillus actinomycetemcomitans
```

-continued

```
<400> SEQUENCE: 136

Met Trp Ile Phe Tyr Asn Thr Arg Thr Phe Val Pro Asn Tyr Arg Leu
1               5                   10                  15

Met Pro Thr Gly Arg His Ser Arg Asn Tyr Gly Trp Lys Ala Ser Ser
            20                  25                  30

Ser Val Val Ala Thr Ser Cys Trp Lys Cys Thr Asn Lys Val Ser Leu
        35                  40                  45

Lys Pro Cys Tyr Lys Arg Leu Pro Gln Asp Ile Arg Lys Arg Lys Asn
    50                  55                  60

Ala Phe Gln Asn Asp Arg Thr Leu Val Ser Gly Val Arg Phe Phe Ala
65                  70                  75                  80

Ala Trp Arg Arg Glu Lys Gln Ala Val Cys Ala Ile Ile Leu Arg Lys
                85                  90                  95

Phe Leu Pro His Phe Arg Ile Asn Met Ser Phe Gln Phe Asn Ala Ile
            100                 105                 110

Ala Leu Leu Leu Val Ile Leu Ile Leu Leu Gly Val Leu Ser His Asn
        115                 120                 125

Ser Ser Ile Thr Ile Ser Ala Ala Val Leu Leu Ile Met Gln Gln Thr
130                 135                 140

Leu Leu Ala Lys Tyr Ile Pro Tyr Leu Glu Lys Tyr Gly Leu Ser Ile
145                 150                 155                 160

Gly Ile Val Ile Leu Thr Ile Gly Val Leu Ser Pro Leu Val Ser Gly
                165                 170                 175

Arg Ile Gln Leu Pro Gly Leu Ser Ala Phe Phe Ser Trp Arg Met Phe
            180                 185                 190

Val Ala Ile Gly Val Gly Val Leu Val Ala Trp Leu Ala Gly Lys Gly
        195                 200                 205

Val Pro Leu Met Gly Glu Glu Pro Val Leu Val Thr Gly Leu Val Ile
    210                 215                 220

Gly Thr Ile Ile Gly Val Ser Phe Leu Gly Gly Ile Pro Val Gly Pro
225                 230                 235                 240

Leu Ile Ala Ala Gly Ile Leu Ala Leu Leu Ile Gly Lys Phe
                245                 250

<210> SEQ ID NO 137
<211> LENGTH: 387
<212> TYPE: DNA
<213> ORGANISM: Actinobacillus actinomycetemcomitans
<220> FEATURE:
<221> NAME/KEY: CDS
<222> LOCATION: (1)..(387)

<400> SEQUENCE: 137 atg aaa aac aaa tgg tta ttg att gcc gcc gtg agc ggt ttt tta tgt     48
Met Lys Asn Lys Trp Leu Leu Ile Ala Ala Val Ser Gly Phe Leu Cys
1               5                   10                  15 gtg act atc ggt gcg ttt gcg gcg cac ggt tta agc caa gtg ttg gac     96
Val Thr Ile Gly Ala Phe Ala Ala His Gly Leu Ser Gln Val Leu Asp
            20                  25                  30 gcg aaa gcc tta gcg tgg att gac acc ggc gtg aaa tat caa atg ttc    144
Ala Lys Ala Leu Ala Trp Ile Asp Thr Gly Val Lys Tyr Gln Met Phe
        35                  40                  45 cac acc ctc gcc atc atg gga atc ggc atc gca caa tta tgt cgc gaa    192
His Thr Leu Ala Ile Met Gly Ile Gly Ile Ala Gln Leu Cys Arg Glu
    50                  55                  60 cca ttt gcc gcc aac aaa agc gcc aat gtt gcc gcc ggc gcg tgg tca    240
Pro Phe Ala Ala Asn Lys Ser Ala Asn Val Ala Ala Gly Ala Trp Ser
```

```
                65                  70                  75                  80
ttc gga atc ctt ctc ttt agc ggc agt tta tac gcc ctc gca ctt ggc        288
Phe Gly Ile Leu Leu Phe Ser Gly Ser Leu Tyr Ala Leu Ala Leu Gly
                    85                  90                  95 tca ggt aaa ttt atg gtt tgg ctc acg ccc atc ggc ggc acg cta ttt        336
Ser Gly Lys Phe Met Val Trp Leu Thr Pro Ile Gly Gly Thr Leu Phe
                100                 105                 110 tta atc ggc tgg ctt ggt tta gct tac ggc gct ttc aaa agt aaa tca        384
Leu Ile Gly Trp Leu Gly Leu Ala Tyr Gly Ala Phe Lys Ser Lys Ser
            115                 120                 125 gaa                                                                    387
Glu

<210> SEQ ID NO 138
<211> LENGTH: 129
<212> TYPE: PRT
<213> ORGANISM: Actinobacillus actinomycetemcomitans

<400> SEQUENCE: 138

Met Lys Asn Lys Trp Leu Leu Ile Ala Ala Val Ser Gly Phe Leu Cys
1               5                   10                  15

Val Thr Ile Gly Ala Phe Ala Ala His Gly Leu Ser Gln Val Leu Asp
                20                  25                  30

Ala Lys Ala Leu Ala Trp Ile Asp Thr Gly Val Lys Tyr Gln Met Phe
            35                  40                  45

His Thr Leu Ala Ile Met Gly Ile Gly Ile Ala Gln Leu Cys Arg Glu
        50                  55                  60

Pro Phe Ala Ala Asn Lys Ser Ala Asn Val Ala Ala Gly Ala Trp Ser
65                  70                  75                  80

Phe Gly Ile Leu Leu Phe Ser Gly Ser Leu Tyr Ala Leu Ala Leu Gly
                85                  90                  95

Ser Gly Lys Phe Met Val Trp Leu Thr Pro Ile Gly Gly Thr Leu Phe
                100                 105                 110

Leu Ile Gly Trp Leu Gly Leu Ala Tyr Gly Ala Phe Lys Ser Lys Ser
            115                 120                 125

Glu

<210> SEQ ID NO 139
<211> LENGTH: 684
<212> TYPE: DNA
<213> ORGANISM: Actinobacillus actinomycetemcomitans
<220> FEATURE:
<221> NAME/KEY: CDS
<222> LOCATION: (1)..(684)

<400> SEQUENCE: 139 atc aat ttg gca cat aat tat cag caa aaa tgg cag gcg gac atc ggt        48
Ile Asn Leu Ala His Asn Tyr Gln Gln Lys Trp Gln Ala Asp Ile Gly
1               5                   10                  15 cgg cac gcc gtg cag tat ttt gct tac gat aac ccg cgg gcg gat ttt        96
Arg His Ala Val Gln Tyr Phe Ala Tyr Asp Asn Pro Arg Ala Asp Phe
                20                  25                  30 tac gcc gaa caa att cat ttc tcc gaa caa ggc gcc tat ttc tta ctc       144
Tyr Ala Glu Gln Ile His Phe Ser Glu Gln Gly Ala Tyr Phe Leu Leu
            35                  40                  45 cac acg ccg caa ggc cgc gtg caa atc aat tca ccg tat ttg ggt gag       192
His Thr Pro Gln Gly Arg Val Gln Ile Asn Ser Pro Tyr Leu Gly Glu
        50                  55                  60 cat aat atc tct aat gcg ttg gcg gca act gcc ttg gcg atg aac gtg       240
```

-continued

| | | |
|---|---|---|
| His Asn Ile Ser Asn Ala Leu Ala Ala Thr Ala Leu Ala Met Asn Val<br>65                     70                         75                      80 | | |
| ggt gcc acc acg gcg cag gtg aaa aaa ggg ttg gaa acg ccc tct ttg<br>Gly Ala Thr Thr Ala Gln Val Lys Lys Gly Leu Glu Thr Pro Ser Leu<br>                         85                         90                       95 | 288 |
| gtg aaa ggg cgt ttg ttc ccg att cag cct tgt gaa aat ctg tta ttg<br>Val Lys Gly Arg Leu Phe Pro Ile Gln Pro Cys Glu Asn Leu Leu Leu<br>                 100                      105                     110 | 336 |
| ctg gac gat act tac aac gcc aat gtg gga tct atg aaa tcg gcg att<br>Leu Asp Asp Thr Tyr Asn Ala Asn Val Gly Ser Met Lys Ser Ala Ile<br>                 115                      120                     125 | 384 |
| tcc gtg tta caa aaa tat cct gct ttt cgc gtc ttt gtt gtt ggt gat<br>Ser Val Leu Gln Lys Tyr Pro Ala Phe Arg Val Phe Val Val Gly Asp<br>130                      135                       140 | 432 |
| atg ggc gaa tta ggc gat aat gcg caa ctt tgc cat caa gag gtg ggg<br>Met Gly Glu Leu Gly Asp Asn Ala Gln Leu Cys His Gln Glu Val Gly<br>145                      150                       155                     160 | 480 |
| gag ttc gct cat gcc gcc aag tta gac tta gtg ctt tct ttc ggg tgt<br>Glu Phe Ala His Ala Ala Lys Leu Asp Leu Val Leu Ser Phe Gly Cys<br>                 165                      170                     175 | 528 |
| tcc agt ggc gtt ata agt gcg gtt aat tcg gga cgc cat ttt acc gat<br>Ser Ser Gly Val Ile Ser Ala Val Asn Ser Gly Arg His Phe Thr Asp<br>                    180                      185                     190 | 576 |
| aaa acg gaa ctt gta act tat tta aca ccg att att caa caa caa tta<br>Lys Thr Glu Leu Val Thr Tyr Leu Thr Pro Ile Ile Gln Gln Gln Leu<br>                 195                      200                     205 | 624 |
| gca caa caa aaa gtc gtt gtt ttg gtg aaa gga tca cgc agc atg aaa<br>Ala Gln Gln Lys Val Val Val Leu Val Lys Gly Ser Arg Ser Met Lys<br>210                      215                       220 | 672 |
| atg gaa gaa gtg<br>Met Glu Glu Val<br>225 | 684 |

<210> SEQ ID NO 140
<211> LENGTH: 228
<212> TYPE: PRT
<213> ORGANISM: Actinobacillus actinomycetemcomitans

<400> SEQUENCE: 140

Ile Asn Leu Ala His Asn Tyr Gln Gln Lys Trp Gln Ala Asp Ile Gly
1                 5                     10                   15

Arg His Ala Val Gln Tyr Phe Ala Tyr Asp Asn Pro Arg Ala Asp Phe
                 20                     25                     30

Tyr Ala Glu Gln Ile His Phe Ser Glu Gln Gly Ala Tyr Phe Leu Leu
                   35                     40                     45

His Thr Pro Gln Gly Arg Val Gln Ile Asn Ser Pro Tyr Leu Gly Glu
     50                     55                     60

His Asn Ile Ser Asn Ala Leu Ala Ala Thr Ala Leu Ala Met Asn Val
65                     70                         75                      80

Gly Ala Thr Thr Ala Gln Val Lys Lys Gly Leu Glu Thr Pro Ser Leu
                 85                     90                     95

Val Lys Gly Arg Leu Phe Pro Ile Gln Pro Cys Glu Asn Leu Leu Leu
                 100                      105                     110

Leu Asp Asp Thr Tyr Asn Ala Asn Val Gly Ser Met Lys Ser Ala Ile
                 115                      120                     125

Ser Val Leu Gln Lys Tyr Pro Ala Phe Arg Val Phe Val Val Gly Asp
130                     135                      140

Met Gly Glu Leu Gly Asp Asn Ala Gln Leu Cys His Gln Glu Val Gly

```
                145                 150                 155                 160
Glu Phe Ala His Ala Ala Lys Leu Asp Leu Val Leu Ser Phe Gly Cys
                    165                 170                 175

Ser Ser Gly Val Ile Ser Ala Val Asn Ser Gly Arg His Phe Thr Asp
            180                 185                 190

Lys Thr Glu Leu Val Thr Tyr Leu Thr Pro Ile Ile Gln Gln Gln Leu
        195                 200                 205

Ala Gln Gln Lys Val Val Leu Val Lys Gly Ser Arg Ser Met Lys
    210                 215                 220

Met Glu Glu Val
225

<210> SEQ ID NO 141
<211> LENGTH: 267
<212> TYPE: DNA
<213> ORGANISM: Actinobacillus actinomycetemcomitans
<220> FEATURE:
<221> NAME/KEY: CDS
<222> LOCATION: (1)..(267)

<400> SEQUENCE: 141 gat ggc ggt aag gcg ggt tcg agg tat gca ggt att atc tat aaa tct        48
Asp Gly Gly Lys Ala Gly Ser Arg Tyr Ala Gly Ile Ile Tyr Lys Ser
1               5                   10                  15 gtg aag cca tat ttt cgt ggt gat agt cgt ttt ttt ggt aag gtc tgt        96
Val Lys Pro Tyr Phe Arg Gly Asp Ser Arg Phe Phe Gly Lys Val Cys
            20                  25                  30 gat att aga att gag ctt tct agt gat ggc act att tta tct tac caa       144
Asp Ile Arg Ile Glu Leu Ser Ser Asp Gly Thr Ile Leu Ser Tyr Gln
        35                  40                  45 aag gtc tcc ggg cca aat gat tta tgt ggg gcg gct tta aat gct att       192
Lys Val Ser Gly Pro Asn Asp Leu Cys Gly Ala Ala Leu Asn Ala Ile
    50                  55                  60 ggt caa acc aga aaa atg aac gaa ccg cct acg ccg gaa gaa tat gaa       240
Gly Gln Thr Arg Lys Met Asn Glu Pro Pro Thr Pro Glu Glu Tyr Glu
65                  70                  75                  80 ata ttt aaa agg tcc att gta acc ttt                                   267
Ile Phe Lys Arg Ser Ile Val Thr Phe
                85

<210> SEQ ID NO 142
<211> LENGTH: 89
<212> TYPE: PRT
<213> ORGANISM: Actinobacillus actinomycetemcomitans

<400> SEQUENCE: 142

Asp Gly Gly Lys Ala Gly Ser Arg Tyr Ala Gly Ile Ile Tyr Lys Ser
1               5                   10                  15

Val Lys Pro Tyr Phe Arg Gly Asp Ser Arg Phe Phe Gly Lys Val Cys
            20                  25                  30

Asp Ile Arg Ile Glu Leu Ser Ser Asp Gly Thr Ile Leu Ser Tyr Gln
        35                  40                  45

Lys Val Ser Gly Pro Asn Asp Leu Cys Gly Ala Ala Leu Asn Ala Ile
    50                  55                  60

Gly Gln Thr Arg Lys Met Asn Glu Pro Pro Thr Pro Glu Glu Tyr Glu
65                  70                  75                  80

Ile Phe Lys Arg Ser Ile Val Thr Phe
                85
```

<210> SEQ ID NO 143
<211> LENGTH: 683
<212> TYPE: DNA
<213> ORGANISM: Actinobacillus actinomycetemcomitans
<220> FEATURE:
<221> NAME/KEY: CDS
<222> LOCATION: (1)..(681)

<400> SEQUENCE: 143

| ggt | gcc | tta | tat | ttt | gta | ttc | agt | ctg | atg | ggc | gtg | ttc | gcc | agt | ttg | 48 |
|---|---|---|---|---|---|---|---|---|---|---|---|---|---|---|---|---|
| Gly | Ala | Leu | Tyr | Phe | Val | Phe | Ser | Leu | Met | Gly | Val | Phe | Ala | Ser | Leu | |
| 1 | | | | 5 | | | | | 10 | | | | | 15 | | |

| tta | tcc | acc | gcg | cgc | ggc | ggc | tgg | att | ggt | atc | cct | ttt | gtt | ctc | ctg | 96 |
|---|---|---|---|---|---|---|---|---|---|---|---|---|---|---|---|---|
| Leu | Ser | Thr | Ala | Arg | Gly | Gly | Trp | Ile | Gly | Ile | Pro | Phe | Val | Leu | Leu | |
| | | | 20 | | | | | 25 | | | | | 30 | | | |

| tta | atc | ctc | ttt | gct | tat | cgt | cgt | tat | tta | tcg | aaa | aaa | ttc | gtc | gcc | 144 |
|---|---|---|---|---|---|---|---|---|---|---|---|---|---|---|---|---|
| Leu | Ile | Leu | Phe | Ala | Tyr | Arg | Arg | Tyr | Leu | Ser | Lys | Lys | Phe | Val | Ala | |
| | 35 | | | | | 40 | | | | | 45 | | | | | |

| ggc | ttt | ttt | att | gtg | ctt | gcc | ctg | att | gta | aca | acc | gtt | gcg | atg | ttg | 192 |
|---|---|---|---|---|---|---|---|---|---|---|---|---|---|---|---|---|
| Gly | Phe | Phe | Ile | Val | Leu | Ala | Leu | Ile | Val | Thr | Thr | Val | Ala | Met | Leu | |
| 50 | | | | | 55 | | | | | 60 | | | | | | |

| cca | aat | acc | aaa | att | aaa | gaa | cgc | att | gcc | gcc | gca | gaa | tac | gac | atc | 240 |
|---|---|---|---|---|---|---|---|---|---|---|---|---|---|---|---|---|
| Pro | Asn | Thr | Lys | Ile | Lys | Glu | Arg | Ile | Ala | Ala | Ala | Glu | Tyr | Asp | Ile | |
| 65 | | | | 70 | | | | | 75 | | | | | 80 | | |

| atc | gcc | tat | ttt | caa | caa | aat | aac | ggt | tct | acc | tcc | gtc | ggc | gcc | cgt | 288 |
|---|---|---|---|---|---|---|---|---|---|---|---|---|---|---|---|---|
| Ile | Ala | Tyr | Phe | Gln | Gln | Asn | Asn | Gly | Ser | Thr | Ser | Val | Gly | Ala | Arg | |
| | | | 85 | | | | | 90 | | | | | 95 | | | |

| ttt | gat | atg | tgg | aaa | agc | gtg | atg | tta | atg | acg | cag | gaa | aaa | ccg | att | 336 |
|---|---|---|---|---|---|---|---|---|---|---|---|---|---|---|---|---|
| Phe | Asp | Met | Trp | Lys | Ser | Val | Met | Leu | Met | Thr | Gln | Glu | Lys | Pro | Ile | |
| | | 100 | | | | | 105 | | | | | 110 | | | | |

| ttc | ggt | tgg | ggc | gta | caa | ggg | gtc | agc | gaa | aaa | cgc | aaa | ctg | caa | tat | 384 |
|---|---|---|---|---|---|---|---|---|---|---|---|---|---|---|---|---|
| Phe | Gly | Trp | Gly | Val | Gln | Gly | Val | Ser | Glu | Lys | Arg | Lys | Leu | Gln | Tyr | |
| 115 | | | | | 120 | | | | | 125 | | | | | | |

| gag | caa | ggt | ttg | ata | agc | caa | tat | gcc | gcc | gcc | ttt | aac | cac | gcg | cac | 432 |
|---|---|---|---|---|---|---|---|---|---|---|---|---|---|---|---|---|
| Glu | Gln | Gly | Leu | Ile | Ser | Gln | Tyr | Ala | Ala | Ala | Phe | Asn | His | Ala | His | |
| 130 | | | | | 135 | | | | | 140 | | | | | | |

| aac | caa | tat | ttt | gat | gat | tta | tcc | aaa | cgc | ggc | gca | tta | ggt | tta | ctc | 480 |
|---|---|---|---|---|---|---|---|---|---|---|---|---|---|---|---|---|
| Asn | Gln | Tyr | Phe | Asp | Asp | Leu | Ser | Lys | Arg | Gly | Ala | Leu | Gly | Leu | Leu | |
| 145 | | | | 150 | | | | | 155 | | | | | 160 | | |

| gcc | tta | ctc | ggc | gta | ttt | tta | gtg | ccg | ttg | cgt | ttc | ttt | ata | cgg | cat | 528 |
|---|---|---|---|---|---|---|---|---|---|---|---|---|---|---|---|---|
| Ala | Leu | Leu | Gly | Val | Phe | Leu | Val | Pro | Leu | Arg | Phe | Phe | Ile | Arg | His | |
| | | | 165 | | | | | 170 | | | | | 175 | | | |

| ctc | aaa | agc | gtc | gat | tta | gaa | ctg | aaa | ctc | gtt | tcg | ttg | tta | ggt | gcg | 576 |
|---|---|---|---|---|---|---|---|---|---|---|---|---|---|---|---|---|
| Leu | Lys | Ser | Val | Asp | Leu | Glu | Leu | Lys | Leu | Val | Ser | Leu | Leu | Gly | Ala | |
| | | | 180 | | | | | 185 | | | | | 190 | | | |

| gtt | cat | att | gtc | tcc | gtg | atg | ttc | tac | tgt | ttc | agc | caa | ggc | ttt | ttc | 624 |
|---|---|---|---|---|---|---|---|---|---|---|---|---|---|---|---|---|
| Val | His | Ile | Val | Ser | Val | Met | Phe | Tyr | Cys | Phe | Ser | Gln | Gly | Phe | Phe | |
| | | 195 | | | | | 200 | | | | | 205 | | | | |

| agc | cat | aac | tcg | ggc | aat | att | ttc | tat | ttt | ttc | ccg | gtg | att | gtg | ttt | 672 |
|---|---|---|---|---|---|---|---|---|---|---|---|---|---|---|---|---|
| Ser | His | Asn | Ser | Gly | Asn | Ile | Phe | Tyr | Phe | Phe | Pro | Val | Ile | Val | Phe | |
| 210 | | | | | 215 | | | | | 220 | | | | | | |

| tac | gcc | ttg | gt | | | | | | | | | | | | | 683 |
|---|---|---|---|---|---|---|---|---|---|---|---|---|---|---|---|---|
| Tyr | Ala | Leu | | | | | | | | | | | | | | |
| 225 | | | | | | | | | | | | | | | | |

<210> SEQ ID NO 144
<211> LENGTH: 227
<212> TYPE: PRT
<213> ORGANISM: Actinobacillus actinomycetemcomitans

<400> SEQUENCE: 144

Gly Ala Leu Tyr Phe Val Phe Ser Leu Met Gly Val Phe Ala Ser Leu

```
  1               5               10              15
Leu Ser Thr Ala Arg Gly Gly Trp Ile Gly Ile Pro Phe Val Leu Leu
                20              25              30

Leu Ile Leu Phe Ala Tyr Arg Arg Tyr Leu Ser Lys Lys Phe Val Ala
                35              40              45

Gly Phe Phe Ile Val Leu Ala Leu Ile Val Thr Thr Val Ala Met Leu
 50              55              60

Pro Asn Thr Lys Ile Lys Glu Arg Ile Ala Ala Ala Glu Tyr Asp Ile
65              70              75              80

Ile Ala Tyr Phe Gln Gln Asn Asn Gly Ser Thr Ser Val Gly Ala Arg
                85              90              95

Phe Asp Met Trp Lys Ser Val Met Leu Met Thr Gln Glu Lys Pro Ile
                100             105             110

Phe Gly Trp Gly Val Gln Gly Val Ser Glu Lys Arg Lys Leu Gln Tyr
                115             120             125

Glu Gln Gly Leu Ile Ser Gln Tyr Ala Ala Ala Phe Asn His Ala His
            130             135             140

Asn Gln Tyr Phe Asp Asp Leu Ser Lys Arg Gly Ala Leu Gly Leu Leu
145             150             155             160

Ala Leu Leu Gly Val Phe Leu Val Pro Leu Arg Phe Ile Arg His
                165             170             175

Leu Lys Ser Val Asp Leu Glu Leu Lys Leu Val Ser Leu Leu Gly Ala
                180             185             190

Val His Ile Val Ser Val Met Phe Tyr Cys Phe Ser Gln Gly Phe Phe
            195             200             205

Ser His Asn Ser Gly Asn Ile Phe Tyr Phe Pro Val Ile Val Phe
    210             215             220

Tyr Ala Leu
225

<210> SEQ ID NO 145
<211> LENGTH: 408
<212> TYPE: DNA
<213> ORGANISM: Actinobacillus actinomycetemcomitans
<220> FEATURE:
<221> NAME/KEY: CDS
<222> LOCATION: (1)..(408)

<400> SEQUENCE: 145 gcc gat tat ggc atc gac tat ggt aac gat ttc gta ggt atc att gaa      48
Ala Asp Tyr Gly Ile Asp Tyr Gly Asn Asp Phe Val Gly Ile Ile Glu
 1               5              10              15 gga aaa ttg aag tta aac aaa tca acg tta cat gat aat aac gcc tcc      96
Gly Lys Leu Lys Leu Asn Lys Ser Thr Leu His Asp Asn Asn Ala Ser
                20              25              30 ggc tac cgt ggc aaa ctg aac gaa aag gca cgt ttg ggc gta agt tac     144
Gly Tyr Arg Gly Lys Leu Asn Glu Lys Ala Arg Leu Gly Val Ser Tyr
            35              40              45 tta caa ggc tat cgc gta aca cca agc att ctt cct tat gcc aaa gtt     192
Leu Gln Gly Tyr Arg Val Thr Pro Ser Ile Leu Pro Tyr Ala Lys Val
 50              55              60 ggg gtg caa act gct aaa ttt gaa agt gag gtt cgt aca cgc aac tac     240
Gly Val Gln Thr Ala Lys Phe Glu Ser Glu Val Arg Thr Arg Asn Tyr
65              70              75              80 tca gct acg cat agt gat acc aaa aac ggt ata ggt ttt ggt gcg ggt     288
Ser Ala Thr His Ser Asp Thr Lys Asn Gly Ile Gly Phe Gly Ala Gly
                85              90              95
```

```
gtt aag gtc aat ctg gta ccg gac ttt gag cta agc ttg gaa tat tta         336
Val Lys Val Asn Leu Val Pro Asp Phe Glu Leu Ser Leu Glu Tyr Leu
            100                 105                 110 agg act cat aac aaa ttt gat ggt caa aag tta aga ggt aat gta tat         384
Arg Thr His Asn Lys Phe Asp Gly Gln Lys Leu Arg Gly Asn Val Tyr
        115                 120                 125 agc acc aac gct aca tat cgt ttc                                         408
Ser Thr Asn Ala Thr Tyr Arg Phe
    130                 135

<210> SEQ ID NO 146
<211> LENGTH: 136
<212> TYPE: PRT
<213> ORGANISM: Actinobacillus actinomycetemcomitans

<400> SEQUENCE: 146

Ala Asp Tyr Gly Ile Asp Tyr Gly Asn Asp Phe Val Gly Ile Ile Glu
1               5                   10                  15

Gly Lys Leu Lys Leu Asn Lys Ser Thr Leu His Asp Asn Asn Ala Ser
            20                  25                  30

Gly Tyr Arg Gly Lys Leu Asn Glu Lys Ala Arg Leu Gly Val Ser Tyr
        35                  40                  45

Leu Gln Gly Tyr Arg Val Thr Pro Ser Ile Leu Pro Tyr Ala Lys Val
    50                  55                  60

Gly Val Gln Thr Ala Lys Phe Glu Ser Glu Val Arg Thr Arg Asn Tyr
65                  70                  75                  80

Ser Ala Thr His Ser Asp Thr Lys Asn Gly Ile Gly Phe Gly Ala Gly
                85                  90                  95

Val Lys Val Asn Leu Val Pro Asp Phe Glu Leu Ser Leu Glu Tyr Leu
            100                 105                 110

Arg Thr His Asn Lys Phe Asp Gly Gln Lys Leu Arg Gly Asn Val Tyr
        115                 120                 125

Ser Thr Asn Ala Thr Tyr Arg Phe
    130                 135

<210> SEQ ID NO 147
<211> LENGTH: 426
<212> TYPE: DNA
<213> ORGANISM: Actinobacillus actinomycetemcomitans
<220> FEATURE:
<221> NAME/KEY: CDS
<222> LOCATION: (1)..(426)

<400> SEQUENCE: 147 atg aaa aaa att ctt acc gca ctt ttt tgc agt tgt ctc att tcc cct         48
Met Lys Lys Ile Leu Thr Ala Leu Phe Cys Ser Cys Leu Ile Ser Pro
1               5                   10                  15 ctc aca aac gct gaa acc ttg tct gat ggt tta cca cca cag gca gct         96
Leu Thr Asn Ala Glu Thr Leu Ser Asp Gly Leu Pro Pro Gln Ala Ala
            20                  25                  30 ggt gat tat gtg ttc ttg gac ccg cat caa aac aat acg gat ata caa         144
Gly Asp Tyr Val Phe Leu Asp Pro His Gln Asn Asn Thr Asp Ile Gln
        35                  40                  45 ttt cgt tta aaa ctt aaa ggc aaa caa tgg ctg gca gac ggt tcc caa         192
Phe Arg Leu Lys Leu Lys Gly Lys Gln Trp Leu Ala Asp Gly Ser Gln
    50                  55                  60 aat gcc ggc aaa agc tgg tcg cct gtg tgc gaa gtc agt ggc gaa tgc         240
Asn Ala Gly Lys Ser Trp Ser Pro Val Cys Glu Val Ser Gly Glu Cys
65                  70                  75                  80 aaa ctg gag aca tcc tcc aaa gcg gaa atc gaa cgc ttc ttt gag caa         288
```

```
Lys Leu Glu Thr Ser Ser Lys Ala Glu Ile Glu Arg Phe Phe Glu Gln
                85                  90                  95 tat ccg caa gta cta aac cga aca gat gtc agc tgc att cac aat atg    336
Tyr Pro Gln Val Leu Asn Arg Thr Asp Val Ser Cys Ile His Asn Met
            100                 105                 110 gcg ttc gct ttc tgc ggg tta act tta gat aaa aaa acc gat tat gtg    384
Ala Phe Ala Phe Cys Gly Leu Thr Leu Asp Lys Lys Thr Asp Tyr Val
        115                 120                 125 atg gtc gca tta gtg acc aat ccg cca caa gtc aca tcg tat            426
Met Val Ala Leu Val Thr Asn Pro Pro Gln Val Thr Ser Tyr
    130                 135                 140

<210> SEQ ID NO 148
<211> LENGTH: 142
<212> TYPE: PRT
<213> ORGANISM: Actinobacillus actinomycetemcomitans

<400> SEQUENCE: 148

Met Lys Lys Ile Leu Thr Ala Leu Phe Cys Ser Cys Leu Ile Ser Pro
1               5                   10                  15

Leu Thr Asn Ala Glu Thr Leu Ser Asp Gly Leu Pro Pro Gln Ala Ala
                20                  25                  30

Gly Asp Tyr Val Phe Leu Asp Pro His Gln Asn Asn Thr Asp Ile Gln
            35                  40                  45

Phe Arg Leu Lys Leu Lys Gly Lys Gln Trp Leu Ala Asp Gly Ser Gln
        50                  55                  60

Asn Ala Gly Lys Ser Trp Ser Pro Val Cys Glu Val Ser Gly Glu Cys
65                  70                  75                  80

Lys Leu Glu Thr Ser Ser Lys Ala Glu Ile Glu Arg Phe Phe Glu Gln
                85                  90                  95

Tyr Pro Gln Val Leu Asn Arg Thr Asp Val Ser Cys Ile His Asn Met
            100                 105                 110

Ala Phe Ala Phe Cys Gly Leu Thr Leu Asp Lys Lys Thr Asp Tyr Val
        115                 120                 125

Met Val Ala Leu Val Thr Asn Pro Pro Gln Val Thr Ser Tyr
    130                 135                 140

<210> SEQ ID NO 149
<211> LENGTH: 679
<212> TYPE: DNA
<213> ORGANISM: Actinobacillus actinomycetemcomitans
<220> FEATURE:
<221> NAME/KEY: CDS
<222> LOCATION: (1)..(678)

<400> SEQUENCE: 149 cgc cga att att ggc aca acg aca aca gga tat tca cta atg cgc gca    48
Arg Arg Ile Ile Gly Thr Thr Thr Thr Gly Tyr Ser Leu Met Arg Ala
1               5                   10                  15 tta ttg cct ttt ctt cgt tta ttt aaa ttc gcc aaa ctg ccg tta att    96
Leu Leu Pro Phe Leu Arg Leu Phe Lys Phe Ala Lys Leu Pro Leu Ile
                20                  25                  30 tta ggc ggc ttg ctg atg att tta ggg ctg gcg tcc agt atc ggg ttg    144
Leu Gly Gly Leu Leu Met Ile Leu Gly Leu Ala Ser Ser Ile Gly Leu
            35                  40                  45 ctc acc ctt tcc ggc tgg ttt ctt gcc gcc acc gcc atc gcc ggt ttc    192
Leu Thr Leu Ser Gly Trp Phe Leu Ala Ala Thr Ala Ile Ala Gly Phe
        50                  55                  60 ggc tcg cta ttt aac ttt ttc tac cca tcc gcc agc gta cgc ggt ttg    240
Gly Ser Leu Phe Asn Phe Phe Tyr Pro Ser Ala Ser Val Arg Gly Leu
```

-continued

```
                65                  70                  75                  80
gca atc ggg cgt acc gtg gcg cgc tac ctt gaa aaa gtg gtc acc cat         288
Ala Ile Gly Arg Thr Val Ala Arg Tyr Leu Glu Lys Val Val Thr His
                85                  90                  95 gac gcc acc ttc cgc gta ttg gca aaa ctg cgt gtg cag gtg ttt gac         336
Asp Ala Thr Phe Arg Val Leu Ala Lys Leu Arg Val Gln Val Phe Asp
            100                 105                 110 aaa atc att ccg tta agc cct gcg ctg ctc aac cgt tat cgt aac agc         384
Lys Ile Ile Pro Leu Ser Pro Ala Leu Leu Asn Arg Tyr Arg Asn Ser
        115                 120                 125 gat tta tta aac cgc ttg gtt gcc gat gtg gac acc ctc gac agc cta         432
Asp Leu Leu Asn Arg Leu Val Ala Asp Val Asp Thr Leu Asp Ser Leu
    130                 135                 140 tat ctt cgc ctc att gcg ccc ttt atc agc gcc ata gtg gtg att gcg         480
Tyr Leu Arg Leu Ile Ala Pro Phe Ile Ser Ala Ile Val Val Ile Ala
145                 150                 155                 160 ttc att acc ttt ggc ttg agt ttt att aat gcc ccg ctc gcg ctg ttt         528
Phe Ile Thr Phe Gly Leu Ser Phe Ile Asn Ala Pro Leu Ala Leu Phe
                165                 170                 175 atc ggt ttc aca tta ctg gcg ctc ttg ctg gtt atc ccg acg att ttt         576
Ile Gly Phe Thr Leu Leu Ala Leu Leu Leu Val Ile Pro Thr Ile Phe
            180                 185                 190 tac cat ttg ggt aac aaa ttc ggc gcc aaa ctt acc caa tcc cgc gcc         624
Tyr His Leu Gly Asn Lys Phe Gly Ala Lys Leu Thr Gln Ser Arg Ala
        195                 200                 205 ctt tac cgc acg caa ttt atc gaa ttt att cag gcg caa gcg gaa tta         672
Leu Tyr Arg Thr Gln Phe Ile Glu Phe Ile Gln Ala Gln Ala Glu Leu
    210                 215                 220 ttg ctg t                                                               679
Leu Leu
225
```

<210> SEQ ID NO 150
<211> LENGTH: 226
<212> TYPE: PRT
<213> ORGANISM: Actinobacillus actinomycetemcomitans

<400> SEQUENCE: 150

```
Arg Arg Ile Ile Gly Thr Thr Thr Gly Tyr Ser Leu Met Arg Ala
1               5                   10                  15

Leu Leu Pro Phe Leu Arg Leu Phe Lys Phe Ala Lys Leu Pro Leu Ile
                20                  25                  30

Leu Gly Gly Leu Leu Met Ile Leu Gly Leu Ala Ser Ser Ile Gly Leu
            35                  40                  45

Leu Thr Leu Ser Gly Trp Phe Leu Ala Ala Thr Ala Ile Ala Gly Phe
    50                  55                  60

Gly Ser Leu Phe Asn Phe Phe Tyr Pro Ser Ala Ser Val Arg Gly Leu
65                  70                  75                  80

Ala Ile Gly Arg Thr Val Ala Arg Tyr Leu Glu Lys Val Val Thr His
                85                  90                  95

Asp Ala Thr Phe Arg Val Leu Ala Lys Leu Arg Val Gln Val Phe Asp
            100                 105                 110

Lys Ile Ile Pro Leu Ser Pro Ala Leu Leu Asn Arg Tyr Arg Asn Ser
        115                 120                 125

Asp Leu Leu Asn Arg Leu Val Ala Asp Val Asp Thr Leu Asp Ser Leu
    130                 135                 140

Tyr Leu Arg Leu Ile Ala Pro Phe Ile Ser Ala Ile Val Val Ile Ala
145                 150                 155                 160
```

```
Phe Ile Thr Phe Gly Leu Ser Phe Ile Asn Ala Pro Leu Ala Leu Phe
            165                 170                 175

Ile Gly Phe Thr Leu Leu Ala Leu Leu Leu Val Ile Pro Thr Ile Phe
            180                 185                 190

Tyr His Leu Gly Asn Lys Phe Gly Ala Lys Leu Thr Gln Ser Arg Ala
            195                 200                 205

Leu Tyr Arg Thr Gln Phe Ile Glu Phe Ile Gln Ala Gln Ala Glu Leu
        210                 215                 220

Leu Leu
225

<210> SEQ ID NO 151
<211> LENGTH: 323
<212> TYPE: DNA
<213> ORGANISM: Actinobacillus actinomycetemcomitans
<220> FEATURE:
<221> NAME/KEY: CDS
<222> LOCATION: (1)..(321)

<400> SEQUENCE: 151 cct tcc aaa ttg acg tta gct ctt gct att gca agt ggc tta agt gta    48
Pro Ser Lys Leu Thr Leu Ala Leu Ala Ile Ala Ser Gly Leu Ser Val
1               5                   10                  15 aca aat tta agc tat gcc act aac gat act att caa gcg ggc aac ggc    96
Thr Asn Leu Ser Tyr Ala Thr Asn Asp Thr Ile Gln Ala Gly Asn Gly
                20                  25                  30 att gcc gtg gta caa acc caa tcg ggt gaa atc caa ggt tat att cat   144
Ile Ala Val Val Gln Thr Gln Ser Gly Glu Ile Gln Gly Tyr Ile His
            35                  40                  45 aac gat att ttg acc tat aaa ggc att ccg tat gcc aca gca gaa cgt   192
Asn Asp Ile Leu Thr Tyr Lys Gly Ile Pro Tyr Ala Thr Ala Glu Arg
        50                  55                  60 ttt atg cca cca aaa ccg gtg gag aat tgg caa ggg aca aaa atg gcg   240
Phe Met Pro Pro Lys Pro Val Glu Asn Trp Gln Gly Thr Lys Met Ala
65                  70                  75                  80 ttg act tat ggc gat gtc tgc ccg caa gtg ccg atg ggc ggt cgt agt   288
Leu Thr Tyr Gly Asp Val Cys Pro Gln Val Pro Met Gly Gly Arg Ser
                85                  90                  95 ttc ttc ttt acc gga cct gaa atg acg gaa agt ga                    323
Phe Phe Phe Thr Gly Pro Glu Met Thr Glu Ser
                100                 105

<210> SEQ ID NO 152
<211> LENGTH: 107
<212> TYPE: PRT
<213> ORGANISM: Actinobacillus actinomycetemcomitans

<400> SEQUENCE: 152

Pro Ser Lys Leu Thr Leu Ala Leu Ala Ile Ala Ser Gly Leu Ser Val
1               5                   10                  15

Thr Asn Leu Ser Tyr Ala Thr Asn Asp Thr Ile Gln Ala Gly Asn Gly
                20                  25                  30

Ile Ala Val Val Gln Thr Gln Ser Gly Glu Ile Gln Gly Tyr Ile His
            35                  40                  45

Asn Asp Ile Leu Thr Tyr Lys Gly Ile Pro Tyr Ala Thr Ala Glu Arg
        50                  55                  60

Phe Met Pro Pro Lys Pro Val Glu Asn Trp Gln Gly Thr Lys Met Ala
65                  70                  75                  80

Leu Thr Tyr Gly Asp Val Cys Pro Gln Val Pro Met Gly Gly Arg Ser
```

```
                    85                  90                  95
Phe Phe Phe Thr Gly Pro Glu Met Thr Glu Ser
                    100                 105

<210> SEQ ID NO 153
<211> LENGTH: 177
<212> TYPE: DNA
<213> ORGANISM: Actinobacillus actinomycetemcomitans
<220> FEATURE:
<221> NAME/KEY: CDS
<222> LOCATION: (1)..(177)

<400> SEQUENCE: 153 ggc ggc ggt gcc tgg gtt cag gcg gat ttg aag atg ttc caa atg cac       48
Gly Gly Gly Ala Trp Val Gln Ala Asp Leu Lys Met Phe Gln Met His
1               5                   10                  15 agg atg tcg ttt ggt tca tcg gtg gcc gcg caa aat acc ttg aac gtg       96
Arg Met Ser Phe Gly Ser Ser Val Ala Ala Gln Asn Thr Leu Asn Val
            20                  25                  30 gtt gat att tac gcc gtg tca ctc aaa acc atc caa tgt cag ctg aaa      144
Val Asp Ile Tyr Ala Val Ser Leu Lys Thr Ile Gln Cys Gln Leu Lys
        35                  40                  45 gcc att gtg aca gat ttt gat att tcg cac ctt                          177
Ala Ile Val Thr Asp Phe Asp Ile Ser His Leu
    50                  55

<210> SEQ ID NO 154
<211> LENGTH: 59
<212> TYPE: PRT
<213> ORGANISM: Actinobacillus actinomycetemcomitans

<400> SEQUENCE: 154

Gly Gly Gly Ala Trp Val Gln Ala Asp Leu Lys Met Phe Gln Met His
1               5                   10                  15

Arg Met Ser Phe Gly Ser Ser Val Ala Ala Gln Asn Thr Leu Asn Val
            20                  25                  30

Val Asp Ile Tyr Ala Val Ser Leu Lys Thr Ile Gln Cys Gln Leu Lys
        35                  40                  45

Ala Ile Val Thr Asp Phe Asp Ile Ser His Leu
    50                  55

<210> SEQ ID NO 155
<211> LENGTH: 469
<212> TYPE: DNA
<213> ORGANISM: Actinobacillus actinomycetemcomitans
<220> FEATURE:
<221> NAME/KEY: CDS
<222> LOCATION: (1)..(468)

<400> SEQUENCE: 155 atg gag aaa aaa caa acc tca cgg gta caa aaa ctg gaa ttt ttg ctc       48
Met Glu Lys Lys Gln Thr Ser Arg Val Gln Lys Leu Glu Phe Leu Leu
1               5                   10                  15 aaa caa aca gat aaa atc cat ctg cgc gac gcg gca caa atg ctt gat       96
Lys Gln Thr Asp Lys Ile His Leu Arg Asp Ala Ala Gln Met Leu Asp
            20                  25                  30 gtg tcg gaa atg act tta cgt cgg gat tta agt tcc gac agc ggc aat      144
Val Ser Glu Met Thr Leu Arg Arg Asp Leu Ser Ser Asp Ser Gly Asn
        35                  40                  45 gtg gtg tta ttg ggc ggc tat atc gtg atg aac cca caa aaa agc ggc      192
Val Val Leu Leu Gly Gly Tyr Ile Val Met Asn Pro Gln Lys Ser Gly
    50                  55                  60
```

```
aat cat tat cag att ttt gac caa caa acg cgc cac att acg gaa aaa        240
Asn His Tyr Gln Ile Phe Asp Gln Gln Thr Arg His Ile Thr Glu Lys
 65              70                  75                  80 atg tgg ctc ggt aaa ctc gcc gcc aat ctc gtc aag gac gga gat acc        288
Met Trp Leu Gly Lys Leu Ala Ala Asn Leu Val Lys Asp Gly Asp Thr
                 85                  90                  95 gtg ttc ttc gat tgc ggt agc acc att ccg ttt atc att tcg caa atc        336
Val Phe Phe Asp Cys Gly Ser Thr Ile Pro Phe Ile Ile Ser Gln Ile
                100                 105                 110 gat ccg cag ata aaa ttc acc gca ctt ttt tgc tcc atc aat agt ttt        384
Asp Pro Gln Ile Lys Phe Thr Ala Leu Phe Cys Ser Ile Asn Ser Phe
            115                 120                 125 atg gcg ttg cag gac aaa ccg cac tgc gaa gtg att ctg tgc ggc gga        432
Met Ala Leu Gln Asp Lys Pro His Cys Glu Val Ile Leu Cys Gly Gly
130                 135                 140 cat tat tcg cgc cac aat tct ttc ctg act tcc gtg c                     469
His Tyr Ser Arg His Asn Ser Phe Leu Thr Ser Val
145                 150                 155

<210> SEQ ID NO 156
<211> LENGTH: 156
<212> TYPE: PRT
<213> ORGANISM: Actinobacillus actinomycetemcomitans

<400> SEQUENCE: 156

Met Glu Lys Lys Gln Thr Ser Arg Val Gln Lys Leu Glu Phe Leu Leu
1               5                   10                  15

Lys Gln Thr Asp Lys Ile His Leu Arg Asp Ala Ala Gln Met Leu Asp
            20                  25                  30

Val Ser Glu Met Thr Leu Arg Arg Asp Leu Ser Ser Asp Ser Gly Asn
        35                  40                  45

Val Val Leu Leu Gly Gly Tyr Ile Val Met Asn Pro Gln Lys Ser Gly
    50                  55                  60

Asn His Tyr Gln Ile Phe Asp Gln Gln Thr Arg His Ile Thr Glu Lys
65              70                  75                  80

Met Trp Leu Gly Lys Leu Ala Ala Asn Leu Val Lys Asp Gly Asp Thr
                85                  90                  95

Val Phe Phe Asp Cys Gly Ser Thr Ile Pro Phe Ile Ile Ser Gln Ile
                100                 105                 110

Asp Pro Gln Ile Lys Phe Thr Ala Leu Phe Cys Ser Ile Asn Ser Phe
            115                 120                 125

Met Ala Leu Gln Asp Lys Pro His Cys Glu Val Ile Leu Cys Gly Gly
130                 135                 140

His Tyr Ser Arg His Asn Ser Phe Leu Thr Ser Val
145                 150                 155

<210> SEQ ID NO 157
<211> LENGTH: 340
<212> TYPE: DNA
<213> ORGANISM: Actinobacillus actinomycetemcomitans
<220> FEATURE:
<221> NAME/KEY: CDS
<222> LOCATION: (1)..(339)

<400> SEQUENCE: 157 atg aca tat cca ggt gga aaa ggt aaa tgt ttc caa aaa atc att aat         48
Met Thr Tyr Pro Gly Gly Lys Gly Lys Cys Phe Gln Lys Ile Ile Asn
1               5                   10                  15 tta atg cct ccg cat gac gta tat att gaa act cat ctt ggt agt ggt         96
Leu Met Pro Pro His Asp Val Tyr Ile Glu Thr His Leu Gly Ser Gly
```

```
                20                  25                  30
gca gta cta cga aat aaa aaa cca gca cta aaa aat att gga ata gat       144
Ala Val Leu Arg Asn Lys Lys Pro Ala Leu Lys Asn Ile Gly Ile Asp
        35                  40                  45 cta gat ttt gat gtt att caa tca tgg att ggt tat tct cct gaa aat       192
Leu Asp Phe Asp Val Ile Gln Ser Trp Ile Gly Tyr Ser Pro Glu Asn
 50                  55                  60 cat aag ttt ttt aat aat gat gca ttg gcg ttt cta act aag tac ctg       240
His Lys Phe Phe Asn Asn Asp Ala Leu Ala Phe Leu Thr Lys Tyr Leu
 65                  70                  75                  80 ttt act ggg aaa gag tta gta tat tgt gat cct cca tat gtt ctt tca       288
Phe Thr Gly Lys Glu Leu Val Tyr Cys Asp Pro Pro Tyr Val Leu Ser
                 85                  90                  95 act aga aga aga caa aaa ata tat aaa tat gaa tac act gat gag cag       336
Thr Arg Arg Arg Gln Lys Ile Tyr Lys Tyr Glu Tyr Thr Asp Glu Gln
            100                 105                 110 cat g                                                                 340
His
```

<210> SEQ ID NO 158
<211> LENGTH: 113
<212> TYPE: PRT
<213> ORGANISM: Actinobacillus actinomycetemcomitans

<400> SEQUENCE: 158

```
Met Thr Tyr Pro Gly Gly Lys Gly Lys Cys Phe Gln Lys Ile Ile Asn
 1               5                  10                  15

Leu Met Pro Pro His Asp Val Tyr Ile Glu Thr His Leu Gly Ser Gly
                20                  25                  30

Ala Val Leu Arg Asn Lys Lys Pro Ala Leu Lys Asn Ile Gly Ile Asp
            35                  40                  45

Leu Asp Phe Asp Val Ile Gln Ser Trp Ile Gly Tyr Ser Pro Glu Asn
 50                  55                  60

His Lys Phe Phe Asn Asn Asp Ala Leu Ala Phe Leu Thr Lys Tyr Leu
 65                  70                  75                  80

Phe Thr Gly Lys Glu Leu Val Tyr Cys Asp Pro Pro Tyr Val Leu Ser
                 85                  90                  95

Thr Arg Arg Arg Gln Lys Ile Tyr Lys Tyr Glu Tyr Thr Asp Glu Gln
            100                 105                 110

His
```

<210> SEQ ID NO 159
<211> LENGTH: 771
<212> TYPE: DNA
<213> ORGANISM: Actinobacillus actinomycetemcomitans
<220> FEATURE:
<221> NAME/KEY: CDS
<222> LOCATION: (1)..(771)

<400> SEQUENCE: 159

```
atc gac gct ttt ttc tct cgc caa aac aat caa ttt cac ttg gaa caa        48
Ile Asp Ala Phe Phe Ser Arg Gln Asn Asn Gln Phe His Leu Glu Gln
 1               5                  10                  15 caa agc cat tgc gtt aac caa att atc gag caa tgg cgt tat aac ggg        96
Gln Ser His Cys Val Asn Gln Ile Ile Glu Gln Trp Arg Tyr Asn Gly
                20                  25                  30 caa att atc ggg cgt gaa att ccg caa ttt gtc gcc gaa cag aaa aac       144
Gln Ile Ile Gly Arg Glu Ile Pro Gln Phe Val Ala Glu Gln Lys Asn
            35                  40                  45
```

| | | |
|---|---|---|
| caa caa ggc ttg gca gtg cgt gtc acc tgc ccc gag caa acc tct ctt<br>Gln Gln Gly Leu Ala Val Arg Val Thr Cys Pro Glu Gln Thr Ser Leu<br>          50                         55                      60 | | 192 |
| tta gcg gaa ttt aac aat caa ccg gtg aac gat gcc ctt caa acg gca<br>Leu Ala Glu Phe Asn Asn Gln Pro Val Asn Asp Ala Leu Gln Thr Ala<br>65                        70                         75                      80 | | 240 |
| gaa aag tgc ggt gta tct ttt gag agt ttt cat att gtg gcg gaa gat<br>Glu Lys Cys Gly Val Ser Phe Glu Ser Phe His Ile Val Ala Glu Asp<br>                        85                         90                      95 | | 288 |
| ctc aat tct gaa atc acc gcc acg gaa aca ccc gct tgg caa ctg ctc<br>Leu Asn Ser Glu Ile Thr Ala Thr Glu Thr Pro Ala Trp Gln Leu Leu<br>                  100                       105                      110 | | 336 |
| tac acc acc tat ttg cag tct tgt tct ccc ctg caa agc ggt gaa tcc<br>Tyr Thr Thr Tyr Leu Gln Ser Cys Ser Pro Leu Gln Ser Gly Glu Ser<br>            115                      120                      125 | | 384 |
| ctg caa ccg att ccg ctg tat aaa caa ctg aaa aac ata ccg cac tta<br>Leu Gln Pro Ile Pro Leu Tyr Lys Gln Leu Lys Asn Ile Pro His Leu<br>130                      135                      140 | | 432 |
| gca atg gat ttg gtt aaa tgg cag gaa aat tgg cag gcg tgc gat caa<br>Ala Met Asp Leu Val Lys Trp Gln Glu Asn Trp Gln Ala Cys Asp Gln<br>145                      150                      155                      160 | | 480 |
| ttg caa atg aac ggt tcc gtg ttg gaa caa cag gct ttg gtg caa att<br>Leu Gln Met Asn Gly Ser Val Leu Glu Gln Gln Ala Leu Val Gln Ile<br>                        165                      170                      175 | | 528 |
| tca gac acc caa agc acg ctg ttt aag cat ggt tac cat cta acg cag<br>Ser Asp Thr Gln Ser Thr Leu Phe Lys His Gly Tyr His Leu Thr Gln<br>            180                      185                      190 | | 576 |
| gaa att gag cga cac agc ggc att cct act tac tat tat tta tac cgc<br>Glu Ile Glu Arg His Ser Gly Ile Pro Thr Tyr Tyr Tyr Leu Tyr Arg<br>                        195                      200                      205 | | 624 |
| atc ggt gga aaa agc tgt gaa gcg gag ctg caa tca cgc tgt ccg tta<br>Ile Gly Gly Lys Ser Cys Glu Ala Glu Leu Gln Ser Arg Cys Pro Leu<br>210                      215                      220 | | 672 |
| tgt aaa aga aaa tgg acg tta agc cac ccg ctt ttt gac ttc tta tat<br>Cys Lys Arg Lys Trp Thr Leu Ser His Pro Leu Phe Asp Phe Leu Tyr<br>225                      230                      235                      240 | | 720 |
| ttt aaa tgt gat cat tgt cgc ctc gtt tca aac ctc tca tgg cat tgg<br>Phe Lys Cys Asp His Cys Arg Leu Val Ser Asn Leu Ser Trp His Trp<br>                        245                      250                      255 | | 768 |
| caa<br>Gln | | 771 |

<210> SEQ ID NO 160
<211> LENGTH: 257
<212> TYPE: PRT
<213> ORGANISM: Actinobacillus actinomycetemcomitans

<400> SEQUENCE: 160

Ile Asp Ala Phe Phe Ser Arg Gln Asn Asn Gln Phe His Leu Glu Gln
1                   5                        10                         15

Gln Ser His Cys Val Asn Gln Ile Ile Glu Gln Trp Arg Tyr Asn Gly
                  20                        25                        30

Gln Ile Ile Gly Arg Glu Ile Pro Gln Phe Val Ala Glu Lys Asn
                      35                       40                        45

Gln Gln Gly Leu Ala Val Arg Val Thr Cys Pro Glu Gln Thr Ser Leu
          50                         55                      60

Leu Ala Glu Phe Asn Asn Gln Pro Val Asn Asp Ala Leu Gln Thr Ala
65                   70                        75                        80

Glu Lys Cys Gly Val Ser Phe Glu Ser Phe His Ile Val Ala Glu Asp

```
                    85                  90                  95
Leu Asn Ser Glu Ile Thr Ala Thr Glu Thr Pro Ala Trp Gln Leu Leu
            100                 105                 110
Tyr Thr Thr Tyr Leu Gln Ser Cys Ser Pro Leu Gln Ser Gly Glu Ser
        115                 120                 125
Leu Gln Pro Ile Pro Leu Tyr Lys Gln Leu Lys Asn Ile Pro His Leu
    130                 135                 140
Ala Met Asp Leu Val Lys Trp Gln Glu Asn Trp Gln Ala Cys Asp Gln
145                 150                 155                 160
Leu Gln Met Asn Gly Ser Val Leu Glu Gln Ala Leu Val Gln Ile
                165                 170                 175
Ser Asp Thr Gln Ser Thr Leu Phe Lys His Gly Tyr His Leu Thr Gln
            180                 185                 190
Glu Ile Glu Arg His Ser Gly Ile Pro Thr Tyr Tyr Leu Tyr Arg
        195                 200                 205
Ile Gly Gly Lys Ser Cys Glu Ala Glu Leu Gln Ser Arg Cys Pro Leu
    210                 215                 220
Cys Lys Arg Lys Trp Thr Leu Ser His Pro Leu Phe Asp Phe Leu Tyr
225                 230                 235                 240
Phe Lys Cys Asp His Cys Arg Leu Val Ser Asn Leu Ser Trp His Trp
                245                 250                 255
Gln

<210> SEQ ID NO 161
<211> LENGTH: 330
<212> TYPE: DNA
<213> ORGANISM: Actinobacillus actinomycetemcomitans
<220> FEATURE:
<221> NAME/KEY: CDS
<222> LOCATION: (1)..(330)

<400> SEQUENCE: 161 gag gcg gat aaa ttt aaa gtg gat att ccg tct atg gca aga ctg aga     48
Glu Ala Asp Lys Phe Lys Val Asp Ile Pro Ser Met Ala Arg Leu Arg
1               5                   10                  15 atc agc ccg aat atc gac atc agt gcg aca ccg aag ctg ttg gaa ctt    96
Ile Ser Pro Asn Ile Asp Ile Ser Ala Thr Pro Lys Leu Leu Glu Leu
                20                  25                  30 tcc ggc aat att gat att ccc tgg gcg cgc att gcc att gaa aac ctg   144
Ser Gly Asn Ile Asp Ile Pro Trp Ala Arg Ile Ala Ile Glu Asn Leu
            35                  40                  45 ccg gac agt gca gtg gcg gtc agc tcc gat gaa gtg att tta aat ggc   192
Pro Asp Ser Ala Val Ala Val Ser Ser Asp Glu Val Ile Leu Asn Gly
    50                  55                  60 aat aag aag agt act ctg ccg aaa aca ttg ccg agc gaa acc caa agc   240
Asn Lys Lys Ser Thr Leu Pro Lys Thr Leu Pro Ser Glu Thr Gln Ser
65                  70                  75                  80 ggc atg gca att cgt tct gat tta aga atc aat atc ggc gat gat gtc   288
Gly Met Ala Ile Arg Ser Asp Leu Arg Ile Asn Ile Gly Asp Asp Val
                85                  90                  95 agt tta aat gcc tat ggc ttg aaa acc cat ctc cac ggg ttg           330
Ser Leu Asn Ala Tyr Gly Leu Lys Thr His Leu His Gly Leu
            100                 105                 110

<210> SEQ ID NO 162
<211> LENGTH: 110
<212> TYPE: PRT
<213> ORGANISM: Actinobacillus actinomycetemcomitans
```

<400> SEQUENCE: 162

```
Glu Ala Asp Lys Phe Lys Val Asp Ile Pro Ser Met Ala Arg Leu Arg
1               5                  10                  15

Ile Ser Pro Asn Ile Asp Ile Ser Ala Thr Pro Lys Leu Leu Glu Leu
            20                  25                  30

Ser Gly Asn Ile Asp Ile Pro Trp Ala Arg Ile Ala Ile Glu Asn Leu
        35                  40                  45

Pro Asp Ser Ala Val Ala Val Ser Ser Asp Glu Val Ile Leu Asn Gly
    50                  55                  60

Asn Lys Lys Ser Thr Leu Pro Lys Thr Leu Pro Ser Glu Thr Gln Ser
65                  70                  75                  80

Gly Met Ala Ile Arg Ser Asp Leu Arg Ile Asn Ile Gly Asp Asp Val
                85                  90                  95

Ser Leu Asn Ala Tyr Gly Leu Lys Thr His Leu His Gly Leu
            100                 105                 110
```

<210> SEQ ID NO 163
<211> LENGTH: 625
<212> TYPE: DNA
<213> ORGANISM: Actinobacillus actinomycetemcomitans
<220> FEATURE:
<221> NAME/KEY: CDS
<222> LOCATION: (1)..(624)

<400> SEQUENCE: 163

| | |
|---|---:|
| gat aag aca gaa acg atg caa caa aat gaa gaa aaa atc acg ccg tca <br> Asp Lys Thr Glu Thr Met Gln Gln Asn Glu Glu Lys Ile Thr Pro Ser <br> 1                 5                10              15 | 48 |
| gag caa aaa ccg atc gtg cat gaa acc gtt gtg gtg aag aaa acc ggt <br> Glu Gln Lys Pro Ile Val His Glu Thr Val Val Lys Lys Thr Gly <br>                  20                25              30 | 96 |
| tcc gcg tta ggt ttg ctg gca ctt tta att gcg ttg ggt tta ggc ggc <br> Ser Ala Leu Gly Leu Leu Ala Leu Leu Ile Ala Leu Gly Leu Gly Gly <br>          35                 40              45 | 144 |
| gcg ggc tat tat ttc ggt cag cta cag gtt gac gaa ata cag caa aaa <br> Ala Gly Tyr Tyr Phe Gly Gln Leu Gln Val Asp Glu Ile Gln Gln Lys <br> 50                55              60 | 192 |
| ctg acc gca ctt gaa aac caa ttg caa caa aaa ggc act tcc gcc gat <br> Leu Thr Ala Leu Glu Asn Gln Leu Gln Gln Lys Gly Thr Ser Ala Asp <br> 65                70              75              80 | 240 |
| gtt gcc ggc atg ccg gat ttt agt gca gag aaa aat cag ctg gcg aaa <br> Val Ala Gly Met Pro Asp Phe Ser Ala Glu Lys Asn Gln Leu Ala Lys <br>                 85              90              95 | 288 |
| tta acg gaa ttt tcc caa gtg gca agt gat caa atc agc gcc ttg aat <br> Leu Thr Glu Phe Ser Gln Val Ala Ser Asp Gln Ile Ser Ala Leu Asn <br>                  100            105           110 | 336 |
| cag aat ttg tcc gcc aaa gaa caa agc ctg tcg gca ttg caa caa cag <br> Gln Asn Leu Ser Ala Lys Glu Gln Ser Leu Ser Ala Leu Gln Gln Gln <br>                115            120           125 | 384 |
| gtg caa cgt ttg tcc aat caa gcc aaa gcg gag cag ccg aat gac tgg <br> Val Gln Arg Leu Ser Asn Gln Ala Lys Ala Glu Gln Pro Asn Asp Trp <br> 130             135            140 | 432 |
| tta ctg acc gaa gcg gat ttt ctg tta aat aac gct ttg cgc aaa ctg <br> Leu Leu Thr Glu Ala Asp Phe Leu Leu Asn Asn Ala Leu Arg Lys Leu <br> 145             150            155           160 | 480 |
| gtg ttg gat aac gac gtg gat acc agt gtg tcc ttg ttg aaa gtt gcc <br> Val Leu Asp Asn Asp Val Asp Thr Ser Val Ser Leu Leu Lys Val Ala <br>                165            170           175 | 528 |
| gat gaa acc ctt tcc aaa gtc gcc atg cca caa gtg gcg cag gtg cgt | 576 |

```
Asp Glu Thr Leu Ser Lys Val Ala Met Pro Gln Val Ala Gln Val Arg
            180                 185                 190 agc gcc att aac gcc gat tta aaa cag ttg ttg tcc ctg aac aat gtg g    625
Ser Ala Ile Asn Ala Asp Leu Lys Gln Leu Leu Ser Leu Asn Asn Val
        195                 200                 205

<210> SEQ ID NO 164
<211> LENGTH: 208
<212> TYPE: PRT
<213> ORGANISM: Actinobacillus actinomycetemcomitans

<400> SEQUENCE: 164

Asp Lys Thr Glu Thr Met Gln Gln Asn Glu Glu Lys Ile Thr Pro Ser
1               5                   10                  15

Glu Gln Lys Pro Ile Val His Glu Thr Val Val Lys Lys Thr Gly
            20                  25                  30

Ser Ala Leu Gly Leu Leu Ala Leu Leu Ile Ala Leu Gly Leu Gly Gly
        35                  40                  45

Ala Gly Tyr Tyr Phe Gly Gln Leu Gln Val Asp Glu Ile Gln Gln Lys
    50                  55                  60

Leu Thr Ala Leu Glu Asn Gln Leu Gln Gln Lys Gly Thr Ser Ala Asp
65                  70                  75                  80

Val Ala Gly Met Pro Asp Phe Ser Ala Glu Lys Asn Gln Leu Ala Lys
                85                  90                  95

Leu Thr Glu Phe Ser Gln Val Ala Ser Asp Gln Ile Ser Ala Leu Asn
            100                 105                 110

Gln Asn Leu Ser Ala Lys Glu Gln Ser Leu Ser Ala Leu Gln Gln Gln
        115                 120                 125

Val Gln Arg Leu Ser Asn Gln Ala Lys Ala Glu Gln Pro Asn Asp Trp
    130                 135                 140

Leu Leu Thr Glu Ala Asp Phe Leu Leu Asn Asn Ala Leu Arg Lys Leu
145                 150                 155                 160

Val Leu Asp Asn Asp Val Asp Thr Ser Val Ser Leu Leu Lys Val Ala
                165                 170                 175

Asp Glu Thr Leu Ser Lys Val Ala Met Pro Gln Val Ala Gln Val Arg
            180                 185                 190

Ser Ala Ile Asn Ala Asp Leu Lys Gln Leu Leu Ser Leu Asn Asn Val
        195                 200                 205

<210> SEQ ID NO 165
<211> LENGTH: 684
<212> TYPE: DNA
<213> ORGANISM: Actinobacillus actinomycetemcomitans
<220> FEATURE:
<221> NAME/KEY: CDS
<222> LOCATION: (1)..(684)

<400> SEQUENCE: 165 atg acg att tta gtt ctg ggt atc aat cac aaa act gct tcc gtg gca    48
Met Thr Ile Leu Val Leu Gly Ile Asn His Lys Thr Ala Ser Val Ala
1               5                   10                  15 ttg cgg gaa aag gtg gcg ttt tcc gac gaa aag cgc act ttt gct ttg    96
Leu Arg Glu Lys Val Ala Phe Ser Asp Glu Lys Arg Thr Phe Ala Leu
            20                  25                  30 cgt cac att caa caa acg cag ttg gcg gaa agt gcg gtg att tta tcc    144
Arg His Ile Gln Gln Thr Gln Leu Ala Glu Ser Ala Val Ile Leu Ser
        35                  40                  45 acc tgt aat cgc acg gaa gtt tat ctg cac aat aaa agc gtt ccg ccg    192
Thr Cys Asn Arg Thr Glu Val Tyr Leu His Asn Lys Ser Val Pro Pro
```

```
            50                  55                  60
caa gag acg caa acc tgg atc aca ctg gcg gtg cag tgg ttt gcc ggc      240
Gln Glu Thr Gln Thr Trp Ile Thr Leu Ala Val Gln Trp Phe Ala Gly
 65                  70                  75                  80 att cat caa cta gcg ttg gcg gag ctg cag cac tgt gtt tat act cac      288
Ile His Gln Leu Ala Leu Ala Glu Leu Gln His Cys Val Tyr Thr His
                 85                  90                  95 gaa aat ctt cag gcg gcg aat cat tta atg gaa gtg gcg tgc ggt ttg      336
Glu Asn Leu Gln Ala Ala Asn His Leu Met Glu Val Ala Cys Gly Leu
            100                 105                 110 gat tcg ctg att tta ggc gaa ccg cag att ttg ggg cag gtg aag caa      384
Asp Ser Leu Ile Leu Gly Glu Pro Gln Ile Leu Gly Gln Val Lys Gln
        115                 120                 125 gcc tac cac atg agc gag cag cat tat caa cag gaa ggg caa acc att      432
Ala Tyr His Met Ser Glu Gln His Tyr Gln Gln Glu Gly Gln Thr Ile
    130                 135                 140 tcc ggc gaa cta tcc cgt tta ttc caa aaa acc ttt gct acc gct aaa      480
Ser Gly Glu Leu Ser Arg Leu Phe Gln Lys Thr Phe Ala Thr Ala Lys
145                 150                 155                 160 cgg gtg cgc acc gaa acc aac atc ggc gag agt gcg gtg tcc gtt gcc      528
Arg Val Arg Thr Glu Thr Asn Ile Gly Glu Ser Ala Val Ser Val Ala
                165                 170                 175 tat gcc gcc tgt agc cta gca cgt cag att ttt gaa tcc ctg cgt gac      576
Tyr Ala Ala Cys Ser Leu Ala Arg Gln Ile Phe Glu Ser Leu Arg Asp
            180                 185                 190 ttg acg att tta tta gtg ggc gca ggt gaa acc att gaa ctg gtg aac      624
Leu Thr Ile Leu Leu Val Gly Ala Gly Glu Thr Ile Glu Leu Val Asn
        195                 200                 205 cgc cat ttg tta cgt cac ggc gtg aaa aac tta ttt atc gcc aac cgt      672
Arg His Leu Leu Arg His Gly Val Lys Asn Leu Phe Ile Ala Asn Arg
    210                 215                 220 aca ttg gcg cgc                                                      684
Thr Leu Ala Arg
225
```

<210> SEQ ID NO 166
<211> LENGTH: 228
<212> TYPE: PRT
<213> ORGANISM: Actinobacillus actinomycetemcomitans

<400> SEQUENCE: 166

```
Met Thr Ile Leu Val Leu Gly Ile Asn His Lys Thr Ala Ser Val Ala
  1               5                  10                  15

Leu Arg Glu Lys Val Ala Phe Ser Asp Glu Lys Arg Thr Phe Ala Leu
                 20                  25                  30

Arg His Ile Gln Gln Thr Gln Leu Ala Glu Ser Ala Val Ile Leu Ser
             35                  40                  45

Thr Cys Asn Arg Thr Glu Val Tyr Leu His Asn Lys Ser Val Pro Pro
 50                  55                  60

Gln Glu Thr Gln Thr Trp Ile Thr Leu Ala Val Gln Trp Phe Ala Gly
 65                  70                  75                  80

Ile His Gln Leu Ala Leu Ala Glu Leu Gln His Cys Val Tyr Thr His
                 85                  90                  95

Glu Asn Leu Gln Ala Ala Asn His Leu Met Glu Val Ala Cys Gly Leu
            100                 105                 110

Asp Ser Leu Ile Leu Gly Glu Pro Gln Ile Leu Gly Gln Val Lys Gln
        115                 120                 125

Ala Tyr His Met Ser Glu Gln His Tyr Gln Gln Glu Gly Gln Thr Ile
```

```
            130                 135                 140
Ser Gly Glu Leu Ser Arg Leu Phe Gln Lys Thr Phe Ala Thr Ala Lys
145                 150                 155                 160

Arg Val Arg Thr Glu Thr Asn Ile Gly Glu Ser Ala Val Ser Val Ala
                165                 170                 175

Tyr Ala Ala Cys Ser Leu Ala Arg Gln Ile Phe Glu Ser Leu Arg Asp
            180                 185                 190

Leu Thr Ile Leu Leu Val Gly Ala Gly Glu Thr Ile Glu Leu Val Asn
        195                 200                 205

Arg His Leu Leu Arg His Gly Val Lys Asn Leu Phe Ile Ala Asn Arg
    210                 215                 220

Thr Leu Ala Arg
225

<210> SEQ ID NO 167
<211> LENGTH: 138
<212> TYPE: DNA
<213> ORGANISM: Actinobacillus actinomycetemcomitans
<220> FEATURE:
<221> NAME/KEY: CDS
<222> LOCATION: (1)..(138)

<400> SEQUENCE: 167 atg cgc cgt tgg aag ctg aaa atc ttc cgc aaa atg aac cgc act ttg      48
Met Arg Arg Trp Lys Leu Lys Ile Phe Arg Lys Met Asn Arg Thr Leu
1               5                   10                  15 cgc gtt cgc ctt tcg ttc cca atg cac cga ttc gtg ccg gac ctt aat      96
Arg Val Arg Leu Ser Phe Pro Met His Arg Phe Val Pro Asp Leu Asn
            20                  25                  30 tta ttt aac ttc gat ctt tgt ata ttc cgt cgt tta att cgt              138
Leu Phe Asn Phe Asp Leu Cys Ile Phe Arg Arg Leu Ile Arg
        35                  40                  45

<210> SEQ ID NO 168
<211> LENGTH: 46
<212> TYPE: PRT
<213> ORGANISM: Actinobacillus actinomycetemcomitans

<400> SEQUENCE: 168

Met Arg Arg Trp Lys Leu Lys Ile Phe Arg Lys Met Asn Arg Thr Leu
1               5                   10                  15

Arg Val Arg Leu Ser Phe Pro Met His Arg Phe Val Pro Asp Leu Asn
            20                  25                  30

Leu Phe Asn Phe Asp Leu Cys Ile Phe Arg Arg Leu Ile Arg
        35                  40                  45

<210> SEQ ID NO 169
<211> LENGTH: 1950
<212> TYPE: DNA
<213> ORGANISM: Actinobacillus actinomycetemcomitans
<220> FEATURE:
<221> NAME/KEY: CDS
<222> LOCATION: (1)..(1950)

<400> SEQUENCE: 169 atg gct gat gta tta acc cgt ttc aac agt ggc aag ctt tgg gaa ttc      48
Met Ala Asp Val Leu Thr Arg Phe Asn Ser Gly Lys Leu Trp Glu Phe
1               5                   10                  15 gat ggc ggc att cat ccg ccc gac atg aaa tcc caa tcc aac cgc gcg      96
Asp Gly Gly Ile His Pro Pro Asp Met Lys Ser Gln Ser Asn Arg Ala
            20                  25                  30
```

```
cct att cgt acc ttg ccg ttg ccc gat aat ttc tac gtt ctt ctg aaa        144
Pro Ile Arg Thr Leu Pro Leu Pro Asp Asn Phe Tyr Val Leu Leu Lys
        35                  40                  45 caa cac gcc ggc aca gcg ggc aat tta ttg gta aaa tgc ggc gat cat        192
Gln His Ala Gly Thr Ala Gly Asn Leu Leu Val Lys Cys Gly Asp His
 50                  55                  60 gtt ttg aaa ggt caa ccg ctc acc cag ggg gac ggt ttg cgt tcg ctg        240
Val Leu Lys Gly Gln Pro Leu Thr Gln Gly Asp Gly Leu Arg Ser Leu
 65                  70                  75                  80 ccg gtt cat gcg cct act tca ggc acg gtc att gat gtg atg cct tat        288
Pro Val His Ala Pro Thr Ser Gly Thr Val Ile Asp Val Met Pro Tyr
                 85                  90                  95 gtc acc gcc cat cct tcc ggt cta ccg gaa acc tgt gtg cat att aaa        336
Val Thr Ala His Pro Ser Gly Leu Pro Glu Thr Cys Val His Ile Lys
                100                 105                 110 gcg gat gga tta gat caa tgg cgc gag caa acc ccg ttg gag gat ttc        384
Ala Asp Gly Leu Asp Gln Trp Arg Glu Gln Thr Pro Leu Glu Asp Phe
            115                 120                 125 ctt agc caa acg ccg gaa cag tta atc gaa aaa att tat cag gcg ggc        432
Leu Ser Gln Thr Pro Glu Gln Leu Ile Glu Lys Ile Tyr Gln Ala Gly
    130                 135                 140 att gcc ggt ctg ggt ggc gcg gta ttc ccg acc gcg gca aaa att cat        480
Ile Ala Gly Leu Gly Gly Ala Val Phe Pro Thr Ala Ala Lys Ile His
145                 150                 155                 160 tcc gcc gag aaa cag gtg aaa tta ctg att att aac ggc gcg gaa tgt        528
Ser Ala Glu Lys Gln Val Lys Leu Leu Ile Ile Asn Gly Ala Glu Cys
                165                 170                 175 gaa cct tac att acc tgc gac gat cgc tta atg cat gat tat gct gat        576
Glu Pro Tyr Ile Thr Cys Asp Asp Arg Leu Met His Asp Tyr Ala Asp
                180                 185                 190 gaa att atc gaa ggc gtg cgt att ttg cgc tac att tta cgc cct gag        624
Glu Ile Ile Glu Gly Val Arg Ile Leu Arg Tyr Ile Leu Arg Pro Glu
            195                 200                 205 aaa gtg gtg atc gcc gtt gaa gat aat aaa cca aaa gcg gtg aaa tcc        672
Lys Val Val Ile Ala Val Glu Asp Asn Lys Pro Lys Ala Val Lys Ser
    210                 215                 220 ttg gaa cgc gcc tta cac ggc gcc aac gat att gaa atc cga gtg att        720
Leu Glu Arg Ala Leu His Gly Ala Asn Asp Ile Glu Ile Arg Val Ile
225                 230                 235                 240 ccg acc aaa tac cct tcc ggc gcg gca aaa cag tta att caa gtg ctg        768
Pro Thr Lys Tyr Pro Ser Gly Ala Ala Lys Gln Leu Ile Gln Val Leu
                245                 250                 255 acc ggc atg gag gta cct agc ggt caa cgc tcc tcc ggt atc ggc gtg        816
Thr Gly Met Glu Val Pro Ser Gly Gln Arg Ser Ser Gly Ile Gly Val
                260                 265                 270 ctg atg caa aac atc ggc acc gct ttt gct att aaa cgc gca gtg atg        864
Leu Met Gln Asn Ile Gly Thr Ala Phe Ala Ile Lys Arg Ala Val Met
            275                 280                 285 gat gat gaa ccg ctg att gag cgc gtc gtc acc ctc acc ggt gat aaa        912
Asp Asp Glu Pro Leu Ile Glu Arg Val Val Thr Leu Thr Gly Asp Lys
    290                 295                 300 atc gcc gat aaa ggc aac tat tgg gcg cgt ttt gga acg ccg att tat        960
Ile Ala Asp Lys Gly Asn Tyr Trp Ala Arg Phe Gly Thr Pro Ile Tyr
305                 310                 315                 320 cac ttg ttg cgc gaa acg ggc tat caa tac gac gat cgt ttc ccg gtc       1008
His Leu Leu Arg Glu Thr Gly Tyr Gln Tyr Asp Asp Arg Phe Pro Val
                325                 330                 335 ttc atg ggc ggt ccg atg atg ggc ttt att ctg ccc gat tta aat gcg       1056
Phe Met Gly Gly Pro Met Met Gly Phe Ile Leu Pro Asp Leu Asn Ala
                340                 345                 350
```

| | | |
|---|---|---|
| ccg atg acc aaa gtg acc aac tgc ctg ttg gcg ccg gat cat ttt gaa<br>Pro Met Thr Lys Val Thr Asn Cys Leu Leu Ala Pro Asp His Phe Glu<br>355 360 365 | | 1104 |
| tac gcc ccg ccg gaa gaa gaa aaa aat tgt att cgc tgt tct gcc tgt<br>Tyr Ala Pro Pro Glu Glu Glu Lys Asn Cys Ile Arg Cys Ser Ala Cys<br>370 375 380 | | 1152 |
| tcc gat gcc tgc ccg gtg aaa ctc atg ccg cag caa ttg tat tgg ttt<br>Ser Asp Ala Cys Pro Val Lys Leu Met Pro Gln Gln Leu Tyr Trp Phe<br>385 390 395 400 | | 1200 |
| gca cgc agc gaa gat cac gaa aaa tcg gaa gaa tat tcc ctc aaa gat<br>Ala Arg Ser Glu Asp His Glu Lys Ser Glu Glu Tyr Ser Leu Lys Asp<br>405 410 415 | | 1248 |
| tgt att gaa tgc ggc gtg tgc gct tat gtt tgc cca agt cac att ccg<br>Cys Ile Glu Cys Gly Val Cys Ala Tyr Val Cys Pro Ser His Ile Pro<br>420 425 430 | | 1296 |
| tta att caa tat ttc cgc cgg gaa aaa gct aaa atc tgg gaa atc aaa<br>Leu Ile Gln Tyr Phe Arg Arg Glu Lys Ala Lys Ile Trp Glu Ile Lys<br>435 440 445 | | 1344 |
| cac aaa gcc aaa ttg gcg gaa gaa gct aaa ata cgt ttt gaa caa cgc<br>His Lys Ala Lys Leu Ala Glu Glu Ala Lys Ile Arg Phe Glu Gln Arg<br>450 455 460 | | 1392 |
| caa gcc cgt ttg gaa cgg gaa gaa cag gaa cgc aaa gat cgc tca caa<br>Gln Ala Arg Leu Glu Arg Glu Glu Gln Glu Arg Lys Asp Arg Ser Gln<br>465 470 475 480 | | 1440 |
| cgt gct gca gcc gcc cgt cgt gaa gaa ttg gcg caa caa aaa ggc gtg<br>Arg Ala Ala Ala Arg Arg Glu Glu Leu Ala Gln Gln Lys Gly Val<br>485 490 495 | | 1488 |
| gat ccg gtg gct gcc gcc tta gcg cgc tta aaa gcg aaa aaa gcc gaa<br>Asp Pro Val Ala Ala Ala Leu Ala Arg Leu Lys Ala Lys Lys Ala Glu<br>500 505 510 | | 1536 |
| acg acg gaa gct acg cag gca gaa cag aaa acc att gtt gac gaa aaa<br>Thr Thr Glu Ala Thr Gln Ala Glu Gln Lys Thr Ile Val Asp Glu Lys<br>515 520 525 | | 1584 |
| ggt cat atc ctg cct gac aac agc gac atc atg gca caa cgc aaa gcc<br>Gly His Ile Leu Pro Asp Asn Ser Asp Ile Met Ala Gln Arg Lys Ala<br>530 535 540 | | 1632 |
| cgt cgt tta gcc cgt cag gcg gaa gcg gca cac tcg ccg tcg cag aaa<br>Arg Arg Leu Ala Arg Gln Ala Glu Ala Ala His Ser Pro Ser Gln Lys<br>545 550 555 560 | | 1680 |
| aca gaa aaa acg cta gaa aaa acg cta gaa aaa acc acc gca ctt gag<br>Thr Glu Lys Thr Leu Glu Lys Thr Leu Glu Lys Thr Thr Ala Leu Glu<br>565 570 575 | | 1728 |
| gat aaa aaa tct acc gtt gcc gcc gcc att gcc cgt gcg aaa gcc aag<br>Asp Lys Lys Ser Thr Val Ala Ala Ala Ile Ala Arg Ala Lys Ala Lys<br>580 585 590 | | 1776 |
| aaa gcg gcg cag caa acg gaa gcc gtc gaa gca aac gaa cct gaa acg<br>Lys Ala Ala Gln Gln Thr Glu Ala Val Glu Ala Asn Glu Pro Glu Thr<br>595 600 605 | | 1824 |
| gca aaa agt gcg gtc aat att tcc ggt gaa aat ggc gca gag aac gat<br>Ala Lys Ser Ala Val Asn Ile Ser Gly Glu Asn Gly Ala Glu Asn Asp<br>610 615 620 | | 1872 |
| ccg cgc aaa gcc gct gtt gcc gcc gct att gcc cgt gcg aaa gcg aag<br>Pro Arg Lys Ala Ala Val Ala Ala Ala Ile Ala Arg Ala Lys Ala Lys<br>625 630 635 640 | | 1920 |
| aaa gcc caa cgt gaa aac acg caa caa gat<br>Lys Ala Gln Arg Glu Asn Thr Gln Gln Asp<br>645 650 | | 1950 |

<210> SEQ ID NO 170

```
<211> LENGTH: 650
<212> TYPE: PRT
<213> ORGANISM: Actinobacillus actinomycetemcomitans

<400> SEQUENCE: 170

Met Ala Asp Val Leu Thr Arg Phe Asn Ser Gly Lys Leu Trp Glu Phe
1               5                   10                  15

Asp Gly Gly Ile His Pro Pro Asp Met Lys Ser Gln Ser Asn Arg Ala
            20                  25                  30

Pro Ile Arg Thr Leu Pro Leu Pro Asp Asn Phe Tyr Val Leu Leu Lys
        35                  40                  45

Gln His Ala Gly Thr Ala Gly Asn Leu Leu Val Lys Cys Gly Asp His
    50                  55                  60

Val Leu Lys Gly Gln Pro Leu Thr Gln Gly Asp Gly Leu Arg Ser Leu
65                  70                  75                  80

Pro Val His Ala Pro Thr Ser Gly Thr Val Ile Asp Val Met Pro Tyr
                85                  90                  95

Val Thr Ala His Pro Ser Gly Leu Pro Glu Thr Cys Val His Ile Lys
            100                 105                 110

Ala Asp Gly Leu Asp Gln Trp Arg Glu Gln Thr Pro Leu Glu Asp Phe
        115                 120                 125

Leu Ser Gln Thr Pro Glu Gln Leu Ile Glu Lys Ile Tyr Gln Ala Gly
    130                 135                 140

Ile Ala Gly Leu Gly Gly Ala Val Phe Pro Thr Ala Ala Lys Ile His
145                 150                 155                 160

Ser Ala Glu Lys Gln Val Lys Leu Leu Ile Ile Asn Gly Ala Glu Cys
                165                 170                 175

Glu Pro Tyr Ile Thr Cys Asp Asp Arg Leu Met His Asp Tyr Ala Asp
            180                 185                 190

Glu Ile Ile Glu Gly Val Arg Ile Leu Arg Tyr Ile Leu Arg Pro Glu
        195                 200                 205

Lys Val Val Ile Ala Val Glu Asp Asn Lys Pro Lys Ala Val Lys Ser
    210                 215                 220

Leu Glu Arg Ala Leu His Gly Ala Asn Asp Ile Glu Ile Arg Val Ile
225                 230                 235                 240

Pro Thr Lys Tyr Pro Ser Gly Ala Ala Lys Gln Leu Ile Gln Val Leu
                245                 250                 255

Thr Gly Met Glu Val Pro Ser Gly Gln Arg Ser Ser Gly Ile Gly Val
            260                 265                 270

Leu Met Gln Asn Ile Gly Thr Ala Phe Ala Ile Lys Arg Ala Val Met
        275                 280                 285

Asp Asp Glu Pro Leu Ile Glu Arg Val Val Thr Leu Thr Gly Asp Lys
    290                 295                 300

Ile Ala Asp Lys Gly Asn Tyr Trp Ala Arg Phe Gly Thr Pro Ile Tyr
305                 310                 315                 320

His Leu Leu Arg Glu Thr Gly Tyr Gln Tyr Asp Asp Arg Phe Pro Val
                325                 330                 335

Phe Met Gly Gly Pro Met Met Gly Phe Ile Leu Pro Asp Leu Asn Ala
            340                 345                 350

Pro Met Thr Lys Val Thr Asn Cys Leu Leu Ala Pro Asp His Phe Glu
        355                 360                 365

Tyr Ala Pro Pro Glu Glu Lys Asn Cys Ile Arg Cys Ser Ala Cys
    370                 375                 380

Ser Asp Ala Cys Pro Val Lys Leu Met Pro Gln Gln Leu Tyr Trp Phe
```

```
                385                 390                 395                 400
            Ala Arg Ser Glu Asp His Glu Lys Ser Glu Glu Tyr Ser Leu Lys Asp
                            405                 410                 415
            Cys Ile Glu Cys Gly Val Cys Ala Tyr Val Cys Pro Ser His Ile Pro
                        420                 425                 430
            Leu Ile Gln Tyr Phe Arg Arg Glu Lys Ala Lys Ile Trp Glu Ile Lys
                        435                 440                 445
            His Lys Ala Lys Leu Ala Glu Glu Ala Lys Ile Arg Phe Glu Gln Arg
                    450                 455                 460
            Gln Ala Arg Leu Glu Arg Glu Glu Gln Glu Arg Lys Asp Arg Ser Gln
            465                 470                 475                 480
            Arg Ala Ala Ala Arg Arg Glu Glu Leu Ala Gln Gln Lys Gly Val
                            485                 490                 495
            Asp Pro Val Ala Ala Leu Ala Arg Leu Lys Ala Lys Ala Glu
                        500                 505                 510
            Thr Thr Glu Ala Thr Gln Ala Glu Gln Lys Thr Ile Val Asp Glu Lys
                    515                 520                 525
            Gly His Ile Leu Pro Asp Asn Ser Asp Ile Met Ala Gln Arg Lys Ala
                530                 535                 540
            Arg Arg Leu Ala Arg Gln Ala Glu Ala His Ser Pro Ser Gln Lys
            545                 550                 555                 560
            Thr Glu Lys Thr Leu Glu Lys Thr Leu Glu Lys Thr Thr Ala Leu Glu
                            565                 570                 575
            Asp Lys Lys Ser Thr Val Ala Ala Ile Ala Arg Ala Lys Ala Lys
                        580                 585                 590
            Lys Ala Ala Gln Gln Thr Glu Ala Val Glu Ala Asn Glu Pro Glu Thr
                    595                 600                 605
            Ala Lys Ser Ala Val Asn Ile Ser Gly Glu Asn Gly Ala Glu Asn Asp
                610                 615                 620
            Pro Arg Lys Ala Ala Val Ala Ala Ile Ala Arg Ala Lys Ala Lys
            625                 630                 635                 640
            Lys Ala Gln Arg Glu Asn Thr Gln Gln Asp
                            645                 650

<210> SEQ ID NO 171
<211> LENGTH: 525
<212> TYPE: DNA
<213> ORGANISM: Actinobacillus actinomycetemcomitans
<220> FEATURE:
<221> NAME/KEY: CDS
<222> LOCATION: (1)..(525)

<400> SEQUENCE: 171 atg aag ttt aaa acg cta ctt ggc gcg ctc tta ttg agc gtg ttt tcc      48
Met Lys Phe Lys Thr Leu Leu Gly Ala Leu Leu Leu Ser Val Phe Ser
1               5                   10                  15 act tcc gtt tgg gct gat cgc gtg att acc gat caa ctt gat cga caa      96
Thr Ser Val Trp Ala Asp Arg Val Ile Thr Asp Gln Leu Asp Arg Gln
                20                  25                  30 gtg acc atc ccc gac cat att cat cgc gct gtg ata tta cag cac cag     144
Val Thr Ile Pro Asp His Ile His Arg Ala Val Ile Leu Gln His Gln
            35                  40                  45 acc tta aat ctc gcg gtg caa ctg gat gcc acc aaa caa att gcg ggc     192
Thr Leu Asn Leu Ala Val Gln Leu Asp Ala Thr Lys Gln Ile Ala Gly
        50                  55                  60 gtg ctt tcc aac tgg caa aaa cag ctg ggc aaa gac ttc gtg cgc ctt     240
Val Leu Ser Asn Trp Gln Lys Gln Leu Gly Lys Asp Phe Val Arg Leu
```

```
                65                  70                  75                  80
gcg ccg gaa ttg gca aat tta ccg atg ccc ggt gat ttg aat acg gtc            288
Ala Pro Glu Leu Ala Asn Leu Pro Met Pro Gly Asp Leu Asn Thr Val
                    85                  90                  95 aat att gaa agc cta atg gaa atc aaa ccg gat gtt gtt ttc gtg acc            336
Asn Ile Glu Ser Leu Met Glu Ile Lys Pro Asp Val Val Phe Val Thr
                    100                 105                 110 aat tac gcg ccg aaa gaa atg att gaa aaa atc agc caa atg aac gtg            384
Asn Tyr Ala Pro Lys Glu Met Ile Glu Lys Ile Ser Gln Met Asn Val
                    115                 120                 125 ccg gtg att gcc att tcg tta cgc agc ggc gat aaa acc gaa caa agc            432
Pro Val Ile Ala Ile Ser Leu Arg Ser Gly Asp Lys Thr Glu Gln Ser
            130                 135                 140 aaa ctc aac ccg acc ctt gcc gat gaa aac aat gcc tac aac gaa ggg            480
Lys Leu Asn Pro Thr Leu Ala Asp Glu Asn Asn Ala Tyr Asn Glu Gly
145                 150                 155                 160 tta aaa cgc ggg att gaa att att gcc gat gtt ttt gat aaa aaa                525
Leu Lys Arg Gly Ile Glu Ile Ile Ala Asp Val Phe Asp Lys Lys
                    165                 170                 175

<210> SEQ ID NO 172
<211> LENGTH: 175
<212> TYPE: PRT
<213> ORGANISM: Actinobacillus actinomycetemcomitans

<400> SEQUENCE: 172

Met Lys Phe Lys Thr Leu Leu Gly Ala Leu Leu Leu Ser Val Phe Ser
1               5                   10                  15

Thr Ser Val Trp Ala Asp Arg Val Ile Thr Asp Gln Leu Asp Arg Gln
            20                  25                  30

Val Thr Ile Pro Asp His Ile His Arg Ala Val Ile Leu Gln His Gln
        35                  40                  45

Thr Leu Asn Leu Ala Val Gln Leu Asp Ala Thr Lys Gln Ile Ala Gly
    50                  55                  60

Val Leu Ser Asn Trp Gln Lys Gln Leu Gly Lys Asp Phe Val Arg Leu
65                  70                  75                  80

Ala Pro Glu Leu Ala Asn Leu Pro Met Pro Gly Asp Leu Asn Thr Val
                85                  90                  95

Asn Ile Glu Ser Leu Met Glu Ile Lys Pro Asp Val Val Phe Val Thr
            100                 105                 110

Asn Tyr Ala Pro Lys Glu Met Ile Glu Lys Ile Ser Gln Met Asn Val
        115                 120                 125

Pro Val Ile Ala Ile Ser Leu Arg Ser Gly Asp Lys Thr Glu Gln Ser
    130                 135                 140

Lys Leu Asn Pro Thr Leu Ala Asp Glu Asn Asn Ala Tyr Asn Glu Gly
145                 150                 155                 160

Leu Lys Arg Gly Ile Glu Ile Ile Ala Asp Val Phe Asp Lys Lys
                165                 170                 175

<210> SEQ ID NO 173
<211> LENGTH: 391
<212> TYPE: DNA
<213> ORGANISM: Actinobacillus actinomycetemcomitans
<220> FEATURE:
<221> NAME/KEY: CDS
<222> LOCATION: (1)..(390)

<400> SEQUENCE: 173 atg gcg gag ttg gtg tat aaa ccg ctt gag caa cct gtg gaa gca cca            48
```

```
Met Ala Glu Leu Val Tyr Lys Pro Leu Glu Gln Pro Val Glu Ala Pro
1               5                   10                  15 aat ccg aat cta aaa att gaa gcg gta aac gaa cag ttt gcg gca aaa      96
Asn Pro Asn Leu Lys Ile Glu Ala Val Asn Glu Gln Phe Ala Ala Lys
            20                  25                  30 tac ccg aaa caa ttt gcg tct tgg aaa gcc acc gaa aaa ggc gac aag     144
Tyr Pro Lys Gln Phe Ala Ser Trp Lys Ala Thr Glu Lys Gly Asp Lys
        35                  40                  45 att att tat gca gat gag gaa aat cca cgt tta atc ata tta tgg ggc     192
Ile Ile Tyr Ala Asp Glu Glu Asn Pro Arg Leu Ile Ile Leu Trp Gly
    50                  55                  60 ggt tat gcc ttt gcg aaa gaa tat aac gca ccg cgc gga cac att tat     240
Gly Tyr Ala Phe Ala Lys Glu Tyr Asn Ala Pro Arg Gly His Ile Tyr
65                  70                  75                  80 gcc att aaa gat tta cgc aat att ttg cgt acc ggt gcg ccg aaa acc     288
Ala Ile Lys Asp Leu Arg Asn Ile Leu Arg Thr Gly Ala Pro Lys Thr
                85                  90                  95 gct aac gac ggt cca caa ccg atg gcg tgt tgg acc tgt aaa ggt ccg     336
Ala Asn Asp Gly Pro Gln Pro Met Ala Cys Trp Thr Cys Lys Gly Pro
            100                 105                 110 gat gtg ccg cgt tta atc gcc gaa tgg gga gaa gaa ggc tat ttc aat     384
Asp Val Pro Arg Leu Ile Ala Glu Trp Gly Glu Glu Gly Tyr Phe Asn
        115                 120                 125 ggt aaa t                                                            391
Gly Lys
    130

<210> SEQ ID NO 174
<211> LENGTH: 130
<212> TYPE: PRT
<213> ORGANISM: Actinobacillus actinomycetemcomitans

<400> SEQUENCE: 174

Met Ala Glu Leu Val Tyr Lys Pro Leu Glu Gln Pro Val Glu Ala Pro
1               5                   10                  15

Asn Pro Asn Leu Lys Ile Glu Ala Val Asn Glu Gln Phe Ala Ala Lys
            20                  25                  30

Tyr Pro Lys Gln Phe Ala Ser Trp Lys Ala Thr Glu Lys Gly Asp Lys
        35                  40                  45

Ile Ile Tyr Ala Asp Glu Glu Asn Pro Arg Leu Ile Ile Leu Trp Gly
    50                  55                  60

Gly Tyr Ala Phe Ala Lys Glu Tyr Asn Ala Pro Arg Gly His Ile Tyr
65                  70                  75                  80

Ala Ile Lys Asp Leu Arg Asn Ile Leu Arg Thr Gly Ala Pro Lys Thr
                85                  90                  95

Ala Asn Asp Gly Pro Gln Pro Met Ala Cys Trp Thr Cys Lys Gly Pro
            100                 105                 110

Asp Val Pro Arg Leu Ile Ala Glu Trp Gly Glu Glu Gly Tyr Phe Asn
        115                 120                 125

Gly Lys
    130

<210> SEQ ID NO 175
<211> LENGTH: 540
<212> TYPE: DNA
<213> ORGANISM: Actinobacillus actinomycetemcomitans
<220> FEATURE:
<221> NAME/KEY: CDS
<222> LOCATION: (1)..(540)
```

```
<400> SEQUENCE: 175 aaa gcc atg ccg gca tta gac tta aat aaa gac ggc aaa atc caa tat      48
Lys Ala Met Pro Ala Leu Asp Leu Asn Lys Asp Gly Lys Ile Gln Tyr
1               5                   10                  15 gtg tta tta aaa ggc gaa ccg ggc cac cct gat gcg gaa gca cgt acc      96
Val Leu Leu Lys Gly Glu Pro Gly His Pro Asp Ala Glu Ala Arg Thr
            20                  25                  30 aag tat gtg att gag caa cta aac gcg caa ggc att cca acg gaa caa     144
Lys Tyr Val Ile Glu Gln Leu Asn Ala Gln Gly Ile Pro Thr Glu Gln
        35                  40                  45 ctc ttt atc gac acc ggg atg tgg gat gcg gca ctg gca aaa gac aaa     192
Leu Phe Ile Asp Thr Gly Met Trp Asp Ala Ala Leu Ala Lys Asp Lys
    50                  55                  60 atg gat gcg tgg tta tcc agc tct aaa gcc aat gac att gaa gtc att     240
Met Asp Ala Trp Leu Ser Ser Ser Lys Ala Asn Asp Ile Glu Val Ile
65                  70                  75                  80 att tcc aac aac gac ggc atg gcg atg ggc gca ttg gaa gca acc aaa     288
Ile Ser Asn Asn Asp Gly Met Ala Met Gly Ala Leu Glu Ala Thr Lys
                85                  90                  95 gca cac ggc aaa aaa tta ccg att ttc ggg gta gat gcg ttg cct gaa     336
Ala His Gly Lys Lys Leu Pro Ile Phe Gly Val Asp Ala Leu Pro Glu
            100                 105                 110 gta tta caa ctc atc aag aaa ggc gac att gca ggt acc gta ttg aat     384
Val Leu Gln Leu Ile Lys Lys Gly Asp Ile Ala Gly Thr Val Leu Asn
        115                 120                 125 gac ggc gcg act caa ggt aaa gcg att gtg gat tta tcc aac aac ctg     432
Asp Gly Ala Thr Gln Gly Lys Ala Ile Val Asp Leu Ser Asn Asn Leu
    130                 135                 140 gca aac ggc aaa ccg gct acc gaa ggc acc aaa tgg gag ctt aaa gat     480
Ala Asn Gly Lys Pro Ala Thr Glu Gly Thr Lys Trp Glu Leu Lys Asp
145                 150                 155                 160 cgc gtt gtg cgc att cct tat gtt ggc gta gat aaa gac aac ttg tct     528
Arg Val Val Arg Ile Pro Tyr Val Gly Val Asp Lys Asp Asn Leu Ser
                165                 170                 175 caa ttc tta aaa                                                     540
Gln Phe Leu Lys
            180

<210> SEQ ID NO 176
<211> LENGTH: 180
<212> TYPE: PRT
<213> ORGANISM: Actinobacillus actinomycetemcomitans

<400> SEQUENCE: 176

Lys Ala Met Pro Ala Leu Asp Leu Asn Lys Asp Gly Lys Ile Gln Tyr
1               5                   10                  15

Val Leu Leu Lys Gly Glu Pro Gly His Pro Asp Ala Glu Ala Arg Thr
            20                  25                  30

Lys Tyr Val Ile Glu Gln Leu Asn Ala Gln Gly Ile Pro Thr Glu Gln
        35                  40                  45

Leu Phe Ile Asp Thr Gly Met Trp Asp Ala Ala Leu Ala Lys Asp Lys
    50                  55                  60

Met Asp Ala Trp Leu Ser Ser Lys Ala Asn Asp Ile Glu Val Ile
65                  70                  75                  80

Ile Ser Asn Asn Asp Gly Met Ala Met Gly Ala Leu Glu Ala Thr Lys
                85                  90                  95

Ala His Gly Lys Lys Leu Pro Ile Phe Gly Val Asp Ala Leu Pro Glu
            100                 105                 110
```

-continued

```
Val Leu Gln Leu Ile Lys Lys Gly Asp Ile Ala Gly Thr Val Leu Asn
        115                 120                 125

Asp Gly Ala Thr Gln Gly Lys Ala Ile Val Asp Leu Ser Asn Asn Leu
    130                 135                 140

Ala Asn Gly Lys Pro Ala Thr Glu Gly Thr Lys Trp Glu Leu Lys Asp
145                 150                 155                 160

Arg Val Val Arg Ile Pro Tyr Val Gly Val Asp Lys Asp Asn Leu Ser
                165                 170                 175

Gln Phe Leu Lys
            180
```

<210> SEQ ID NO 177
<211> LENGTH: 1071
<212> TYPE: DNA
<213> ORGANISM: Actinobacillus actinomycetemcomitans
<220> FEATURE:
<221> NAME/KEY: CDS
<222> LOCATION: (1)..(1071)

<400> SEQUENCE: 177

```
atg gca gga aat acc atc gga caa tta ttt cgc gtc acc acc ttc ggc      48
Met Ala Gly Asn Thr Ile Gly Gln Leu Phe Arg Val Thr Thr Phe Gly
1               5                   10                  15 gag tcc cac ggc att gcc ttg ggt tgc att gtg gac ggc gta ccg ccg      96
Glu Ser His Gly Ile Ala Leu Gly Cys Ile Val Asp Gly Val Pro Pro
            20                  25                  30 aac atg gca tta tcg gaa gcg gat att caa ccg gat ttg gat cgt cgt     144
Asn Met Ala Leu Ser Glu Ala Asp Ile Gln Pro Asp Leu Asp Arg Arg
        35                  40                  45 aaa ccc ggc acc tcg cgc tat acc aca ccg cgc cgc gaa gac gat gaa     192
Lys Pro Gly Thr Ser Arg Tyr Thr Thr Pro Arg Arg Glu Asp Asp Glu
    50                  55                  60 gtg cag att tta tcc ggt gtc ttt gaa gga aaa acc acc ggc acc agt     240
Val Gln Ile Leu Ser Gly Val Phe Glu Gly Lys Thr Thr Gly Thr Ser
65                  70                  75                  80 att ggc ata atc att aag aac ggc gat caa cgc tcg cag gac tat ggc     288
Ile Gly Ile Ile Ile Lys Asn Gly Asp Gln Arg Ser Gln Asp Tyr Gly
                85                  90                  95 gaa att aaa gat cgc ttc cgt ccg gga cat gca gat ttt act tat caa     336
Glu Ile Lys Asp Arg Phe Arg Pro Gly His Ala Asp Phe Thr Tyr Gln
            100                 105                 110 caa aaa tac ggc att cgt gat tat cgc ggc ggc ggt cgt tct tcc gcc     384
Gln Lys Tyr Gly Ile Arg Asp Tyr Arg Gly Gly Gly Arg Ser Ser Ala
        115                 120                 125 cgc gaa act gcc atg cgc gtg gcg gcg ggt gcc atc gcg aaa aaa tat     432
Arg Glu Thr Ala Met Arg Val Ala Ala Gly Ala Ile Ala Lys Lys Tyr
    130                 135                 140 tta cgc gaa caa ttc ggc att gaa gtg cgt ggt ttc tta agc caa atc     480
Leu Arg Glu Gln Phe Gly Ile Glu Val Arg Gly Phe Leu Ser Gln Ile
145                 150                 155                 160 ggc gat gtc aaa att gcg ccg caa tcc gtg gaa cat att gat tgg gca     528
Gly Asp Val Lys Ile Ala Pro Gln Ser Val Glu His Ile Asp Trp Ala
                165                 170                 175 gaa gta aat agc aat ctg ttt ttc tgc ccc gat aaa agt gcg gtg gaa     576
Glu Val Asn Ser Asn Leu Phe Phe Cys Pro Asp Lys Ser Ala Val Glu
            180                 185                 190 aaa ttc gat gaa tta att cgt gat ctg aaa aaa caa ggg gat tct atc     624
Lys Phe Asp Glu Leu Ile Arg Asp Leu Lys Lys Gln Gly Asp Ser Ile
        195                 200                 205 ggt gct aaa ttg acc gtg gtg gcg gaa aac gtc ccc gtc ggg ttg ggc     672
```

```
Gly Ala Lys Leu Thr Val Val Ala Glu Asn Val Pro Val Gly Leu Gly
    210                 215                 220 gaa ccg gtg ttt gat cgt ttg gat gcg gat tta gcc cac gca tta atg      720
Glu Pro Val Phe Asp Arg Leu Asp Ala Asp Leu Ala His Ala Leu Met
225                 230                 235                 240 agc att aat gcg gta aaa ggc gtg gaa att ggt gac ggt ttc gct gtg      768
Ser Ile Asn Ala Val Lys Gly Val Glu Ile Gly Asp Gly Phe Ala Val
                245                 250                 255 gta gaa caa aaa ggt agc caa cat cgt gac gaa atg atc ccg caa gga      816
Val Glu Gln Lys Gly Ser Gln His Arg Asp Glu Met Ile Pro Gln Gly
            260                 265                 270 ttt ctt tcc aac tat gcc ggc ggg att ttg ggc ggc atc agt tca gga      864
Phe Leu Ser Asn Tyr Ala Gly Gly Ile Leu Gly Gly Ile Ser Ser Gly
        275                 280                 285 caa ccg att atc gcc acg att gcc ctc aaa ccc act tcc agc att acc      912
Gln Pro Ile Ile Ala Thr Ile Ala Leu Lys Pro Thr Ser Ser Ile Thr
    290                 295                 300 att ccg ggg cgc tcg gtg aat ctc gac aat gaa tct gtc gaa gtt gtt      960
Ile Pro Gly Arg Ser Val Asn Leu Asp Asn Glu Ser Val Glu Val Val
305                 310                 315                 320 act aaa ggt cgc cac gat cct tgt gtc ggc atc cgc gcc gtg ccg att     1008
Thr Lys Gly Arg His Asp Pro Cys Val Gly Ile Arg Ala Val Pro Ile
                325                 330                 335 gcg gaa gct atg acg gcg att gta ttg ttg gat cat ttg ttg cgt ttt     1056
Ala Glu Ala Met Thr Ala Ile Val Leu Leu Asp His Leu Leu Arg Phe
            340                 345                 350 aaa gcg caa tgc cga                                                 1071
Lys Ala Gln Cys Arg
        355

<210> SEQ ID NO 178
<211> LENGTH: 357
<212> TYPE: PRT
<213> ORGANISM: Actinobacillus actinomycetemcomitans

<400> SEQUENCE: 178

Met Ala Gly Asn Thr Ile Gly Gln Leu Phe Arg Val Thr Thr Phe Gly
1               5                   10                  15

Glu Ser His Gly Ile Ala Leu Gly Cys Ile Val Asp Gly Val Pro Pro
                20                  25                  30

Asn Met Ala Leu Ser Glu Ala Asp Ile Gln Pro Asp Leu Asp Arg Arg
            35                  40                  45

Lys Pro Gly Thr Ser Arg Tyr Thr Thr Pro Arg Arg Glu Asp Asp Glu
        50                  55                  60

Val Gln Ile Leu Ser Gly Val Phe Glu Gly Lys Thr Thr Gly Thr Ser
65                  70                  75                  80

Ile Gly Ile Ile Ile Lys Asn Gly Asp Gln Arg Ser Gln Asp Tyr Gly
                85                  90                  95

Glu Ile Lys Asp Arg Phe Arg Pro Gly His Ala Asp Phe Thr Tyr Gln
            100                 105                 110

Gln Lys Tyr Gly Ile Arg Asp Tyr Arg Gly Gly Arg Ser Ser Ala
        115                 120                 125

Arg Glu Thr Ala Met Arg Val Ala Ala Gly Ala Ile Ala Lys Lys Tyr
    130                 135                 140

Leu Arg Glu Gln Phe Gly Ile Glu Val Arg Gly Phe Leu Ser Gln Ile
145                 150                 155                 160

Gly Asp Val Lys Ile Ala Pro Gln Ser Val Glu His Ile Asp Trp Ala
                165                 170                 175
```

```
Glu Val Asn Ser Asn Leu Phe Phe Cys Pro Asp Lys Ser Ala Val Glu
            180                 185                 190

Lys Phe Asp Glu Leu Ile Arg Asp Leu Lys Lys Gln Gly Asp Ser Ile
        195                 200                 205

Gly Ala Lys Leu Thr Val Val Ala Glu Asn Val Pro Val Gly Leu Gly
    210                 215                 220

Glu Pro Val Phe Asp Arg Leu Asp Ala Asp Leu Ala His Ala Leu Met
225                 230                 235                 240

Ser Ile Asn Ala Val Lys Gly Val Glu Ile Gly Asp Gly Phe Ala Val
                245                 250                 255

Val Glu Gln Lys Gly Ser Gln His Arg Asp Glu Met Ile Pro Gln Gly
            260                 265                 270

Phe Leu Ser Asn Tyr Ala Gly Gly Ile Leu Gly Gly Ile Ser Ser Gly
        275                 280                 285

Gln Pro Ile Ile Ala Thr Ile Ala Leu Lys Pro Thr Ser Ser Ile Thr
    290                 295                 300

Ile Pro Gly Arg Ser Val Asn Leu Asp Asn Glu Ser Val Glu Val Val
305                 310                 315                 320

Thr Lys Gly Arg His Asp Pro Cys Val Gly Ile Arg Ala Val Pro Ile
                325                 330                 335

Ala Glu Ala Met Thr Ala Ile Val Leu Leu Asp His Leu Leu Arg Phe
            340                 345                 350

Lys Ala Gln Cys Arg
        355

<210> SEQ ID NO 179
<211> LENGTH: 633
<212> TYPE: DNA
<213> ORGANISM: Actinobacillus actinomycetemcomitans
<220> FEATURE:
<221> NAME/KEY: CDS
<222> LOCATION: (1)..(633)

<400> SEQUENCE: 179 gac ctc ttg gtg gat tcc tac gtg aaa tgg cgt atc aat gat tta ggt      48
Asp Leu Leu Val Asp Ser Tyr Val Lys Trp Arg Ile Asn Asp Leu Gly
1               5                   10                  15 cgt ttc ttc acc acg acc ggt ggt ggc gat tat gca caa gca gcc aac      96
Arg Phe Phe Thr Thr Thr Gly Gly Gly Asp Tyr Ala Gln Ala Ala Asn
            20                  25                  30 tta tta cgt cgt aaa gtc aat gac cgt ttg cgt tcc gaa atc ggt tcc     144
Leu Leu Arg Arg Lys Val Asn Asp Arg Leu Arg Ser Glu Ile Gly Ser
        35                  40                  45 cgc acc att aaa gac atc gtt tcc ggt aca cga ggc gaa ctc atg gta     192
Arg Thr Ile Lys Asp Ile Val Ser Gly Thr Arg Gly Glu Leu Met Val
    50                  55                  60 ggc acg aaa aaa gcg ctc aac agt ggg caa gac agc acc gcc gaa ctg     240
Gly Thr Lys Lys Ala Leu Asn Ser Gly Gln Asp Ser Thr Ala Glu Leu
65                  70                  75                  80 ggg att gaa gtg ctc gac gta cgg att aaa caa att aac ttg ccg gat     288
Gly Ile Glu Val Leu Asp Val Arg Ile Lys Gln Ile Asn Leu Pro Asp
                85                  90                  95 gaa gtg tct tcc tcc att tac cag cgt atg cgc gcc gaa cgg gat gcg     336
Glu Val Ser Ser Ser Ile Tyr Gln Arg Met Arg Ala Glu Arg Asp Ala
            100                 105                 110 gta gcc cgt gaa cac cgc tct caa ggt aaa gaa aaa gcg gca ttt att     384
Val Ala Arg Glu His Arg Ser Gln Gly Lys Glu Lys Ala Ala Phe Ile
        115                 120                 125
```

```
cag gcg gat gta gat cgt aaa gtc acc tta att atc gcc aat gcg gaa        432
Gln Ala Asp Val Asp Arg Lys Val Thr Leu Ile Ile Ala Asn Ala Glu
    130                 135                 140 aaa acc gca cag gaa tta cgc ggt gac ggc gac gcg acc gca gcc aaa        480
Lys Thr Ala Gln Glu Leu Arg Gly Asp Gly Asp Ala Thr Ala Ala Lys
145                 150                 155                 160 atc ttt gcc gat gcc ttt ggt aaa gag cct gaa ttt tac agc ttc att        528
Ile Phe Ala Asp Ala Phe Gly Lys Glu Pro Glu Phe Tyr Ser Phe Ile
                165                 170                 175 cgt agc ctg aaa gcc tat gaa agc agc ttc gcc gac tcg gac aat ttg        576
Arg Ser Leu Lys Ala Tyr Glu Ser Ser Phe Ala Asp Ser Asp Asn Leu
            180                 185                 190 ttg att tta aaa ccg gac agt gac ttc ttc cgt ttt atg caa tca cca        624
Leu Ile Leu Lys Pro Asp Ser Asp Phe Phe Arg Phe Met Gln Ser Pro
        195                 200                 205 agt aaa taa                                                            633
Ser Lys
    210
```

<210> SEQ ID NO 180
<211> LENGTH: 210
<212> TYPE: PRT
<213> ORGANISM: Actinobacillus actinomycetemcomitans

<400> SEQUENCE: 180

```
Asp Leu Leu Val Asp Ser Tyr Val Lys Trp Arg Ile Asn Asp Leu Gly
1               5                   10                  15

Arg Phe Phe Thr Thr Gly Gly Asp Tyr Ala Gln Ala Ala Asn
            20                  25                  30

Leu Leu Arg Arg Lys Val Asn Asp Arg Leu Arg Ser Glu Ile Gly Ser
        35                  40                  45

Arg Thr Ile Lys Asp Ile Val Ser Gly Thr Arg Gly Glu Leu Met Val
    50                  55                  60

Gly Thr Lys Lys Ala Leu Asn Ser Gly Gln Asp Ser Thr Ala Glu Leu
65                  70                  75                  80

Gly Ile Glu Val Leu Asp Val Arg Ile Lys Gln Ile Asn Leu Pro Asp
                85                  90                  95

Glu Val Ser Ser Ile Tyr Gln Arg Met Arg Ala Glu Arg Asp Ala
            100                 105                 110

Val Ala Arg Glu His Arg Ser Gln Gly Lys Glu Lys Ala Ala Phe Ile
        115                 120                 125

Gln Ala Asp Val Asp Arg Lys Val Thr Leu Ile Ile Ala Asn Ala Glu
    130                 135                 140

Lys Thr Ala Gln Glu Leu Arg Gly Asp Gly Asp Ala Thr Ala Ala Lys
145                 150                 155                 160

Ile Phe Ala Asp Ala Phe Gly Lys Glu Pro Glu Phe Tyr Ser Phe Ile
                165                 170                 175

Arg Ser Leu Lys Ala Tyr Glu Ser Ser Phe Ala Asp Ser Asp Asn Leu
            180                 185                 190

Leu Ile Leu Lys Pro Asp Ser Asp Phe Phe Arg Phe Met Gln Ser Pro
        195                 200                 205

Ser Lys
    210
```

<210> SEQ ID NO 181
<211> LENGTH: 582
<212> TYPE: DNA

-continued

```
<213> ORGANISM: Actinobacillus actinomycetemcomitans
<220> FEATURE:
<221> NAME/KEY: CDS
<222> LOCATION: (1)..(582)

<400> SEQUENCE: 181 atg atc gac aac atc aac gaa ctt cgc acc ttt atc acc gcg gcg caa        48
Met Ile Asp Asn Ile Asn Glu Leu Arg Thr Phe Ile Thr Ala Ala Gln
1               5                   10                  15 gaa ggc agt ttc acc aaa gcc gcc gca aaa tta aac gtt tcc acc tcc        96
Glu Gly Ser Phe Thr Lys Ala Ala Ala Lys Leu Asn Val Ser Thr Ser
            20                  25                  30 gca tta agc cat tcc att cgc aag ctg gaa gaa cag ctc aac atc aaa       144
Ala Leu Ser His Ser Ile Arg Lys Leu Glu Glu Gln Leu Asn Ile Lys
        35                  40                  45 ctg ttc aac cgc acc aca cgc agc att gcc acc acg gag gcg ggc gag       192
Leu Phe Asn Arg Thr Thr Arg Ser Ile Ala Thr Thr Glu Ala Gly Glu
50                  55                  60 cag ttg ttt caa aat ctc ttg ccg ttg ttt gaa agt att gaa gat aat       240
Gln Leu Phe Gln Asn Leu Leu Pro Leu Phe Glu Ser Ile Glu Asp Asn
65                  70                  75                  80 ctc aac gca tta agc acc ttt cgc aac acg ttg aaa ggg aaa tta tgc       288
Leu Asn Ala Leu Ser Thr Phe Arg Asn Thr Leu Lys Gly Lys Leu Cys
                85                  90                  95 att aac ggt aac gat cat gtt ttt tta tcc att ttg tgg gat aaa ttg       336
Ile Asn Gly Asn Asp His Val Phe Leu Ser Ile Leu Trp Asp Lys Leu
            100                 105                 110 atg gcg ttc gcg gaa caa tac ccc gaa atg gaa ttg gaa ttg acc agt       384
Met Ala Phe Ala Glu Gln Tyr Pro Glu Met Glu Leu Glu Leu Thr Ser
        115                 120                 125 gac acc aaa ttt gtg gat atc gtg gcg ggg cgg ttt gat gcg ggt att       432
Asp Thr Lys Phe Val Asp Ile Val Ala Gly Arg Phe Asp Ala Gly Ile
130                 135                 140 cgc tta gga tcg gac gtg gca caa gat atg atc gcc gtg aga tta agc       480
Arg Leu Gly Ser Asp Val Ala Gln Asp Met Ile Ala Val Arg Leu Ser
145                 150                 155                 160 gac aaa atg caa atg gcg gtg gtc ggc acg cca gag tat ttc gcc aaa       528
Asp Lys Met Gln Met Ala Val Val Gly Thr Pro Glu Tyr Phe Ala Lys
                165                 170                 175 aaa gcc aca ccg aag aaa gta gaa gac ttg ggc gaa cac gag tgc ttg       576
Lys Ala Thr Pro Lys Lys Val Glu Asp Leu Gly Glu His Glu Cys Leu
            180                 185                 190 ctg gtg                                                                582
Leu Val <210> SEQ ID NO 182
<211> LENGTH: 194
<212> TYPE: PRT
<213> ORGANISM: Actinobacillus actinomycetemcomitans

<400> SEQUENCE: 182

Met Ile Asp Asn Ile Asn Glu Leu Arg Thr Phe Ile Thr Ala Ala Gln
1               5                   10                  15

Glu Gly Ser Phe Thr Lys Ala Ala Ala Lys Leu Asn Val Ser Thr Ser
            20                  25                  30

Ala Leu Ser His Ser Ile Arg Lys Leu Glu Glu Gln Leu Asn Ile Lys
        35                  40                  45

Leu Phe Asn Arg Thr Thr Arg Ser Ile Ala Thr Thr Glu Ala Gly Glu
    50                  55                  60

Gln Leu Phe Gln Asn Leu Leu Pro Leu Phe Glu Ser Ile Glu Asp Asn
```

```
                65                  70                  75                  80
Leu Asn Ala Leu Ser Thr Phe Arg Asn Thr Leu Lys Gly Lys Leu Cys
                    85                  90                  95

Ile Asn Gly Asn Asp His Val Phe Leu Ser Ile Leu Trp Asp Lys Leu
                100                 105                 110

Met Ala Phe Ala Glu Gln Tyr Pro Glu Met Glu Leu Glu Leu Thr Ser
            115                 120                 125

Asp Thr Lys Phe Val Asp Ile Val Ala Gly Arg Phe Asp Ala Gly Ile
        130                 135                 140

Arg Leu Gly Ser Asp Val Ala Gln Asp Met Ile Ala Val Arg Leu Ser
145                 150                 155                 160

Asp Lys Met Gln Met Ala Val Val Gly Thr Pro Glu Tyr Phe Ala Lys
                165                 170                 175

Lys Ala Thr Pro Lys Lys Val Glu Asp Leu Gly Glu His Glu Cys Leu
                180                 185                 190

Leu Val

<210> SEQ ID NO 183
<211> LENGTH: 662
<212> TYPE: DNA
<213> ORGANISM: Actinobacillus actinomycetemcomitans
<220> FEATURE:
<221> NAME/KEY: CDS
<222> LOCATION: (1)..(660)

<400> SEQUENCE: 183 taa tct cgg caa tgt tcg cca cct tgc ttt ttt tgc ctg cat tat ttc      48
    Ser Arg Gln Cys Ser Pro Pro Cys Phe Phe Cys Leu His Tyr Phe
    1               5                   10                  15 gcc gtt atc aaa aca aac cgc gca ccc cga acc caa aag tgc ggt gga      96
Ala Val Ile Lys Thr Asn Arg Ala Pro Arg Thr Gln Lys Cys Gly Gly
                20                  25                  30 ttt tgg atg cgt ttt tta cgc atg ggc gtg gtt tca atc ctg tta ggg     144
Phe Trp Met Arg Phe Leu Arg Met Gly Val Val Ser Ile Leu Leu Gly
            35                  40                  45 ggg att ttt atc gtc ggc ggt ttg tat cgt tcc gaa tgg cgt gat gat     192
Gly Ile Phe Ile Val Gly Gly Leu Tyr Arg Ser Glu Trp Arg Asp Asp
        50                  55                  60 att cgt caa tgg gtt tct atg ccg cag gtg atg tta gac gag gcg aag     240
Ile Arg Gln Trp Val Ser Met Pro Gln Val Met Leu Asp Glu Ala Lys
65                  70                  75 caa atc gct gac ttg acc ggc gtg gat ttg ggc aac cgt tat ttc ctg     288
Gln Ile Ala Asp Leu Thr Gly Val Asp Leu Gly Asn Arg Tyr Phe Leu
80                  85                  90                  95 gtg ctt gcc gac aac gac gat gcc tta ctg gaa aaa gaa cgg gcg ctg     336
Val Leu Ala Asp Asn Asp Asp Ala Leu Leu Lys Glu Arg Ala Leu
                100                 105                 110 aca aca aaa ctg gat gaa cag cac atc cct tat cgc gcc ctt tcc caa     384
Thr Thr Lys Leu Asp Glu Gln His Ile Pro Tyr Arg Ala Leu Ser Gln
            115                 120                 125 tgg atg atg tcg gaa gcg caa cag cgg caa ttt ata gtg gaa ttg cag     432
Trp Met Met Ser Glu Ala Gln Gln Arg Gln Phe Ile Val Glu Leu Gln
        130                 135                 140 gca aaa ctc aaa ccg cag gat tat gcc gta ttg gat gag att ggc gtg     480
Ala Lys Leu Lys Pro Gln Asp Tyr Ala Val Leu Asp Glu Ile Gly Val
145                 150                 155 ccg tcg gaa aga tta caa cag gca ctg cgg gaa ttg aac acg cag ccg     528
Pro Ser Glu Arg Leu Gln Gln Ala Leu Arg Glu Leu Asn Thr Gln Pro
160                 165                 170                 175
```

```
ccg tta tcc ttg cag cag gcg ttg caa tct acc gtc ggg caa gca tgg      576
Pro Leu Ser Leu Gln Gln Ala Leu Gln Ser Thr Val Gly Gln Ala Trp
            180                 185                 190 ctg ccg ctc tat tta ggc aaa tta gcg gaa aat cag gtg gct ggc atc      624
Leu Pro Leu Tyr Leu Gly Lys Leu Ala Glu Asn Gln Val Ala Gly Ile
        195                 200                 205 gtg cag gta agc gga cac agt gcc gtt tcc ctt gcg ca                   662
Val Gln Val Ser Gly His Ser Ala Val Ser Leu Ala
    210                 215
```

<210> SEQ ID NO 184
<211> LENGTH: 219
<212> TYPE: PRT
<213> ORGANISM: Actinobacillus actinomycetemcomitans

<400> SEQUENCE: 184

```
Ser Arg Gln Cys Ser Pro Pro Cys Phe Phe Cys Leu His Tyr Phe Ala
1               5                   10                  15

Val Ile Lys Thr Asn Arg Ala Pro Arg Thr Gln Lys Cys Gly Gly Phe
            20                  25                  30

Trp Met Arg Phe Leu Arg Met Gly Val Val Ser Ile Leu Leu Gly Gly
        35                  40                  45

Ile Phe Ile Val Gly Gly Leu Tyr Arg Ser Glu Trp Arg Asp Asp Ile
    50                  55                  60

Arg Gln Trp Val Ser Met Pro Gln Val Met Leu Asp Glu Ala Lys Gln
65                  70                  75                  80

Ile Ala Asp Leu Thr Gly Val Asp Leu Gly Asn Arg Tyr Phe Leu Val
                85                  90                  95

Leu Ala Asp Asn Asp Asp Ala Leu Leu Glu Lys Glu Arg Ala Leu Thr
            100                 105                 110

Thr Lys Leu Asp Glu Gln His Ile Pro Tyr Arg Ala Leu Ser Gln Trp
        115                 120                 125

Met Met Ser Glu Ala Gln Gln Arg Gln Phe Ile Val Glu Leu Gln Ala
    130                 135                 140

Lys Leu Lys Pro Gln Asp Tyr Ala Val Leu Asp Glu Ile Gly Val Pro
145                 150                 155                 160

Ser Glu Arg Leu Gln Gln Ala Leu Arg Glu Leu Asn Thr Gln Pro Pro
                165                 170                 175

Leu Ser Leu Gln Gln Ala Leu Gln Ser Thr Val Gly Gln Ala Trp Leu
            180                 185                 190

Pro Leu Tyr Leu Gly Lys Leu Ala Glu Asn Gln Val Ala Gly Ile Val
        195                 200                 205

Gln Val Ser Gly His Ser Ala Val Ser Leu Ala
    210                 215
```

<210> SEQ ID NO 185
<211> LENGTH: 247
<212> TYPE: DNA
<213> ORGANISM: Actinobacillus actinomycetemcomitans
<220> FEATURE:
<221> NAME/KEY: CDS
<222> LOCATION: (1)..(246)

<400> SEQUENCE: 185

```
ggg gtg ttt atg tcc gcg cat aat ttc ccg aaa tcc cgt gaa acc cgt      48
Gly Val Phe Met Ser Ala His Asn Phe Pro Lys Ser Arg Glu Thr Arg
1               5                   10                  15 gca cct aaa gtg gcg gaa ttg gcg tta tat cgt gag cgg ctg ccg gaa      96
```

```
                Ala Pro Lys Val Ala Glu Leu Ala Leu Tyr Arg Glu Arg Leu Pro Glu
                             20                  25                  30 aaa tta agc tat ctg gct gac gca cca caa acg gat ccg gaa ggc agt         144
Lys Leu Ser Tyr Leu Ala Asp Ala Pro Gln Thr Asp Pro Glu Gly Ser
             35                  40                  45 gaa gcc atc att cgc ttt agt cgt aaa gaa aaa cgt caa tat gtc acc         192
Glu Ala Ile Ile Arg Phe Ser Arg Lys Glu Lys Arg Gln Tyr Val Thr
 50                  55                  60 tcc gaa aag aat ggc aag gcg aca aaa tgg ata gtg gat ttt gtt gat         240
Ser Glu Lys Asn Gly Lys Ala Thr Lys Trp Ile Val Asp Phe Val Asp
 65                  70                  75                  80 ggg aag t                                                               247
Gly Lys <210> SEQ ID NO 186
<211> LENGTH: 82
<212> TYPE: PRT
<213> ORGANISM: Actinobacillus actinomycetemcomitans

<400> SEQUENCE: 186

Gly Val Phe Met Ser Ala His Asn Phe Pro Lys Ser Arg Glu Thr Arg
 1               5                  10                  15

Ala Pro Lys Val Ala Glu Leu Ala Leu Tyr Arg Glu Arg Leu Pro Glu
             20                  25                  30

Lys Leu Ser Tyr Leu Ala Asp Ala Pro Gln Thr Asp Pro Glu Gly Ser
             35                  40                  45

Glu Ala Ile Ile Arg Phe Ser Arg Lys Glu Lys Arg Gln Tyr Val Thr
 50                  55                  60

Ser Glu Lys Asn Gly Lys Ala Thr Lys Trp Ile Val Asp Phe Val Asp
 65                  70                  75                  80

Gly Lys

<210> SEQ ID NO 187
<211> LENGTH: 357
<212> TYPE: DNA
<213> ORGANISM: Actinobacillus actinomycetemcomitans
<220> FEATURE:
<221> NAME/KEY: CDS
<222> LOCATION: (1)..(357)

<400> SEQUENCE: 187 tgc gtc cac tcc ggt cct ctc gta cta gga gca gcc cca acc aat tct         48
Cys Val His Ser Gly Pro Leu Val Leu Gly Ala Ala Pro Thr Asn Ser
 1               5                  10                  15 cct acg ccc acg gca gat agg gac cga act gtc tca cgt tct aaa             96
Pro Thr Pro Thr Ala Asp Arg Asp Arg Thr Val Ser Arg Ser Lys
             20                  25                  30 ccc agc tcg cgt acc act tta aat ggc gaa cag cca tac cct tgg gac        144
Pro Ser Ser Arg Thr Thr Leu Asn Gly Glu Gln Pro Tyr Pro Trp Asp
             35                  40                  45 cta ctt cag ccc cag gat gtg atg agc cga cat cga ggt gcc aaa cac        192
Leu Leu Gln Pro Gln Asp Val Met Ser Arg His Arg Gly Ala Lys His
 50                  55                  60 cgc cgt cga tat gaa ctc ttg ggc ggt atc agc ctg tta tcc ccg gag        240
Arg Arg Arg Tyr Glu Leu Leu Gly Gly Ile Ser Leu Leu Ser Pro Glu
 65                  70                  75                  80 tac ctt tta tcc gtt gag cga tgg ccc ttc cat gca gaa cca ccg gat        288
Tyr Leu Leu Ser Val Glu Arg Trp Pro Phe His Ala Glu Pro Pro Asp
                 85                  90                  95 cac tat gac cta ctt tcg tac ctg ccc gac ctg tcc gtc tcg cag tta        336
```

His Tyr Asp Leu Leu Ser Tyr Leu Pro Asp Leu Ser Val Ser Gln Leu
            100                 105                 110 agc ttg ctt ata cca ttg cac                                          357
Ser Leu Leu Ile Pro Leu His
        115

<210> SEQ ID NO 188
<211> LENGTH: 119
<212> TYPE: PRT
<213> ORGANISM: Actinobacillus actinomycetemcomitans

<400> SEQUENCE: 188

Cys Val His Ser Gly Pro Leu Val Leu Gly Ala Ala Pro Thr Asn Ser
1               5                   10                  15

Pro Thr Pro Thr Ala Asp Arg Asp Arg Thr Val Ser Arg Arg Ser Lys
            20                  25                  30

Pro Ser Ser Arg Thr Thr Leu Asn Gly Glu Gln Pro Tyr Pro Trp Asp
        35                  40                  45

Leu Leu Gln Pro Gln Asp Val Met Ser Arg His Arg Gly Ala Lys His
    50                  55                  60

Arg Arg Arg Tyr Glu Leu Leu Gly Gly Ile Ser Leu Leu Ser Pro Glu
65                  70                  75                  80

Tyr Leu Leu Ser Val Glu Arg Trp Pro Phe His Ala Glu Pro Pro Asp
                85                  90                  95

His Tyr Asp Leu Leu Ser Tyr Leu Pro Asp Leu Ser Val Ser Gln Leu
            100                 105                 110

Ser Leu Leu Ile Pro Leu His
        115

<210> SEQ ID NO 189
<211> LENGTH: 222
<212> TYPE: DNA
<213> ORGANISM: Actinobacillus actinomycetemcomitans
<220> FEATURE:
<221> NAME/KEY: CDS
<222> LOCATION: (1)..(222)

<400> SEQUENCE: 189 gaa acc gtg tgc tat gaa atc atg cgc gaa atc att cgc gta cac cat    48
Glu Thr Val Cys Tyr Glu Ile Met Arg Glu Ile Ile Arg Val His His
1               5                   10                  15 gta ttt gcc agc gaa caa ttc gtg gtt tat gcc tct cac gcc gtc gcc    96
Val Phe Ala Ser Glu Gln Phe Val Val Tyr Ala Ser His Ala Val Ala
            20                  25                  30 gat tat ctg att aac gaa gaa tcc cac ggc tta ctg gct gaa ctg gaa    144
Asp Tyr Leu Ile Asn Glu Glu Ser His Gly Leu Leu Ala Glu Leu Glu
        35                  40                  45 gtg ttc atc ggc aaa caa atc caa gta aaa act gaa gtg ttt tat act    192
Val Phe Ile Gly Lys Gln Ile Gln Val Lys Thr Glu Val Phe Tyr Thr
    50                  55                  60 cag gaa cag ttt gat gtg gtg gtg atg tag                            222
Gln Glu Gln Phe Asp Val Val Val Met
65                  70

<210> SEQ ID NO 190
<211> LENGTH: 73
<212> TYPE: PRT
<213> ORGANISM: Actinobacillus actinomycetemcomitans

<400> SEQUENCE: 190

Glu Thr Val Cys Tyr Glu Ile Met Arg Glu Ile Ile Arg Val His His

```
                    1               5                  10                      15
                Val Phe Ala Ser Glu Gln Phe Val Val Tyr Ala Ser His Ala Val Ala
                           20                  25                      30
                Asp Tyr Leu Ile Asn Glu Glu Ser His Gly Leu Leu Ala Glu Leu Glu
                           35                  40                      45
                Val Phe Ile Gly Lys Gln Ile Gln Val Lys Thr Glu Val Phe Tyr Thr
                           50                  55                      60
                Gln Glu Gln Phe Asp Val Val Met
                 65                  70

<210> SEQ ID NO 191
<211> LENGTH: 1670
<212> TYPE: DNA
<213> ORGANISM: Actinobacillus actinomycetemcomitans
<220> FEATURE:
<221> NAME/KEY: CDS
<222> LOCATION: (1)..(1668)

<400> SEQUENCE: 191 atc gaa cgt tat caa cgt tat aac aac acc tca tac aat ctt gag ccg      48
Ile Glu Arg Tyr Gln Arg Tyr Asn Asn Thr Ser Tyr Asn Leu Glu Pro
 1               5                  10                  15 gac atc aaa tac agt ccg ggc ggg ttg cgc gat ttg cat ttg ttg tat      96
Asp Ile Lys Tyr Ser Pro Gly Gly Leu Arg Asp Leu His Leu Leu Tyr
             20                  25                  30 tgg atc gcg ttg cgc cat aac ggg gct aaa aat tta cag gaa att tta     144
Trp Ile Ala Leu Arg His Asn Gly Ala Lys Asn Leu Gln Glu Ile Leu
         35                  40                  45 cag gcg ggg ttt att cat ccg gca gaa cac gcc ttg tta cta aaa agc     192
Gln Ala Gly Phe Ile His Pro Ala Glu His Ala Leu Leu Leu Lys Ser
     50                  55                  60 caa ttt ctg ttt aaa gtg cgg tac gct ttg cac tta att tta aag          240
Gln Gln Phe Leu Phe Lys Val Arg Tyr Ala Leu His Leu Ile Leu Lys
 65                  70                  75                  80 cgt tat gac aac cgc ctg ttg ttt gat cgc caa ctg aaa gtc agc gaa     288
Arg Tyr Asp Asn Arg Leu Leu Phe Asp Arg Gln Leu Lys Val Ser Glu
                 85                  90                  95 ttg ttg ggt ttc cag ggg gaa ggc aat caa ggc gtg gaa gcc atg atg     336
Leu Leu Gly Phe Gln Gly Glu Gly Asn Gln Gly Val Glu Ala Met Met
            100                 105                 110 aag cgc ttt ttt cag gcg ttg cat tcc att tcg tta cta agc gaa ttg     384
Lys Arg Phe Phe Gln Ala Leu His Ser Ile Ser Leu Leu Ser Glu Leu
        115                 120                 125 ttg gta aaa cat tat cag gaa cat ttt tta acc cgt cat gca gtg gtg     432
Leu Val Lys His Tyr Gln Glu His Phe Leu Thr Arg His Ala Val Val
    130                 135                 140 agc gag caa ata ctc gat gac aat ttc agc ctg atc aat caa tcc att     480
Ser Glu Gln Ile Leu Asp Asp Asn Phe Ser Leu Ile Asn Gln Ser Ile
145                 150                 155                 160 tgc tta cgt aat cat caa tgc ttt gag cag cag ccg gaa agc att ctt     528
Cys Leu Arg Asn His Gln Cys Phe Glu Gln Gln Pro Glu Ser Ile Leu
                165                 170                 175 gac ctt ttt tat cat tta acc caa tat ccg cag gcg gaa att cat tcc     576
Asp Leu Phe Tyr His Leu Thr Gln Tyr Pro Gln Ala Glu Ile His Ser
            180                 185                 190 ttt gtc ttg cgc gag ctt tat ttg gcg ctg gag caa cgg cag ggc tat     624
Phe Val Leu Arg Glu Leu Tyr Leu Ala Leu Glu Gln Arg Gln Gly Tyr
        195                 200                 205 ttg tgt gat ttg cca gcg gcg cgg gaa aaa ttc gtg cgc ctg ttt aat     672
Leu Cys Asp Leu Pro Ala Ala Arg Glu Lys Phe Val Arg Leu Phe Asn
```

-continued

```
         210                 215                 220
cag ccg aat gcg att aaa cgt gct ttt ttc cct atg cac caa tac ggc      720
Gln Pro Asn Ala Ile Lys Arg Ala Phe Phe Pro Met His Gln Tyr Gly
225                 230                 235                 240 gtg ctt acc gcc tat tta ccg caa tgg ggc aac gtc gtc ggt tta atg      768
Val Leu Thr Ala Tyr Leu Pro Gln Trp Gly Asn Val Val Gly Leu Met
                245                 250                 255 cag ttt gat tta ttt cat tgt tac acc gtg gac gag cat att ctg cgc      816
Gln Phe Asp Leu Phe His Cys Tyr Thr Val Asp Glu His Ile Leu Arg
            260                 265                 270 gtg atg tta aaa ctg gaa agt ttt tta gag ggc gct tcg gca caa agc      864
Val Met Leu Lys Leu Glu Ser Phe Leu Glu Gly Ala Ser Ala Gln Ser
        275                 280                 285 cat ccc att tgc cat caa ata ttc agc cga att tcc gac cgc act ttg      912
His Pro Ile Cys His Gln Ile Phe Ser Arg Ile Ser Asp Arg Thr Leu
    290                 295                 300 ttg tat att gcc gct tta ttt cac gac atc gcc aaa ggg cgc ggc ggt      960
Leu Tyr Ile Ala Ala Leu Phe His Asp Ile Ala Lys Gly Arg Gly Gly
305                 310                 315                 320 tct cat gaa tta ttg ggt gcg gtg gat gtg cgc gaa ttt gcc gtt cgg     1008
Ser His Glu Leu Leu Gly Ala Val Asp Val Arg Glu Phe Ala Val Arg
                325                 330                 335 cac ggt ttt gat caa cgg gaa acg gaa acc atg gtg tgg ctg gtg gag     1056
His Gly Phe Asp Gln Arg Glu Thr Glu Thr Met Val Trp Leu Val Glu
            340                 345                 350 cag cat ttg ctt atg tcg gtc acg gca caa cgg cgg gat att cat gat     1104
Gln His Leu Leu Met Ser Val Thr Ala Gln Arg Arg Asp Ile His Asp
        355                 360                 365 ccg gaa att gta ctg aat ttc gcc gaa ctg gtg cgt aat cag gtg cgt     1152
Pro Glu Ile Val Leu Asn Phe Ala Glu Leu Val Arg Asn Gln Val Arg
    370                 375                 380 ttg gat tat tta acc tgc ctg acc gtc gcc gat att gtg gcg acc aat     1200
Leu Asp Tyr Leu Thr Cys Leu Thr Val Ala Asp Ile Val Ala Thr Asn
385                 390                 395                 400 gaa act ttg tgg aat agc tgg aag cgt tct ttg ctg gcg act ttg tac     1248
Glu Thr Leu Trp Asn Ser Trp Lys Arg Ser Leu Leu Ala Thr Leu Tyr
                405                 410                 415 gat tac gcc acc caa caa ttc gcc caa ggg ctg gaa agt atc ttg gat     1296
Asp Tyr Ala Thr Gln Gln Phe Ala Gln Gly Leu Glu Ser Ile Leu Asp
            420                 425                 430 aat caa gcg aaa gcg aaa gga cac cgc cga tta gca ctg cag gaa ata     1344
Asn Gln Ala Lys Ala Lys Gly His Arg Arg Leu Ala Leu Gln Glu Ile
        435                 440                 445 cgt gaa aaa acc acc gca ctt tcc gac aaa cac atc gaa aaa ttg tgg     1392
Arg Glu Lys Thr Thr Ala Leu Ser Asp Lys His Ile Glu Lys Leu Trp
    450                 455                 460 cag cgt ttt ccg ata gat tat ttc ttg cgc aat tcg cca caa caa att     1440
Gln Arg Phe Pro Ile Asp Tyr Phe Leu Arg Asn Ser Pro Gln Gln Ile
465                 470                 475                 480 ggt tgg cat acc cgt ttg ctt gcc gaa ttt gaa ggg gaa ttg ttg gtg     1488
Gly Trp His Thr Arg Leu Leu Ala Glu Phe Glu Gly Glu Leu Leu Val
                485                 490                 495 aaa gtc agt aac cgg ttt tct gcc ggc ggc acg gaa att ttc att tat     1536
Lys Val Ser Asn Arg Phe Ser Ala Gly Gly Thr Glu Ile Phe Ile Tyr
            500                 505                 510 acc aaa gac cga ccg aac ctg ttt cac aaa gtg gta agt act atc ggc     1584
Thr Lys Asp Arg Pro Asn Leu Phe His Lys Val Val Ser Thr Ile Gly
        515                 520                 525 gcg aaa aaa ctc agt atc cat gat gcg caa att atc acc gcc aaa gac     1632
```

```
Ala Lys Lys Leu Ser Ile His Asp Ala Gln Ile Ile Thr Ala Lys Asp
            530                 535                 540
ggc tat gtg ttg gac agt ttt att gtg acg gaa tta ga                      1670
Gly Tyr Val Leu Asp Ser Phe Ile Val Thr Glu Leu
545                 550                 555
```

<210> SEQ ID NO 192
<211> LENGTH: 556
<212> TYPE: PRT
<213> ORGANISM: Actinobacillus actinomycetemcomitans

<400> SEQUENCE: 192

```
Ile Glu Arg Tyr Gln Arg Tyr Asn Asn Thr Ser Tyr Asn Leu Glu Pro
1               5                   10                  15

Asp Ile Lys Tyr Ser Pro Gly Gly Leu Arg Asp Leu His Leu Leu Tyr
                20                  25                  30

Trp Ile Ala Leu Arg His Asn Gly Ala Lys Asn Leu Gln Glu Ile Leu
            35                  40                  45

Gln Ala Gly Phe Ile His Pro Ala Glu His Ala Leu Leu Leu Lys Ser
    50                  55                  60

Gln Gln Phe Leu Phe Lys Val Arg Tyr Ala Leu His Leu Ile Leu Lys
65                  70                  75                  80

Arg Tyr Asp Asn Arg Leu Leu Phe Asp Arg Gln Leu Lys Val Ser Glu
                85                  90                  95

Leu Leu Gly Phe Gln Gly Glu Gly Asn Gln Gly Val Glu Ala Met Met
            100                 105                 110

Lys Arg Phe Phe Gln Ala Leu His Ser Ile Ser Leu Leu Ser Glu Leu
        115                 120                 125

Leu Val Lys His Tyr Gln Glu His Phe Leu Thr Arg His Ala Val Val
    130                 135                 140

Ser Glu Gln Ile Leu Asp Asp Asn Phe Ser Leu Ile Asn Gln Ser Ile
145                 150                 155                 160

Cys Leu Arg Asn His Gln Cys Phe Glu Gln Gln Pro Glu Ser Ile Leu
                165                 170                 175

Asp Leu Phe Tyr His Leu Thr Gln Tyr Pro Gln Ala Glu Ile His Ser
            180                 185                 190

Phe Val Leu Arg Glu Leu Tyr Leu Ala Leu Glu Gln Arg Gln Gly Tyr
        195                 200                 205

Leu Cys Asp Leu Pro Ala Ala Arg Glu Lys Phe Val Arg Leu Phe Asn
    210                 215                 220

Gln Pro Asn Ala Ile Lys Arg Ala Phe Phe Pro Met His Gln Tyr Gly
225                 230                 235                 240

Val Leu Thr Ala Tyr Leu Pro Gln Trp Gly Asn Val Val Gly Leu Met
                245                 250                 255

Gln Phe Asp Leu Phe His Cys Tyr Thr Val Asp Glu His Ile Leu Arg
            260                 265                 270

Val Met Leu Lys Leu Glu Ser Phe Leu Glu Gly Ala Ser Ala Gln Ser
        275                 280                 285

His Pro Ile Cys His Gln Ile Phe Ser Arg Ile Ser Asp Arg Thr Leu
    290                 295                 300

Leu Tyr Ile Ala Ala Leu Phe Asp Ile Ala Lys Gly Arg Gly
305                 310                 315                 320

Ser His Glu Leu Leu Gly Ala Val Asp Val Arg Glu Phe Ala Val Arg
                325                 330                 335

His Gly Phe Asp Gln Arg Glu Thr Glu Thr Met Val Trp Leu Val Glu
```

```
                       340                 345                 350
        Gln His Leu Leu Met Ser Val Thr Ala Gln Arg Arg Asp Ile His Asp
                        355                 360                 365

Pro Glu Ile Val Leu Asn Phe Ala Glu Leu Val Arg Asn Gln Val Arg
            370                 375                 380

Leu Asp Tyr Leu Thr Cys Leu Thr Val Ala Asp Ile Val Ala Thr Asn
        385                 390                 395                 400

Glu Thr Leu Trp Asn Ser Trp Lys Arg Ser Leu Leu Ala Thr Leu Tyr
                        405                 410                 415

Asp Tyr Ala Thr Gln Gln Phe Ala Gln Gly Leu Glu Ser Ile Leu Asp
                    420                 425                 430

Asn Gln Ala Lys Ala Lys Gly His Arg Arg Leu Ala Leu Gln Glu Ile
                    435                 440                 445

Arg Glu Lys Thr Thr Ala Leu Ser Asp Lys His Ile Glu Lys Leu Trp
            450                 455                 460

Gln Arg Phe Pro Ile Asp Tyr Phe Leu Arg Asn Ser Pro Gln Gln Ile
        465                 470                 475                 480

Gly Trp His Thr Arg Leu Leu Ala Glu Phe Glu Gly Glu Leu Leu Val
                        485                 490                 495

Lys Val Ser Asn Arg Phe Ser Ala Gly Gly Thr Glu Ile Phe Ile Tyr
                    500                 505                 510

Thr Lys Asp Arg Pro Asn Leu Phe His Lys Val Val Ser Thr Ile Gly
                    515                 520                 525

Ala Lys Lys Leu Ser Ile His Asp Ala Gln Ile Ile Thr Ala Lys Asp
        530                 535                 540

Gly Tyr Val Leu Asp Ser Phe Ile Val Thr Glu Leu
        545                 550                 555

<210> SEQ ID NO 193
<211> LENGTH: 567
<212> TYPE: DNA
<213> ORGANISM: Actinobacillus actinomycetemcomitans
<220> FEATURE:
<221> NAME/KEY: CDS
<222> LOCATION: (1)..(567)

<400> SEQUENCE: 193 gtc aac cat tcg ctt tat tcc gta ttg aga ccg att aat ggc gaa agc      48
Val Asn His Ser Leu Tyr Ser Val Leu Arg Pro Ile Asn Gly Glu Ser
1               5                   10                  15 acc ctt att aaa ggt caa gcg aag tgg gtg att tca aga ggt tcg cgt      96
Thr Leu Ile Lys Gly Gln Ala Lys Trp Val Ile Ser Arg Gly Ser Arg
            20                  25                  30 aat cgc act ttt cgt gtc ggt caa tct tat tgt cct tgt tgt tta ggg     144
Asn Arg Thr Phe Arg Val Gly Gln Ser Tyr Cys Pro Cys Cys Leu Gly
        35                  40                  45 gaa aca cct tat ttg cgt aat gaa tgg cgt ttt gcg tgg cat ttt ggt     192
Glu Thr Pro Tyr Leu Arg Asn Glu Trp Arg Phe Ala Trp His Phe Gly
    50                  55                  60 tgt tcg aaa cat caa gtt tta ctt gaa tct aaa tgc cct tgt tgt ggc     240
Cys Ser Lys His Gln Val Leu Leu Glu Ser Lys Cys Pro Cys Cys Gly
65                  70                  75                  80 gaa ctg tat caa cct cat ttg ctt tcc gca gaa aaa cga cac tta aat     288
Glu Leu Tyr Gln Pro His Leu Leu Ser Ala Glu Lys Arg His Leu Asn
                85                  90                  95 tac tgt cat caa tgt ggt gag aaa tta cag gtt gtt aca aca ccg ctt     336
Tyr Cys His Gln Cys Gly Glu Lys Leu Gln Val Val Thr Thr Pro Leu
            100                 105                 110
```

```
aat gaa gta gaa att gca aca atg gaa aca ctt aat aac gta ttt atg      384
Asn Glu Val Glu Ile Ala Thr Met Glu Thr Leu Asn Asn Val Phe Met
            115                 120                 125 act aac tca ggt gaa tgt ttc agg aaa cgt gtg aat gca caa gtg tac      432
Thr Asn Ser Gly Glu Cys Phe Arg Lys Arg Val Asn Ala Gln Val Tyr
130                 135                 140 ttt gct ata ttg cgt tac ttc atc aat ctt att cgg cgt gct acg gtc      480
Phe Ala Ile Leu Arg Tyr Phe Ile Asn Leu Ile Arg Arg Ala Thr Val
145                 150                 155                 160 gta aaa tct act cac gct ttt gca aaa ttt gtg gaa gaa tgt ggt att      528
Val Lys Ser Thr His Ala Phe Ala Lys Phe Val Glu Glu Cys Gly Ile
                165                 170                 175 tct caa gcg gaa ata tgc caa acc aaa acc gcc ctt gca                  567
Ser Gln Ala Glu Ile Cys Gln Thr Lys Thr Ala Leu Ala
            180                 185

<210> SEQ ID NO 194
<211> LENGTH: 189
<212> TYPE: PRT
<213> ORGANISM: Actinobacillus actinomycetemcomitans

<400> SEQUENCE: 194

Val Asn His Ser Leu Tyr Ser Val Leu Arg Pro Ile Asn Gly Glu Ser
1               5                   10                  15

Thr Leu Ile Lys Gly Gln Ala Lys Trp Val Ile Ser Arg Gly Ser Arg
            20                  25                  30

Asn Arg Thr Phe Arg Val Gly Gln Ser Tyr Cys Pro Cys Cys Leu Gly
        35                  40                  45

Glu Thr Pro Tyr Leu Arg Asn Glu Trp Arg Phe Ala Trp His Phe Gly
    50                  55                  60

Cys Ser Lys His Gln Val Leu Leu Glu Ser Lys Cys Pro Cys Cys Gly
65                  70                  75                  80

Glu Leu Tyr Gln Pro His Leu Leu Ser Ala Glu Lys Arg His Leu Asn
                85                  90                  95

Tyr Cys His Gln Cys Gly Glu Lys Leu Gln Val Val Thr Thr Pro Leu
            100                 105                 110

Asn Glu Val Glu Ile Ala Thr Met Glu Thr Leu Asn Asn Val Phe Met
        115                 120                 125

Thr Asn Ser Gly Glu Cys Phe Arg Lys Arg Val Asn Ala Gln Val Tyr
    130                 135                 140

Phe Ala Ile Leu Arg Tyr Phe Ile Asn Leu Ile Arg Arg Ala Thr Val
145                 150                 155                 160

Val Lys Ser Thr His Ala Phe Ala Lys Phe Val Glu Glu Cys Gly Ile
                165                 170                 175

Ser Gln Ala Glu Ile Cys Gln Thr Lys Thr Ala Leu Ala
            180                 185

<210> SEQ ID NO 195
<211> LENGTH: 492
<212> TYPE: DNA
<213> ORGANISM: Actinobacillus actinomycetemcomitans
<220> FEATURE:
<221> NAME/KEY: CDS
<222> LOCATION: (1)..(492)

<400> SEQUENCE: 195 acc ttg gat gtg ctt cgt tcc gaa act ttc gtt tcc gaa tta aaa ggc       48
Thr Leu Asp Val Leu Arg Ser Glu Thr Phe Val Ser Glu Leu Lys Gly
1               5                   10                  15
```

```
tta aat gct tat cgc acc acc gtg cct gtc atc ggc gga cac tcc ggt      96
Leu Asn Ala Tyr Arg Thr Thr Val Pro Val Ile Gly Gly His Ser Gly
             20                  25                  30 gtg act att ctt ccg tta tta tct caa gtg caa tac gtt gaa tgg aaa     144
Val Thr Ile Leu Pro Leu Leu Ser Gln Val Gln Tyr Val Glu Trp Lys
         35                  40                  45 gag gac gaa att gaa ccg tta acc aaa cgc att caa aat gcc ggc acc     192
Glu Asp Glu Ile Glu Pro Leu Thr Lys Arg Ile Gln Asn Ala Gly Thr
 50                  55                  60 gaa gta gta aac gcg aaa gcc ggc ggt tcc gca acc tta tcc atg         240
Glu Val Val Asn Ala Lys Ala Gly Gly Gly Ser Ala Thr Leu Ser Met
 65                  70                  75                  80 gcg cag gcg gca gcc cgt ttt gct aat gct gta gtc cgc ggt tta caa     288
Ala Gln Ala Ala Ala Arg Phe Ala Asn Ala Val Val Arg Gly Leu Gln
                 85                  90                  95 ggt gaa acc gtc gta gaa tgc agc tat gtg gaa ggc gac ggc aaa tac     336
Gly Glu Thr Val Val Glu Cys Ser Tyr Val Glu Gly Asp Gly Lys Tyr
            100                 105                 110 gcc cgc ttc ttc gca caa ccg gtt cgc ttc ggc aag gaa ggt gtg gaa     384
Ala Arg Phe Phe Ala Gln Pro Val Arg Phe Gly Lys Glu Gly Val Glu
        115                 120                 125 gaa atc cta cca atc ggt aaa ctc agc gcc ttg gaa caa cag gct tta     432
Glu Ile Leu Pro Ile Gly Lys Leu Ser Ala Leu Glu Gln Gln Ala Leu
130                 135                 140 gaa acc atg tta ccg aca ttg cgt gca gat att gaa tta ggt gag aag     480
Glu Thr Met Leu Pro Thr Leu Arg Ala Asp Ile Glu Leu Gly Glu Lys
145                 150                 155                 160 ttt att aat cca                                                     492
Phe Ile Asn Pro
```

<210> SEQ ID NO 196
<211> LENGTH: 164
<212> TYPE: PRT
<213> ORGANISM: Actinobacillus actinomycetemcomitans

<400> SEQUENCE: 196

```
Thr Leu Asp Val Leu Arg Ser Glu Thr Phe Val Ser Glu Leu Lys Gly
 1               5                  10                  15

Leu Asn Ala Tyr Arg Thr Thr Val Pro Val Ile Gly Gly His Ser Gly
             20                  25                  30

Val Thr Ile Leu Pro Leu Leu Ser Gln Val Gln Tyr Val Glu Trp Lys
         35                  40                  45

Glu Asp Glu Ile Glu Pro Leu Thr Lys Arg Ile Gln Asn Ala Gly Thr
 50                  55                  60

Glu Val Val Asn Ala Lys Ala Gly Gly Gly Ser Ala Thr Leu Ser Met
 65                  70                  75                  80

Ala Gln Ala Ala Ala Arg Phe Ala Asn Ala Val Val Arg Gly Leu Gln
                 85                  90                  95

Gly Glu Thr Val Val Glu Cys Ser Tyr Val Glu Gly Asp Gly Lys Tyr
            100                 105                 110

Ala Arg Phe Phe Ala Gln Pro Val Arg Phe Gly Lys Glu Gly Val Glu
        115                 120                 125

Glu Ile Leu Pro Ile Gly Lys Leu Ser Ala Leu Glu Gln Gln Ala Leu
130                 135                 140

Glu Thr Met Leu Pro Thr Leu Arg Ala Asp Ile Glu Leu Gly Glu Lys
145                 150                 155                 160

Phe Ile Asn Pro
```

<210> SEQ ID NO 197
<211> LENGTH: 667
<212> TYPE: DNA
<213> ORGANISM: Actinobacillus actinomycetemcomitans
<220> FEATURE:
<221> NAME/KEY: CDS
<222> LOCATION: (1)..(666)

<400> SEQUENCE: 197

| | | | | | | | | | | | | | | | | |
|---|---|---|---|---|---|---|---|---|---|---|---|---|---|---|---|---|
| gca | tta | agc | ctg | caa | agt | ttc | aac | ctt | gaa | gtg | ccg | gtt | gat | gat | aaa | 48 |
| Ala | Leu | Ser | Leu | Gln | Ser | Phe | Asn | Leu | Glu | Val | Pro | Val | Asp | Asp | Lys | |
| 1 | | | | 5 | | | | | 10 | | | | | 15 | | |
| gaa | cgt | atc | gaa | aac | atc | aaa | cgt | tac | acc | ggt | gaa | aaa | tta | gat | acg | 96 |
| Glu | Arg | Ile | Glu | Asn | Ile | Lys | Arg | Tyr | Thr | Gly | Glu | Lys | Leu | Asp | Thr | |
| | | | 20 | | | | | 25 | | | | | 30 | | | |
| gcg | ttt | gtc | aac | gga | tta | gtg | gaa | gcc | tcg | agc | cgt | tta | cgt | cgc | tta | 144 |
| Ala | Phe | Val | Asn | Gly | Leu | Val | Glu | Ala | Ser | Ser | Arg | Leu | Arg | Arg | Leu | |
| | | 35 | | | | | 40 | | | | | 45 | | | | |
| tcc | ccg | ccg | gca | ttc | cgt | ttc | caa | tta | acc | gaa | tta | gcc | cgc | gcc | gcc | 192 |
| Ser | Pro | Pro | Ala | Phe | Arg | Phe | Gln | Leu | Thr | Glu | Leu | Ala | Arg | Ala | Ala | |
| 50 | | | | | 55 | | | | | 60 | | | | | | |
| caa | aaa | cgc | atc | gtc | tta | ccg | gaa | ggc | gac | gaa | ccg | cgc | acc | att | aaa | 240 |
| Gln | Lys | Arg | Ile | Val | Leu | Pro | Glu | Gly | Asp | Glu | Pro | Arg | Thr | Ile | Lys | |
| 65 | | | | | 70 | | | | | 75 | | | | | 80 | |
| gcg | gcg | att | tta | tgt | gcc | gaa | cgc | ggt | atc | gca | gaa | tgt | gtg | ctg | tta | 288 |
| Ala | Ala | Ile | Leu | Cys | Ala | Glu | Arg | Gly | Ile | Ala | Glu | Cys | Val | Leu | Leu | |
| | | | | 85 | | | | | 90 | | | | | 95 | | |
| gcc | aaa | ccg | gaa | gac | gta | caa | cgc | gtg | gcg | gaa | tcc | caa | ggc | gtt | aag | 336 |
| Ala | Lys | Pro | Glu | Asp | Val | Gln | Arg | Val | Ala | Glu | Ser | Gln | Gly | Val | Lys | |
| | | | 100 | | | | | 105 | | | | | 110 | | | |
| ttg | gta | aac | ggc | att | acc | gtt | atc | gac | ccg | gcg | agc | gtg | cgt | gaa | aac | 384 |
| Leu | Val | Asn | Gly | Ile | Thr | Val | Ile | Asp | Pro | Ala | Ser | Val | Arg | Glu | Asn | |
| | | 115 | | | | | 120 | | | | | 125 | | | | |
| tat | gtg | gca | cgt | ttg | gtt | gag | cta | cgc | aaa | gcc | aaa | ggc | atg | acc | gaa | 432 |
| Tyr | Val | Ala | Arg | Leu | Val | Glu | Leu | Arg | Lys | Ala | Lys | Gly | Met | Thr | Glu | |
| | 130 | | | | | 135 | | | | | 140 | | | | | |
| acc | atg | gcg | cgt | gaa | caa | ttg | gaa | gac | aat | gtt | gtg | ctc | ggt | acc | atg | 480 |
| Thr | Met | Ala | Arg | Glu | Gln | Leu | Glu | Asp | Asn | Val | Val | Leu | Gly | Thr | Met | |
| 145 | | | | | 150 | | | | | 155 | | | | | 160 | |
| atg | ttg | gaa | gcc | aac | caa | gta | gac | ggt | ttg | gta | tcc | ggc | gcc | gta | cac | 528 |
| Met | Leu | Glu | Ala | Asn | Gln | Val | Asp | Gly | Leu | Val | Ser | Gly | Ala | Val | His | |
| | | | | 165 | | | | | 170 | | | | | 175 | | |
| acc | acc | gcc | aac | acc | att | cgc | ccg | cca | atg | caa | atc | atc | aaa | acc | gca | 576 |
| Thr | Thr | Ala | Asn | Thr | Ile | Arg | Pro | Pro | Met | Gln | Ile | Ile | Lys | Thr | Ala | |
| | | | 180 | | | | | 185 | | | | | 190 | | | |
| ccg | ggc | agc | tcc | att | att | tct | tcc | atc | ttc | ttc | atg | ttg | cta | ccg | gat | 624 |
| Pro | Gly | Ser | Ser | Ile | Ile | Ser | Ser | Ile | Phe | Phe | Met | Leu | Leu | Pro | Asp | |
| | | 195 | | | | | 200 | | | | | 205 | | | | |
| caa | gta | ttg | gtc | tat | ggc | gat | tgc | gca | gtg | aac | ccg | gat | ccg | a | | 667 |
| Gln | Val | Leu | Val | Tyr | Gly | Asp | Cys | Ala | Val | Asn | Pro | Asp | Pro | | | |
| | 210 | | | | | 215 | | | | | 220 | | | | | |

<210> SEQ ID NO 198
<211> LENGTH: 222
<212> TYPE: PRT
<213> ORGANISM: Actinobacillus actinomycetemcomitans

<400> SEQUENCE: 198

| | | | | | | | | | | | | | | | |
|---|---|---|---|---|---|---|---|---|---|---|---|---|---|---|---|
| Ala | Leu | Ser | Leu | Gln | Ser | Phe | Asn | Leu | Glu | Val | Pro | Val | Asp | Asp | Lys |
| 1 | | | | 5 | | | | | 10 | | | | | 15 | |

```
Glu Arg Ile Glu Asn Ile Lys Arg Tyr Thr Gly Glu Lys Leu Asp Thr
                20                  25                  30

Ala Phe Val Asn Gly Leu Val Glu Ala Ser Ser Arg Leu Arg Arg Leu
            35                  40                  45

Ser Pro Pro Ala Phe Arg Phe Gln Leu Thr Glu Leu Ala Arg Ala Ala
    50                  55                  60

Gln Lys Arg Ile Val Leu Pro Glu Gly Asp Glu Pro Arg Thr Ile Lys
65                  70                  75                  80

Ala Ala Ile Leu Cys Ala Glu Arg Gly Ile Ala Glu Cys Val Leu Leu
                85                  90                  95

Ala Lys Pro Glu Asp Val Gln Arg Val Ala Glu Ser Gln Gly Val Lys
            100                 105                 110

Leu Val Asn Gly Ile Thr Val Ile Asp Pro Ala Ser Val Arg Glu Asn
        115                 120                 125

Tyr Val Ala Arg Leu Val Glu Leu Arg Lys Ala Lys Gly Met Thr Glu
    130                 135                 140

Thr Met Ala Arg Glu Gln Leu Glu Asp Asn Val Val Leu Gly Thr Met
145                 150                 155                 160

Met Leu Glu Ala Asn Gln Val Asp Gly Leu Val Ser Gly Ala Val His
                165                 170                 175

Thr Thr Ala Asn Thr Ile Arg Pro Pro Met Gln Ile Ile Lys Thr Ala
            180                 185                 190

Pro Gly Ser Ser Ile Ile Ser Ser Ile Phe Phe Met Leu Leu Pro Asp
        195                 200                 205

Gln Val Leu Val Tyr Gly Asp Cys Ala Val Asn Pro Asp Pro
    210                 215                 220
```

<210> SEQ ID NO 199
<211> LENGTH: 267
<212> TYPE: DNA
<213> ORGANISM: Actinobacillus actinomycetemcomitans
<220> FEATURE:
<221> NAME/KEY: CDS
<222> LOCATION: (1)..(267)

<400> SEQUENCE: 199

```
ggt ata cgc cct gag cat tta att ccg tct gat gag gca gaa gtt acg      48
Gly Ile Arg Pro Glu His Leu Ile Pro Ser Asp Glu Ala Glu Val Thr
1               5                   10                  15 ttg cgc agc aat gtg cag gtg gtg gaa ttg ctt ggt aac gaa acg caa      96
Leu Arg Ser Asn Val Gln Val Val Glu Leu Leu Gly Asn Glu Thr Gln
                20                  25                  30 att cac ctt gaa atc cct gaa att aaa caa ccg acc tta att tat cgc     144
Ile His Leu Glu Ile Pro Glu Ile Lys Gln Pro Thr Leu Ile Tyr Arg
            35                  40                  45 caa aat gat gtg gtg ttg gtg aag gag ggg gaa acg atg gac atc ggc     192
Gln Asn Asp Val Val Leu Val Lys Glu Gly Glu Thr Met Asp Ile Gly
50                  55                  60 atc att ccg gaa cgt tgc cat ctg ttt aaa gaa gac ggc acc gcc tgc     240
Ile Ile Pro Glu Arg Cys His Leu Phe Lys Glu Asp Gly Thr Ala Cys
65                  70                  75                  80 caa cgt ttg tat aaa gaa aaa ggc gtt                                  267
Gln Arg Leu Tyr Lys Glu Lys Gly Val
                85
```

<210> SEQ ID NO 200
<211> LENGTH: 89
<212> TYPE: PRT
<213> ORGANISM: Actinobacillus actinomycetemcomitans

```
<400> SEQUENCE: 200

Gly Ile Arg Pro Glu His Leu Ile Pro Ser Asp Glu Ala Glu Val Thr
1               5                   10                  15

Leu Arg Ser Asn Val Gln Val Val Glu Leu Leu Gly Asn Glu Thr Gln
            20                  25                  30

Ile His Leu Glu Ile Pro Glu Ile Lys Gln Pro Thr Leu Ile Tyr Arg
        35                  40                  45

Gln Asn Asp Val Val Leu Val Lys Glu Gly Glu Thr Met Asp Ile Gly
    50                  55                  60

Ile Ile Pro Glu Arg Cys His Leu Phe Lys Glu Asp Gly Thr Ala Cys
65                  70                  75                  80

Gln Arg Leu Tyr Lys Glu Lys Gly Val
                85

<210> SEQ ID NO 201
<211> LENGTH: 219
<212> TYPE: DNA
<213> ORGANISM: Actinobacillus actinomycetemcomitans
<220> FEATURE:
<221> NAME/KEY: CDS
<222> LOCATION: (1)..(219)

<400> SEQUENCE: 201 tac atc gtc atc gcc ttt gtg gtg tca cag tta ttg gac gga aat ctg      48
Tyr Ile Val Ile Ala Phe Val Val Ser Gln Leu Leu Asp Gly Asn Leu
1               5                   10                  15 ctg gtg ccg ttt ttg ttc tcc gaa gcg gtc aat ctg cac ccg ttg gtg     96
Leu Val Pro Phe Leu Phe Ser Glu Ala Val Asn Leu His Pro Leu Val
            20                  25                  30 atc atc att gcc gtt ttg att ttc ggt ggc ttg tgg gga ttc tgg ggc    144
Ile Ile Ile Ala Val Leu Ile Phe Gly Gly Leu Trp Gly Phe Trp Gly
        35                  40                  45 gta ttt ttt gcc att ccg ctg gcg act ttg gtg aaa gcg gtg gtg aac    192
Val Phe Phe Ala Ile Pro Leu Ala Thr Leu Val Lys Ala Val Val Asn
    50                  55                  60 gct tgg cct tcc aat gaa gcg gtg gaa                                219
Ala Trp Pro Ser Asn Glu Ala Val Glu
65                  70

<210> SEQ ID NO 202
<211> LENGTH: 73
<212> TYPE: PRT
<213> ORGANISM: Actinobacillus actinomycetemcomitans

<400> SEQUENCE: 202

Tyr Ile Val Ile Ala Phe Val Val Ser Gln Leu Leu Asp Gly Asn Leu
1               5                   10                  15

Leu Val Pro Phe Leu Phe Ser Glu Ala Val Asn Leu His Pro Leu Val
            20                  25                  30

Ile Ile Ile Ala Val Leu Ile Phe Gly Gly Leu Trp Gly Phe Trp Gly
        35                  40                  45

Val Phe Phe Ala Ile Pro Leu Ala Thr Leu Val Lys Ala Val Val Asn
    50                  55                  60

Ala Trp Pro Ser Asn Glu Ala Val Glu
65                  70

<210> SEQ ID NO 203
<211> LENGTH: 631
<212> TYPE: DNA
```

```
<213> ORGANISM: Actinobacillus actinomycetemcomitans
<220> FEATURE:
<221> NAME/KEY: CDS
<222> LOCATION: (1)..(630)

<400> SEQUENCE: 203 cct ttc gcc atc gaa agt gac gag aaa ttt gcc tcc gcc tgc att cgt      48
Pro Phe Ala Ile Glu Ser Asp Glu Lys Phe Ala Ser Ala Cys Ile Arg
1               5                   10                  15 tgc ggt cag tgc gtg caa gcc tgc cct tat gat atg ttg cat ttg gca      96
Cys Gly Gln Cys Val Gln Ala Cys Pro Tyr Asp Met Leu His Leu Ala
                20                  25                  30 tcg ttg cta tca cca atg gaa gcg ggg acg ccg tat ttt atc gcg cgc     144
Ser Leu Leu Ser Pro Met Glu Ala Gly Thr Pro Tyr Phe Ile Ala Arg
            35                  40                  45 gat aaa cct tgc gaa atg tgt ccg gat att cct tgc gcc cat gcg tgt     192
Asp Lys Pro Cys Glu Met Cys Pro Asp Ile Pro Cys Ala His Ala Cys
        50                  55                  60 ccg agc ggt gcg tta gat cgt gag gcg cag gat att aat caa tcc cgt     240
Pro Ser Gly Ala Leu Asp Arg Glu Ala Gln Asp Ile Asn Gln Ser Arg
65                  70                  75                  80 atg ggg ctg gcg gtg ttg ctg gat cat gaa acc tgc ttg aac tgg caa     288
Met Gly Leu Ala Val Leu Leu Asp His Glu Thr Cys Leu Asn Trp Gln
                85                  90                  95 ggc ttg cgt tgc gat gtg tgt tat cgg gtt tgt ccg ttg att gat aaa     336
Gly Leu Arg Cys Asp Val Cys Tyr Arg Val Cys Pro Leu Ile Asp Lys
                100                 105                 110 gcc att acg ctg gaa agc cat cgt aat gag cgc acc ggc aag cac gcg     384
Ala Ile Thr Leu Glu Ser His Arg Asn Glu Arg Thr Gly Lys His Ala
            115                 120                 125 gtg ttt att ccg acg gtg cat tcc gat ggc tgt acc ggc tgt ggc aaa     432
Val Phe Ile Pro Thr Val His Ser Asp Gly Cys Thr Gly Cys Gly Lys
        130                 135                 140 tgc gaa caa gcg tgt gtc ttg gaa gaa gcg gca atc aaa gta tta ccg     480
Cys Glu Gln Ala Cys Val Leu Glu Glu Ala Ala Ile Lys Val Leu Pro
145                 150                 155                 160 atg cat ttg gcg aaa ggc atg tta ggc aaa cat tat cgt ttg ggt tgg     528
Met His Leu Ala Lys Gly Met Leu Gly Lys His Tyr Arg Leu Gly Trp
                165                 170                 175 gaa gaa aag gcg aaa gcc gga cat tcc ttg gcg ccg aaa gat ttg att     576
Glu Glu Lys Ala Lys Ala Gly His Ser Leu Ala Pro Lys Asp Leu Ile
                180                 185                 190 tcg atg ccg acc cgt atg ccg gaa gcc aca atg ccg gta atg ggc gca     624
Ser Met Pro Thr Arg Met Pro Glu Ala Thr Met Pro Val Met Gly Ala
            195                 200                 205 gaa gac a                                                           631
Glu Asp
    210

<210> SEQ ID NO 204
<211> LENGTH: 210
<212> TYPE: PRT
<213> ORGANISM: Actinobacillus actinomycetemcomitans

<400> SEQUENCE: 204

Pro Phe Ala Ile Glu Ser Asp Glu Lys Phe Ala Ser Ala Cys Ile Arg
1               5                   10                  15

Cys Gly Gln Cys Val Gln Ala Cys Pro Tyr Asp Met Leu His Leu Ala
                20                  25                  30

Ser Leu Leu Ser Pro Met Glu Ala Gly Thr Pro Tyr Phe Ile Ala Arg
            35                  40                  45
```

```
Asp Lys Pro Cys Glu Met Cys Pro Asp Ile Pro Cys Ala His Ala Cys
     50                  55                  60

Pro Ser Gly Ala Leu Asp Arg Glu Ala Gln Asp Ile Asn Gln Ser Arg
 65                  70                  75                  80

Met Gly Leu Ala Val Leu Leu Asp His Glu Thr Cys Leu Asn Trp Gln
                 85                  90                  95

Gly Leu Arg Cys Asp Val Cys Tyr Arg Val Cys Pro Leu Ile Asp Lys
            100                 105                 110

Ala Ile Thr Leu Glu Ser His Arg Asn Glu Arg Thr Gly Lys His Ala
        115                 120                 125

Val Phe Ile Pro Thr Val His Ser Asp Gly Cys Thr Gly Cys Gly Lys
    130                 135                 140

Cys Glu Gln Ala Cys Val Leu Glu Glu Ala Ala Ile Lys Val Leu Pro
145                 150                 155                 160

Met His Leu Ala Lys Gly Met Leu Gly Lys His Tyr Arg Leu Gly Trp
                165                 170                 175

Glu Glu Lys Ala Lys Ala Gly His Ser Leu Ala Pro Lys Asp Leu Ile
            180                 185                 190

Ser Met Pro Thr Arg Met Pro Glu Ala Thr Met Pro Val Met Gly Ala
        195                 200                 205

Glu Asp
    210

<210> SEQ ID NO 205
<211> LENGTH: 354
<212> TYPE: DNA
<213> ORGANISM: Actinobacillus actinomycetemcomitans
<220> FEATURE:
<221> NAME/KEY: CDS
<222> LOCATION: (1)..(354)

<400> SEQUENCE: 205 tgc ctg gaa cgg gtg aaa cgg ttg gag aag caa ggg gtg att atg ggg      48
Cys Leu Glu Arg Val Lys Arg Leu Glu Lys Gln Gly Val Ile Met Gly
 1               5                  10                  15 tat cgt gct ttg ctg aat ccc gca tta ttg gat tcg ccg ttg ttg gtg      96
Tyr Arg Ala Leu Leu Asn Pro Ala Leu Leu Asp Ser Pro Leu Leu Val
             20                  25                  30 atc gtg gaa att acg ctg gta cgt ggc aag ccc gat gtg ttt gaa gaa     144
Ile Val Glu Ile Thr Leu Val Arg Gly Lys Pro Asp Val Phe Glu Glu
         35                  40                  45 ttt aac gcg gcg gtg cag cag tta gat gaa att cag gaa tgc cat ttg     192
Phe Asn Ala Ala Val Gln Gln Leu Asp Glu Ile Gln Glu Cys His Leu
     50                  55                  60 gtt tcc ggt gat ttc gat tat tta ttg aaa aca cgg gtg gcg gat atg     240
Val Ser Gly Asp Phe Asp Tyr Leu Leu Lys Thr Arg Val Ala Asp Met
 65                  70                  75                  80 gcg gcg tat cgt aaa ttg ctg ggg acc acc ttg ctg cgc ctg ccc ggg     288
Ala Ala Tyr Arg Lys Leu Leu Gly Thr Thr Leu Leu Arg Leu Pro Gly
                 85                  90                  95 gtg aac gac acg cgc act tat gtg gtg atg gaa gaa gtg aaa caa acg     336
Val Asn Asp Thr Arg Thr Tyr Val Val Met Glu Glu Val Lys Gln Thr
            100                 105                 110 aat ttt tta cag tta aaa                                             354
Asn Phe Leu Gln Leu Lys
        115

<210> SEQ ID NO 206
```

```
<211> LENGTH: 118
<212> TYPE: PRT
<213> ORGANISM: Actinobacillus actinomycetemcomitans

<400> SEQUENCE: 206

Cys Leu Glu Arg Val Lys Arg Leu Glu Lys Gln Gly Val Ile Met Gly
1               5                   10                  15

Tyr Arg Ala Leu Leu Asn Pro Ala Leu Leu Asp Ser Pro Leu Leu Val
            20                  25                  30

Ile Val Glu Ile Thr Leu Val Arg Gly Lys Pro Asp Val Phe Glu Glu
        35                  40                  45

Phe Asn Ala Ala Val Gln Gln Leu Asp Glu Ile Gln Glu Cys His Leu
    50                  55                  60

Val Ser Gly Asp Phe Asp Tyr Leu Leu Lys Thr Arg Val Ala Asp Met
65                  70                  75                  80

Ala Ala Tyr Arg Lys Leu Leu Gly Thr Thr Leu Leu Arg Leu Pro Gly
                85                  90                  95

Val Asn Asp Thr Arg Thr Tyr Val Val Met Glu Glu Val Lys Gln Thr
            100                 105                 110

Asn Phe Leu Gln Leu Lys
        115

<210> SEQ ID NO 207
<211> LENGTH: 613
<212> TYPE: DNA
<213> ORGANISM: Actinobacillus actinomycetemcomitans
<220> FEATURE:
<221> NAME/KEY: CDS
<222> LOCATION: (1)..(612)

<400> SEQUENCE: 207 atg agt tta aaa ata tta tta aat cag ccg caa tac gat ccg att cgt     48
Met Ser Leu Lys Ile Leu Leu Asn Gln Pro Gln Tyr Asp Pro Ile Arg
1               5                   10                  15 gac aaa aaa gcc gag cgc aac tta ttt gcc cgt cgc gct ttg gtg tca     96
Asp Lys Lys Ala Glu Arg Asn Leu Phe Ala Arg Arg Ala Leu Val Ser
            20                  25                  30 ttt atc ggc gtg ttg gtg ttg tcg gtg gtg tta att tta aac ttg tat    144
Phe Ile Gly Val Leu Val Leu Ser Val Val Leu Ile Leu Asn Leu Tyr
        35                  40                  45 gat ttg cag gtg gtc aat tat gac ggt tat caa acc cgt tcc aac ggc    192
Asp Leu Gln Val Val Asn Tyr Asp Gly Tyr Gln Thr Arg Ser Asn Gly
    50                  55                  60 aat cgt att aag ttg ttg ccg ctg ccg ccg act cgc ggg ttg att tat    240
Asn Arg Ile Lys Leu Leu Pro Leu Pro Pro Thr Arg Gly Leu Ile Tyr
65                  70                  75                  80 gat cgc aac ggc aaa ctg ctg gcg gaa aat ctg acc ttt ttc ggg ctt    288
Asp Arg Asn Gly Lys Leu Leu Ala Glu Asn Leu Thr Phe Phe Gly Leu
                85                  90                  95 tat atc gtg cct gaa aag gtg gaa aat tta gac cgc act ttt gag gag    336
Tyr Ile Val Pro Glu Lys Val Glu Asn Leu Asp Arg Thr Phe Glu Glu
            100                 105                 110 ctg agg gtg ttg gta ggc tta act gat gaa gat att gcg aat ttt aac    384
Leu Arg Val Leu Val Gly Leu Thr Asp Glu Asp Ile Ala Asn Phe Asn
        115                 120                 125 aag gaa cgg cgt cgc tcc tcc cgt tat atg ccg att atg ctg aaa cga    432
Lys Glu Arg Arg Arg Ser Ser Arg Tyr Met Pro Ile Met Leu Lys Arg
    130                 135                 140 aat cta acg gaa gag caa att gcc cgt ttt gcg gtg aat caa tac aat    480
Asn Leu Thr Glu Glu Gln Ile Ala Arg Phe Ala Val Asn Gln Tyr Asn
```

```
                145                 150                 155                 160
ttc cag agt ttg gat gtg aaa ccc tac ttt aag cgc cat tat tta tac      528
Phe Gln Ser Leu Asp Val Lys Pro Tyr Phe Lys Arg His Tyr Leu Tyr
                165                 170                 175 ggc gaa ccg ctg acc cat gtt ttg ggc tat gtg tca aaa att aac gat      576
Gly Glu Pro Leu Thr His Val Leu Gly Tyr Val Ser Lys Ile Asn Asp
            180                 185                 190 cgt gat gta gaa cgc ttg aaa aaa gag gaa aag tac g                    613
Arg Asp Val Glu Arg Leu Lys Lys Glu Glu Lys Tyr
            195                 200

<210> SEQ ID NO 208
<211> LENGTH: 204
<212> TYPE: PRT
<213> ORGANISM: Actinobacillus actinomycetemcomitans

<400> SEQUENCE: 208

Met Ser Leu Lys Ile Leu Leu Asn Gln Pro Gln Tyr Asp Pro Ile Arg
1               5                   10                  15

Asp Lys Lys Ala Glu Arg Asn Leu Phe Ala Arg Arg Ala Leu Val Ser
                20                  25                  30

Phe Ile Gly Val Leu Val Leu Ser Val Val Leu Ile Leu Asn Leu Tyr
            35                  40                  45

Asp Leu Gln Val Val Asn Tyr Asp Gly Tyr Gln Thr Arg Ser Asn Gly
        50                  55                  60

Asn Arg Ile Lys Leu Leu Pro Leu Pro Pro Thr Arg Gly Leu Ile Tyr
65                  70                  75                  80

Asp Arg Asn Gly Lys Leu Leu Ala Glu Asn Leu Thr Phe Phe Gly Leu
                85                  90                  95

Tyr Ile Val Pro Glu Lys Val Glu Asn Leu Asp Arg Thr Phe Glu Glu
                100                 105                 110

Leu Arg Val Leu Val Gly Leu Thr Asp Glu Asp Ile Ala Asn Phe Asn
            115                 120                 125

Lys Glu Arg Arg Arg Ser Ser Arg Tyr Met Pro Ile Met Leu Lys Arg
        130                 135                 140

Asn Leu Thr Glu Glu Gln Ile Ala Arg Phe Ala Val Asn Gln Tyr Asn
145                 150                 155                 160

Phe Gln Ser Leu Asp Val Lys Pro Tyr Phe Lys Arg His Tyr Leu Tyr
                165                 170                 175

Gly Glu Pro Leu Thr His Val Leu Gly Tyr Val Ser Lys Ile Asn Asp
            180                 185                 190

Arg Asp Val Glu Arg Leu Lys Lys Glu Glu Lys Tyr
            195                 200

<210> SEQ ID NO 209
<211> LENGTH: 631
<212> TYPE: DNA
<213> ORGANISM: Actinobacillus actinomycetemcomitans
<220> FEATURE:
<221> NAME/KEY: CDS
<222> LOCATION: (1)..(630)

<400> SEQUENCE: 209 cgc tta gca caa cat tca tcg gaa aaa ctg acc gca ctt tcc cat gca      48
Arg Leu Ala Gln His Ser Ser Glu Lys Leu Thr Ala Leu Ser His Ala
1               5                   10                  15 acc acg cat tct gac gcc caa agt gcg gta gaa aat cag agt gaa tct      96
Thr Thr His Ser Asp Ala Gln Ser Ala Val Glu Asn Gln Ser Glu Ser
            20                  25                  30
```

| | | |
|---|---|---|
| gat agc gac gaa act gat gcg gat gtg ttg tta ggc gag gat tat cgt<br>Asp Ser Asp Glu Thr Asp Ala Asp Val Leu Leu Gly Glu Asp Tyr Arg<br>        35                      40                     45 | | 144 |
| tgg gag tgg agc aac ccc gag ctt gcc aat att gag caa ggc cct aag<br>Trp Glu Trp Ser Asn Pro Glu Leu Ala Asn Ile Glu Gln Gly Pro Lys<br>50                     55                     60 | | 192 |
| ccc tcc gaa atc aaa gcc gcc att ttg cag gac atc act cct gaa tta<br>Pro Ser Glu Ile Lys Ala Ala Ile Leu Gln Asp Ile Thr Pro Glu Leu<br>65                   70                   75                 80 | | 240 |
| cag caa aaa atc gtc aat tta act caa acg caa gat cgc tgg gcg cag<br>Gln Gln Lys Ile Val Asn Leu Thr Gln Thr Gln Asp Arg Trp Ala Gln<br>        85                      90                     95 | | 288 |
| ctg att gag caa agc ggt gta gaa aat ctc acc aaa gag ttc gcc tta<br>Leu Ile Glu Gln Ser Gly Val Glu Asn Leu Thr Lys Glu Phe Ala Leu<br>            100                   105                110 | | 336 |
| aat acc ttc att tgg cag gaa aat gac gcg gag ttt aaa ctt ggt gtg<br>Asn Thr Phe Ile Trp Gln Glu Asn Asp Ala Glu Phe Lys Leu Gly Val<br>            115                   120                125 | | 384 |
| cgt tcc agc cac ggg cat tta aat cag gat aag cat cgg aag ctg tta<br>Arg Ser Ser His Gly His Leu Asn Gln Asp Lys His Arg Lys Leu Leu<br>130                    135                   140 | | 432 |
| caa cag gca ctt tca gtg gtg tta cag aaa gaa att gca ctg acc gtg<br>Gln Gln Ala Leu Ser Val Val Leu Gln Lys Glu Ile Ala Leu Thr Val<br>145                    150                   155                160 | | 480 |
| gaa att aac gac gac gaa caa tat ctg acg ccg acg gat tat cgc cgt<br>Glu Ile Asn Asp Asp Glu Gln Tyr Leu Thr Pro Thr Asp Tyr Arg Arg<br>                  165                   170                175 | | 528 |
| aaa acc tat gct caa ttg cgt gag cag gcg aaa cag gat ttg ttg caa<br>Lys Thr Tyr Ala Gln Leu Arg Glu Gln Ala Lys Gln Asp Leu Leu Gln<br>            180                   185                190 | | 576 |
| gat gaa aag ttg caa cta ttg gag cgt gaa ttt gat tgt cag gtt gat<br>Asp Glu Lys Leu Gln Leu Leu Glu Arg Glu Phe Asp Cys Gln Val Asp<br>            195                   200                205 | | 624 |
| gtg aaa a<br>Val Lys<br>    210 | | 631 |

<210> SEQ ID NO 210
<211> LENGTH: 210
<212> TYPE: PRT
<213> ORGANISM: Actinobacillus actinomycetemcomitans

<400> SEQUENCE: 210

Arg Leu Ala Gln His Ser Ser Glu Lys Leu Thr Ala Leu Ser His Ala
1                   5                   10                  15

Thr Thr His Ser Asp Ala Gln Ser Ala Val Glu Asn Gln Ser Glu Ser
               20                   25                   30

Asp Ser Asp Glu Thr Asp Ala Asp Val Leu Leu Gly Glu Asp Tyr Arg
        35                      40                     45

Trp Glu Trp Ser Asn Pro Glu Leu Ala Asn Ile Glu Gln Gly Pro Lys
50                     55                     60

Pro Ser Glu Ile Lys Ala Ala Ile Leu Gln Asp Ile Thr Pro Glu Leu
65                   70                   75                 80

Gln Gln Lys Ile Val Asn Leu Thr Gln Thr Gln Asp Arg Trp Ala Gln
        85                      90                     95

Leu Ile Glu Gln Ser Gly Val Glu Asn Leu Thr Lys Glu Phe Ala Leu
            100                   105                110

Asn Thr Phe Ile Trp Gln Glu Asn Asp Ala Glu Phe Lys Leu Gly Val

```
                115                 120                 125
Arg Ser Ser His Gly His Leu Asn Gln Asp Lys His Arg Lys Leu Leu
    130                 135                 140

Gln Gln Ala Leu Ser Val Val Leu Gln Lys Glu Ile Ala Leu Thr Val
145                 150                 155                 160

Glu Ile Asn Asp Asp Glu Gln Tyr Leu Thr Pro Thr Asp Tyr Arg Arg
                165                 170                 175

Lys Thr Tyr Ala Gln Leu Arg Glu Gln Ala Lys Gln Asp Leu Leu Gln
                180                 185                 190

Asp Glu Lys Leu Gln Leu Leu Glu Arg Glu Phe Asp Cys Gln Val Asp
                195                 200                 205

Val Lys
    210

<210> SEQ ID NO 211
<211> LENGTH: 1155
<212> TYPE: DNA
<213> ORGANISM: Actinobacillus actinomycetemcomitans
<220> FEATURE:
<221> NAME/KEY: CDS
<222> LOCATION: (1)..(1155)

<400> SEQUENCE: 211 ccc gaa cat ata aaa gac aag gta tcg aga ggt ttc att atg gca agt      48
Pro Glu His Ile Lys Asp Lys Val Ser Arg Gly Phe Ile Met Ala Ser
1               5                   10                  15 gta aca ttg cgc aat gtg ggc aaa tct tac gga aac gta cat att tcc     96
Val Thr Leu Arg Asn Val Gly Lys Ser Tyr Gly Asn Val His Ile Ser
            20                  25                  30 aaa gat att aat ttg gat att gaa gaa ggc gaa ttt gtc gtc ttt gtc    144
Lys Asp Ile Asn Leu Asp Ile Glu Glu Gly Glu Phe Val Val Phe Val
        35                  40                  45 gga ccg tcc ggt tgc ggt aaa tcc aca tta ttg cga atg att gcc gga    192
Gly Pro Ser Gly Cys Gly Lys Ser Thr Leu Leu Arg Met Ile Ala Gly
    50                  55                  60 ctt gag gat att acc acc ggt gaa ctt tac atc ggt gaa aaa cgg atg    240
Leu Glu Asp Ile Thr Thr Gly Glu Leu Tyr Ile Gly Glu Lys Arg Met
65                  70                  75                  80 aac gat gtg ccg ccg gca aag cgc ggt atc ggt atg gtg ttc caa tct    288
Asn Asp Val Pro Pro Ala Lys Arg Gly Ile Gly Met Val Phe Gln Ser
                85                  90                  95 tac gcc ctg tac ccg cac ttg gat gtg gca gaa aat atg tct ttc ggg    336
Tyr Ala Leu Tyr Pro His Leu Asp Val Ala Glu Asn Met Ser Phe Gly
            100                 105                 110 ctg aaa tta gcc ggt gta aat aaa acg gaa cgg gat cag cgc gtt aat    384
Leu Lys Leu Ala Gly Val Asn Lys Thr Glu Arg Asp Gln Arg Val Asn
        115                 120                 125 cag gtt gcc gaa att tta cag ctt gcc cat ttg ctt gaa cgt aaa ccg    432
Gln Val Ala Glu Ile Leu Gln Leu Ala His Leu Leu Glu Arg Lys Pro
    130                 135                 140 aaa gcc ttg tcg ggc ggt cag cgt caa cgt gtg gcg att ggg cga acc    480
Lys Ala Leu Ser Gly Gly Gln Arg Gln Arg Val Ala Ile Gly Arg Thr
145                 150                 155                 160 ctt gtt tcc cag cca gaa gta ttc ttg ctg gac gaa ccg ctt tcc aac    528
Leu Val Ser Gln Pro Glu Val Phe Leu Leu Asp Glu Pro Leu Ser Asn
                165                 170                 175 tta gat gcc gcc ttg cgc gta caa atg cgg gtg gaa atc tcc aaa tta    576
Leu Asp Ala Ala Leu Arg Val Gln Met Arg Val Glu Ile Ser Lys Leu
            180                 185                 190
```

```
cac aaa aaa ctc aac cgc acc atg att tat gtt acc cat gac caa gtg      624
His Lys Lys Leu Asn Arg Thr Met Ile Tyr Val Thr His Asp Gln Val
        195                 200                 205 gaa gcc atg acc ctg gcg gac aaa atc gtg gtg ttg aat gcg ggc ggt      672
Glu Ala Met Thr Leu Ala Asp Lys Ile Val Val Leu Asn Ala Gly Gly
210                 215                 220 att gcg cag gtg ggg aaa ccg ctg gaa ctt tac cat tat ccg caa aat      720
Ile Ala Gln Val Gly Lys Pro Leu Glu Leu Tyr His Tyr Pro Gln Asn
225                 230                 235                 240 cgt ttc gtg gcc ggt ttt atc ggt tca ccg aaa atg aat ttc ctg ccg      768
Arg Phe Val Ala Gly Phe Ile Gly Ser Pro Lys Met Asn Phe Leu Pro
        245                 250                 255 gtg aaa gtg act gct gtg gaa aaa gag cgg gtg caa atc gaa ttg ccc      816
Val Lys Val Thr Ala Val Glu Lys Glu Arg Val Gln Ile Glu Leu Pro
        260                 265                 270 gac gcc aac cat cat aac ttc tgg atc ccg gtt tcc ggt aat ggc gtg      864
Asp Ala Asn His His Asn Phe Trp Ile Pro Val Ser Gly Asn Gly Val
        275                 280                 285 aaa gtg ggt gaa aac ctt tca tta ggt ata cgc cct gag cat tta att      912
Lys Val Gly Glu Asn Leu Ser Leu Gly Ile Arg Pro Glu His Leu Ile
290                 295                 300 ccg tct gat gag gca gaa gtt acg ttg cgc agc aat gtg cag gtg gtg      960
Pro Ser Asp Glu Ala Glu Val Thr Leu Arg Ser Asn Val Gln Val Val
305                 310                 315                 320 gaa ttg ctt ggt aac gaa acg caa att cac ctt gaa atc cct gaa att     1008
Glu Leu Leu Gly Asn Glu Thr Gln Ile His Leu Glu Ile Pro Glu Ile
                325                 330                 335 aaa caa ccg acc tta att tat cgc caa aat gat gtg gtg ttg gtg aag     1056
Lys Gln Pro Thr Leu Ile Tyr Arg Gln Asn Asp Val Val Leu Val Lys
            340                 345                 350 gag ggg gaa acg atg gac atc ggc atc att ccg gaa cgt tgc cat ctg     1104
Glu Gly Glu Thr Met Asp Ile Gly Ile Ile Pro Glu Arg Cys His Leu
            355                 360                 365 ttt aaa gaa gac ggc acc gcc tgc caa cgt ttg tat aaa gaa aaa ggc     1152
Phe Lys Glu Asp Gly Thr Ala Cys Gln Arg Leu Tyr Lys Glu Lys Gly
370                 375                 380 gtt                                                                  1155
Val
385

<210> SEQ ID NO 212
<211> LENGTH: 385
<212> TYPE: PRT
<213> ORGANISM: Actinobacillus actinomycetemcomitans

<400> SEQUENCE: 212

Pro Glu His Ile Lys Asp Lys Val Ser Arg Gly Phe Ile Met Ala Ser
1               5                   10                  15

Val Thr Leu Arg Asn Val Gly Lys Ser Tyr Gly Asn Val His Ile Ser
            20                  25                  30

Lys Asp Ile Asn Leu Asp Ile Glu Glu Gly Glu Phe Val Val Phe Val
        35                  40                  45

Gly Pro Ser Gly Cys Gly Lys Ser Thr Leu Leu Arg Met Ile Ala Gly
    50                  55                  60

Leu Glu Asp Ile Thr Thr Gly Glu Leu Tyr Ile Gly Glu Lys Arg Met
65                  70                  75                  80

Asn Asp Val Pro Pro Ala Lys Arg Gly Ile Gly Met Val Phe Gln Ser
                85                  90                  95

Tyr Ala Leu Tyr Pro His Leu Asp Val Ala Glu Asn Met Ser Phe Gly
```

```
                    100                 105                 110
Leu Lys Leu Ala Gly Val Asn Lys Thr Glu Arg Asp Gln Arg Val Asn
            115                 120                 125

Gln Val Ala Glu Ile Leu Gln Leu Ala His Leu Leu Glu Arg Lys Pro
        130                 135                 140

Lys Ala Leu Ser Gly Gly Gln Arg Gln Arg Val Ala Ile Gly Arg Thr
145                 150                 155                 160

Leu Val Ser Gln Pro Glu Val Phe Leu Leu Asp Glu Pro Leu Ser Asn
                165                 170                 175

Leu Asp Ala Ala Leu Arg Val Gln Met Arg Val Glu Ile Ser Lys Leu
            180                 185                 190

His Lys Lys Leu Asn Arg Thr Met Ile Tyr Val Thr His Asp Gln Val
        195                 200                 205

Glu Ala Met Thr Leu Ala Asp Lys Ile Val Leu Asn Ala Gly Gly
    210                 215                 220

Ile Ala Gln Val Gly Lys Pro Leu Glu Leu Tyr His Tyr Pro Gln Asn
225                 230                 235                 240

Arg Phe Val Ala Gly Phe Ile Gly Ser Pro Lys Met Asn Phe Leu Pro
                245                 250                 255

Val Lys Val Thr Ala Val Glu Lys Glu Arg Val Gln Ile Glu Leu Pro
            260                 265                 270

Asp Ala Asn His His Asn Phe Trp Ile Pro Val Ser Gly Asn Gly Val
        275                 280                 285

Lys Val Gly Glu Asn Leu Ser Leu Gly Ile Arg Pro Glu His Leu Ile
    290                 295                 300

Pro Ser Asp Glu Ala Glu Val Thr Leu Arg Ser Asn Val Gln Val Val
305                 310                 315                 320

Glu Leu Leu Gly Asn Glu Thr Gln Ile His Leu Glu Ile Pro Glu Ile
                325                 330                 335

Lys Gln Pro Thr Leu Ile Tyr Arg Gln Asn Asp Val Val Leu Val Lys
            340                 345                 350

Glu Gly Glu Thr Met Asp Ile Gly Ile Ile Pro Glu Arg Cys His Leu
        355                 360                 365

Phe Lys Glu Asp Gly Thr Ala Cys Gln Arg Leu Tyr Lys Glu Lys Gly
    370                 375                 380
Val
385
```

<210> SEQ ID NO 213
<211> LENGTH: 447
<212> TYPE: DNA
<213> ORGANISM: Actinobacillus actinomycetemcomitans
<220> FEATURE:
<221> NAME/KEY: CDS
<222> LOCATION: (1)..(447)

<400> SEQUENCE: 213

```
atg cca aaa aat gcg caa ttc tac ctg ctt tcc gat gcc tct ccc gca        48
Met Pro Lys Asn Ala Gln Phe Tyr Leu Leu Ser Asp Ala Ser Pro Ala
1               5                   10                  15 cag acg aat ttg tct gcg gtg gaa agc ctt gcc tgc aat ttg gcg gcg        96
Gln Thr Asn Leu Ser Ala Val Glu Ser Leu Ala Cys Asn Leu Ala Ala
            20                  25                  30 tcc gcc tgg cgt ttg gga aaa cgg gtt ctg ttg gcg tgt gaa aat gaa       144
Ser Ala Trp Arg Leu Gly Lys Arg Val Leu Leu Ala Cys Glu Asn Glu
        35                  40                  45
```

```
gcg cag gcg ctc aat att gat gaa gcc ctt tgg caa cgg gaa ccg gac      192
Ala Gln Ala Leu Asn Ile Asp Glu Ala Leu Trp Gln Arg Glu Pro Asp
 50                  55                  60 gaa ttc gtc ccg cac aac ctt tcc ggc gaa gcc acg acg tat gcc acg      240
Glu Phe Val Pro His Asn Leu Ser Gly Glu Ala Thr Thr Tyr Ala Thr
 65                  70                  75                  80 ccc atc gaa atc agc tgg acg ggc aaa cgc aac gca caa agc cgc gat      288
Pro Ile Glu Ile Ser Trp Thr Gly Lys Arg Asn Ala Gln Ser Arg Asp
                 85                  90                  95 ttg ctg att aat tta caa ccg cag ctg ccg gaa ttc atc aac agc ttt      336
Leu Leu Ile Asn Leu Gln Pro Gln Leu Pro Glu Phe Ile Asn Ser Phe
            100                 105                 110 aac caa att atc gat ttc gta ccc gcc gaa gaa caa caa aaa gct tta      384
Asn Gln Ile Ile Asp Phe Val Pro Ala Glu Glu Gln Gln Lys Ala Leu
        115                 120                 125 gcg cgg gaa cgt tat aaa caa ttg agg cag ttg ggc tgg gaa ttg agt      432
Ala Arg Glu Arg Tyr Lys Gln Leu Arg Gln Leu Gly Trp Glu Leu Ser
130                 135                 140 acg gag cag gcg ggg                                                  447
Thr Glu Gln Ala Gly
145

<210> SEQ ID NO 214
<211> LENGTH: 149
<212> TYPE: PRT
<213> ORGANISM: Actinobacillus actinomycetemcomitans

<400> SEQUENCE: 214

Met Pro Lys Asn Ala Gln Phe Tyr Leu Leu Ser Asp Ala Ser Pro Ala
 1               5                  10                  15

Gln Thr Asn Leu Ser Ala Val Glu Ser Leu Ala Cys Asn Leu Ala Ala
            20                  25                  30

Ser Ala Trp Arg Leu Gly Lys Arg Val Leu Leu Ala Cys Glu Asn Glu
        35                  40                  45

Ala Gln Ala Leu Asn Ile Asp Glu Ala Leu Trp Gln Arg Glu Pro Asp
 50                  55                  60

Glu Phe Val Pro His Asn Leu Ser Gly Glu Ala Thr Thr Tyr Ala Thr
 65                  70                  75                  80

Pro Ile Glu Ile Ser Trp Thr Gly Lys Arg Asn Ala Gln Ser Arg Asp
                 85                  90                  95

Leu Leu Ile Asn Leu Gln Pro Gln Leu Pro Glu Phe Ile Asn Ser Phe
            100                 105                 110

Asn Gln Ile Ile Asp Phe Val Pro Ala Glu Glu Gln Gln Lys Ala Leu
        115                 120                 125

Ala Arg Glu Arg Tyr Lys Gln Leu Arg Gln Leu Gly Trp Glu Leu Ser
    130                 135                 140

Thr Glu Gln Ala Gly
145

<210> SEQ ID NO 215
<211> LENGTH: 774
<212> TYPE: DNA
<213> ORGANISM: Actinobacillus actinomycetemcomitans
<220> FEATURE:
<221> NAME/KEY: CDS
<222> LOCATION: (1)..(774)

<400> SEQUENCE: 215 aaa gac aac aaa atc tgg cac ttc acc tta cga aaa gaa gca ata tgg       48
Lys Asp Asn Lys Ile Trp His Phe Thr Leu Arg Lys Glu Ala Ile Trp
```

```
tct aac ggc gaa ccg gtg act gcg cag caa ttt gtt gca agc tgg caa        96
Ser Asn Gly Glu Pro Val Thr Ala Gln Gln Phe Val Ala Ser Trp Gln
         20                  25                  30 cgg ctg gcg caa tcg gat tct cct tta aag cac tat tta cgc tac ctt       144
Arg Leu Ala Gln Ser Asp Ser Pro Leu Lys His Tyr Leu Arg Tyr Leu
     35                  40                  45 aac tta gtc aac gcg gag aaa gtg tta cag caa act ctg ctg cca gag       192
Asn Leu Val Asn Ala Glu Lys Val Leu Gln Gln Thr Leu Leu Pro Glu
 50                  55                  60 cag ttg gga att gtc gcg gaa aat gac cgc act tta cgc tta act tta       240
Gln Leu Gly Ile Val Ala Glu Asn Asp Arg Thr Leu Arg Leu Thr Leu
 65                  70                  75                  80 gat aaa gcg acc cct tac ttg ccg caa atg ctg gcg cat atc agc ctg       288
Asp Lys Ala Thr Pro Tyr Leu Pro Gln Met Leu Ala His Ile Ser Leu
                 85                  90                  95 ttg cca caa tat ttg tcg cca cat gaa ggc att gtg acc aac ggg gcg       336
Leu Pro Gln Tyr Leu Ser Pro His Glu Gly Ile Val Thr Asn Gly Ala
            100                 105                 110 tat caa gtg atg ggg cag caa ggc aat ctc atc cat ttg gaa aag aac       384
Tyr Gln Val Met Gly Gln Gln Gly Asn Leu Ile His Leu Glu Lys Asn
        115                 120                 125 ccg caa tat tgg gcg aaa gaa aaa gtg gcg ttt aaa aat gtg gat tat       432
Pro Gln Tyr Trp Ala Lys Glu Lys Val Ala Phe Lys Asn Val Asp Tyr
    130                 135                 140 cag aaa atc gca ctg caa cag gac gtc agc gcc tta gat gtg gtg tgg       480
Gln Lys Ile Ala Leu Gln Gln Asp Val Ser Ala Leu Asp Val Val Trp
145                 150                 155                 160 cag ccg cag caa caa acg gat caa acg caa tac ttc ccg caa ctt tgc       528
Gln Pro Gln Gln Gln Thr Asp Gln Thr Gln Tyr Phe Pro Gln Leu Cys
                165                 170                 175 acc tat ttt tac acc ttt aat ttt aac atg cca caa ctg gcg caa agc       576
Thr Tyr Phe Tyr Thr Phe Asn Phe Asn Met Pro Gln Leu Ala Gln Ser
            180                 185                 190 ccg gtg cgt aag gca ttg gca atg atg aca tct gcc cgc agt tta ttg       624
Pro Val Arg Lys Ala Leu Ala Met Met Thr Ser Ala Arg Ser Leu Leu
        195                 200                 205 ccg gaa agt aaa aac agg att cct tta acg gat aat ttt tta cca att       672
Pro Glu Ser Lys Asn Arg Ile Pro Leu Thr Asp Asn Phe Leu Pro Ile
    210                 215                 220 tcc atg caa acc atc gat agc cgg tgg gag caa acg ccg gtt gaa caa       720
Ser Met Gln Thr Ile Asp Ser Arg Trp Glu Gln Thr Pro Val Glu Gln
225                 230                 235                 240 tta tta agc caa gcg cga att gga gag aag gca ccg ctc aaa ctg acc       768
Leu Leu Ser Gln Ala Arg Ile Gly Glu Lys Ala Pro Leu Lys Leu Thr
                245                 250                 255 cta agt                                                                774
Leu Ser
```

<210> SEQ ID NO 216
<211> LENGTH: 258
<212> TYPE: PRT
<213> ORGANISM: Actinobacillus actinomycetemcomitans

<400> SEQUENCE: 216

```
Lys Asp Asn Lys Ile Trp His Phe Thr Leu Arg Lys Glu Ala Ile Trp
 1               5                  10                  15

Ser Asn Gly Glu Pro Val Thr Ala Gln Gln Phe Val Ala Ser Trp Gln
             20                  25                  30
```

```
Arg Leu Ala Gln Ser Asp Ser Pro Leu Lys His Tyr Leu Arg Tyr Leu
            35                  40                  45

Asn Leu Val Asn Ala Glu Lys Val Leu Gln Gln Thr Leu Leu Pro Glu
 50                  55                  60

Gln Leu Gly Ile Val Ala Glu Asn Asp Arg Thr Leu Arg Leu Thr Leu
 65                  70                  75                  80

Asp Lys Ala Thr Pro Tyr Leu Pro Gln Met Leu Ala His Ile Ser Leu
                 85                  90                  95

Leu Pro Gln Tyr Leu Ser Pro His Glu Gly Ile Val Thr Asn Gly Ala
            100                 105                 110

Tyr Gln Val Met Gly Gln Gly Asn Leu Ile His Leu Glu Lys Asn
            115                 120                 125

Pro Gln Tyr Trp Ala Lys Glu Lys Val Ala Phe Lys Asn Val Asp Tyr
            130                 135                 140

Gln Lys Ile Ala Leu Gln Gln Asp Val Ser Ala Leu Asp Val Val Trp
145                 150                 155                 160

Gln Pro Gln Gln Gln Thr Asp Gln Thr Gln Tyr Phe Pro Gln Leu Cys
                165                 170                 175

Thr Tyr Phe Tyr Thr Phe Asn Phe Asn Met Pro Gln Leu Ala Gln Ser
            180                 185                 190

Pro Val Arg Lys Ala Leu Ala Met Met Thr Ser Ala Arg Ser Leu Leu
            195                 200                 205

Pro Glu Ser Lys Asn Arg Ile Pro Leu Thr Asp Asn Phe Leu Pro Ile
            210                 215                 220

Ser Met Gln Thr Ile Asp Ser Arg Trp Glu Gln Thr Pro Val Glu Gln
225                 230                 235                 240

Leu Leu Ser Gln Ala Arg Ile Gly Glu Lys Ala Pro Leu Lys Leu Thr
                245                 250                 255

Leu Ser

<210> SEQ ID NO 217
<211> LENGTH: 363
<212> TYPE: DNA
<213> ORGANISM: Actinobacillus actinomycetemcomitans
<220> FEATURE:
<221> NAME/KEY: CDS
<222> LOCATION: (1)..(363)

<400> SEQUENCE: 217 atc cgt att caa ccg gac gaa ggc att tct atg cgt ttt ggc ttg aaa      48
Ile Arg Ile Gln Pro Asp Glu Gly Ile Ser Met Arg Phe Gly Leu Lys
 1               5                  10                  15 aaa ccg ggc gcc ggc ttt gaa gcc aaa gaa gtg tcg atg gat ttc cgc      96
Lys Pro Gly Ala Gly Phe Glu Ala Lys Glu Val Ser Met Asp Phe Arg
             20                  25                  30 tat gcc gat ctt gcg ggt gcc acc gtc atg acc gct tat gag cgt tta     144
Tyr Ala Asp Leu Ala Gly Ala Thr Val Met Thr Ala Tyr Glu Arg Leu
         35                  40                  45 ttg ctt gat gcc atg aaa ggc gac gcg acc cta ttt gcg cgt acc gat     192
Leu Leu Asp Ala Met Lys Gly Asp Ala Thr Leu Phe Ala Arg Thr Asp
 50                  55                  60 gcc gta cac gcc gcc tgg aaa ttc gtt caa ccg att ttg aac tat aaa     240
Ala Val His Ala Ala Trp Lys Phe Val Gln Pro Ile Leu Asn Tyr Lys
 65                  70                  75                  80 gcc caa ggc ggc aga ctt tat gat tac gag gcc ggc acc tgg gga ccg     288
Ala Gln Gly Gly Arg Leu Tyr Asp Tyr Glu Ala Gly Thr Trp Gly Pro
                 85                  90                  95
```

```
acg gca gcc gat aaa ctc atc gcc aaa agc ggt cgt gta tgg cgc cgc      336
Thr Ala Ala Asp Lys Leu Ile Ala Lys Ser Gly Arg Val Trp Arg Arg
            100                 105                 110 cca agc ggg ttg atg aag aaa aaa gtg                                   363
Pro Ser Gly Leu Met Lys Lys Lys Val
        115                 120
```

<210> SEQ ID NO 218
<211> LENGTH: 121
<212> TYPE: PRT
<213> ORGANISM: Actinobacillus actinomycetemcomitans

<400> SEQUENCE: 218

```
Ile Arg Ile Gln Pro Asp Glu Gly Ile Ser Met Arg Phe Gly Leu Lys
1               5                   10                  15

Lys Pro Gly Ala Gly Phe Glu Ala Lys Glu Val Ser Met Asp Phe Arg
            20                  25                  30

Tyr Ala Asp Leu Ala Gly Ala Thr Val Met Thr Ala Tyr Glu Arg Leu
        35                  40                  45

Leu Leu Asp Ala Met Lys Gly Asp Ala Thr Leu Phe Ala Arg Thr Asp
50                  55                  60

Ala Val His Ala Ala Trp Lys Phe Val Gln Pro Ile Leu Asn Tyr Lys
65                  70                  75                  80

Ala Gln Gly Gly Arg Leu Tyr Asp Tyr Glu Ala Gly Thr Trp Gly Pro
                85                  90                  95

Thr Ala Ala Asp Lys Leu Ile Ala Lys Ser Gly Arg Val Trp Arg Arg
            100                 105                 110

Pro Ser Gly Leu Met Lys Lys Lys Val
        115                 120
```

<210> SEQ ID NO 219
<211> LENGTH: 159
<212> TYPE: DNA
<213> ORGANISM: Actinobacillus actinomycetemcomitans
<220> FEATURE:
<221> NAME/KEY: CDS
<222> LOCATION: (1)..(159)

<400> SEQUENCE: 219

```
atg gca aca ggc aaa agc att att tta atg gga gtt tcc agt aca gga      48
Met Ala Thr Gly Lys Ser Ile Ile Leu Met Gly Val Ser Ser Thr Gly
1               5                   10                  15 aaa aca tca gtg ggg acg gaa gta gca cgt cgt ttg gag ata aaa ctg      96
Lys Thr Ser Val Gly Thr Glu Val Ala Arg Arg Leu Glu Ile Lys Leu
            20                  25                  30 att gat ggc gat gat ctg cac ccg cgc gcc aat atc ata aaa atg ggc      144
Ile Asp Gly Asp Asp Leu His Pro Arg Ala Asn Ile Ile Lys Met Gly
        35                  40                  45 gaa gga cat ccg ctc                                                   159
Glu Gly His Pro Leu
    50
```

<210> SEQ ID NO 220
<211> LENGTH: 53
<212> TYPE: PRT
<213> ORGANISM: Actinobacillus actinomycetemcomitans

<400> SEQUENCE: 220

```
Met Ala Thr Gly Lys Ser Ile Ile Leu Met Gly Val Ser Ser Thr Gly
1               5                   10                  15

Lys Thr Ser Val Gly Thr Glu Val Ala Arg Arg Leu Glu Ile Lys Leu
```

```
                    20                  25                  30
Ile Asp Gly Asp Asp Leu His Pro Arg Ala Asn Ile Ile Lys Met Gly
            35                  40                  45

Gly Gly His Pro Leu
    50
```

<210> SEQ ID NO 221
<211> LENGTH: 289
<212> TYPE: DNA
<213> ORGANISM: Actinobacillus actinomycetemcomitans
<220> FEATURE:
<221> NAME/KEY: CDS
<222> LOCATION: (1)..(288)

<400> SEQUENCE: 221

```
aac att gct tat gcg gcg aaa gac aaa tac agt cgt gaa gaa atc atc      48
Asn Ile Ala Tyr Ala Ala Lys Asp Lys Tyr Ser Arg Glu Glu Ile Ile
1               5                   10                  15 aaa gcg gca aaa gcg gcg cac gcc atg gaa ttt atc gag cat ttg gaa      96
Lys Ala Ala Lys Ala Ala His Ala Met Glu Phe Ile Glu His Leu Glu
                20                  25                  30 aac ggt ctg gat acg gtt atc ggc gaa aac ggc gcc agc tta tcc ggc      144
Asn Gly Leu Asp Thr Val Ile Gly Glu Asn Gly Ala Ser Leu Ser Gly
            35                  40                  45 ggt caa cgc cag cgt tta gcc atc gcc cgc gcc ttg ttg cgt aac tcg      192
Gly Gln Arg Gln Arg Leu Ala Ile Ala Arg Ala Leu Leu Arg Asn Ser
        50                  55                  60 ccg gta ttg att tta gat gaa gcc acc tcg gca ttg gat acg gaa tcc      240
Pro Val Leu Ile Leu Asp Glu Ala Thr Ser Ala Leu Asp Thr Glu Ser
65                  70                  75                  80 gaa cgc gca att caa gcg gca ttg gaa gaa atc caa aaa gat cgc acg g    289
Glu Arg Ala Ile Gln Ala Ala Leu Glu Glu Ile Gln Lys Asp Arg Thr
                85                  90                  95
```

<210> SEQ ID NO 222
<211> LENGTH: 96
<212> TYPE: PRT
<213> ORGANISM: Actinobacillus actinomycetemcomitans

<400> SEQUENCE: 222

```
Asn Ile Ala Tyr Ala Ala Lys Asp Lys Tyr Ser Arg Glu Glu Ile Ile
1               5                   10                  15

Lys Ala Ala Lys Ala Ala His Ala Met Glu Phe Ile Glu His Leu Glu
                20                  25                  30

Asn Gly Leu Asp Thr Val Ile Gly Glu Asn Gly Ala Ser Leu Ser Gly
            35                  40                  45

Gly Gln Arg Gln Arg Leu Ala Ile Ala Arg Ala Leu Leu Arg Asn Ser
        50                  55                  60

Pro Val Leu Ile Leu Asp Glu Ala Thr Ser Ala Leu Asp Thr Glu Ser
65                  70                  75                  80

Glu Arg Ala Ile Gln Ala Ala Leu Glu Glu Ile Gln Lys Asp Arg Thr
                85                  90                  95
```

<210> SEQ ID NO 223
<211> LENGTH: 353
<212> TYPE: DNA
<213> ORGANISM: Actinobacillus actinomycetemcomitans
<220> FEATURE:
<221> NAME/KEY: CDS
<222> LOCATION: (1)..(351)

<400> SEQUENCE: 223

```
tcg aac atc aac cct gat gat cca agt gcg att atc gaa ggc aac gaa       48
Ser Asn Ile Asn Pro Asp Asp Pro Ser Ala Ile Ile Glu Gly Asn Glu
1               5                  10                  15 aaa gtg gtt cgc cct cgt tta acc gac gcg gaa ttc ttc tcc aaa acc       96
Lys Val Val Arg Pro Arg Leu Thr Asp Ala Glu Phe Phe Ser Lys Thr
                20                  25                  30 gac tta aaa caa aaa tta gtg gat cgc tta ccg cgc ttg gaa act gtg      144
Asp Leu Lys Gln Lys Leu Val Asp Arg Leu Pro Arg Leu Glu Thr Val
            35                  40                  45 ttg ttc caa caa caa ctt ggc aca ttg cgt gat aaa acc gac cgc atc      192
Leu Phe Gln Gln Gln Leu Gly Thr Leu Arg Asp Lys Thr Asp Arg Ile
        50                  55                  60 gaa caa ctt gcg ggt gca atc gcc aaa caa atc ggt gcc gac gaa gcg      240
Glu Gln Leu Ala Gly Ala Ile Ala Lys Gln Ile Gly Ala Asp Glu Ala
65                  70                  75                  80 aaa gca aaa cgt gcg ggc ttg ctg tca aaa tgc gat ttg atg acc aat      288
Lys Ala Lys Arg Ala Gly Leu Leu Ser Lys Cys Asp Leu Met Thr Asn
                85                  90                  95 atg gtg ttt gaa ttc acc gac acc caa ggc gta atg ggt atg cac tat      336
Met Val Phe Glu Phe Thr Asp Thr Gln Gly Val Met Gly Met His Tyr
                100                 105                 110 gcc cgt cac gac ggc ga                                               353
Ala Arg His Asp Gly
        115

<210> SEQ ID NO 224
<211> LENGTH: 117
<212> TYPE: PRT
<213> ORGANISM: Actinobacillus actinomycetemcomitans

<400> SEQUENCE: 224

Ser Asn Ile Asn Pro Asp Asp Pro Ser Ala Ile Ile Glu Gly Asn Glu
1               5                   10                  15

Lys Val Val Arg Pro Arg Leu Thr Asp Ala Glu Phe Phe Ser Lys Thr
                20                  25                  30

Asp Leu Lys Gln Lys Leu Val Asp Arg Leu Pro Arg Leu Glu Thr Val
            35                  40                  45

Leu Phe Gln Gln Gln Leu Gly Thr Leu Arg Asp Lys Thr Asp Arg Ile
        50                  55                  60

Glu Gln Leu Ala Gly Ala Ile Ala Lys Gln Ile Gly Ala Asp Glu Ala
65                  70                  75                  80

Lys Ala Lys Arg Ala Gly Leu Leu Ser Lys Cys Asp Leu Met Thr Asn
                85                  90                  95

Met Val Phe Glu Phe Thr Asp Thr Gln Gly Val Met Gly Met His Tyr
                100                 105                 110

Ala Arg His Asp Gly
        115

<210> SEQ ID NO 225
<211> LENGTH: 366
<212> TYPE: DNA
<213> ORGANISM: Actinobacillus actinomycetemcomitans
<220> FEATURE:
<221> NAME/KEY: CDS
<222> LOCATION: (1)..(366)

<400> SEQUENCE: 225 cta ttg gaa aaa caa ggg tta att aaa tta aaa gat ccg acc aac ctg       48
Leu Leu Glu Lys Gln Gly Leu Ile Lys Leu Lys Asp Pro Thr Asn Leu
1               5                   10                  15
```

```
ttc tcc act tct ata gat atc att gaa aat ccg aaa aat tta caa atc        96
Phe Ser Thr Ser Ile Asp Ile Ile Glu Asn Pro Lys Asn Leu Gln Ile
         20                  25                  30 aaa gaa gtg gat acc tcc gtt gcg gca cgt gcc tta gat gac gtt gat       144
Lys Glu Val Asp Thr Ser Val Ala Ala Arg Ala Leu Asp Asp Val Asp
             35                  40                  45 ttg gcg gta gtg aat aac aac tac gcc ggt caa gta ggc tta aat gcg       192
Leu Ala Val Val Asn Asn Asn Tyr Ala Gly Gln Val Gly Leu Asn Ala
 50                  55                  60 caa gat cac ggc gta ttt gtg gaa gat aaa gat tca ccg tat gta aat       240
Gln Asp His Gly Val Phe Val Glu Asp Lys Asp Ser Pro Tyr Val Asn
 65                  70                  75                  80 att atc gtg gca cgg acc gat aac aaa gac agc aaa gcc gta cag act       288
Ile Ile Val Ala Arg Thr Asp Asn Lys Asp Ser Lys Ala Val Gln Thr
                 85                  90                  95 ttc gtg aaa gcc tac caa acc ccg gaa gtg gaa caa gaa gcg aaa aaa       336
Phe Val Lys Ala Tyr Gln Thr Pro Glu Val Glu Gln Glu Ala Lys Lys
            100                 105                 110 cac ttt aaa gac ggc gtg gta aaa ggc tgg                               366
His Phe Lys Asp Gly Val Val Lys Gly Trp
            115                 120
```

<210> SEQ ID NO 226
<211> LENGTH: 122
<212> TYPE: PRT
<213> ORGANISM: Actinobacillus actinomycetemcomitans

<400> SEQUENCE: 226

```
Leu Leu Glu Lys Gln Gly Leu Ile Lys Leu Lys Asp Pro Thr Asn Leu
 1               5                  10                  15

Phe Ser Thr Ser Ile Asp Ile Ile Glu Asn Pro Lys Asn Leu Gln Ile
             20                  25                  30

Lys Glu Val Asp Thr Ser Val Ala Ala Arg Ala Leu Asp Asp Val Asp
         35                  40                  45

Leu Ala Val Val Asn Asn Asn Tyr Ala Gly Gln Val Gly Leu Asn Ala
 50                  55                  60

Gln Asp His Gly Val Phe Val Glu Asp Lys Asp Ser Pro Tyr Val Asn
 65                  70                  75                  80

Ile Ile Val Ala Arg Thr Asp Asn Lys Asp Ser Lys Ala Val Gln Thr
                 85                  90                  95

Phe Val Lys Ala Tyr Gln Thr Pro Glu Val Glu Gln Glu Ala Lys Lys
            100                 105                 110

His Phe Lys Asp Gly Val Val Lys Gly Trp
            115                 120
```

<210> SEQ ID NO 227
<211> LENGTH: 465
<212> TYPE: DNA
<213> ORGANISM: Actinobacillus actinomycetemcomitans
<220> FEATURE:
<221> NAME/KEY: CDS
<222> LOCATION: (1)..(465)

<400> SEQUENCE: 227

```
atg act tgg caa aac gtg tcg atc atc gtt agt tat cct caa act gac         48
Met Thr Trp Gln Asn Val Ser Ile Ile Val Ser Tyr Pro Gln Thr Asp
 1               5                  10                  15 ata aaa agg gga tct ttt atg aac ttg aaa aaa tta tta ggc gtc gca        96
Ile Lys Arg Gly Ser Phe Met Asn Leu Lys Lys Leu Leu Gly Val Ala
             20                  25                  30
```

```
aca tta gcc tcc gta ttc gcc tta acg gct tgt aat gaa gag aaa aaa      144
Thr Leu Ala Ser Val Phe Ala Leu Thr Ala Cys Asn Glu Glu Lys Lys
            35                  40                  45 ccg gaa gcc gca ccg gca gac aaa ccg gcg gca gaa gcc ccg gca aca      192
Pro Glu Ala Ala Pro Ala Asp Lys Pro Ala Ala Glu Ala Pro Ala Thr
 50                  55                  60 atc aaa gtg ggc gtg atg gca gga ccg gaa cac caa gtg gct gaa atc      240
Ile Lys Val Gly Val Met Ala Gly Pro Glu His Gln Val Ala Glu Ile
 65                  70                  75                  80 gca gcg aaa gtg gca aaa gaa aaa tac aac tta gac gta gaa tac gtt      288
Ala Ala Lys Val Ala Lys Glu Lys Tyr Asn Leu Asp Val Glu Tyr Val
                 85                  90                  95 tta ttc aat gac tac gcc ttg cca aac act gca gtg tct aaa ggt gat      336
Leu Phe Asn Asp Tyr Ala Leu Pro Asn Thr Ala Val Ser Lys Gly Asp
            100                 105                 110 tta gac gtt aac gca atg caa cat aaa ccg tat tta gac aaa gat tcc      384
Leu Asp Val Asn Ala Met Gln His Lys Pro Tyr Leu Asp Lys Asp Ser
        115                 120                 125 caa gcg aaa gga ttg aac aac tta gtg atc gtg ggt aat acc ttc gtt      432
Gln Ala Lys Gly Leu Asn Asn Leu Val Ile Val Gly Asn Thr Phe Val
130                 135                 140 tac ccg tta gcc ggc tat tca aaa aaa atc aaa                          465
Tyr Pro Leu Ala Gly Tyr Ser Lys Lys Ile Lys
145                 150                 155

<210> SEQ ID NO 228
<211> LENGTH: 155
<212> TYPE: PRT
<213> ORGANISM: Actinobacillus actinomycetemcomitans

<400> SEQUENCE: 228

Met Thr Trp Gln Asn Val Ser Ile Ile Val Ser Tyr Pro Gln Thr Asp
 1               5                  10                  15

Ile Lys Arg Gly Ser Phe Met Asn Leu Lys Lys Leu Leu Gly Val Ala
            20                  25                  30

Thr Leu Ala Ser Val Phe Ala Leu Thr Ala Cys Asn Glu Glu Lys Lys
        35                  40                  45

Pro Glu Ala Ala Pro Ala Asp Lys Pro Ala Ala Glu Ala Pro Ala Thr
 50                  55                  60

Ile Lys Val Gly Val Met Ala Gly Pro Glu His Gln Val Ala Glu Ile
 65                  70                  75                  80

Ala Ala Lys Val Ala Lys Glu Lys Tyr Asn Leu Asp Val Glu Tyr Val
                 85                  90                  95

Leu Phe Asn Asp Tyr Ala Leu Pro Asn Thr Ala Val Ser Lys Gly Asp
            100                 105                 110

Leu Asp Val Asn Ala Met Gln His Lys Pro Tyr Leu Asp Lys Asp Ser
        115                 120                 125

Gln Ala Lys Gly Leu Asn Asn Leu Val Ile Val Gly Asn Thr Phe Val
130                 135                 140

Tyr Pro Leu Ala Gly Tyr Ser Lys Lys Ile Lys
145                 150                 155

<210> SEQ ID NO 229
<211> LENGTH: 1008
<212> TYPE: DNA
<213> ORGANISM: Actinobacillus actinomycetemcomitans
<220> FEATURE:
<221> NAME/KEY: CDS
<222> LOCATION: (1)..(1008)
```

<400> SEQUENCE: 229

```
atg atg gaa ctc gcc tat ttg caa aaa acg ccg cca aaa cag acc gca        48
Met Met Glu Leu Ala Tyr Leu Gln Lys Thr Pro Pro Lys Gln Thr Ala
1               5                   10                  15 ctt tta aaa gcg gaa tgc gcg gat ttt gtc gtc aaa gag caa ctg ggc        96
Leu Leu Lys Ala Glu Cys Ala Asp Phe Val Val Lys Glu Gln Leu Gly
            20                  25                  30 tac gac atg agc ggc gac ggc gaa ttc gtg gcg gtg aaa ata cgc aaa       144
Tyr Asp Met Ser Gly Asp Gly Glu Phe Val Ala Val Lys Ile Arg Lys
        35                  40                  45 acc gat tgc aac acc ttg ttt gta ggc gag caa ctg gcg aaa ttc gcc       192
Thr Asp Cys Asn Thr Leu Phe Val Gly Glu Gln Leu Ala Lys Phe Ala
    50                  55                  60 ggc att tcg gca cgc aac atg agt tat gcc ggt ttg aaa gat cgc aaa       240
Gly Ile Ser Ala Arg Asn Met Ser Tyr Ala Gly Leu Lys Asp Arg Lys
65                  70                  75                  80 gct gtc acc gaa caa tgg ttc agc ctg caa atg ccc ggg caa ccg acg       288
Ala Val Thr Glu Gln Trp Phe Ser Leu Gln Met Pro Gly Gln Pro Thr
                85                  90                  95 ccg gat ttc agc caa ttt cac ctt gac ggc gtg gat att ctt gaa gtg       336
Pro Asp Phe Ser Gln Phe His Leu Asp Gly Val Asp Ile Leu Glu Val
            100                 105                 110 acc cgc cac caa cgc aaa atc cgt atc ggc agc ctg caa ggc aat cat       384
Thr Arg His Gln Arg Lys Ile Arg Ile Gly Ser Leu Gln Gly Asn His
        115                 120                 125 ttt gag att ttg ctg cgc cac gcg gaa gaa acc gac gag ctc aaa gtg       432
Phe Glu Ile Leu Leu Arg His Ala Glu Glu Thr Asp Glu Leu Lys Val
    130                 135                 140 cgg ttg gat ttt ctg gca aaa aac ggc ttc ccc aat tat ttc acc gaa       480
Arg Leu Asp Phe Leu Ala Lys Asn Gly Phe Pro Asn Tyr Phe Thr Glu
145                 150                 155                 160 cag cgt ttc ggg cgc gac ggc aac aat ctc acc caa gcc cta cgc tgg       528
Gln Arg Phe Gly Arg Asp Gly Asn Asn Leu Thr Gln Ala Leu Arg Trp
                165                 170                 175 gcg gcg ggc gaa atc aaa gtg aaa gat cgc aac aag cgc agt ttc tat       576
Ala Ala Gly Glu Ile Lys Val Lys Asp Arg Asn Lys Arg Ser Phe Tyr
            180                 185                 190 att tcc gcc gcc cgc agt gag att ttc aat tta atc gtt gcc aaa cgt       624
Ile Ser Ala Ala Arg Ser Glu Ile Phe Asn Leu Ile Val Ala Lys Arg
        195                 200                 205 att gaa ctc agt ctg gcg cag cag gtc tta aat gga gac gtt ttg caa       672
Ile Glu Leu Ser Leu Ala Gln Gln Val Leu Asn Gly Asp Val Leu Gln
    210                 215                 220 ctg aac ggt tcg cac agt tgg ttt gtg gcg gac gca tcg gaa gat ttg       720
Leu Asn Gly Ser His Ser Trp Phe Val Ala Asp Ala Ser Glu Asp Leu
225                 230                 235                 240 acg caa ctg caa caa cgc ttg gca caa cgg gat att ttg ctt acc gca       768
Thr Gln Leu Gln Gln Arg Leu Ala Gln Arg Asp Ile Leu Leu Thr Ala
                245                 250                 255 ccg ctt atc ggc gaa gag gac aaa agt gcg gtg gat ttt gag aat gaa       816
Pro Leu Ile Gly Glu Glu Asp Lys Ser Ala Val Asp Phe Glu Asn Glu
            260                 265                 270 att ttt gtc gcg cac caa gcc ttg ttc cat ttg atg cgg caa gaa cgc       864
Ile Phe Val Ala His Gln Ala Leu Phe His Leu Met Arg Gln Glu Arg
        275                 280                 285 gtg aaa gcc gcc cgc cgt ccg att tta atg cag gcg caa cag ttt caa       912
Val Lys Ala Ala Arg Arg Pro Ile Leu Met Gln Ala Gln Gln Phe Gln
    290                 295                 300
```

```
tgg caa ttt gaa ccg aac ggt ttg cgc ctt aaa ttt tat ttg ccg gca    960
Trp Gln Phe Glu Pro Asn Gly Leu Arg Leu Lys Phe Tyr Leu Pro Ala
305                 310                 315                 320 ggc agt tac gcc acg gcg ttg gta cgc gag ctg gtg aat gtt gaa aac   1008
Gly Ser Tyr Ala Thr Ala Leu Val Arg Glu Leu Val Asn Val Glu Asn
                325                 330                 335
```

<210> SEQ ID NO 230
<211> LENGTH: 336
<212> TYPE: PRT
<213> ORGANISM: Actinobacillus actinomycetemcomitans

<400> SEQUENCE: 230

```
Met Met Glu Leu Ala Tyr Leu Gln Lys Thr Pro Pro Lys Gln Thr Ala
1               5                   10                  15

Leu Leu Lys Ala Glu Cys Ala Asp Phe Val Val Lys Glu Gln Leu Gly
                20                  25                  30

Tyr Asp Met Ser Gly Asp Gly Glu Phe Val Ala Val Lys Ile Arg Lys
            35                  40                  45

Thr Asp Cys Asn Thr Leu Phe Val Gly Glu Gln Leu Ala Lys Phe Ala
50                  55                  60

Gly Ile Ser Ala Arg Asn Met Ser Tyr Ala Gly Leu Lys Asp Arg Lys
65                  70                  75                  80

Ala Val Thr Glu Gln Trp Phe Ser Leu Gln Met Pro Gly Gln Pro Thr
                85                  90                  95

Pro Asp Phe Ser Gln Phe His Leu Asp Gly Val Asp Ile Leu Glu Val
            100                 105                 110

Thr Arg His Gln Arg Lys Ile Arg Ile Gly Ser Leu Gln Gly Asn His
        115                 120                 125

Phe Glu Ile Leu Leu Arg His Ala Glu Glu Thr Asp Glu Leu Lys Val
    130                 135                 140

Arg Leu Asp Phe Leu Ala Lys Asn Gly Phe Pro Asn Tyr Phe Thr Glu
145                 150                 155                 160

Gln Arg Phe Gly Arg Asp Gly Asn Asn Leu Thr Gln Ala Leu Arg Trp
                165                 170                 175

Ala Ala Gly Glu Ile Lys Val Lys Asp Arg Asn Lys Arg Ser Phe Tyr
            180                 185                 190

Ile Ser Ala Ala Arg Ser Glu Ile Phe Asn Leu Ile Val Ala Lys Arg
        195                 200                 205

Ile Glu Leu Ser Leu Ala Gln Gln Val Leu Asn Gly Asp Val Leu Gln
    210                 215                 220

Leu Asn Gly Ser His Ser Trp Phe Val Ala Asp Ala Ser Glu Asp Leu
225                 230                 235                 240

Thr Gln Leu Gln Gln Arg Leu Ala Gln Arg Asp Ile Leu Leu Thr Ala
                245                 250                 255

Pro Leu Ile Gly Glu Glu Asp Lys Ser Ala Val Asp Phe Glu Asn Glu
            260                 265                 270

Ile Phe Val Ala His Gln Ala Leu Phe His Leu Met Arg Gln Glu Arg
        275                 280                 285

Val Lys Ala Ala Arg Arg Pro Ile Leu Met Gln Ala Gln Gln Phe Gln
    290                 295                 300

Trp Gln Phe Glu Pro Asn Gly Leu Arg Leu Lys Phe Tyr Leu Pro Ala
305                 310                 315                 320

Gly Ser Tyr Ala Thr Ala Leu Val Arg Glu Leu Val Asn Val Glu Asn
                325                 330                 335
```

<210> SEQ ID NO 231
<211> LENGTH: 738
<212> TYPE: DNA
<213> ORGANISM: Actinobacillus actinomycetemcomitans
<220> FEATURE:
<221> NAME/KEY: CDS
<222> LOCATION: (1)..(738)

<400> SEQUENCE: 231

| | | | | | | | | | | | | | | | | |
|---|---|---|---|---|---|---|---|---|---|---|---|---|---|---|---|---|
| atg | aat | att | tta | tta | agt | aac | gat | gac | ggc | att | cac | gcg | ccg | ggc | att | 48 |
| Met | Asn | Ile | Leu | Leu | Ser | Asn | Asp | Asp | Gly | Ile | His | Ala | Pro | Gly | Ile | |
| 1 | | | | 5 | | | | | 10 | | | | | 15 | | |

| cgt | gtg | atg | gca | gaa | gca | ttg | cgt | aag | att | gcc | aat | gtg | acc | atc | gtc | 96 |
|---|---|---|---|---|---|---|---|---|---|---|---|---|---|---|---|---|
| Arg | Val | Met | Ala | Glu | Ala | Leu | Arg | Lys | Ile | Ala | Asn | Val | Thr | Ile | Val | |
| | | 20 | | | | | 25 | | | | | 30 | | | | |

| gcg | ccg | gac | agc | aac | cgc | agc | gcc | gcc | tcc | agt | tcc | tta | acc | ttg | gtg | 144 |
|---|---|---|---|---|---|---|---|---|---|---|---|---|---|---|---|---|
| Ala | Pro | Asp | Ser | Asn | Arg | Ser | Ala | Ala | Ser | Ser | Ser | Leu | Thr | Leu | Val | |
| | | 35 | | | | | 40 | | | | | 45 | | | | |

| aag | ccg | ttg | tat | ccg | tta | cat | ttg | gaa | agc | ggt | gat | tat | tgc | gtc | aac | 192 |
|---|---|---|---|---|---|---|---|---|---|---|---|---|---|---|---|---|
| Lys | Pro | Leu | Tyr | Pro | Leu | His | Leu | Glu | Ser | Gly | Asp | Tyr | Cys | Val | Asn | |
| | 50 | | | | | 55 | | | | | 60 | | | | | |

| ggc | acg | ccg | gcg | gat | tgc | gtg | cat | att | gcg | ctg | aac | ggt | ttt | ctt | tcc | 240 |
|---|---|---|---|---|---|---|---|---|---|---|---|---|---|---|---|---|
| Gly | Thr | Pro | Ala | Asp | Cys | Val | His | Ile | Ala | Leu | Asn | Gly | Phe | Leu | Ser | |
| 65 | | | | | 70 | | | | | 75 | | | | | 80 | |

| ggg | cgc | atc | gat | ttg | gtg | att | tcc | ggc | atc | aac | gcc | ggg | gcg | aac | ctg | 288 |
|---|---|---|---|---|---|---|---|---|---|---|---|---|---|---|---|---|
| Gly | Arg | Ile | Asp | Leu | Val | Ile | Ser | Gly | Ile | Asn | Ala | Gly | Ala | Asn | Leu | |
| | | | | 85 | | | | | 90 | | | | | 95 | | |

| ggc | gat | gat | gtg | cta | tat | tcc | ggc | acg | gtc | gcg | gca | gca | ttt | gaa | ggg | 336 |
|---|---|---|---|---|---|---|---|---|---|---|---|---|---|---|---|---|
| Gly | Asp | Asp | Val | Leu | Tyr | Ser | Gly | Thr | Val | Ala | Ala | Ala | Phe | Glu | Gly | |
| | | | 100 | | | | | 105 | | | | | 110 | | | |

| cgt | cat | ctg | ggc | ttg | ccg | tct | att | gcg | gta | tcg | ctc | gat | ggt | cgt | caa | 384 |
|---|---|---|---|---|---|---|---|---|---|---|---|---|---|---|---|---|
| Arg | His | Leu | Gly | Leu | Pro | Ser | Ile | Ala | Val | Ser | Leu | Asp | Gly | Arg | Gln | |
| | | 115 | | | | | 120 | | | | | 125 | | | | |

| cat | ttt | gaa | acg | gcg | gcg | cgc | gtg | gta | tgc | gat | ttg | gtg | ccg | aaa | tta | 432 |
|---|---|---|---|---|---|---|---|---|---|---|---|---|---|---|---|---|
| His | Phe | Glu | Thr | Ala | Ala | Arg | Val | Val | Cys | Asp | Leu | Val | Pro | Lys | Leu | |
| | 130 | | | | | 135 | | | | | 140 | | | | | |

| cac | gcc | caa | tta | tta | ggc | aaa | cac | gaa | att | ctg | aat | att | aac | gtg | ccc | 480 |
|---|---|---|---|---|---|---|---|---|---|---|---|---|---|---|---|---|
| His | Ala | Gln | Leu | Leu | Gly | Lys | His | Glu | Ile | Leu | Asn | Ile | Asn | Val | Pro | |
| 145 | | | | | 150 | | | | | 155 | | | | | 160 | |

| gat | gtg | cct | tac | gaa | gaa | ctg | aaa | ggc | att | aaa | gtg | tgc | cat | ttg | ggc | 528 |
|---|---|---|---|---|---|---|---|---|---|---|---|---|---|---|---|---|
| Asp | Val | Pro | Tyr | Glu | Glu | Leu | Lys | Gly | Ile | Lys | Val | Cys | His | Leu | Gly | |
| | | | | 165 | | | | | 170 | | | | | 175 | | |

| tac | cgt | tct | tcc | gct | tct | gaa | gtg | att | aaa | cag | caa | agc | ccg | cgt | ggc | 576 |
|---|---|---|---|---|---|---|---|---|---|---|---|---|---|---|---|---|
| Tyr | Arg | Ser | Ser | Ala | Ser | Glu | Val | Ile | Lys | Gln | Gln | Ser | Pro | Arg | Gly | |
| | | | 180 | | | | | 185 | | | | | 190 | | | |

| gaa | gac | atg | tat | tgg | atc | ggg | ctc | agc | ggc | ttg | ccg | gaa | tat | gaa | agc | 624 |
|---|---|---|---|---|---|---|---|---|---|---|---|---|---|---|---|---|
| Glu | Asp | Met | Tyr | Trp | Ile | Gly | Leu | Ser | Gly | Leu | Pro | Glu | Tyr | Glu | Ser | |
| | | 195 | | | | | 200 | | | | | 205 | | | | |

| gaa | ggc | acc | gat | ttc | cac | gcg | gtg | aaa | aac | ggc | tat | gtt | tcc | att | acg | 672 |
|---|---|---|---|---|---|---|---|---|---|---|---|---|---|---|---|---|
| Glu | Gly | Thr | Asp | Phe | His | Ala | Val | Lys | Asn | Gly | Tyr | Val | Ser | Ile | Thr | |
| | 210 | | | | | 215 | | | | | 220 | | | | | |

| ccg | att | cag | gtg | gac | atg | acc | gcg | cac | cac | tca | atc | aac | gct | tta | caa | 720 |
|---|---|---|---|---|---|---|---|---|---|---|---|---|---|---|---|---|
| Pro | Ile | Gln | Val | Asp | Met | Thr | Ala | His | His | Ser | Ile | Asn | Ala | Leu | Gln | |
| 225 | | | | | 230 | | | | | 235 | | | | | 240 | |

| cgt | tgg | tta | gaa | agt | gaa | | | | | | | | | | | 738 |
|---|---|---|---|---|---|---|---|---|---|---|---|---|---|---|---|---|
| Arg | Trp | Leu | Glu | Ser | Glu | | | | | | | | | | | |
| | | | | 245 | | | | | | | | | | | | |

<210> SEQ ID NO 232
<211> LENGTH: 246
<212> TYPE: PRT

<213> ORGANISM: Actinobacillus actinomycetemcomitans

<400> SEQUENCE: 232

```
Met Asn Ile Leu Leu Ser Asn Asp Asp Gly Ile His Ala Pro Gly Ile
1               5                   10                  15

Arg Val Met Ala Glu Ala Leu Arg Lys Ile Ala Asn Val Thr Ile Val
            20                  25                  30

Ala Pro Asp Ser Asn Arg Ser Ala Ala Ser Ser Leu Thr Leu Val
        35                  40                  45

Lys Pro Leu Tyr Pro Leu His Leu Glu Ser Gly Asp Tyr Cys Val Asn
50                  55                  60

Gly Thr Pro Ala Asp Cys Val His Ile Ala Leu Asn Gly Phe Leu Ser
65                  70                  75                  80

Gly Arg Ile Asp Leu Val Ile Ser Gly Ile Asn Ala Gly Ala Asn Leu
                85                  90                  95

Gly Asp Asp Val Leu Tyr Ser Gly Thr Val Ala Ala Phe Glu Gly
            100                 105                 110

Arg His Leu Gly Leu Pro Ser Ile Ala Val Ser Leu Asp Gly Arg Gln
        115                 120                 125

His Phe Glu Thr Ala Ala Arg Val Val Cys Asp Leu Val Pro Lys Leu
130                 135                 140

His Ala Gln Leu Leu Gly Lys His Glu Ile Leu Asn Ile Asn Val Pro
145                 150                 155                 160

Asp Val Pro Tyr Glu Glu Leu Lys Gly Ile Lys Val Cys His Leu Gly
                165                 170                 175

Tyr Arg Ser Ser Ala Ser Glu Val Ile Lys Gln Gln Ser Pro Arg Gly
            180                 185                 190

Glu Asp Met Tyr Trp Ile Gly Leu Ser Gly Leu Pro Glu Tyr Glu Ser
        195                 200                 205

Glu Gly Thr Asp Phe His Ala Val Lys Asn Gly Tyr Val Ser Ile Thr
210                 215                 220

Pro Ile Gln Val Asp Met Thr Ala His His Ser Ile Asn Ala Leu Gln
225                 230                 235                 240

Arg Trp Leu Glu Ser Glu
                245
```

<210> SEQ ID NO 233
<211> LENGTH: 426
<212> TYPE: DNA
<213> ORGANISM: Actinobacillus actinomycetemcomitans
<220> FEATURE:
<221> NAME/KEY: CDS
<222> LOCATION: (1)..(426)

<400> SEQUENCE: 233

```
gat ctg ccg ttg gcg aac cct tac gaa atg ctg atc ctc gcg tcc atc    48
Asp Leu Pro Leu Ala Asn Pro Tyr Glu Met Leu Ile Leu Ala Ser Ile
1               5                   10                  15 gtg gaa aaa gaa acc ggc att gct gca gaa cgc cca caa gtg gcg tcg    96
Val Glu Lys Glu Thr Gly Ile Ala Ala Glu Arg Pro Gln Val Ala Ser
            20                  25                  30 gta ttc att aat cgg tta aaa gcc aaa atg aag ctg caa acc gat ccg   144
Val Phe Ile Asn Arg Leu Lys Ala Lys Met Lys Leu Gln Thr Asp Pro
        35                  40                  45 acc gtc att tac ggc atg ggc gac gac tac aac ggc aat att cgc aaa   192
Thr Val Ile Tyr Gly Met Gly Asp Asp Tyr Asn Gly Asn Ile Arg Lys
50                  55                  60
```

-continued

```
aaa gat ttg gaa acg cca acg cct tat aac acc tat gtg att gac ggc     240
Lys Asp Leu Glu Thr Pro Thr Pro Tyr Asn Thr Tyr Val Ile Asp Gly
 65              70                  75                  80 ttg ccg ccg aca ccg att gcg atg ccg agt gaa gag gcg tta cag gcg     288
Leu Pro Pro Thr Pro Ile Ala Met Pro Ser Glu Glu Ala Leu Gln Ala
                 85                  90                  95 gtg gca cat ccg gcg caa acg gcg ttt tat tat ttc gtg gca gac ggc     336
Val Ala His Pro Ala Gln Thr Ala Phe Tyr Tyr Phe Val Ala Asp Gly
            100                 105                 110 acg ggg gga cac aaa ttc agt cgt aat tta aac gaa cat aac aaa gcg     384
Thr Gly Gly His Lys Phe Ser Arg Asn Leu Asn Glu His Asn Lys Ala
        115                 120                 125 gtg cag caa tat ttg cgc tgg tac cgc gaa caa aac gga aaa             426
Val Gln Gln Tyr Leu Arg Trp Tyr Arg Glu Gln Asn Gly Lys
    130                 135                 140
```

<210> SEQ ID NO 234
<211> LENGTH: 142
<212> TYPE: PRT
<213> ORGANISM: Actinobacillus actinomycetemcomitans

<400> SEQUENCE: 234

```
Asp Leu Pro Leu Ala Asn Pro Tyr Glu Met Leu Ile Leu Ala Ser Ile
 1               5                  10                  15

Val Glu Lys Glu Thr Gly Ile Ala Ala Glu Arg Pro Gln Val Ala Ser
                20                  25                  30

Val Phe Ile Asn Arg Leu Lys Ala Lys Met Lys Leu Gln Thr Asp Pro
            35                  40                  45

Thr Val Ile Tyr Gly Met Gly Asp Asp Tyr Asn Gly Asn Ile Arg Lys
        50                  55                  60

Lys Asp Leu Glu Thr Pro Thr Pro Tyr Asn Thr Tyr Val Ile Asp Gly
 65              70                  75                  80

Leu Pro Pro Thr Pro Ile Ala Met Pro Ser Glu Glu Ala Leu Gln Ala
                 85                  90                  95

Val Ala His Pro Ala Gln Thr Ala Phe Tyr Tyr Phe Val Ala Asp Gly
            100                 105                 110

Thr Gly Gly His Lys Phe Ser Arg Asn Leu Asn Glu His Asn Lys Ala
        115                 120                 125

Val Gln Gln Tyr Leu Arg Trp Tyr Arg Glu Gln Asn Gly Lys
    130                 135                 140
```